United States Patent
Griffin et al.

(10) Patent No.: US 11,014,931 B2
(45) Date of Patent: May 25, 2021

(54) 3-(ETHOXYDIFLUOROMETHYL)-6-(5-FLUORO-6-(2,2,2-TRIFLUOROETHOXY) PYRIDIN-3-YL)-[1,2,4]TRIAZOLO[4,3-A] PYRAZINE AS AN ION CHANNEL MODULATOR

(71) Applicant: Praxis Precision Medicines, Inc., Cambridge, MA (US)

(72) Inventors: Andrew Mark Griffin, L'Ile Bizard (CA); Brian Edward Marron, Ada, MI (US); Gabriel Martinez Botella, Wayland, MA (US)

(73) Assignee: Praxis Precision Medicines, Inc., Cambridge, MA (US)

( * ) Notice: Subject to any disclaimer, the term of this patent is extended or adjusted under 35 U.S.C. 154(b) by 0 days.

(21) Appl. No.: 17/102,586

(22) Filed: Nov. 24, 2020

(65) Prior Publication Data

US 2021/0087197 A1   Mar. 25, 2021

Related U.S. Application Data

(63) Continuation of application No. PCT/US2019/034653, filed on May 30, 2019.

(60) Provisional application No. 62/738,508, filed on Sep. 28, 2018, provisional application No. 62/677,903, filed on May 30, 2018.

(51) Int. Cl.
*A61K 31/4985* (2006.01)
*C07D 487/04* (2006.01)

(52) U.S. Cl.
CPC ........ *C07D 487/04* (2013.01); *C07B 2200/13* (2013.01)

(58) Field of Classification Search
CPC .................... A61K 31/4985; C07D 487/04
USPC ........................................ 514/249; 544/350
See application file for complete search history.

(56) References Cited

U.S. PATENT DOCUMENTS

| | | | |
|---|---|---|---|
| 4,112,095 A | 9/1978 | Allen, Jr. et al. | |
| 4,230,705 A | 10/1980 | Allen, Jr. et al. | |
| 4,242,515 A | 12/1980 | Trust et al. | |
| 5,905,079 A | 5/1999 | Sargent et al. | |
| 6,589,952 B2 | 7/2003 | Bakthavatchalam et al. | |
| 7,863,279 B2 | 1/2011 | Even et al. | |
| 8,030,305 B2 | 10/2011 | Lu et al. | |
| 8,173,654 B2 | 5/2012 | Lu et al. | |
| 8,198,448 B2 | 6/2012 | Albrecht et al. | |
| 8,212,041 B2 | 7/2012 | Albrecht et al. | |
| 8,217,177 B2 | 7/2012 | Albrecht et al. | |
| 8,524,900 B2 | 9/2013 | Albrecht et al. | |
| 8,937,060 B2 | 1/2015 | Cid-Nunez et al. | |
| 8,952,034 B2 | 2/2015 | Corkey et al. | |
| 9,066,954 B2 | 6/2015 | Albrecht et al. | |
| 9,371,329 B2 | 6/2016 | Corkey et al. | |
| 10,280,184 B2 | 5/2019 | Friedman et al. | |
| 2002/0049208 A1 | 4/2002 | Bakthavatchalam et al. | |
| 2009/0124609 A1 | 5/2009 | Albrecht et al. | |
| 2010/0088778 A1 | 4/2010 | Mulley et al. | |
| 2011/0021521 A1 | 1/2011 | Corkey et al. | |
| 2012/0010192 A1 | 1/2012 | Kobayashi et al. | |
| 2012/0065191 A1 | 3/2012 | Kiss et al. | |
| 2012/0245164 A1 | 9/2012 | Auger et al. | |
| 2013/0315895 A1 | 11/2013 | Farrell et al. | |
| 2014/0066443 A1 | 3/2014 | Beshore et al. | |
| 2014/0303158 A1 | 10/2014 | Corkey et al. | |
| 2015/0038503 A1 | 2/2015 | Bourotte et al. | |
| 2016/0159801 A1 | 6/2016 | Quinn et al. | |
| 2016/0235718 A1 | 8/2016 | Baraban | |
| 2016/0297799 A1 | 10/2016 | Brookings et al. | |
| 2016/0317536 A1 | 11/2016 | Reich et al. | |
| 2019/0389868 A1 | 12/2019 | Reddy et al. | |
| 2020/0179358 A1 | 6/2020 | Reddy et al. | |
| 2020/0247793 A1 | 8/2020 | Reddy et al. | |
| 2020/0377499 A1 | 12/2020 | Griffin et al. | |
| 2020/0377506 A1 | 12/2020 | Reddy et al. | |
| 2020/0377507 A1 | 12/2020 | Griffin et al. | |

FOREIGN PATENT DOCUMENTS

| | | |
|---|---|---|
| JP | 2017001991 A | 1/2017 |
| WO | WO-2006061428 A2 | 6/2006 |
| WO | WO-2007075567 A1 | 7/2007 |
| WO | WO-2008008539 A2 | 1/2008 |

(Continued)

OTHER PUBLICATIONS

US 8,754,103 B2, 06/2014, Corkey et al. (withdrawn)
Albright et al. "Synthesis and anxiolytic activity of 6-(substituted-phenyl)-1,2,4-triazolo[4,3-b]pyridazines," *J. Med. Chem.* (1981) vol. 24, pp. 592-600.
Anderson et al. "Unexpected efficacy of a novel sodium channel modulator in Dravet Syndrome," Scientific Reports. 2017.
Anderson et al., "Antiepileptic activity of preferential inhibitors of persistent sodium current," Epilepsia (2014), 55(8), 1274-1283.

(Continued)

*Primary Examiner* — Douglas M Willis
(74) *Attorney, Agent, or Firm* — Goodwin Procter LLP

(57) ABSTRACT

The present invention is directed to, in part, fused heteroaryl compounds, such as the compound:

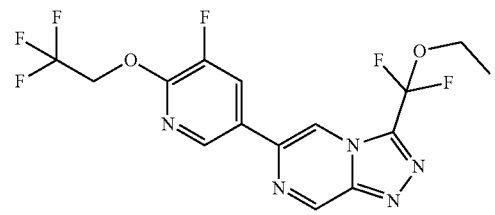

and compositions useful for preventing and/or treating a disease or condition relating to aberrant function of a voltage-gated, sodium ion channel, for example, abnormal late/persistent sodium current. Methods of treating a disease or condition relating to aberrant function of a sodium ion channel including neurological disorders (e.g., Dravet syndrome, epilepsy), pain, and neuromuscular disorders are also provided herein.

18 Claims, 9 Drawing Sheets

(56) References Cited

FOREIGN PATENT DOCUMENTS

| WO | WO-2010053757 A1 | 5/2010 |
| --- | --- | --- |
| WO | WO-2010056865 A1 | 5/2010 |
| WO | WO-2010074807 A1 | 7/2010 |
| WO | WO-2011014462 A1 | 2/2011 |
| WO | WO-2011056985 A2 | 5/2011 |
| WO | WO-2012003392 A1 | 1/2012 |
| WO | WO-2012065546 A1 | 5/2012 |
| WO | WO-2012154760 A1 | 11/2012 |
| WO | WO-2013006463 A1 | 1/2013 |
| WO | WO-2013043925 A1 | 3/2013 |
| WO | WO-2014179492 A1 | 11/2014 |
| WO | WO-2015095370 A1 | 6/2015 |
| WO | WO-2015158283 A1 | 10/2015 |
| WO | WO-2015194670 A1 | 12/2015 |
| WO | WO-2015197567 A1 | 12/2015 |
| WO | WO-2018098491 A1 | 5/2018 |
| WO | WO-2018098499 A1 | 5/2018 |
| WO | WO-2018098500 A1 | 5/2018 |
| WO | WO-2018148745 A1 | 8/2018 |
| WO | WO-2018187480 A1 | 10/2018 |
| WO | WO-2019035951 A1 | 2/2019 |
| WO | WO-2019232209 A1 | 12/2019 |
| WO | WO-2020069322 A1 | 4/2020 |

OTHER PUBLICATIONS

Baker et al. "The novel sodium channel modulator GS-458967 (GS967) is an effective treatment in a mouse model of SCN8A encephalopathy," Epilepsia, 2018, 1166-1176.
Barbieri et al. "Late sodium current blocker GS967 inhibits persistent currents induced by familial hemiplegic migraine type 3 mutations of the SCN1A gene," *The Journal of Headache and Pain* (2019) vol. 20, No. 107, pp. 1-13.
Belardinelli et al. "A Novel, Potent, and Selective Inhibitor of Cardiac Late Sodium Current Suppresses Experimental Arrhythmias," *J. Pharmacol. Exp. Ther.* (2013) vol. 344, pp. 23-32.
Guan et al. "Synthesis and anticonvulsant activity of a new 6-alkoxy-[1,2,4]-triazolo[4,3-b]pyridazine," *Eur. J. Med. Chem.* (2010) vol. 45, pp. 1746-1752.
Koltun et al. "Discovery of triazolopyridinone GS-462808, a late sodium current inhibitor (Late INai) of the cardiac Nav1.5 channel with improved efficacy and potency relative to ranolazine," *Bioorg. Med. Chem. Lett.* (2016) vol. 26, pp. 3207-3211.
PUBCHEM-CID 58763997 Create Date: Aug. 19, 2012 (14 pages).
PUBCHEM-CID 597467 Create Date: Mar. 27, 2005 (15 pages).
PUBCHEM-CID 82381512 Create Date: Oct. 20, 2014 (10 pages).
PUBCHEM-CID 89077556 Create Date: Feb. 13, 2015 (11 pages).
STN Chemical Structure Search Results dated Apr. 14, 2019 (36 pages).
STN Chemical Structure Search Results dated Apr. 2018 (55 pages).
STN Chemical Structure Search Results dated Apr. 23, 2019 (45 pages).
STN Chemical Structure Search Results dated Feb. 2018 (29 pages).
STN Chemical Structure Search Results dated Jan. 15, 2020 (22 pages).
STN Chemical Structure Search Results dated Jan. 2018 (23 pages).
STN Chemical Structure Search Results dated Mar. 20, 2018 (264 pages).
STN Chemical Structure Search Results dated Mar. 20, 2018 (83 pages).
STN Chemical Structure Search Results dated Mar. 6, 2017 (480 pages).
STN Chemical Structure Search Results dated Mar. 6, 2017 (511 pages).
STN Chemical Structure Search Results dated May 18, 2016 (102 pages).
STN Chemical Structure Search Results dated Nov. 1, 2017 (107 pages).
STN Chemical Structure Search Results dated Nov. 21, 2017 (85 pages).
STN Chemical Structure Search Results dated Nov. 3, 2017 (57 pages).
STN Chemical Structure Search Results dated Nov. 6, 2017 (123 pages).
STN Chemical Structure Search Results dated Nov. 6, 2017 (7 pages).
Wengert et al. "Prax330 reduces persistent and resurgent sodium channel currents and neuronal hyperexcitability of subiculum neurons in a mouse model of SCN8A epileptic encephalopathy," *Neuropharmacology* (2019) vol. 158, No. 107699, pp. 1-11.
Written Opinion of the International Searching Authority and International Search Report for PCT/US2017/063507 dated Mar. 29, 2019 (9 pages).
Written Opinion of the International Searching Authority and International Search Report for PCT/US2017/063533 dated Mar. 29, 2019 (10 pages).
Written Opinion of the International Searching Authority and International Search Report for PCT/US2017/063534 dated Mar. 28, 2019 (11 pages).
Written Opinion of the International Searching Authority and International Search Report for PCT/US2018/00224 dated Nov. 5, 2018 (8 pages).
Written Opinion of the International Searching Authority and International Search Report for PCT/US2018/018044 dated May 24, 2018 (10 pages).
Written Opinion of the International Searching Authority and International Search Report for PCT/US2018/026099 dated Aug. 10, 2018 (9 pages).
Written Opinion of the International Searching Authority and International Search Report for PCT/US2019/034653 dated Aug. 9, 2019 (9 pages).
Zablocki et al. "Discovery of Dihydrobenzoxazepinone (GS-6615) Late Sodium Current Inhibitor (Late $I_{Na}i$), a Phase II Agent with Demonstrated Preclinical Anti-Ischemic and Antiarrhythmic Properties," *Journal of Medicinal Chemistry* (2016) vol. 59, pp. 9005-9017.
Written Opinion of the International Searching Authority and International Search Report for PCT/US2019/053467 dated Jan. 14, 2020 (9 pages).

3-(ETHOXYDIFLUOROMETHYL)-6-(5-FLUORO-6-(2,2,2-TRIFLUOROETHOXY)PYRIDIN-3-YL)-[1,2,4]TRIAZOLO[4,3-A]PYRAZINE AS AN ION CHANNEL MODULATOR

CROSS REFERENCE TO RELATED APPLICATIONS

This application is a continuation of International Application No. PCT/US2019/034653, with an international filing date of May 30, 2019, which claims priority to and the benefit of U.S. Provisional Patent Application No. 62/677,903, filed May 30, 2018, and 62/738,508, filed Sep. 28, 2018, each of which is incorporated herein by reference in its entirety.

BACKGROUND

Sodium ion (Na+) channels primarily open in a transient manner and are quickly inactivated, thereby generating a fast Na+ current to initiate the action potential. The late or persistent sodium current (INaL) is a sustained component of the fast Na+ current of cardiac myocytes and neurons. Many common neurological and cardiac conditions are associated with abnormal INaL enhancement, which contributes to the pathogenesis of both electrical and contractile dysfunction in mammals (see, e.g., *Pharmacol Ther* (2008) 119:326-339). Accordingly, pharmaceutical compounds that selectively modulate sodium channel activity, e.g., abnormal INaL, are useful in treating such disease states.

SUMMARY

Described herein are fused heteroaryl compounds and compositions useful for preventing and/or treating a disease, disorder, or condition, e.g., a disease, disorder, or condition relating to aberrant function of a sodium ion channel, e.g., abnormal late sodium current (INaL). In one aspect, the present disclosure features compounds of Formula (I):

In one aspect, the present invention provides a compound having the Formula I:

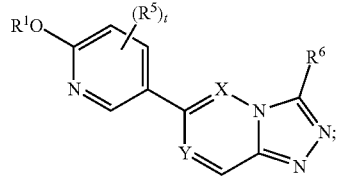

(I)

or a pharmaceutically acceptable salt thereof, wherein
X and Y are each independently $CR^d$ or N;
$R^1$ is

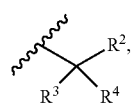

monocyclic $C_{3-6}$ cycloalkyl, or 4- to 7-membered monocyclic heterocyclyl, wherein said cycloalkyl and heterocyclyl are optionally substituted with one or more $R^a$;

$R^2$ is $C_{1-4}$haloalkyl, phenyl, or monocyclic $C_{3-6}$ cycloalkyl optionally substituted with one or more $R^b$;
$R^3$ is hydrogen, $C_{1-4}$alkyl, or $C_{1-4}$haloalkyl;
$R^4$ is hydrogen or $C_{1-4}$alkyl;
$R^5$ is halo;
$R^6$ is $C_{1-4}$alkyl or $C_{1-4}$haloalkyl, wherein said $C_{1-4}$alkyl or $C_{1-4}$haloalkyl are each substituted with $OR^c$;
t is 0, 1, or 2;
$R^a$ and $R^b$ are each independently selected from is selected from halo, $C_{1-4}$alkyl, $C_{1-4}$haloalkyl, $C_{1-4}$alkoxy, and $C_{1-4}$haloalkoxy,
$R^c$ is $C_{1-4}$alkyl optionally substituted with $C_{3-6}$ cycloalkyl or $C_{1-4}$alkoxy, or $C_{3-6}$ cycloalkyl; and
$R^d$ is hydrogen or $C_{1-4}$alkyl;
provided the compound is not a compound having the formula:

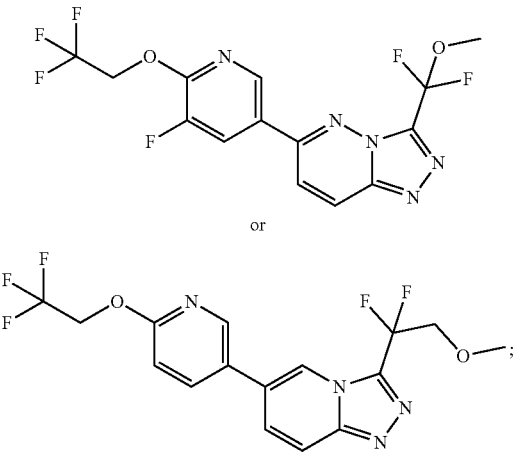

or a pharmaceutically acceptable salt thereof.

In some embodiments, the compound is of the Formula I-a:

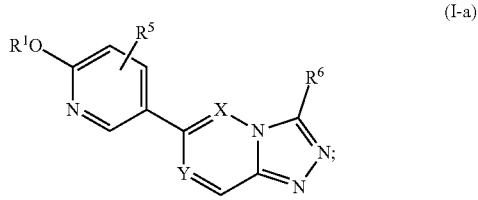

(I-a)

or a pharmaceutically acceptable salt thereof, wherein the variables are as defined herein.

In some embodiments, the compound is of the Formula I-b:

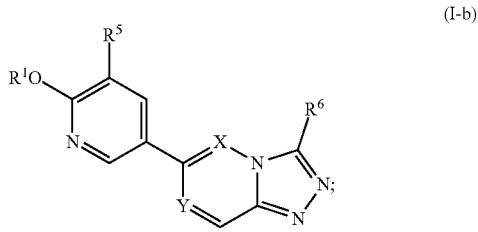

(I-b)

or a pharmaceutically acceptable salt thereof, wherein the variables are as defined herein.

In some embodiments, the compound is of the Formula II:

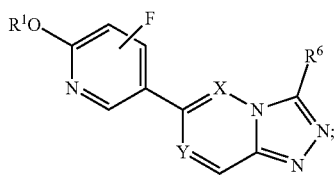
(II)

or a pharmaceutically acceptable salt thereof, wherein the variables are as defined herein.

In some embodiments, the compound is of the Formula III:

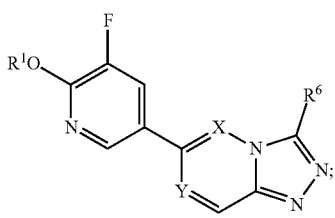
(III)

or a pharmaceutically acceptable salt thereof, wherein the variables are as defined herein.

In some embodiments, the compound is of the Formula I-c:

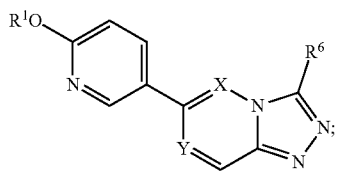
(I-c)

or a pharmaceutically acceptable salt thereof, wherein the variables are as defined herein.

In another aspect, the present disclosure provides a compound having the Formula I-d:

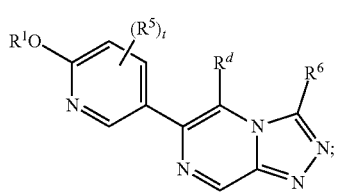
(I-d)

or a pharmaceutically acceptable salt thereof, wherein $R^1$ is

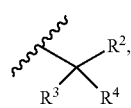

monocyclic $C_{3-6}$ cycloalkyl, or 4- to 7-membered monocyclic heterocyclyl, wherein said cycloalkyl and heterocyclyl are optionally substituted with one or more $R^a$;

$R^2$ is $C_{1-4}$haloalkyl, phenyl, or monocyclic $C_{3-6}$ cycloalkyl optionally substituted with one or more $R^b$;

$R^3$ is hydrogen, $C_{1-4}$alkyl, or $C_{1-4}$haloalkyl;

$R^4$ is hydrogen or $C_{1-4}$alkyl;

$R^5$ is halo;

$R^6$ is $C_{1-4}$alkyl or $C_{1-4}$haloalkyl, wherein said $C_{1-4}$alkyl or $C_{1-4}$haloalkyl are each substituted with $OR^c$;

t is 0, 1, or 2;

$R^a$ and $R^b$ are each independently selected from is selected from halo, $C_{1-4}$alkyl, $C_{1-4}$haloalkyl, $C_{1-4}$alkoxy, and $C_{1-4}$haloalkoxy;

$R^c$ is $C_{1-4}$alkyl optionally substituted with $C_{3-6}$ cycloalkyl or $C_{1-4}$alkoxy, or $C_{3-6}$ cycloalkyl; and $R^d$ is hydrogen or $C_{1-4}$alkyl.

In some embodiments, the compound is of the Formula V:

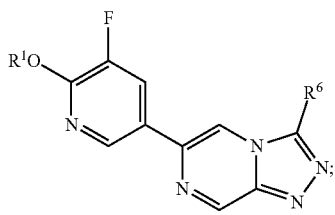
(V)

or a pharmaceutically acceptable salt thereof, wherein the variables are as defined herein.

In some embodiments, the compound is of the Formula VII:

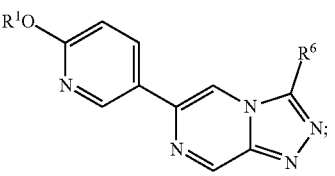
(VII)

or a pharmaceutically acceptable salt thereof, wherein the variables are as defined herein.

In some embodiments, the compound is of the Formula VIII:

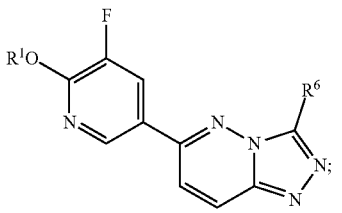
(VIII)

or a pharmaceutically acceptable salt thereof, wherein the variables are as defined herein.

In some embodiments, the compound is of the Formula VIII:

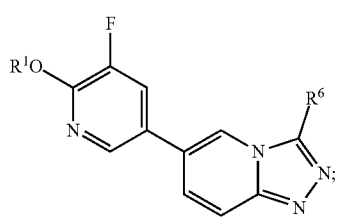

(IX)

or a pharmaceutically acceptable salt thereof, wherein the variables are as defined herein.

In another aspect, provided herein is a crystalline compound of formula:

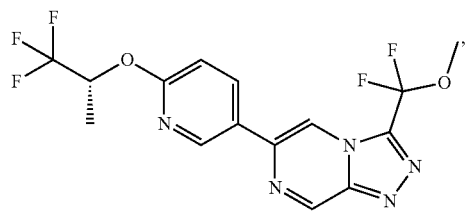 [SMILES: COC(F)(F)c1nnc2cnc(-c3ccc(O[C@H](C)C(F)(F)F)nc3)cn12]

wherein the crystalline compound exhibits an X-ray powder diffraction pattern comprising peaks at the following diffraction angles (2θ): 6.9±0.2, 16.5±0.2, and 20.8±0.2.

In another aspect, provided herein is a crystalline compound of formula:

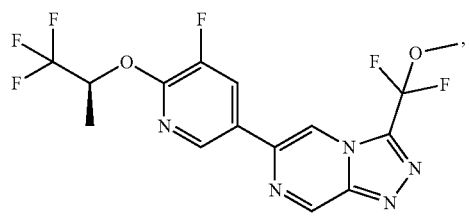 [SMILES: COC(F)(F)c1nnc2cnc(-c3cnc(O[C@@H](C)C(F)(F)F)c(F)c3)cn12]

wherein the crystalline compound exhibits an X-ray powder diffraction pattern comprising peaks at the following diffraction angles (2θ): 16.7±0.2, 19.0±0.2, and 20.4±0.2.

In another aspect, the present invention provides a crystalline compound of formula:

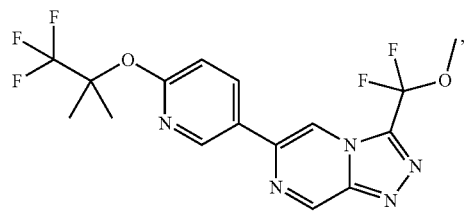 [SMILES: COC(F)(F)c1nnc2cnc(-c3ccc(OC(C)(C)C(F)(F)F)nc3)cn12]

wherein the crystalline compound exhibits an X-ray powder diffraction pattern comprising peaks at the following diffraction angles (2θ): 7.3±0.2, 14.5±0.2, and 21.9±0.2.

In another aspect, the present disclosure provides a crystalline compound of formula:

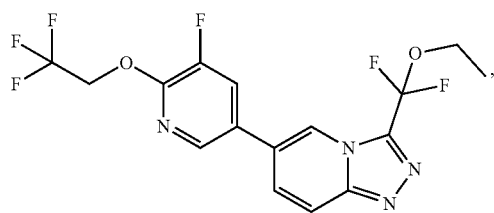

wherein the crystalline compound exhibits an X-ray powder diffraction pattern comprising peaks at the following diffraction angles (2θ): 12.6±0.2, 15.8±0.2, and 18.6±0.2.

In another aspect, the present invention provides a crystalline compound of formula:

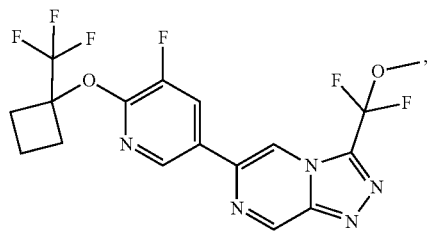 [SMILES: COC(F)(F)c1nnc2cnc(-c3cnc(OC4(C(F)(F)F)CCC4)c(F)c3)cn12]

wherein the crystalline compound exhibits an X-ray powder diffraction pattern comprising peaks at the following diffraction angles (2θ): 5.8±0.2, 19.7±0.2, and 21.0±0.2.

In another aspect, the present invention provides a crystalline compound of formula:

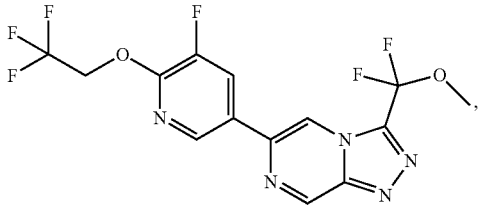 [SMILES: COC(F)(F)c1nnc2cnc(-c3cnc(OCC(F)(F)F)c(F)c3)cn12]

wherein the crystalline compound exhibits an X-ray powder diffraction pattern comprising peaks at the following diffraction angles (2θ): 7.3±0.2, 16.6±0.2, and 18.4±0.2.

In another aspect, the present invention provides a crystalline compound of formula:

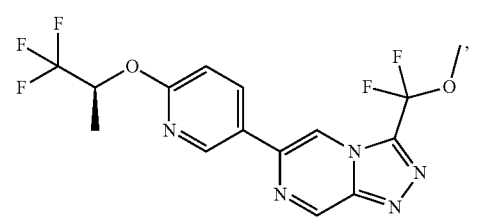 [SMILES: COC(F)(F)c1nnc2cnc(-c3ccc(O[C@@H](C)C(F)(F)F)nc3)cn12]

wherein the crystalline compound exhibits an X-ray powder diffraction pattern comprising peaks at the following diffraction angles (2θ): 6.9±0.2, 16.4±0.2, and 19.5±0.2.

In another aspect, the present invention provides a crystalline compound of formula:

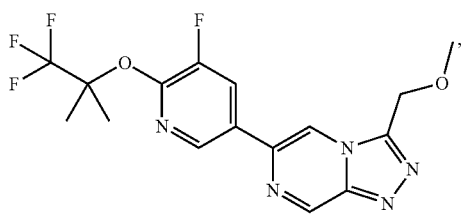 [SMILES: COCc1nnc2cnc(-c3cnc(OC(C)(C)C(F)(F)F)c(F)c3)cn12]

wherein the crystalline compound exhibits an X-ray powder diffraction pattern comprising peaks at the following diffraction angles (2θ): 9.9±0.2, 19.8±0.2, and 23.7±0.2.

In another aspect, the present disclosure provides a crystalline compound of formula:

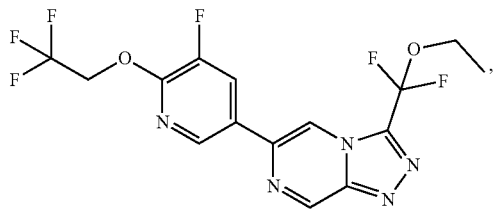 [SMILES: CCOC(F)(F)c1nnc2cnc(-c3cnc(OCC(F)(F)F)c(F)c3)cn12]

wherein the crystalline compound exhibits an X-ray powder diffraction pattern comprising peaks at the following diffraction angles (2θ): 9.3±0.2, 18.8±0.2, and 21.4±0.2.

In another aspect, provided herein is a pharmaceutical composition comprising a compound disclosed herein, or a pharmaceutically acceptable salt thereof; and a pharmaceutically acceptable carrier.

In another aspect of the disclosure, a composition comprising a compound disclosed herein (e.g., a compound of Formula I, I', I-a, I-b, I-c, I-d, II, III, V, VII, VIII, or IX), or a pharmaceutically acceptable salt thereof; and a pharmaceutically acceptable carrier is provided.

Also provided herein is a pharmaceutical composition comprising a compound disclosed herein (e.g., a compound of Formula I, I', I-a, I-b, I-c, I-d, II, III, V, VII, VIII, or IX), or a pharmaceutically acceptable salt thereof; and a pharmaceutically acceptable carrier, for use in medicine.

In another aspect, provided herein is a method of treating a condition relating to aberrant function of a sodium ion channel in a subject, comprising administering to the subject a therapeutically effective amount of a compound disclosed herein (e.g., a compound of Formula I, I', I-a, I-b, I-c, I-d, II, III, V, VII, VIII, or IX), or a pharmaceutically acceptable salt thereof, or a composition or a pharmaceutical composition disclosed herein.

In some embodiments, the condition is a neurological or psychiatric disorder. In some embodiments, the condition is epilepsy or an epilepsy syndrome. In some embodiments, the condition is a genetic epilepsy or a genetic epilepsy syndrome. In some embodiments, the condition is a pediatric epilepsy or a pediatric epilepsy syndrome. In some embodiments, the condition is epileptic encephalopathy. In some embodiments, the epileptic encephalopathy is selected from the group consisting of Dravet syndrome, infantile spasms, and Lennox-Gastaut syndrome.

In some embodiments, the condition is selected from the group consisting of epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

In another aspect, provided herein is a method of treating a neurological disorder or a psychiatric disorder, wherein the method comprises administering to a subject in need thereof a compound disclosed herein (e.g., a compound of Formula I, I', I-a, I-b, I-c, I-d, II, III, V, VII, VIII, or IX), or a pharmaceutically acceptable salt thereof or a composition or a pharmaceutical composition disclosed herein.

In another aspect, the present invention provides a method of treating a pain, wherein the method comprises administering to a subject in need thereof a compound disclosed herein (e.g., a compound of Formula I, I', I-a, I-b, I-c, I-d, II, III, V, VII, VIII, or IX), or a pharmaceutically acceptable salt thereof or a composition or a pharmaceutical composition disclosed herein.

The present disclosure also provides a composition comprising a compound disclosed herein (e.g., a compound of Formula I, I', I-a, I-b, I-c, I-d, II, III, V, VII, VIII, or IX), or a pharmaceutically acceptable salt thereof, or a pharmaceutical composition disclosed herein, or a composition disclosed herein for treating a condition relating to aberrant function of a sodium ion channel in a subject.

In some embodiments, the condition is a neurological or psychiatric disorder. In some embodiments, the condition is a pain. In some embodiments, the condition is epilepsy or an epilepsy syndrome. In some embodiments, the condition is a genetic epilepsy or a genetic epilepsy syndrome. In some embodiments, the condition is a pediatric epilepsy or a pediatric epilepsy syndrome. In some embodiments, the condition is epileptic encephalopathy. In some embodiments, the epileptic encephalopathy is selected from the group consisting of Dravet syndrome, infantile spasms, and Lennox-Gastaut syndrome.

In some embodiments, the condition is selected from the group consisting of epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, and KCNT1 epileptic encephalopathy.

In another aspect, the present disclosure provides a composition comprising a compound disclosed herein (e.g., a compound of Formula I, I', I-a, I-b, I-c, I-d, II, III, V, VII, VIII, or IX), or a pharmaceutically acceptable salt thereof, a pharmaceutical composition disclosed herein, or a composition disclosed herein for treating a neurological disorder or a psychiatric disorder.

Other objects and advantages will become apparent to those skilled in the art from a consideration of the ensuing Detailed Description, Examples, and Claims.

DETAILED DESCRIPTION

Figure 1A:
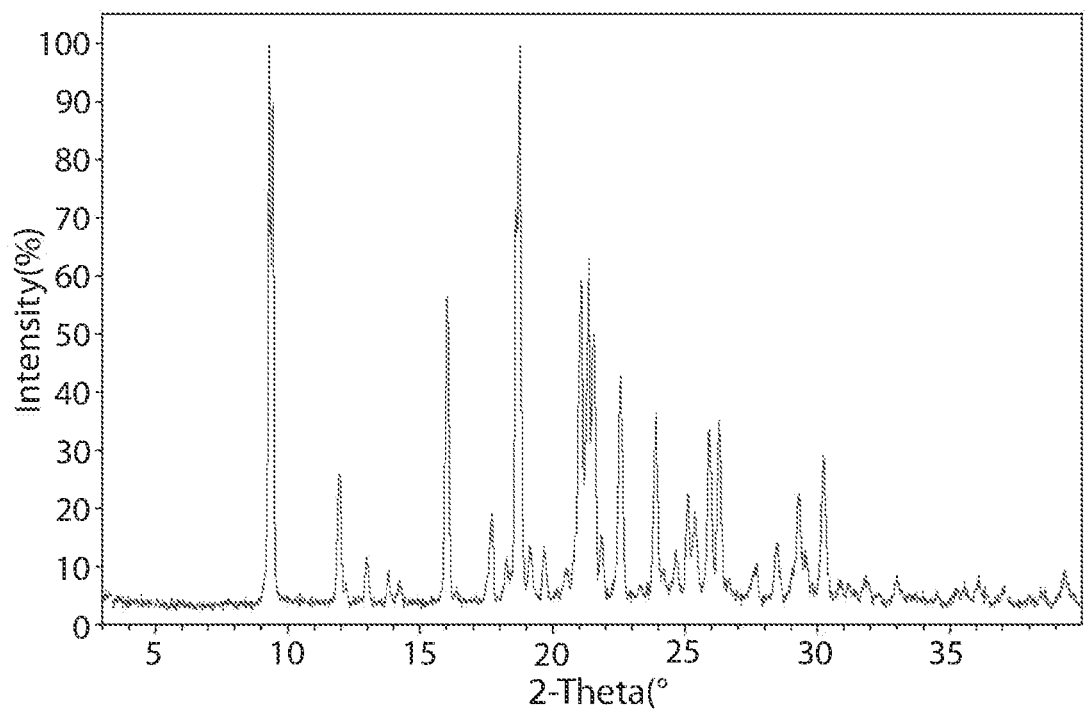
FIG. 1A shows XRPD pattern of Compound 10 raw material.

As generally described herein, the present invention provides compounds and compositions useful for preventing and/or treating a disease, disorder, or condition described herein, e.g., a disease, disorder, or condition relating to aberrant function of a sodium ion channel, such as abnormal late sodium current (INaL). Exemplary diseases, disorders, or conditions include a neurological disorder (e.g., epilepsy or an epilepsy syndrome, a neurodevelopmental disorder or a neuromuscular disorder), a psychiatric disorder, pain, or a gastrointestinal disorder.

Definitions

Chemical Definitions

Definitions of specific functional groups and chemical terms are described in more detail below. The chemical elements are identified in accordance with the Periodic Table of the Elements, CAS version, *Handbook of Chemistry and Physics*, 75*th* Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5th Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3*rd* Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw Hill, N Y, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 75% by weight, more than 80% by weight, more than 85% by weight, more than 90% by weight, more than 91% by weight, more than 92% by weight, more than 93% by weight, more than 94% by weight, more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

In the compositions provided herein, an enantiomerically pure compound can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R compound, by total weight of the compound. In certain embodiments, the active ingredient can be formulated with little or no excipient or carrier.

Compound described herein may also comprise one or more isotopic substitutions. For example, H may be in any isotopic form, including $^1$H, $^2$H (D or deuterium), and $^3$H (T or tritium); C may be in any isotopic form, including $^{12}$C, $^{13}$C, and $^{14}$C; O may be in any isotopic form, including $^{16}$O and $^{18}$O; F may be in any isotopic form, including $^{18}$F and $^{19}$F; and the like.

The following terms are intended to have the meanings presented therewith below and are useful in understanding the description and intended scope of the present invention. When describing the invention, which may include compounds and pharmaceutically acceptable salts thereof, pharmaceutical compositions containing such compounds and methods of using such compounds and compositions, the following terms, if present, have the following meanings unless otherwise indicated. It should also be understood that when described herein any of the moieties defined forth below may be substituted with a variety of substituents, and that the respective definitions are intended to include such substituted moieties within their scope as set out below. Unless otherwise stated, the term "substituted" is to be defined as set out below. It should be further understood that the terms "groups" and "radicals" can be considered interchangeable when used herein. The articles "a" and "an" may be used herein to refer to one or to more than one (i.e. at least one) of the grammatical objects of the article. By way of example "an analogue" means one analogue or more than one analogue.

When a range of values is listed, it is intended to encompass each value and subrange within the range. For example, "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group, e.g., having 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). Examples of $C_{1-6}$ alkyl groups include methyl, ethyl, propyl, isopropyl, butyl, isobutyl, pentyl, hexyl, and the like.

As used herein, "alkenyl" refers to a radical of a straight-chain or branched hydrocarbon group having from 2 to 20 carbon atoms, one or more carbon-carbon double bonds (e.g., 1, 2, 3, or 4 carbon-carbon double bonds), and optionally one or more carbon-carbon triple bonds (e.g., 1, 2, 3, or 4 carbon-carbon triple bonds) ("$C_{2-20}$ alkenyl"). In certain embodiments, alkenyl does not contain any triple bonds. In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_2$-6 alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like.

As used herein, "alkynyl" refers to a radical of a straight-chain or branched hydrocarbon group having from 2 to 20 carbon atoms, one or more carbon-carbon triple bonds (e.g., 1, 2, 3, or 4 carbon-carbon triple bonds), and optionally one or more carbon carbon double bonds (e.g., 1, 2, 3, or 4 carbon-carbon double bonds) ("$C_{2-20}$ alkynyl"). In certain embodiments, alkynyl does not contain any double bonds. In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1 butynyl). Examples of $C_{2-4}$ alkynyl groups include, without limitation, ethynyl ($C_2$), 1 propynyl ($C_3$), 2-propynyl ($C_3$), 1-butynyl ($C_4$), 2-butynyl ($C_4$), and the like. Examples of $C_{2-6}$ alkynyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like.

As used herein, "alkylene," "alkenylene," and "alkynylene," refer to a divalent radical of an alkyl, alkenyl, and alkynyl group respectively. When a range or number of carbons is provided for a particular "alkylene," "alkenylene," or "alkynylene," group, it is understood that the range or number refers to the range or number of carbons in the linear carbon divalent chain. "Alkylene," "alkenylene," and "alkynylene," groups may be substituted or unsubstituted with one or more substituents as described herein.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, and trinaphthalene. Particularly aryl groups include phenyl, naphthyl, indenyl, and tetrahydronaphthyl.

As used herein, "heteroaryl" refers to a radical of a 5-10-membered monocyclic or bicyclic 4n+2 aromatic ring system (e.g., having 6 or 10 electrons shared in a cyclic array) having ring carbon atoms and 1-4 ring heteroatoms provided in the aromatic ring system, wherein each heteroatom is independently selected from nitrogen, oxygen and sulfur ("5-10 -membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10-membered aromatic ring system having ring carbon atoms and 1-4 ring heteroatoms provided in the aromatic ring system, wherein each heteroatom is independently selected from nitrogen, oxygen, and sulfur ("5-10 -membered heteroaryl"). In some embodiments, a heteroaryl group is a 5-8-membered aromatic ring system having ring carbon atoms and 1-4 ring heteroatoms provided in the aromatic ring system, wherein each heteroatom is independently selected from nitrogen, oxygen, and sulfur ("5-8 -membered heteroaryl"). In some embodiments, a heteroaryl group is a 5-6-membered aromatic ring system having ring carbon atoms and 1-4 ring heteroatoms provided in the aromatic ring system, wherein each heteroatom is independently selected from nitrogen, oxygen, and sulfur ("5-6 -membered heteroaryl"). In some embodiments, the 5-6 -membered heteroaryl has 1-3 ring heteroatoms selected from nitrogen, oxygen, and sulfur. In some embodiments, the 5-6 -membered heteroaryl has 1-2 ring heteroatoms selected from nitrogen, oxygen, and sulfur. In some embodiments, the 5-6 -membered heteroaryl has 1 ring heteroatom selected from nitrogen, oxygen, and sulfur.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl.

Examples of representative heteroaryls include the following:

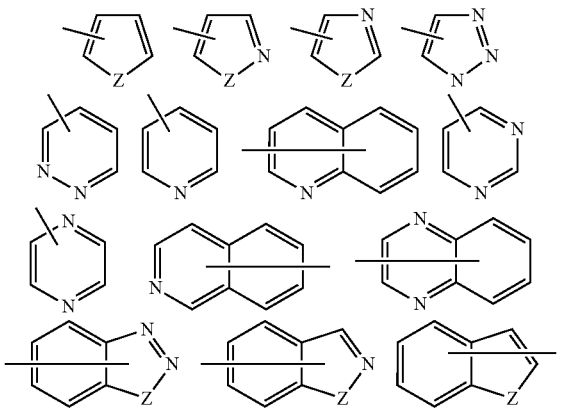

wherein each Z is selected from carbonyl, N, NR$^{65}$, O, and S; and R$^{65}$ is independently hydrogen, $C_{1-8}$ alkyl, $C_{3-10}$ carbocyclyl, 4-10 -membered heterocyclyl, $C_6$-$C_{10}$ aryl, and 5-10 membered heteroaryl.

As used herein, "carbocyclyl" or "carbocyclic" refers to a radical of a non aromatic cyclic hydrocarbon group having from 3 to 10 ring carbon atoms ("$C_{3-10}$ carbocyclyl") and zero heteroatoms in the nonaromatic ring system. In some embodiments, a carbocyclyl group has 3 to 8 ring carbon atoms ("$C_{3-8}$ carbocyclyl"). In some embodiments, a carbocyclyl group has 3 to 7 ring carbon atoms ("$C_{3-7}$ carbocycyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system.

The term "cycloalkyl" refers to a monovalent saturated cyclic, bicyclic, or bridged cyclic (e.g., adamantyl) hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclopentanes, cyclobutanes and cyclopropanes.

As used herein, "$C_{3-6}$ monocyclic cycloalkyl" or "monocyclic $C_{3-6}$ cycloalkyl" refers to a 3- to 7-membered monocyclic hydrocarbon ring system that is saturated. 3- to 7-membered monocyclic cycloalkyl groups include, without limitation, cyclopropyl, cyclobutyl, cyclopentyl, and cyclohexyl. Where specified as being optionally substituted or substituted, substituents on a cycloalkyl (e.g., in the case of an optionally substituted cycloalkyl) may be present on any substitutable position and, include, e.g., the position at which the cycloalkyl group is attached.

As used herein, "heterocyclyl" or "heterocyclic" refers to a radical of a 3 to 10-membered nonaromatic ring system having ring carbon atoms and 1 to 4 ring heteroatoms, wherein each heteroatom is independently selected from nitrogen, oxygen, sulfur, boron, phosphorus, and silicon ("3-10 -membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. The terms "heterocycle," "heterocyclyl," "heterocyclyl ring," "heterocyclic group," "heterocyclic moiety," and "heterocyclic radical," may be used interchangeably.

In some embodiments, a heterocyclyl group is a 4-7 -membered non-aromatic ring system having ring carbon atoms and 1-4 ring heteroatoms, wherein each heteroatom is independently selected from nitrogen, oxygen, and sulfur ("4-7 -membered heterocyclyl"). In some embodiments, a heterocyclyl group is a 5-10 -membered nonaromatic ring system having ring carbon atoms and 1-4 ring heteroatoms, wherein each heteroatom is independently selected from nitrogen, oxygen, sulfur, boron, phosphorus, and silicon ("5-10 membered heterocyclyl"). In some embodiments, a heterocyclyl group is a 5-8 -membered nonaromatic ring system having ring carbon atoms and 1-4 ring heteroatoms, wherein each heteroatom is independently selected from nitrogen, oxygen, and sulfur ("5-8 -membered heterocyclyl"). In some embodiments, a heterocyclyl group is a 5-6 -membered nonaromatic ring system having ring carbon atoms and 1-4 ring heteroatoms, wherein each heteroatom is independently selected from nitrogen, oxygen, and sulfur ("5-6 -membered heterocyclyl"). In some embodiments, the 5-6 -membered heterocyclyl has 1-3 ring heteroatoms selected from nitrogen, oxygen, and sulfur. In some embodiments, the 5-6 -membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, dioxanyl. Exemplary 6-membered heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8 membered heterocyclyl groups containing one heteroatom include, without limitation, azocanyl, oxecanyl and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

Examples of saturated or partially unsaturated heterocyclic radicals include, without limitation, tetrahydrofuranyl, tetrahydrothienyl, terahydropyranyl, pyrrolidinyl, pyridinonyl, pyrrolidonyl, piperidinyl, oxazolidinyl, piperazinyl, dioxanyl, dioxolanyl, morpholinyl, dihydrofuranyl, dihydropyranyl, dihydropyridinyl, tetrahydropyridinyl, dihydropyrimidinyl, oxetanyl, azetidinyl and tetrahydropyrimidinyl. Where specified as being optionally substituted or substituted, substituents on a heterocyclyl (e.g., in the case of an optionally substituted heterocyclyl) may be present on any substitutable position and, include, e.g., the position at which the heterocyclyl group is attached.

"Hetero" when used to describe a compound or a group present on a compound means that one or more carbon atoms in the compound or group have been replaced by a nitrogen, oxygen, or sulfur heteroatom. Hetero may be applied to any of the hydrocarbyl groups described above such as alkyl, e.g., heteroalkyl; carbocyclyl, e.g., heterocyclyl; aryl, e.g, heteroaryl; and the like having from 1 to 5, and particularly from 1 to 3 heteroatoms.

As used herein, "cyano" refers to —CN.

The terms "halo" and "halogen" as used herein refer to an atom selected from fluorine (fluoro, —F), chlorine (chloro, —Cl), bromine (bromo, —Br), and iodine (iodo, —I). In certain embodiments, the halo group is either fluoro or chloro.

The term "alkoxy," as used herein, refers to an alkyl group which is attached to another moiety via an oxygen atom (—O(alkyl)). Non-limiting examples include e.g., methoxy, ethoxy, propoxy, and butoxy.

"Haloalkoxy" is a haloalkyl group which is attached to another moiety via an oxygen atom such as, e.g., but are not limited to —OCHCF$_2$ or —OCF$_3$.

The term "haloalkyl" includes mono, poly, and perhaloalkyl groups substituted with one or more halogen atoms where the halogens are independently selected from fluorine, chlorine, bromine, and iodine. For the group $C_{1-4}$haloalkyl-O—$C_{1-4}$alkyl, the point of attachment occurs on the alkyl moiety which is halogenated.

As used herein, "nitro" refers to —NO$_2$.

As used herein, "oxo" refers to —C=O.

In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, C(=NR$^{cc}$)N(R$^{cc}$)$_2$, —SO$_2$N(R$^{cc}$)$_2$, —SO$_2$R$^{cc}$, —SO$_2$OR$^{cc}$, SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, $C_{1-10}$ alkyl, $C_{1-10}$ perhaloalkyl, $C_{2-10}$ alkenyl, $C_{2-10}$ alkynyl, $C_{3-10}$ carbocyclyl, 3-14-membered heterocyclyl, $C_{6-14}$ aryl, and 5-14-membered heteroaryl, or two R$^{cc}$ groups attached to a nitrogen atom are joined to form a 3-14-membered heterocyclyl or 5-14-membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups, and wherein R$^{aa}$, bb, R$^{cc}$ and R$^{dd}$ are as defined above.

These and other exemplary substituents are described in more detail in the Detailed Description, Examples, and Claims. The invention is not intended to be limited in any manner by the above exemplary listing of substituents.

Other Definitions

As used herein, "pharmaceutically acceptable carrier" refers to a non-toxic carrier, adjuvant, or vehicle that does not destroy the pharmacological activity of the compound with which it is formulated. Pharmaceutically acceptable carriers, adjuvants or vehicles that may be used in the compositions described herein include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

As used herein, "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and N$^+$(C$_{1-4}$alkyl)$_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

Disease, disorder, and condition are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

As used herein, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent.

Compounds

In one aspect, the present invention provides a compound having the Formula I:

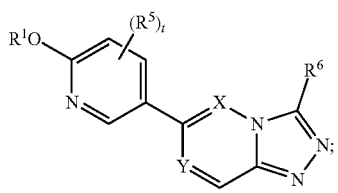

(I)

or a pharmaceutically acceptable salt thereof, wherein
X and Y are each independently CR$^d$ or N;
R$^1$ is

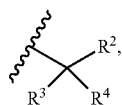

monocyclic C$_{3-6}$ cycloalkyl, or 4- to 7-membered monocyclic heterocyclyl, wherein said cycloalkyl and heterocyclyl are optionally substituted with one or more R$^a$;
R$^2$ is C$_{1-4}$haloalkyl, phenyl, or monocyclic C$_{3-6}$ cycloalkyl optionally substituted with one or more R$^b$;
R$^3$ is hydrogen, C$_{1-4}$alkyl, or C$_{1-4}$haloalkyl;
R$^4$ is hydrogen or C$_{1-4}$alkyl;
R$^5$ is halo;
R$^6$ is C$_{1-4}$alkyl or C$_{1-4}$haloalkyl, wherein said C$_{1-4}$alkyl or C$_{1-4}$haloalkyl are each substituted with OR$^c$;
t is 0, 1, or 2;
R$^a$ and R$^b$ are each independently selected from is selected from halo, C$_{1-4}$alkyl, C$_{1-4}$haloalkyl, C$_{1-4}$alkoxy, and C$_{1-4}$haloalkoxy,
R$^c$ is C$_{1-4}$alkyl optionally substituted with C$_{3-6}$ cycloalkyl or C$_{1-4}$alkoxy, or C$_{3-6}$ cycloalkyl; and
R$^d$ is hydrogen or C$_{1-4}$alkyl;

provided the compound is not a compound having the formula:

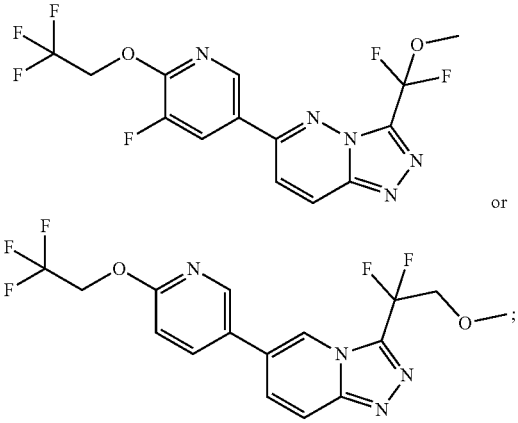

or a pharmaceutically acceptable salt thereof.

In one aspect, the present invention provides a compound having the Formula I':

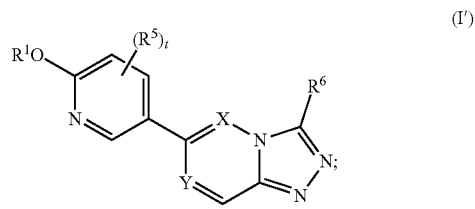

(I')

or a pharmaceutically acceptable salt thereof, wherein
X and Y are each independently CR$^d$ or N;
R$^1$ is

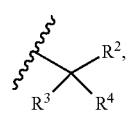

monocyclic C$_{3-6}$ cycloalkyl, or 4- to 7-membered monocyclic heterocyclyl, wherein said cycloalkyl and heterocyclyl are optionally substituted with one or more R$^a$;
R$^2$ is C$_{1-4}$haloalkyl, phenyl, or monocyclic C$_{3-6}$ cycloalkyl optionally substituted with one or more R$^b$;
R$^3$ is hydrogen, C$_{1-4}$alkyl, or C$_{1-4}$haloalkyl;
R$^4$ is hydrogen or C$_{1-4}$alkyl;
R$^5$ is halo;
R$^6$ is C$_{1-4}$alkyl or C$_{1-4}$haloalkyl, wherein said C$_{1-4}$alkyl or C$_{1-4}$haloalkyl are each substituted with OR$^c$;
t is 0, 1, or 2;
R$^a$ and R$^b$ are each independently selected from is selected from halo, C$_{1-4}$alkyl, C$_{1-4}$haloalkyl, C$_{1-4}$alkoxy, and C$_{1-4}$haloalkoxy,
R$^c$ is C$_{1-4}$alkyl optionally substituted with C$_{3-6}$ cycloalkyl or C$_{1-4}$alkoxy, or C$_{3-6}$ cycloalkyl; and
R$^d$ is hydrogen or C$_{1-4}$alkyl;
or a pharmaceutically acceptable salt thereof.

In some embodiments, the compound is of the Formula I-a:

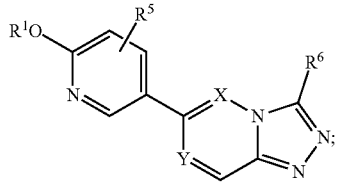
(I-a)

or a pharmaceutically acceptable salt thereof, wherein the variables are as defined herein.

In some embodiments, the compound is of the Formula I-b:

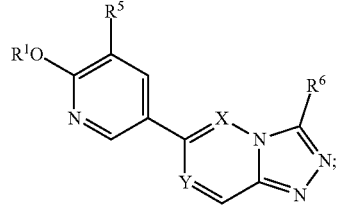
(I-b)

or a pharmaceutically acceptable salt thereof, wherein the variables are as defined herein.

In some embodiments, the compound is of the Formula II:

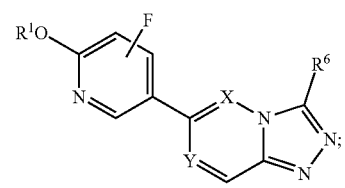
(II)

or a pharmaceutically acceptable salt thereof, wherein the variables are as defined herein.

In some embodiments, the compound is of the Formula III:

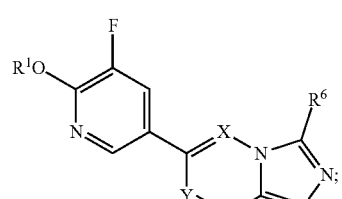
(III)

or a pharmaceutically acceptable salt thereof, wherein the variables are as defined herein.

In some embodiments, the compound is of the Formula I-c:

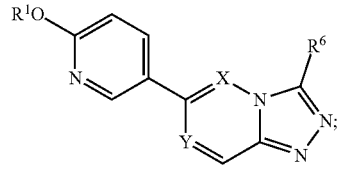
(I-c)

or a pharmaceutically acceptable salt thereof, wherein the variables are as defined herein.

In another aspect, the present disclosure provides a compound having the Formula I-d:

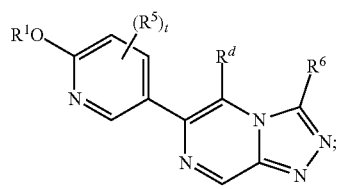
(I-d)

or a pharmaceutically acceptable salt thereof, wherein
$R^1$ is

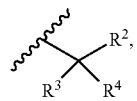

monocyclic $C_{3-6}$ cycloalkyl, or 4- to 7-membered monocyclic heterocyclyl, wherein said cycloalkyl and heterocyclyl are optionally substituted with one or more $R^a$;
$R^2$ is $C_{1-4}$haloalkyl, phenyl, or monocyclic $C_{3-6}$ cycloalkyl optionally substituted with one or more $R^b$;
$R^3$ is hydrogen, $C_{1-4}$alkyl, or $C_{1-4}$haloalkyl;
$R^4$ is hydrogen or $C_{1-4}$alkyl;
$R^5$ is halo;
$R^6$ is $C_{1-4}$alkyl or $C_{1-4}$haloalkyl, wherein said $C_{1-4}$alkyl or $C_{1-4}$haloalkyl are each substituted with $OR^c$;
t is 0, 1, or 2;
$R^a$ and $R^b$ are each independently selected from is selected from halo, $C_{1-4}$alkyl, $C_{1-4}$haloalkyl, $C_{1-4}$alkoxy, and $C_{1-4}$haloalkoxy;
$R^c$ is $C_{1-4}$alkyl optionally substituted with $C_{3-6}$ cycloalkyl or $C_{1-4}$alkoxy, or $C_{3-6}$ cycloalkyl; and
$R^d$ is hydrogen or $C_{1-4}$alkyl.

In some embodiments, the compound is of the Formula V:

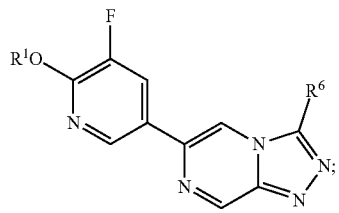
(V)

or a pharmaceutically acceptable salt thereof, wherein the variables are as defined herein.

In some embodiments, the compound is of the Formula VII:

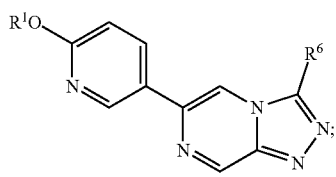
(VII)

or a pharmaceutically acceptable salt thereof, wherein the variables are as defined herein.

In some embodiments, the compound is of the Formula VIII:

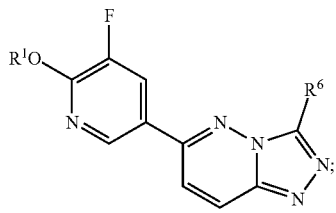
(VIII)

or a pharmaceutically acceptable salt thereof, wherein the variables are as defined herein.

In some embodiments, the compound is of the Formula VIII:

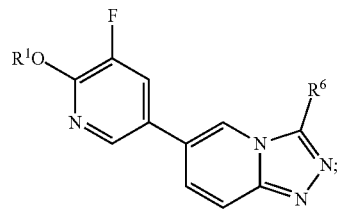
(IX)

or a pharmaceutically acceptable salt thereof, wherein the variables are as defined herein.

In some embodiments, $R^1$ is

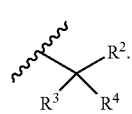

In some embodiments, $R^2$ is cyclobutyl optionally substituted with one or more $R^a$.

In some embodiments, $R^2$ is $C_{1-4}$haloalkyl. In some embodiments, $R^2$ is $CF_3$. In some embodiments, $R^2$ is phenyl.

In some embodiments, $R^3$ is $C_{1-4}$alkyl and $R^4$ is hydrogen or $C_{1-4}$alkyl. In some embodiments, $R^3$ and $R^4$ are each $C_{1-4}$alkyl. In some embodiments, $R^3$ and $R^4$ are each methyl. In some embodiments, $R^3$ is methyl and $R^4$ is hydrogen. In some embodiments, $R^3$ and $R^4$ are each hydrogen.

In some embodiments, $R^6$ is $-CF_2-OR^c$.

In some embodiments, $R^c$ is $C_{1-4}$alkyl optionally substituted with cyclopropyl. In some embodiments, $R^c$ is cyclopropyl.

In some embodiments, $R^6$ is $-C(F_2)OCH_2CH(CH_3)_2$, $-C(F_2)OCH_3$, $-C(F_2)OCH_2CH_3$, $-C(F_2)OCH(CH_3)_2$, or $-C(F_2)OCH_2C_3H_5$.

In some embodiments, $R^6$ is $-CH_2-OR^c$.

In some embodiments, $R^c$ is $C_{1-4}$ alkyl.

In some embodiments, $R^6$ is $-CH_2OCH_3$, $-CH_2OCH_2CH_3$, or $-CH_2OCH_2CH(CH_3)_2$.

In some embodiments, $R^a$ is $C_{1-4}$haloalkyl. In some embodiments, $R^a$ is $CF_3$. In some embodiments, $R^a$ is fluoro.

In some embodiments, t is 1. In some embodiments, t is 0.

In some embodiments, $R^d$ is methyl. In some embodiments, $R^d$ is hydrogen.

In some embodiments, the compound is selected from the group consisting of:

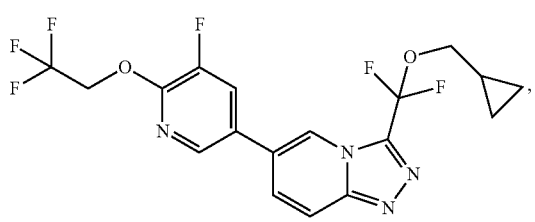

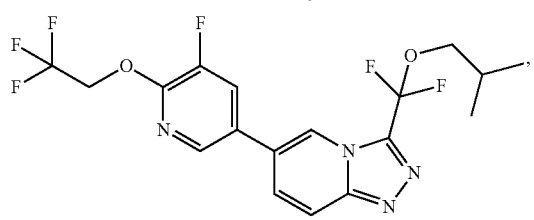

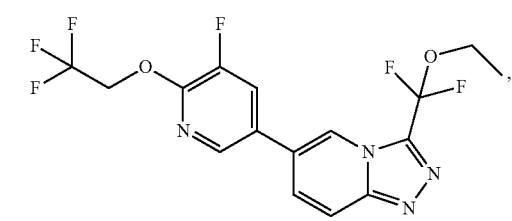 [SMILES: CCOC(F)(F)c1nnc2cnc(-c3cnc(OCC(F)(F)F)c(F)c3)cn12]

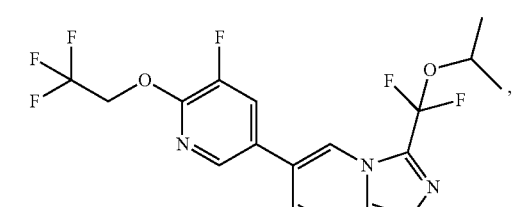

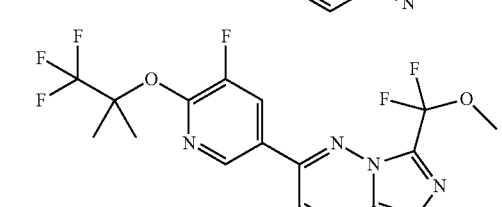

-continued
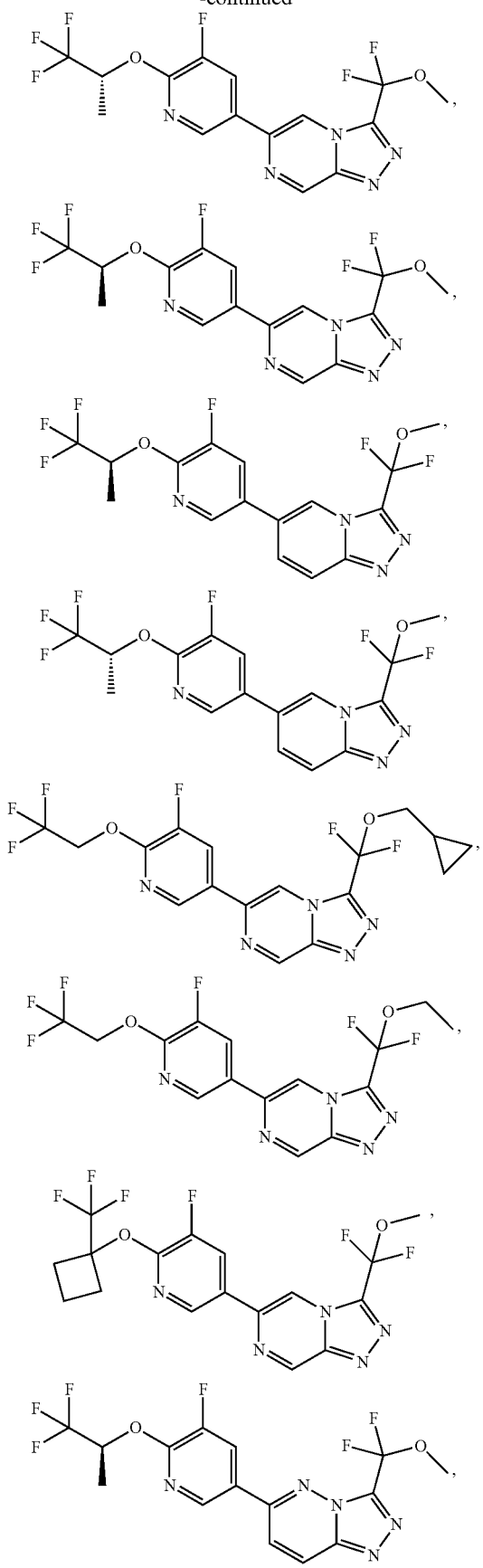
-continued
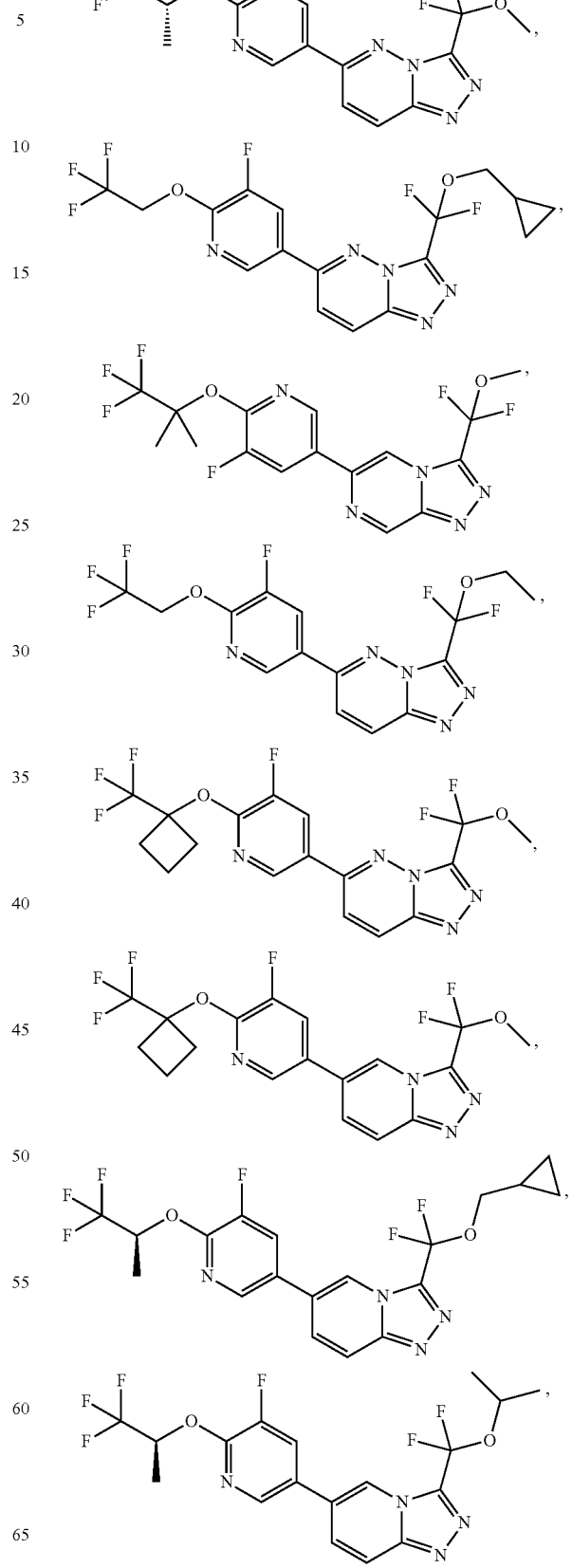

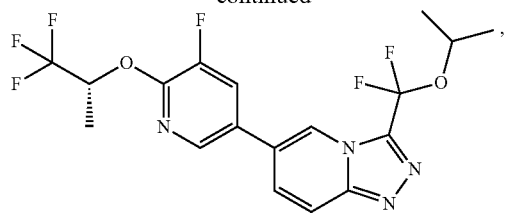
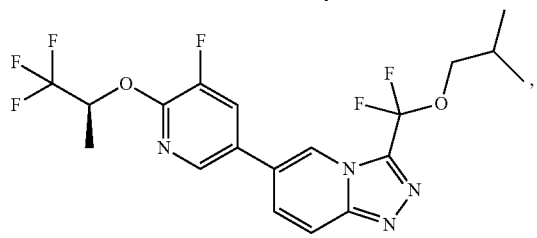
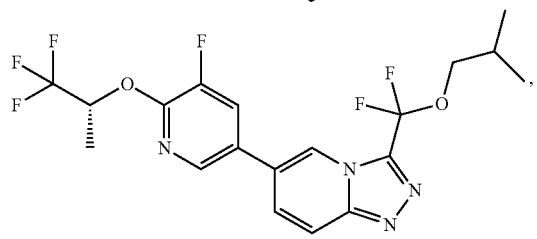
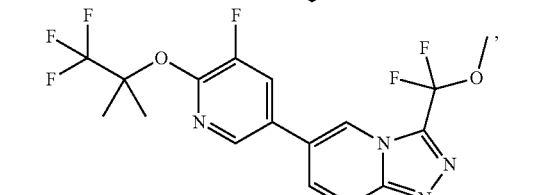
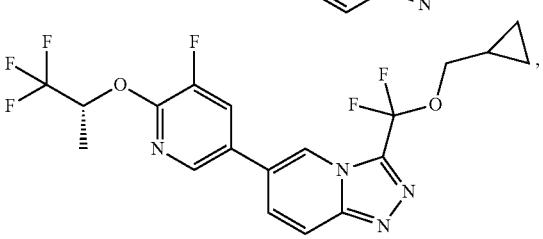
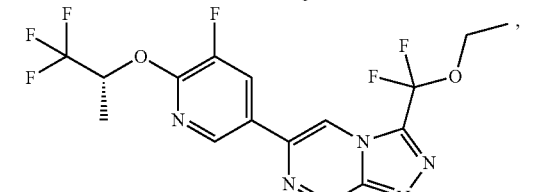
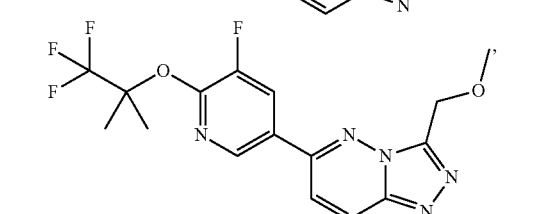
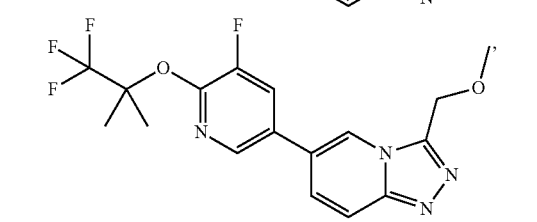
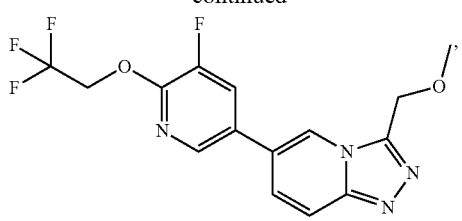
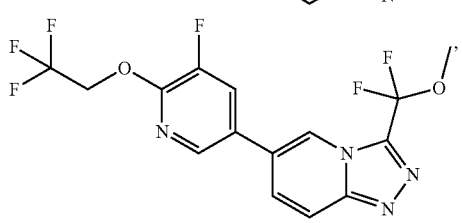
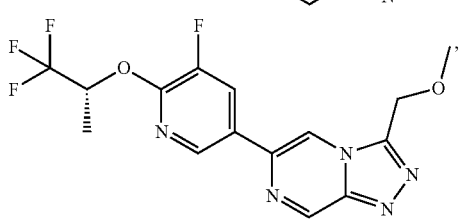
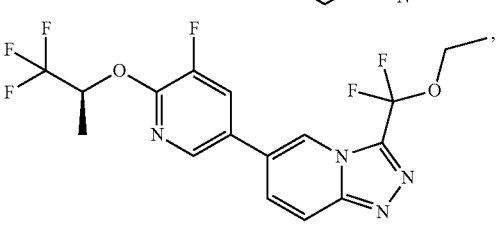
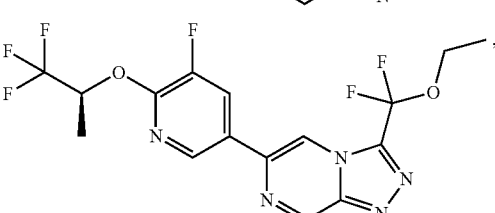
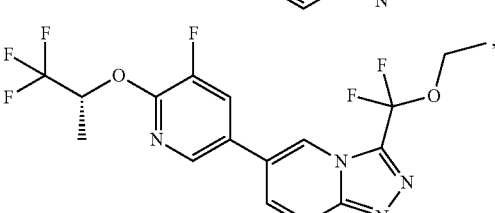
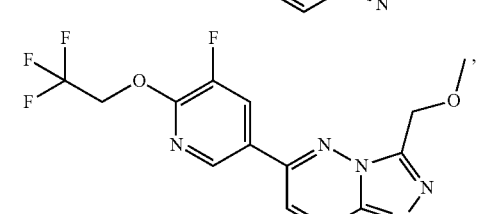
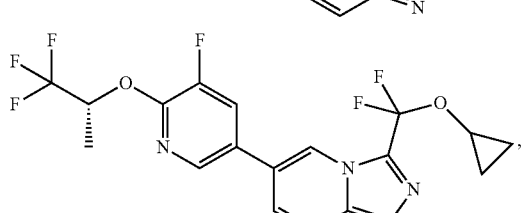

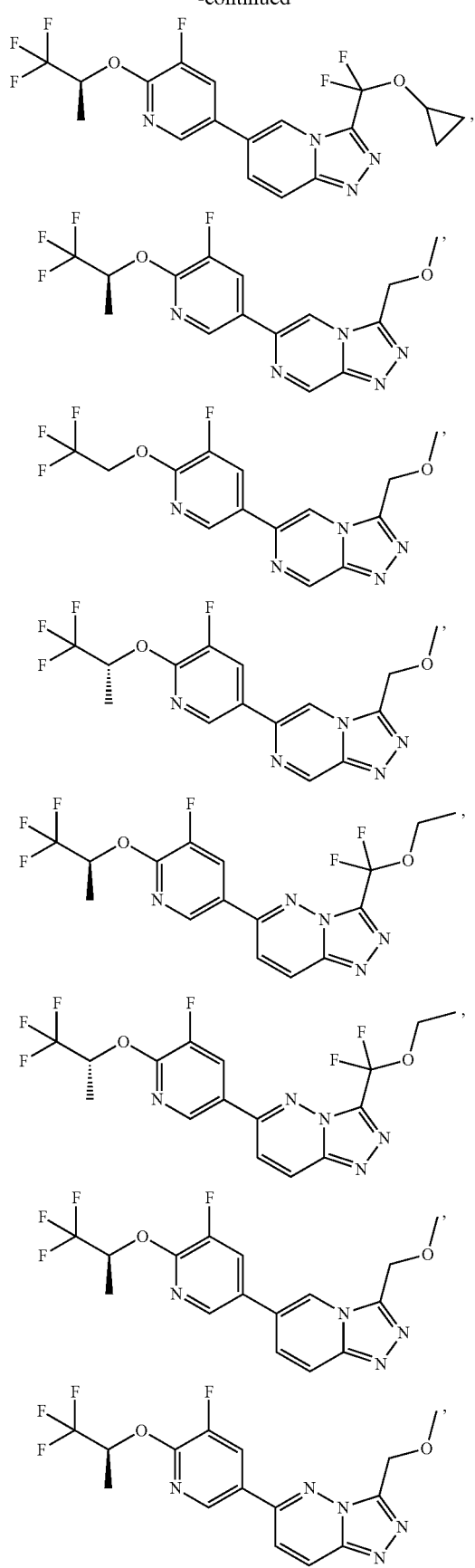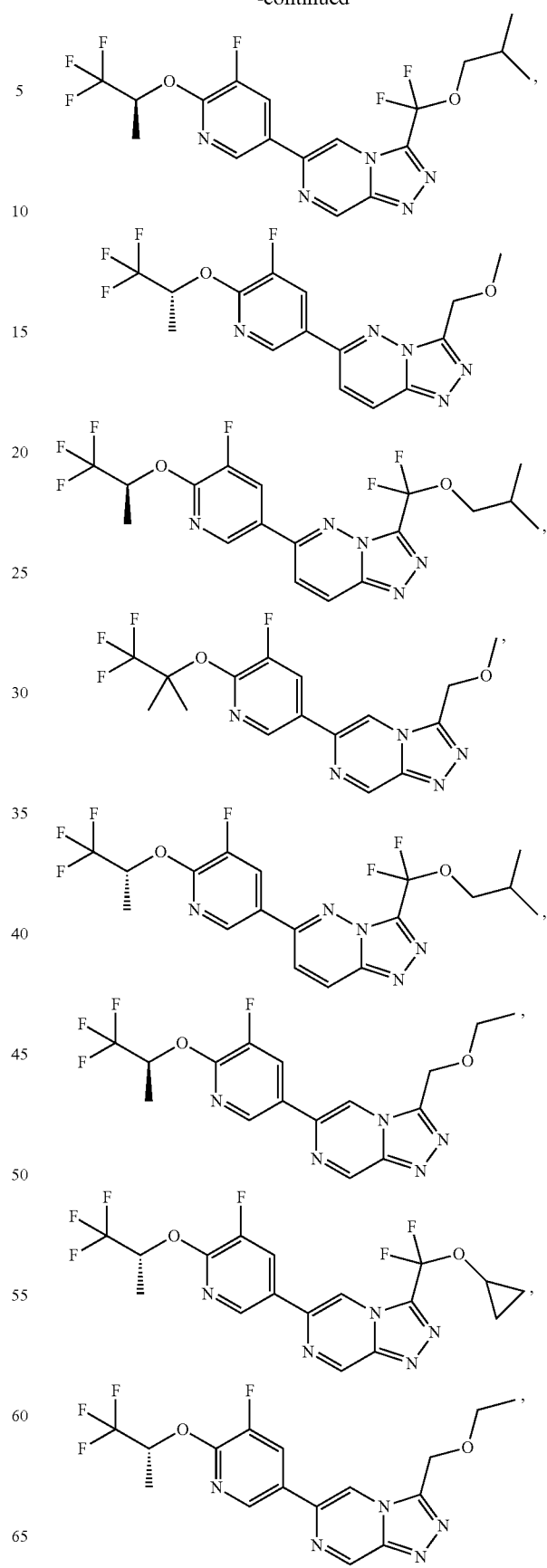

-continued
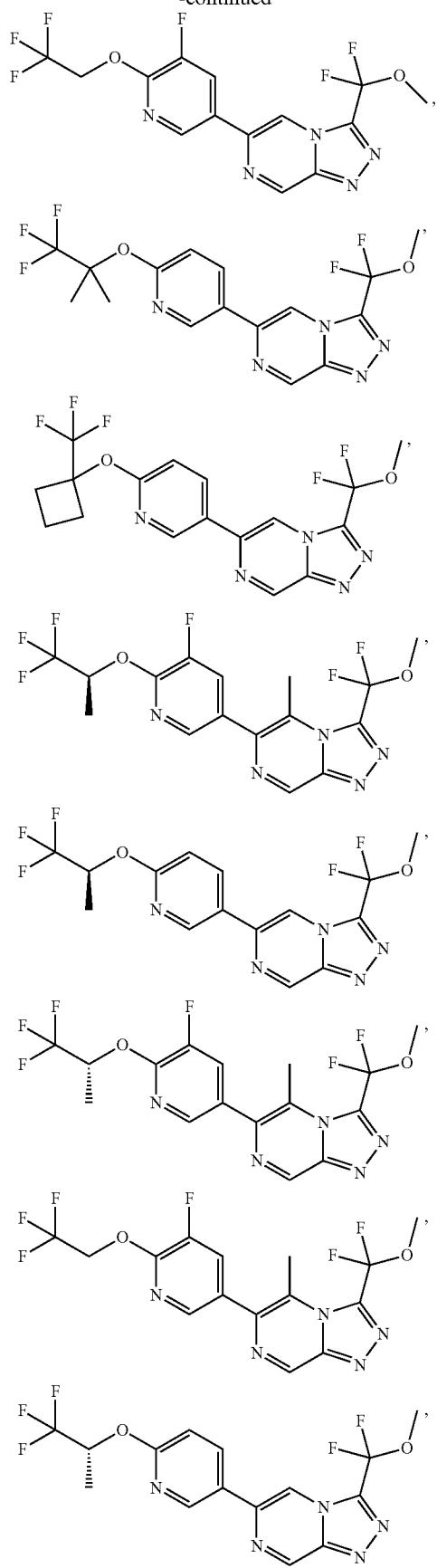
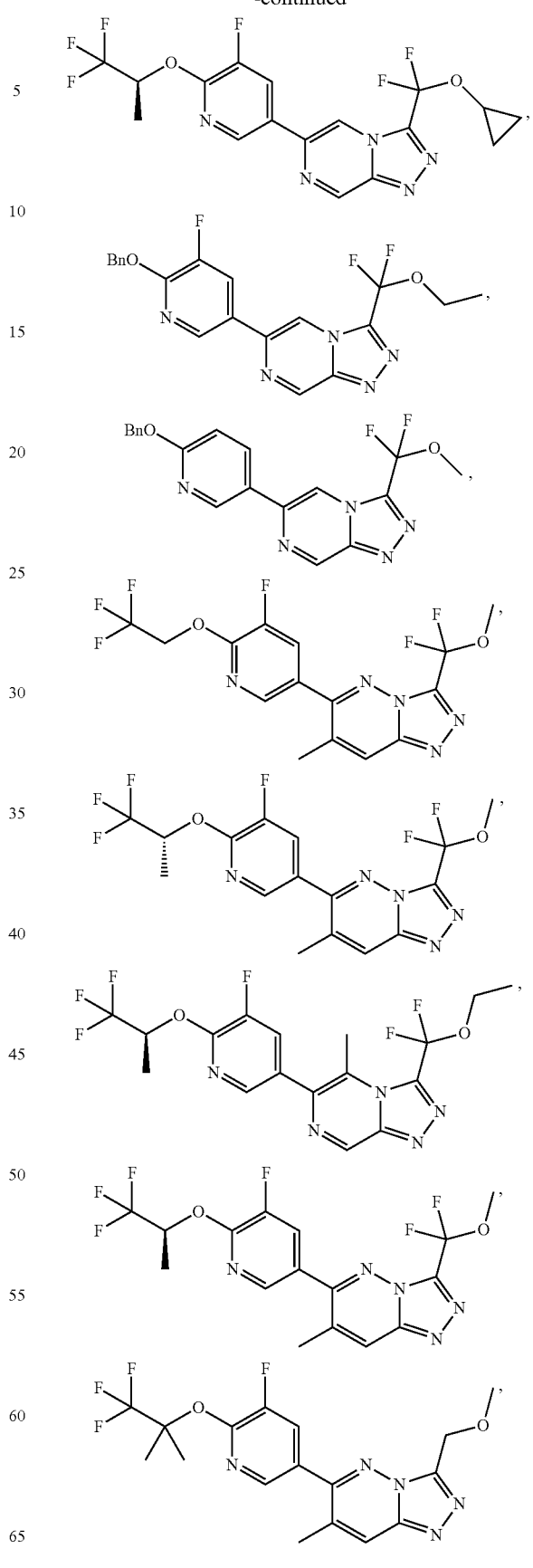

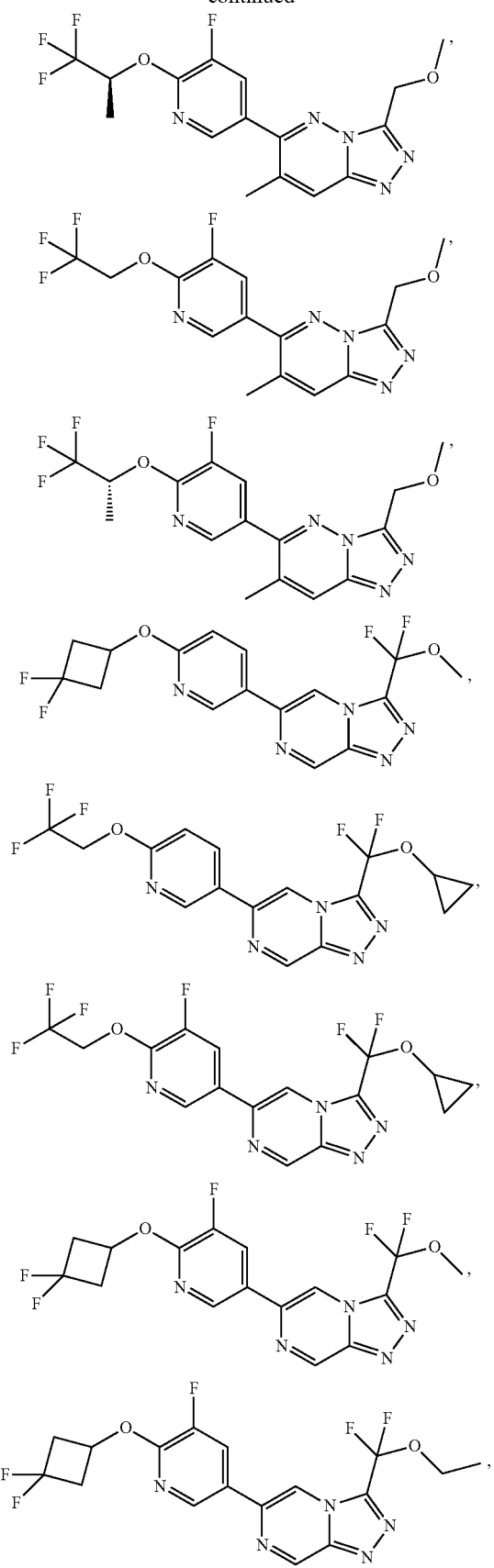
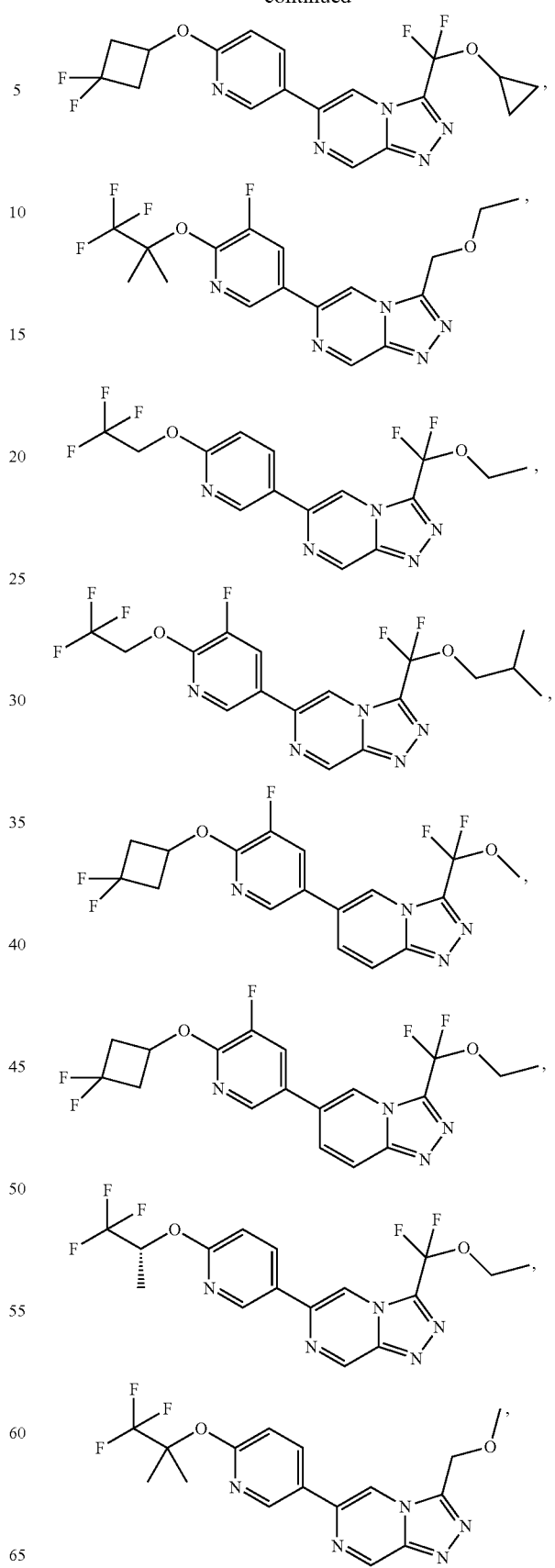

-continued

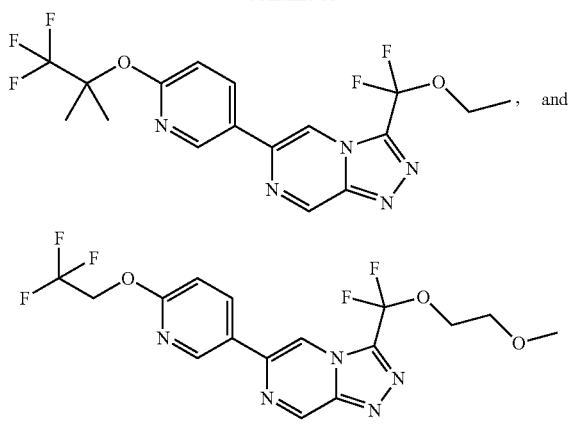

or a pharmaceutically acceptable salt thereof.

In some embodiments, the compound is selected from the group consisting of:

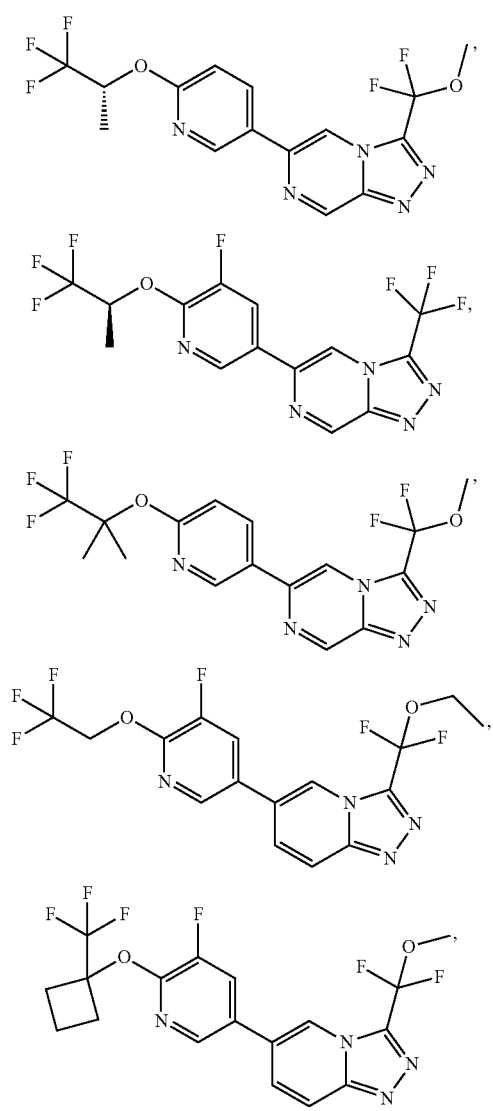

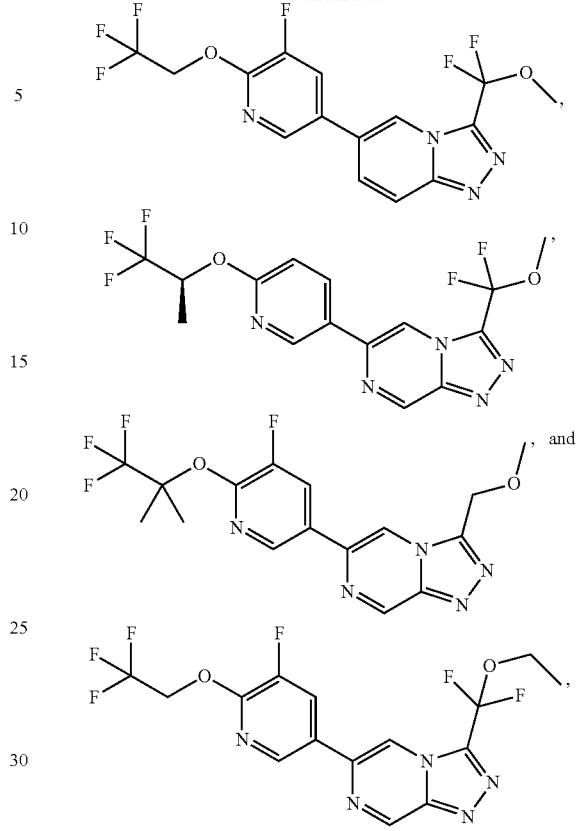

or a pharmaceutically acceptable salt thereof.

In another aspect, the present invention provides a crystalline compound of formula:

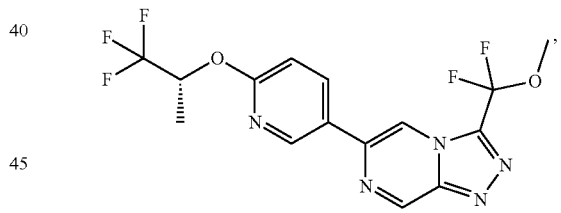

wherein the crystalline compound exhibits an X-ray powder diffraction pattern comprising peaks at the following diffraction angles (2θ): 6.9±0.2, 16.5±0.2, and 20.8±0.2.

In some embodiments, the crystalline compound exhibits an X-ray powder diffraction pattern comprising peaks at the following diffraction angles (2θ): 6.9±0.2, 13.9±0.2, 16.5±0.2, 19.5±0.2, and 20.8±0.2.

In some embodiments, the crystalline compound exhibits an X-ray powder diffraction pattern comprising peaks at the following diffraction angles (2θ): 6.9±0.2, 11.2±0.2, 13.9±0.2, 16.5±0.2, 17.4±0.2, 18.1±0.2, 19.1±0.2, 19.5±0.2, and 20.8±0.2.

Figure 2A:
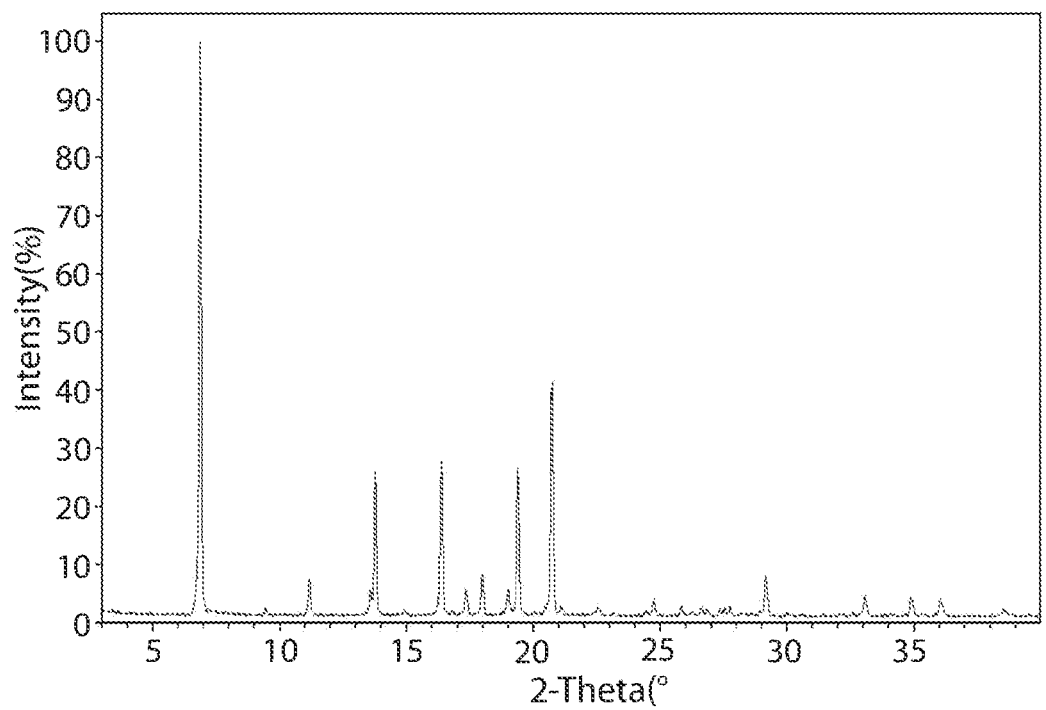
FIG. 2A shows XRPD pattern of Compound 62 raw material.

In some embodiments, the crystalline compound exhibits an X-ray powder diffraction pattern substantially the same as depicted in FIG. 2A.

In some embodiments, the crystalline compound has a melting point onset as determined by differential scanning calorimetry at about 140° C.

Figure 2B:
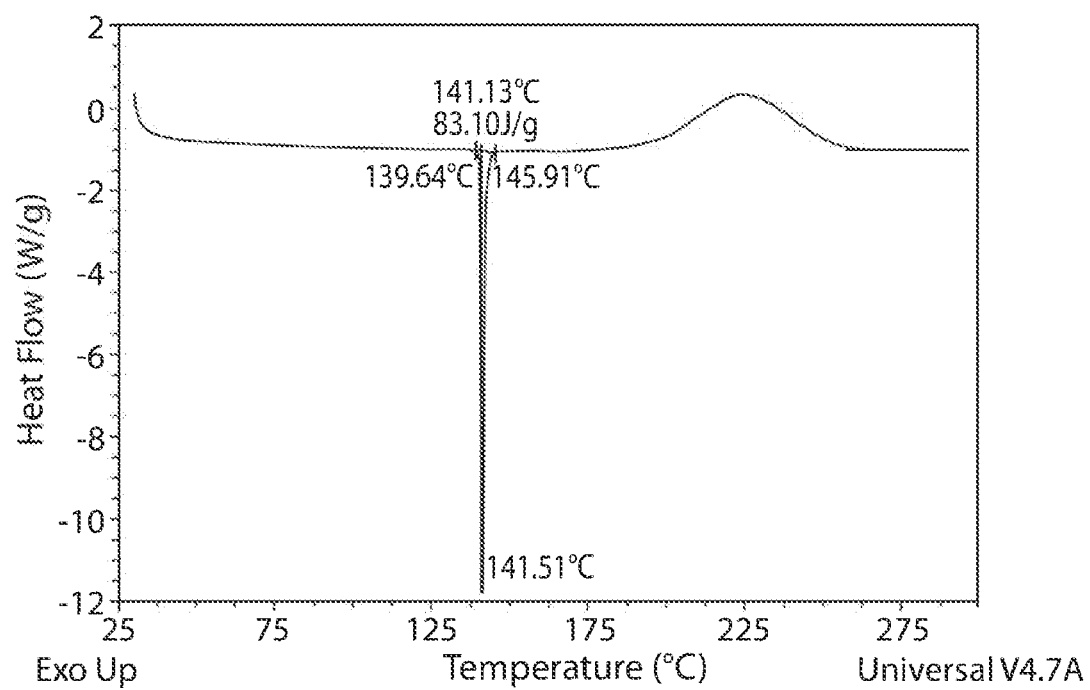
FIG. 2B shows DSC of Compound 62.

In some embodiments, the crystalline compound has a differential scanning calorimetry curve substantially the same as shown in FIG. 2B.

In another aspect, provided herein is a crystalline compound of formula:

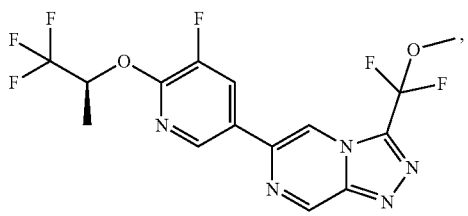 [SMILES: COC(F)(F)c1nnc2cnc(-c3cnc(O[C@@H](C)C(F)(F)F)c(F)c3)cn12]

wherein the crystalline compound exhibits an X-ray powder diffraction pattern comprising peaks at the following diffraction angles (2θ): 16.7±0.2, 19.0±0.2, and 20.4±0.2.

In some embodiments, the crystalline compound exhibits an X-ray powder diffraction pattern comprising peaks at the following diffraction angles (2θ): 7.2±0.2, 14.4±0.2, 16.7±0.2, 19.0±0.2, 20.4±0.2, and 25.7±0.2.

In some embodiments, the crystalline compound exhibits an X-ray powder diffraction pattern comprising peaks at the following diffraction angles (2θ): 7.2±0.2, 14.4±0.2, 16.7±0.2, 17.9±0.2, 19.0±0.2, 20.4±0.2, 20.8±0.2, 23.2±0.2, 25.7±0.2, and 28.0±0.2.

Figure 3A:
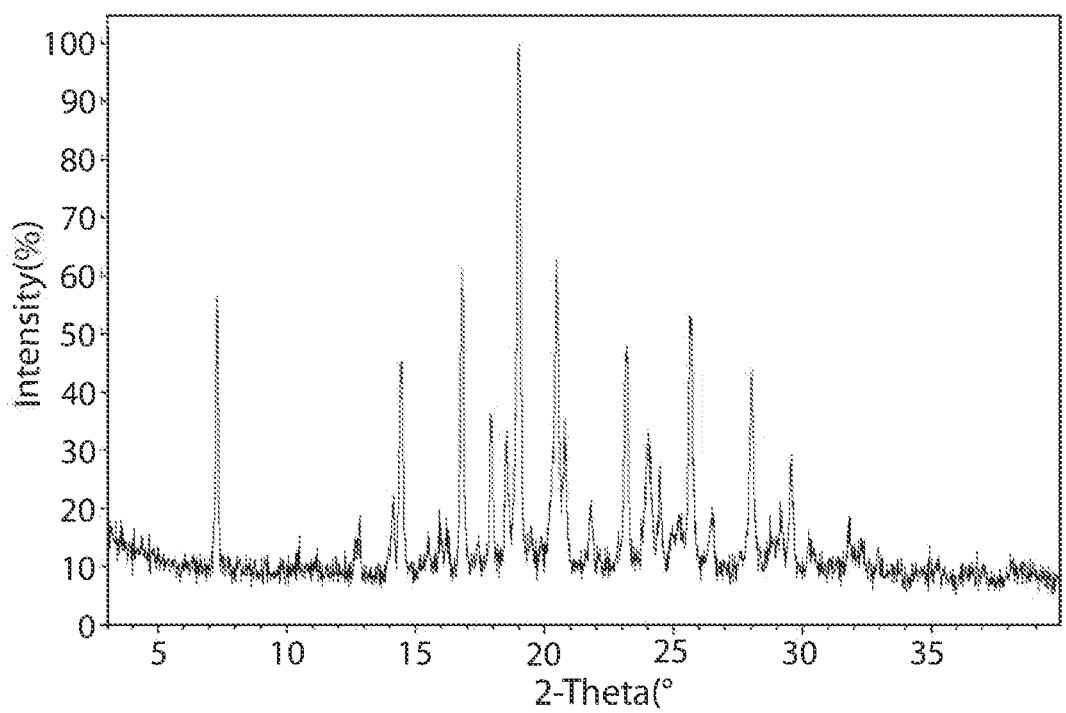
FIG. 3A shows XRPD pattern of Compound 6B raw material.

In some embodiments, the crystalline compound exhibits an X-ray powder diffraction pattern substantially the same as depicted in FIG. 3A.

In some embodiments, the crystalline compound has a melting point onset as determined by differential scanning calorimetry at about 68° C.

Figure 3B:
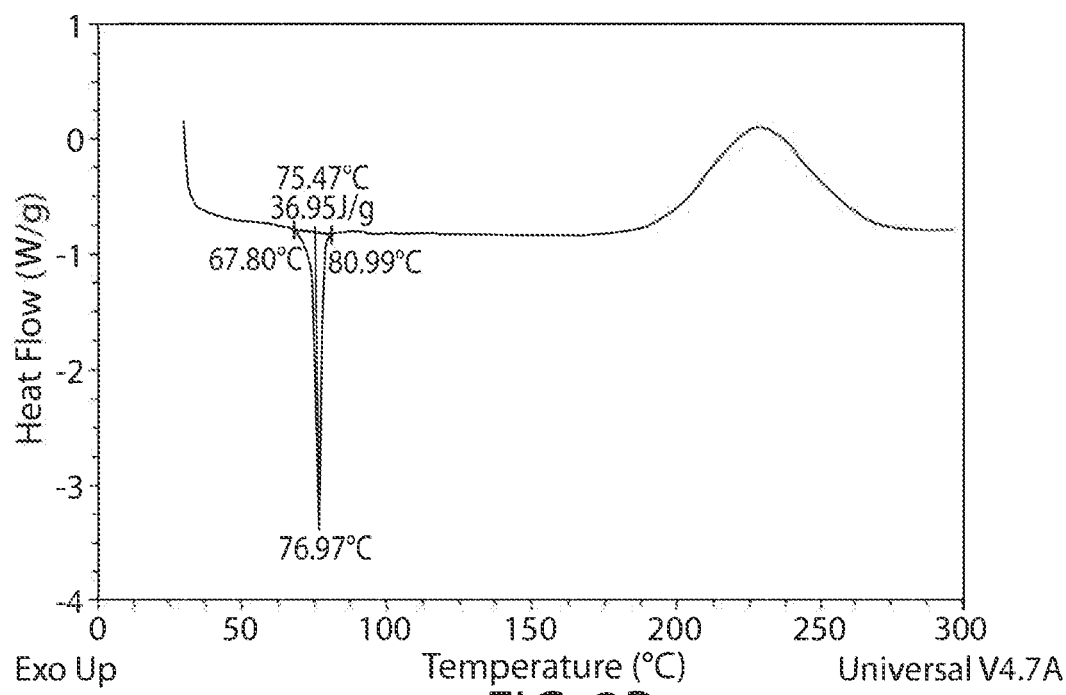
FIG. 3B shows DSC of Compound 6B.

In some embodiments, the crystalline compound has a differential scanning calorimetry curve substantially the same as shown in FIG. 3B.

In another aspect, the present invention provides a crystalline compound of formula:

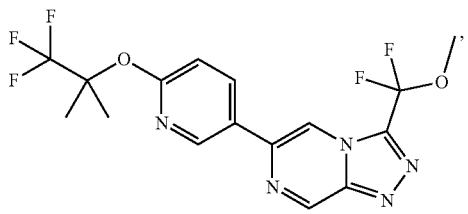 [SMILES: COC(F)(F)c1nnc2cnc(-c3ccc(OC(C)(C)C(F)(F)F)nc3)cn12]

wherein the crystalline compound exhibits an X-ray powder diffraction pattern comprising peaks at the following diffraction angles (2θ): 7.3±0.2, 14.5±0.2, and 21.9±0.2.

In some embodiments, the crystalline compound exhibits an X-ray powder diffraction pattern comprising peaks at the following diffraction angles (2θ): 7.3±0.2, 14.5±0.2, 17.9±0.2, 19.0±0.2, and 21.9±0.2.

In some embodiments, the crystalline compound exhibits an X-ray powder diffraction pattern comprising peaks at the following diffraction angles (2θ): 7.3±0.2, 13.7±0.2, 14.5±0.2, 17.9±0.2, 19.0±0.2, 20.3±0.2, 21.9±0.2, 24.7±0.2, and 25.4±0.2.

Figure 4A:
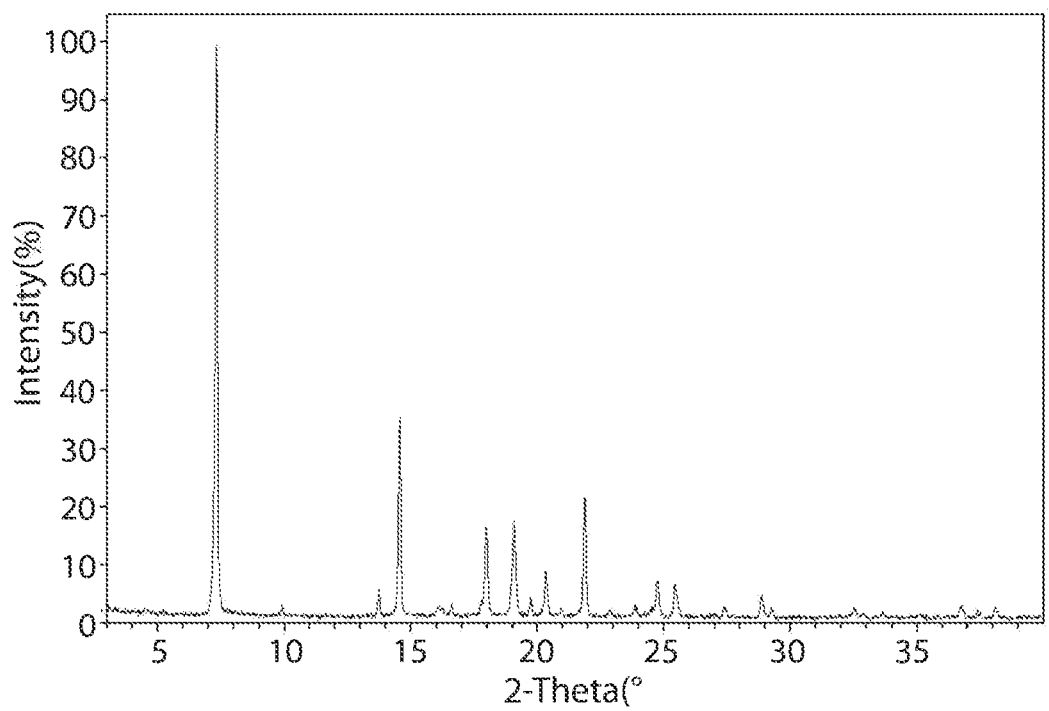
FIG. 4A shows XRPD pattern of Compound 56 raw material.

In some embodiments, the crystalline compound exhibits an X-ray powder diffraction pattern substantially the same as depicted in FIG. 4A.

In some embodiments, the crystalline compound has a melting point onset as determined by differential scanning calorimetry at about 136° C.

Figure 4B:
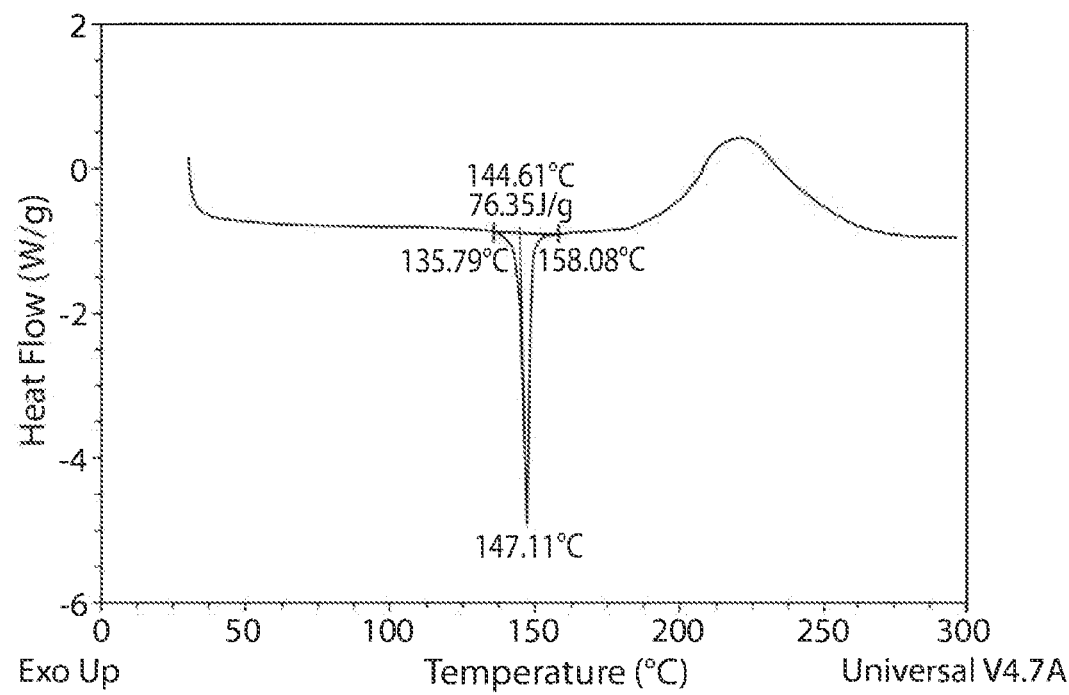
FIG. 4B shows DSC of Compound 56.

In some embodiments, the crystalline compound has a differential scanning calorimetry curve substantially the same as shown in FIG. 4B.

In another aspect, provided herein is a crystalline compound of formula:

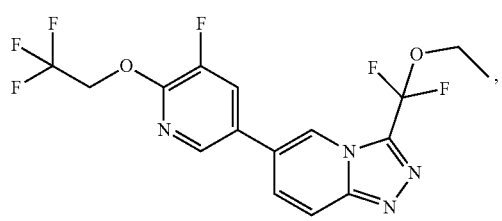 [SMILES: CCOC(F)(F)c1nnc2ccc(-c3cnc(OCC(F)(F)F)c(F)c3)cn12]

wherein the crystalline compound exhibits an X-ray powder diffraction pattern comprising peaks at the following diffraction angles (2θ): 12.6±0.2, 15.8±0.2, and 18.6±0.2.

In some embodiments, the crystalline compound exhibits an X-ray powder diffraction pattern comprising peaks at the following diffraction angles (2θ): 10.7±0.2, 12.3±0.2, 12.6±0.2, 15.8±0.2, 18.6±0.2, and 22.6±0.2.

In some embodiments, the crystalline compound exhibits an X-ray powder diffraction pattern comprising peaks at the following diffraction angles (2θ): 10.7±0.2, 12.3±0.2, 12.6±0.2, 14.9±0.2, 15.8±0.2, 16.6±0.2, 16.8±0.2, 18.6±0.2, 21.0±0.2 and 22.6±0.2.

Figure 5A:
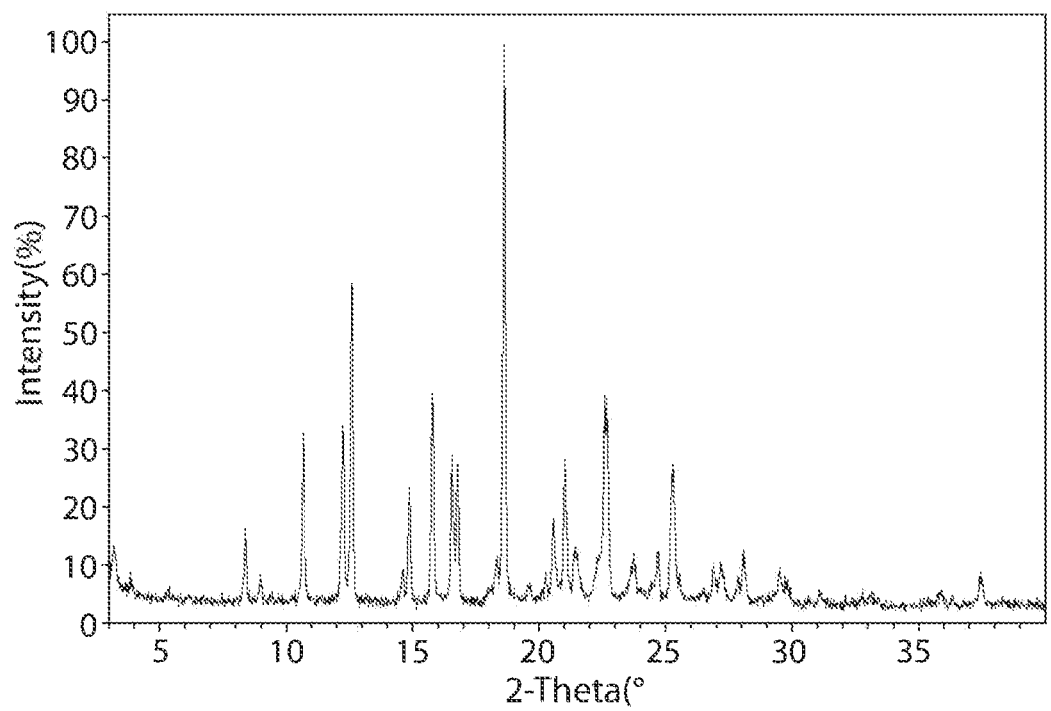
FIG. 5A shows XRPD pattern of Compound 3 raw material.

In some embodiments, the crystalline compound exhibits an X-ray powder diffraction pattern substantially the same as depicted in FIG. 5A.

In some embodiments, the crystalline compound has a melting point onset as determined by differential scanning calorimetry at about 107° C.

Figure 5B:
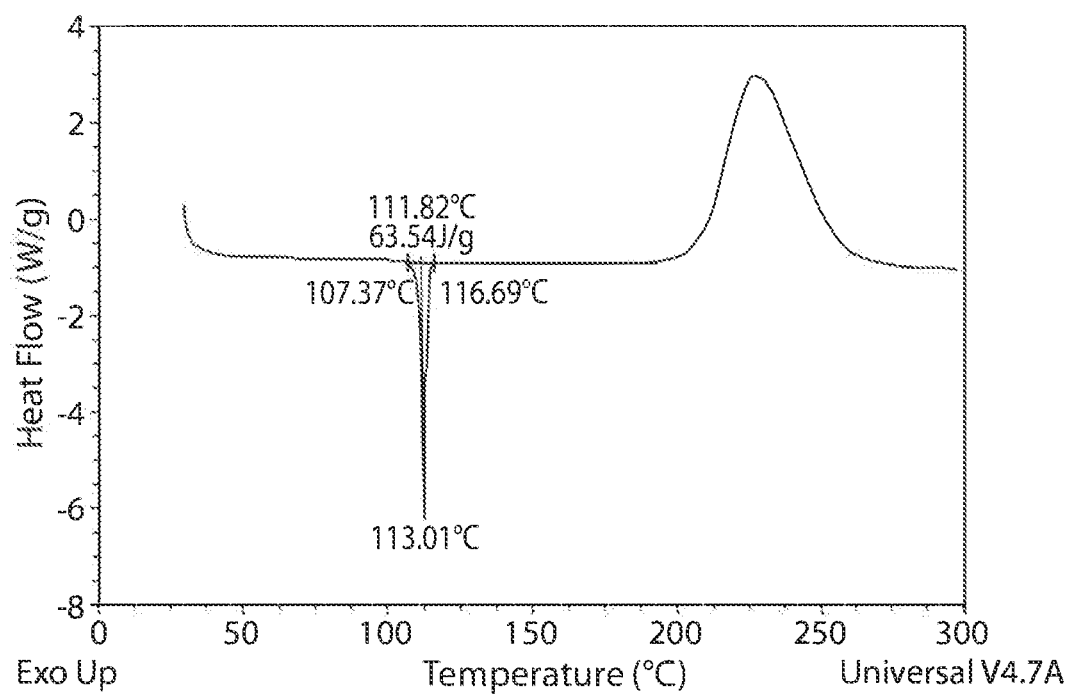
FIG. 5B shows DSC of Compound 3.

In some embodiments, the crystalline compound has a differential scanning calorimetry curve substantially the same as shown in FIG. 5B.

In another aspect, provided herein is a crystalline compound of formula:

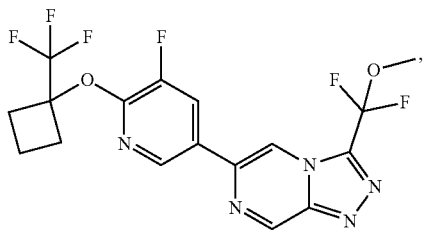 [SMILES: COC(F)(F)c1nnc2cnc(-c3cnc(OC4(C(F)(F)F)CCC4)c(F)c3)cn12]

wherein the crystalline compound exhibits an X-ray powder diffraction pattern comprising peaks at the following diffraction angles (2θ): 5.8±0.2, 19.7±0.2, and 21.0±0.2.

In some embodiments, the crystalline compound exhibits an X-ray powder diffraction pattern comprising peaks at the following diffraction angles (2θ): 5.8±0.2, 14.5±0.2, 15.3±0.2, 19.7±0.2, 21.0±0.2, and 24.2±0.2.

In some embodiments, the crystalline compound exhibits an X-ray powder diffraction pattern comprising peaks at the following diffraction angles (2θ): 5.8±0.2, 11.6±0.2, 12.0±0.2, 14.5±0.2, 15.3±0.2, 19.1±0.2, 19.7±0.2, 21.0±0.2, 22.4±0.2, and 24.2±0.2.

Figure 6A:
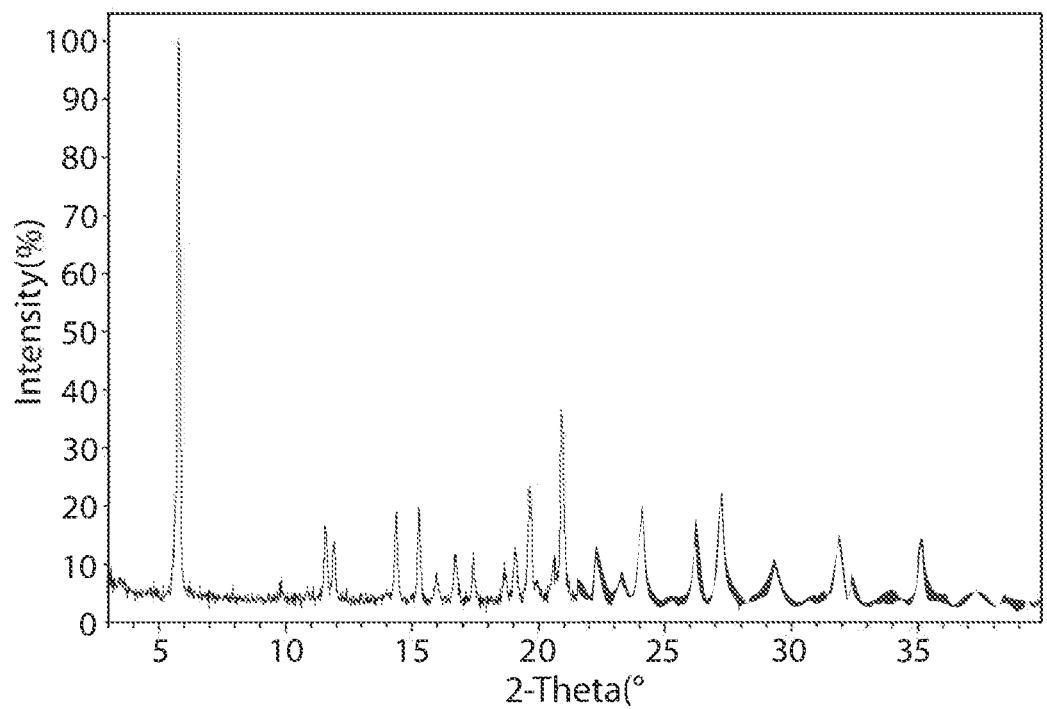
FIG. 6A shows XRPD pattern of Compound 11 raw material.

In some embodiments, the crystalline compound exhibits an X-ray powder diffraction pattern substantially the same as depicted in FIG. 6A.

In some embodiments, the crystalline compound has a melting point onset as determined by differential scanning calorimetry at about 94° C.

Figure 6B:
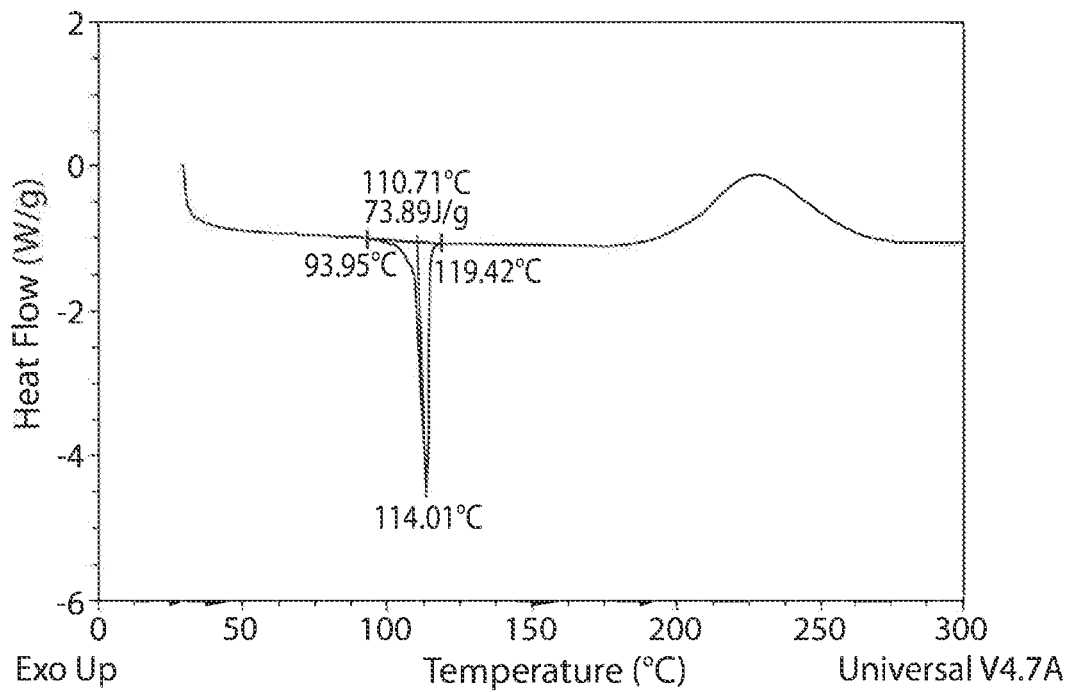
FIG. 6B shows DSC of Compound 11.

In some embodiments, the crystalline compound has a differential scanning calorimetry curve substantially the same as shown in FIG. 6B.

In another aspect, the present invention provides a crystalline compound of formula:

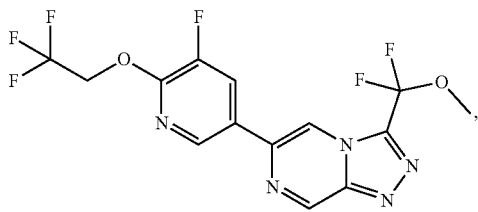 [SMILES: COC(F)(F)c1nnc2cnc(-c3cnc(OCC(F)(F)F)c(F)c3)cn12]

wherein the crystalline compound exhibits an X-ray powder diffraction pattern comprising peaks at the following diffraction angles (2θ): 7.3±0.2, 16.6±0.2, and 18.4±0.2.

In some embodiments, the crystalline compound exhibits an X-ray powder diffraction pattern comprising peaks at the following diffraction angles (2θ): 7.3±0.2, 13.8±0.2, 16.6±0.2, 18.4±0.2, 20.3±0.2, and 24.3±0.2.

In some embodiments, the crystalline compound exhibits an X-ray powder diffraction pattern comprising peaks at the following diffraction angles (2θ): 7.3±0.2, 10.8±0.2, 13.8±0.2, 16.6±0.2, 17.8±0.2, 18.4±0.2, 19.5±0.2, 20.3±0.2, 21.2±0.2, and 24.3±0.2.

Figure 7A:
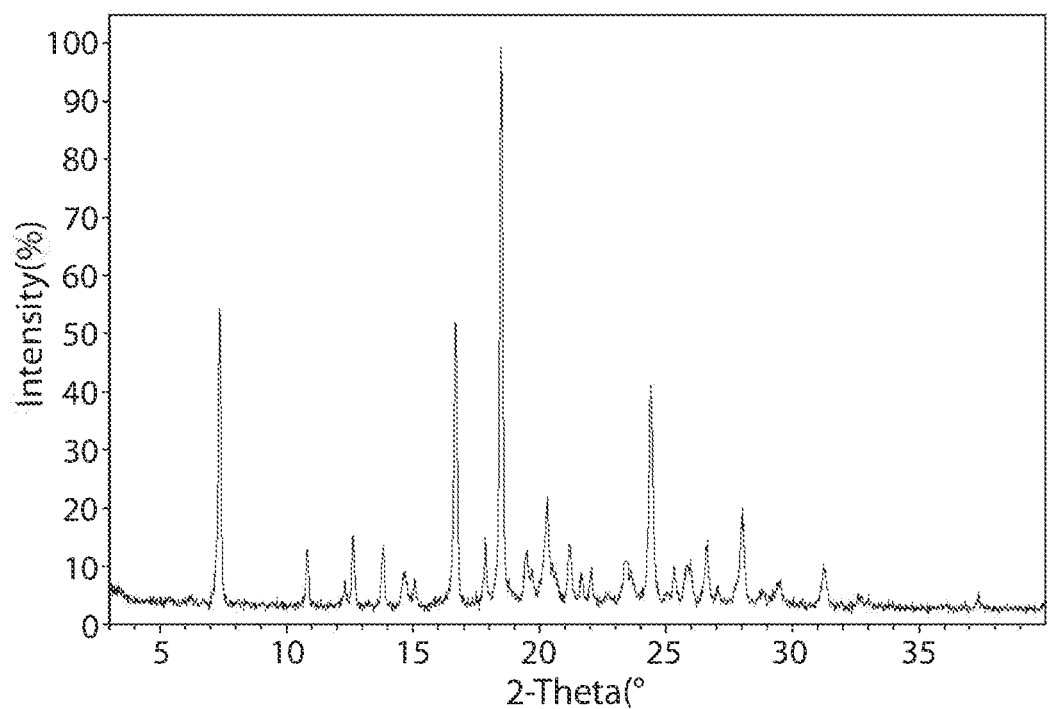
FIG. 7A shows XRPD pattern of Compound 53 raw material.

In some embodiments, the crystalline compound exhibits an X-ray powder diffraction pattern substantially the same as depicted in FIG. 7A.

In some embodiments, the crystalline compound has a melting point onset as determined by differential scanning calorimetry at about 103° C.

Figure 7B:
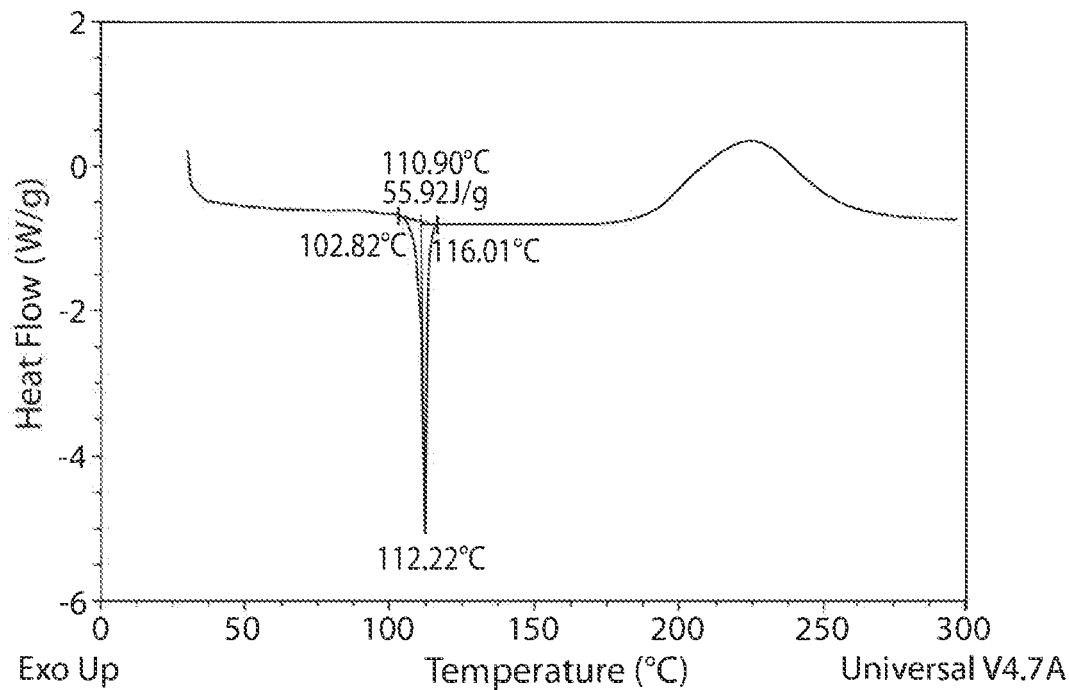
FIG. 7B shows DSC of Compound 53.

In some embodiments, the crystalline compound has a differential scanning calorimetry curve substantially the same as shown in FIG. 7B.

In another aspect, the present invention provides a crystalline compound of formula:

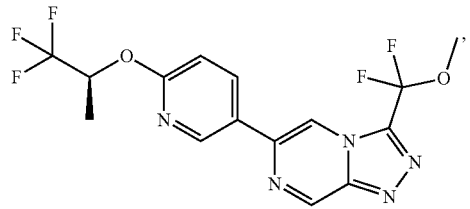 [SMILES: COC(F)(F)c1nnc2cnc(-c3ccc(O[C@@H](C)C(F)(F)F)nc3)cn12]

wherein the crystalline compound exhibits an X-ray powder diffraction pattern comprising peaks at the following diffraction angles (2θ): 6.9±0.2, 16.4±0.2, and 19.5±0.2.

In some embodiments, the crystalline compound exhibits an X-ray powder diffraction pattern comprising peaks at the following diffraction angles (2θ): 6.9±0.2, 16.4±0.2, 17.4±0.2, 18.0±0.2, 19.5±0.2, and 20.8±0.2.

In some embodiments, the crystalline compound exhibits an X-ray powder diffraction pattern comprising peaks at the following diffraction angles (2θ): 6.9±0.2, 11.2±0.2, 13.6±0.2, 13.9±0.2, 16.4±0.2, 17.4±0.2, 18.0±0.2, 19.5±0.2, and 20.8±0.2.

Figure 8A:
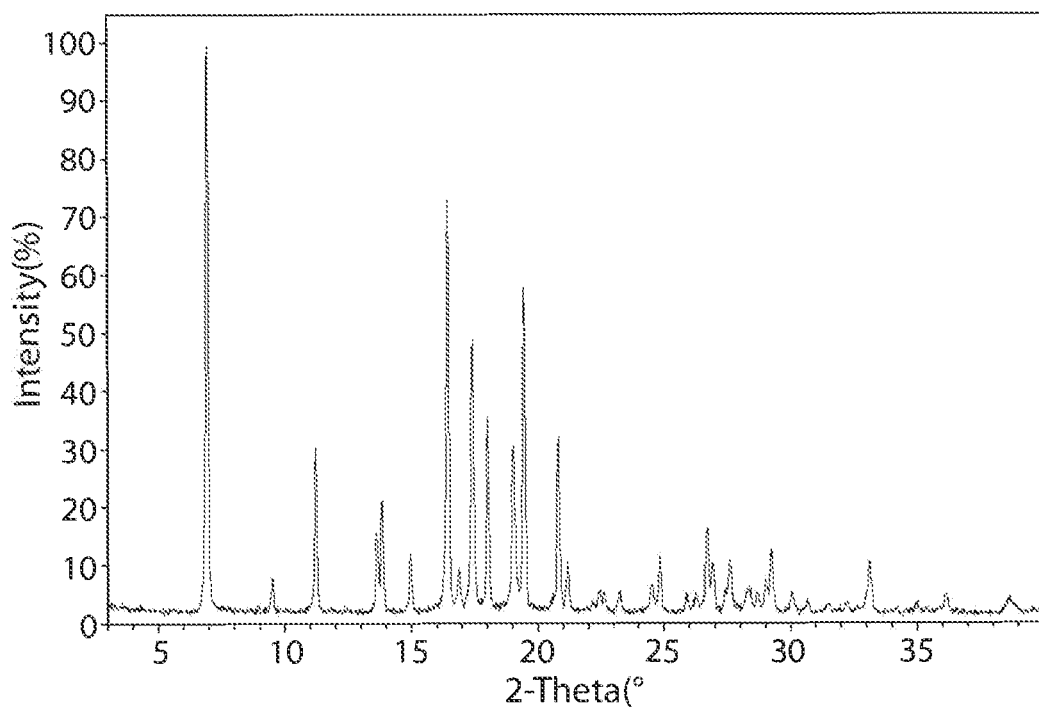
FIG. 8A shows XRPD pattern of Compound 59 raw material.

In some embodiments, the crystalline compound exhibits an X-ray powder diffraction pattern substantially the same as depicted in FIG. 8A.

In some embodiments, the crystalline compound has a melting point onset as determined by differential scanning calorimetry at about 133° C.

Figure 8B:
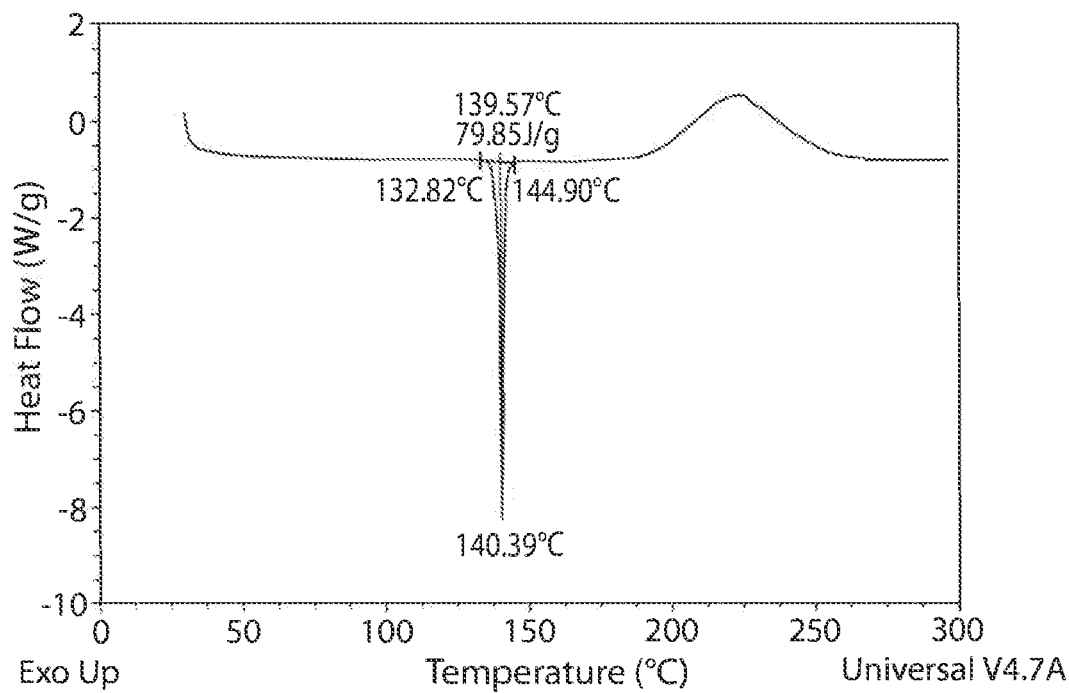
FIG. 8B shows DSC of Compound 59.

In some embodiments, the crystalline compound has a differential scanning calorimetry curve substantially the same as shown in FIG. 8B.

In another aspect, the present disclosure provides a crystalline compound of formula:

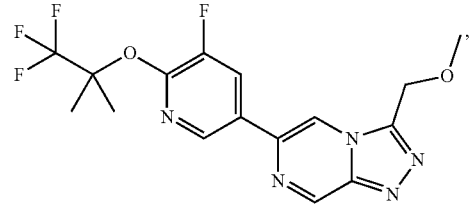

wherein the crystalline compound exhibits an X-ray powder diffraction pattern comprising peaks at the following diffraction angles (2θ): 9.9±0.2, 19.8±0.2, and 23.7±0.2.

In some embodiments, the crystalline compound exhibits an X-ray powder diffraction pattern comprising peaks at the following diffraction angles (2θ): 9.9±0.2, 12.3±0.2, 14.1±0.2, 19.8±0.2, 20.7±0.2, and 23.7±0.2.

In some embodiments, the crystalline compound exhibits an X-ray powder diffraction pattern comprising peaks at the following diffraction angles (2θ): 7.3±0.2, 9.9±0.2, 12.3±0.2, 14.1±0.2, 16.5±0.2, 17.2±0.2, 19.8±0.2, 20.7±0.2, 23.7±0.2, 24.8±0.2, 27.7±0.2, and 29.1±0.2.

Figure 9A:
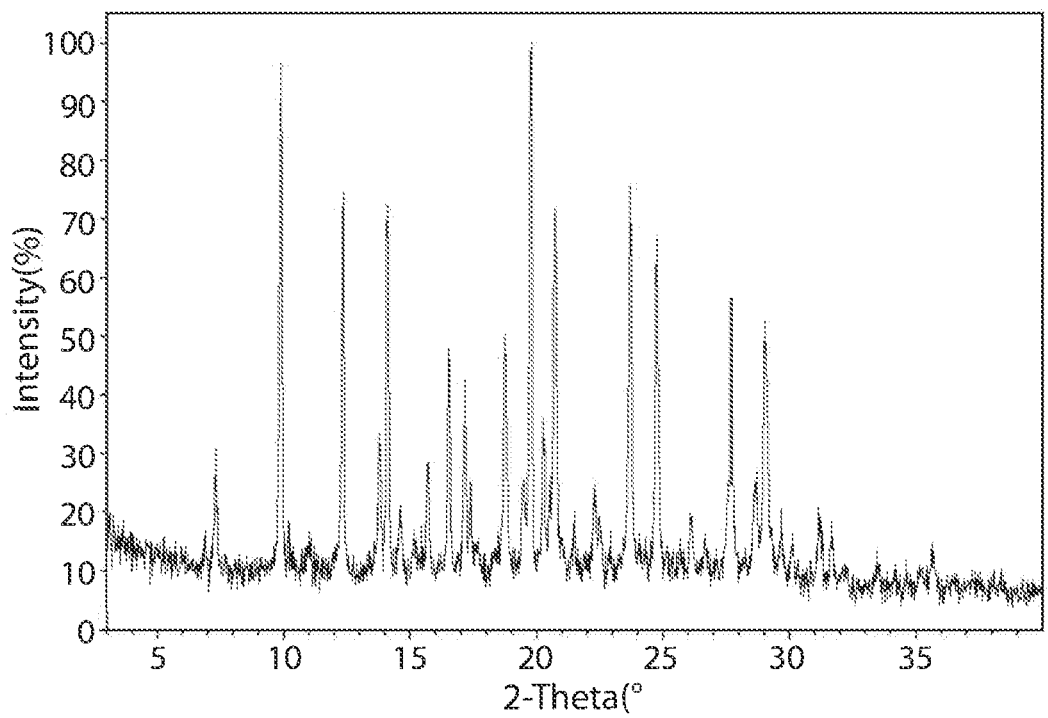
FIG. 9A shows XRPD pattern of Compound 48 raw material.

In some embodiments, the crystalline compound exhibits an X-ray powder diffraction pattern substantially the same as depicted in FIG. 9A.

In some embodiments, the crystalline compound has a melting point onset as determined by differential scanning calorimetry at about 111° C.

Figure 9B:
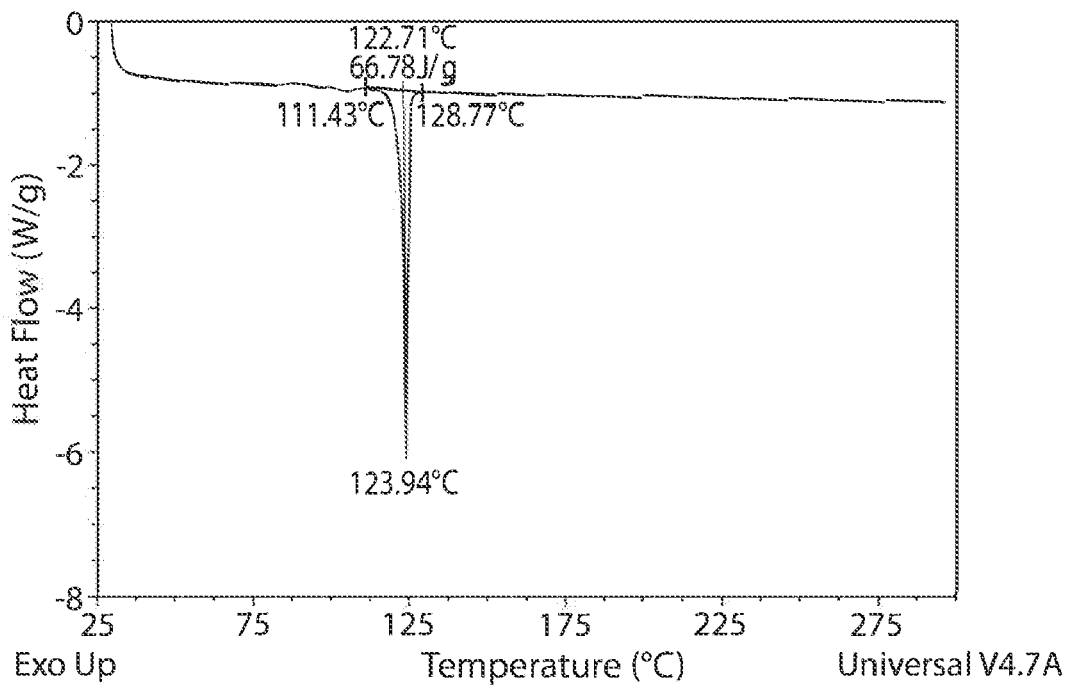
FIG. 9B shows DSC of Compound 48.

In some embodiments, the crystalline compound has a differential scanning calorimetry curve substantially the same as shown in FIG. 9B.

In another aspect, provided herein is a crystalline compound of formula:

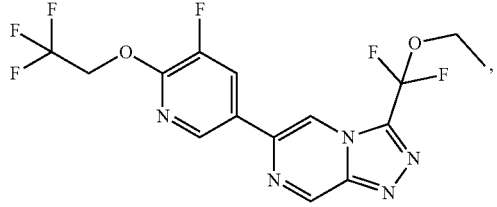

wherein the crystalline compound exhibits an X-ray powder diffraction pattern comprising peaks at the following diffraction angles (2θ): 9.3±0.2, 18.8±0.2, and 21.4±0.2.

In some embodiments, the crystalline compound exhibits an X-ray powder diffraction pattern comprising peaks at the following diffraction angles (2θ): 9.3±0.2, 16.1±0.2, 18.8±0.2, 21.1±0.2, 21.4±0.2, and 21.6±0.2.

In some embodiments, the crystalline compound exhibits an X-ray powder diffraction pattern comprising peaks at the following diffraction angles (2θ): 9.3±0.2, 16.1±0.2, 18.8±0.2, 21.1±0.2, 21.4±0.2, 21.6±0.2, 22.6±0.2, 23.9±0.2, 26.0±0.2, and 26.4±0.2.

In some embodiments, the crystalline compound exhibits an X-ray powder diffraction pattern substantially the same as depicted in FIG. 1A.

In some embodiments, the crystalline compound has a melting point onset as determined by differential scanning calorimetry at about 122° C.

Figure 1B:
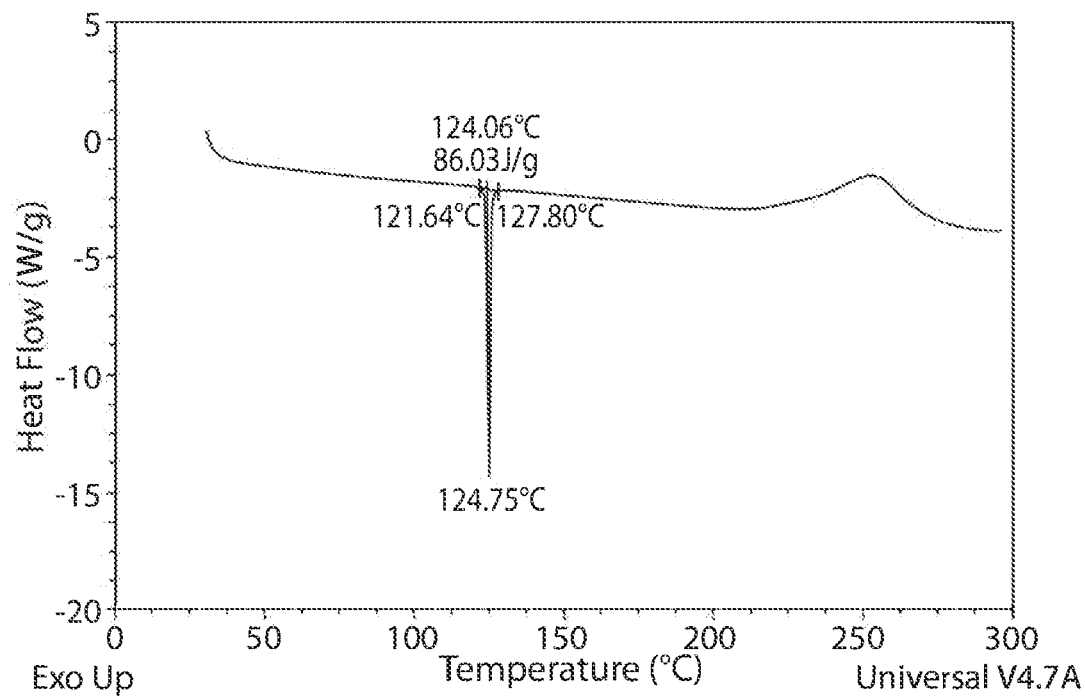
FIG. 1B shows DSC of Compound 10.

In some embodiments, the crystalline compound has a differential scanning calorimetry curve substantially the same as shown in FIG. 1B.

In some embodiments, the X-ray powder diffraction pattern was obtained using Cu Kα radiation.

Pharmaceutical Compositions and Routes of Administration

Compounds provided in accordance with the present invention are usually administered in the form of pharmaceutical compositions. This invention therefore provides pharmaceutical compositions that contain, as the active ingredient, one or more of the compounds described, or a pharmaceutically acceptable salt or ester thereof, and one or more pharmaceutically acceptable excipients, carriers, including inert solid diluents and fillers, diluents, including sterile aqueous solution and various organic solvents, permeation enhancers, solubilizers and adjuvants. The pharmaceutical compositions may be administered alone or in combination with other therapeutic agents. Such compositions are prepared in a manner well known in the pharmaceutical art (see, e.g., Remington's Pharmaceutical Sciences, Mace Publishing Co., Philadelphia, Pa. 17th Ed. (1985); and Modern Pharmaceutics, Marcel Dekker, Inc. 3rd Ed. (G. S. Banker & C. T. Rhodes, Eds.)

The pharmaceutical compositions may be administered in either single or multiple doses by any of the accepted modes of administration of agents having similar utilities, for example as described in those patents and patent applications incorporated by reference, including rectal, buccal, intranasal and transdermal routes, by intra-arterial injection, intravenously, intraperitoneally, parenterally, intramuscularly, subcutaneously, orally, topically, as an inhalant, or via an impregnated or coated device such as a stent, for example, or an artery-inserted cylindrical polymer.

One mode for administration is parenteral, particularly by injection. The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. Aqueous solutions in saline are also conventionally used for injection, but less preferred in the context of the present invention. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating a compound according to the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral administration is another route for administration of compounds in accordance with the invention. Administration may be via capsule or enteric coated tablets, or the like. In making the pharmaceutical compositions that include at least one compound described herein, the active ingredient is usually diluted by an excipient and/or enclosed within such a carrier that can be in the form of a capsule, sachet, paper or other container. When the excipient serves as a diluent, it can be in the form of a solid, semi-solid, or liquid material (as above), which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902,514; and 5,616,345. Another formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The compounds are generally administered in a pharmaceutically effective amount. Preferably, for oral administration, each dosage unit contains from 1 mg to 2 g of a compound described herein, and for parenteral administration, preferably from 0.1 to 700 mg of a compound a compound described herein. It will be understood, however, that the amount of the compound actually administered usually will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action, or to protect from the acid conditions of the stomach. For example, the tablet or pill can comprise an inner dosage and an outer dosage component, the latter being in the form of an envelope over the former. The two components can be separated by an enteric layer that serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably, the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a facemask tent, or intermittent positive pressure breathing machine. Solution, suspension, or powder compositions may be administered, preferably orally or nasally, from devices that deliver the formulation in an appropriate manner.

In some embodiments, a pharmaceutical composition comprising a disclosed compound, or pharmaceutically acceptable salt thereof, and a pharmaceutically acceptable carrier.

Methods of Use

Compounds and compositions described herein are generally useful for the modulating the activity of sodium channels and are useful in treating conditions relating to aberrant function of a sodium channel ion channel, e.g., abnormal late sodium (INaL) current. In some embodiments, a compound provided by the present invention is effective in the treatment of epilepsy or an epilepsy syndrome, a neurodevelopmental disorder, pain, or a neuromuscular disorder. A provided compound, pharmaceutically acceptable salt thereof, or composition may also modulate all sodium ion channels, or may be specific to only one or a plurality of sodium ion channels, e.g., Nav 1.1, 1.2, 1.3, 1.4, 1.5, 1.6, 1.7, 1.8, and/or 1.9.

In typical embodiments, the present invention is intended to encompass the compounds disclosed herein, and the pharmaceutically acceptable salts, pharmaceutically acceptable esters, tautomeric forms, polymorphs, and prodrugs of such compounds. In some embodiments, the present invention includes a pharmaceutically acceptable addition salt, a pharmaceutically acceptable ester, a solvate (e.g., hydrate) of an addition salt, a tautomeric form, a polymorph, an enantiomer, a mixture of enantiomers, a stereoisomer or mixture of stereoisomers (pure or as a racemic or non-racemic mixture) of a compound described herein, e.g. a compound of Formula I, I', I-a, I-b, I-c, I-d, II, III, V, VII, VIII, or IX); such as a compound of Formula named herein.

Epilepsy and Epilepsy Syndromes

The compounds described herein are useful in the treatment of epilepsy and epilepsy syndromes. Epilepsy is a CNS disorder in which nerve cell activity in the brain becomes disrupted, causing seizures or periods of unusual behavior, sensations and sometimes loss of consciousness. Seizure symptoms will vary widely, from a simple blank stare for a few seconds to repeated twitching of their arms or legs during a seizure.

Epilepsy may involve a generalized seizure or a partial or focal seizure. All areas of the brain are involved in a generalized seizure. A person experiencing a generalized seizure may cry out or make some sound, stiffen for several seconds to a minute a then have rhythmic movements of the arms and legs. The eyes are generally open, the person may appear not to be breathing and may actually turn blue. The return to consciousness is gradual and the person maybe confused from minutes to hours. There are six main types of generalized seizures: tonic-clonic, tonic, clonic, myoclonic, absence, and atonic seizures. In a partial or focal seizure, only part of the brain is involved, so only part of the body is affected. Depending on the part of the brain having abnormal electrical activity, symptoms may vary.

Epilepsy, as described herein, includes a generalized, partial, complex partial, tonic clonic, clonic, tonic, refractory seizures, status epilepticus, absence seizures, febrile seizures, or temporal lobe epilepsy.

The compounds described herein (e.g., a compound of Formula I, I', I-a, I-b, I-c, I-d, II, III, V, VII, VIII, or IX) may also be useful in the treatment of epilepsy syndromes. Severe syndromes with diffuse brain dysfunction caused, at least partly, by some aspect of epilepsy, are also referred to as epileptic encephalopathies. These are associated with frequent seizures that are resistant to treatment and severe cognitive dysfunction, for instance West syndrome.

In some embodiments, the epilepsy syndrome comprises an epileptic encephalopathy, such as Dravet syndrome, Angelman syndrome, CDKL5 disorder, frontal lobe epilepsy, infantile spasms, West's syndrome, Juvenile Myoclonic Epilepsy, Landau-Kleffner syndrome, Lennox-Gastaut syndrome, Ohtahara syndrome, PCDH19 epilepsy, or Glut1 deficiency.

In some embodiments, the epilepsy or epilepsy syndrome is a genetic epilepsy or a genetic epilepsy syndrome. In some embodiments, epilepsy or an epilepsy syndrome comprises epileptic encephalopathy, epileptic encephalopathy with SCN1A, SCN2A, SCN8A mutations, early infantile epileptic encephalopathy, Dravet syndrome, Dravet syndrome with SCN1A mutation, generalized epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy.

In some embodiments, the methods described herein further comprise identifying a subject having epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden unexpected death in epilepsy (SUDEP), KCNQ2 epileptic encephalopathy, or KCNT1 epileptic encephalopathy) prior to administration of a compound described herein (e.g., a compound of Formula I, I', I-a, I-b, I-c, I-d, II, III, V, VII, VIII, or IX).

In one aspect, the present invention features a method of treating epilepsy or an epilepsy syndrome (e.g., epileptic encephalopathy, epileptic encephalopathy with SCN1A, SCN2A, SCN8A mutations, early infantile epileptic encephalopathy, Dravet syndrome, Dravet syndrome with SCN1A mutation, generalized Epilepsy with febrile seizures, intractable childhood epilepsy with generalized tonic-clonic seizures, infantile spasms, benign familial neonatal-infantile seizures, SCN2A epileptic encephalopathy, focal epilepsy with SCN3A mutation, cryptogenic pediatric partial epilepsy with SCN3A mutation, SCN8A epileptic encephalopathy, sudden unexpected death in epilepsy, Rasmussen encephalitis, malignant migrating partial seizures of infancy, autosomal dominant nocturnal frontal lobe epilepsy, sudden expected death in epilepsy (SUDEP), KCNQ2 epileptic encephalopathy, or KCNT1 epileptic encephalopathy) comprising administering to a subject in need thereof a compound of Formula (I):

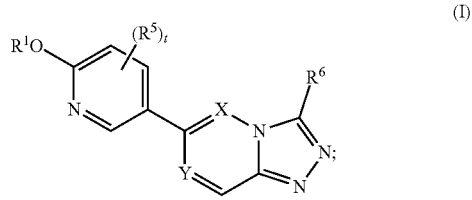

or a pharmaceutically acceptable salt thereof, wherein the variables are as defined herein.

A compound of the present invention (e.g., a compound of Formula I, I', I-a, I-b, I-c, I-d, II, III, V, VII, VIII, or IX) may also be used to treat an epileptic encephalopathy, wherein the subject has a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX.

In some embodiments, the methods described herein further comprise identifying a subject having a mutation in one or more of ALDH7A1, ALG13, ARHGEF9, ARX, ASAH1, CDKL5, CHD2, CHRNA2, CHRNA4, CHRNB2, CLN8, CNTNAP2, CPA6, CSTB, DEPDC5, DNM1, EEF1A2, EPM2A, EPM2B, GABRA1, GABRB3, GABRG2, GNAO1, GOSR2, GRIN1, GRIN2A, GRIN2B, HCN1, IER3IP1, KCNA2, KCNB1, KCNC1, KCNMA1, KCNQ2, KCNQ3, KCNT1, KCTD7, LGI1, MEF2C, NHLRC1, PCDH19, PLCB1, PNKP, PNPO, PRICKLE1, PRICKLE2, PRRT2, RELN, SCARB2, SCN1A, SCN1B, SCN2A, SCN8A, SCN9A, SIAT9, SIK1, SLC13A5, SLC25A22, SLC2A1, SLC35A2, SLC6A1, SNIP1, SPTAN1, SRPX2, ST3GAL3, STRADA, STX1B, STXBP1, SYN1, SYNGAP1, SZT2, TBC1D24, and WWOX prior to administration of a compound described herein (e.g., a compound of Formula I, I', I-a, I-b, I-c, I-d, II, III, V, VII, VIII, or IX).

Neurodevelopmental Disorders

The compounds described herein may be useful in the treatment of a neurodevelopmental disorder. In some embodiments, the neurodevelopmental disorder comprises autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy. In some embodiments, the methods described herein further comprise identifying a subject having a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) prior to administration of a compound described herein (e.g., a compound of Formula I, I', I-a, I-b, I-c, I-d, II, III, V, VII, VIII, or IX).

In one aspect, the present invention features a method of treating a neurodevelopmental disorder (e.g., autism, autism with epilepsy, tuberous sclerosis, Fragile X syndrome, Rett syndrome, Angelman syndrome, Dup15q syndrome, 22q13.3 Deletion syndrome, Prader-Willi syndrome, velocardiofacial syndrome, Smith-Lemli-Opitz syndrome, or a neurodevelopmental disorder with epilepsy) comprising administering to a subject in need thereof a compound of Formula (I):

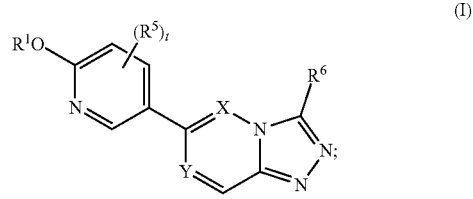

or a pharmaceutically acceptable salt thereof, wherein the variables are as defined herein.

Pain

The compounds described herein may be useful in the treatment of pain. In some embodiments, the pain comprises neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder. In some embodiments, the methods described herein further comprise identifying a subject having pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) prior to administration of a compound described herein (e.g., a compound of Formula I, I', I-a, I-b, I-c, I-d, II, III, V, VII, VIII, or IX).

In one aspect, the present invention features a method of treating pain (e.g., neuropathic pain, trigeminal neuralgia, migraine, hemiplegic migraine, familial hemiplegic migraine, familial hemiplegic migraine type 3, cluster headache, trigeminal neuralgia, cerebellar ataxia, or a related headache disorder) comprising administering to a subject in need thereof a compound of Formula (I):

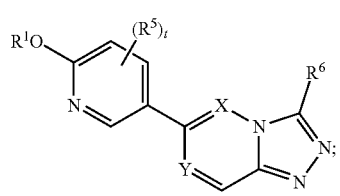

(I)

or a pharmaceutically acceptable salt thereof, wherein the variables are as defined herein.

Neuromuscular Disorders

The compounds described herein may be useful in the treatment of a neuromuscular disorder. In some embodiments, the neuromuscular disorder comprises amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation. In some embodiments, the methods described herein further comprise identifying a subject having a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) prior to administration of a compound described herein (e.g., a compound of Formula I, I', I-a, I-b, I-c, I-d, II, III, V, VII, VIII, or IX).

In one aspect, the present invention features a method of treating a neuromuscular disorder (e.g., amyotrophic lateral sclerosis, multiple sclerosism, myotonia, paramyotonia congenita, potassium-aggravated myotonia, periodic paralysis, hyperkalemic periodic paralysis, hypokalemic periodic paralysis, or laryngospasm with SCN4A mutation) comprising administering to a subject in need thereof a compound of Formula (I):

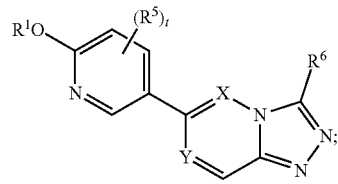

(I)

or a pharmaceutically acceptable salt thereof, wherein the variables are as defined herein.

Other Disorders

In some embodiments, a compound of the present invention (e.g., a compound of Formula I, I', I-a, I-b, I-c, I-d, II, III, V, VII, VIII, or IX) may have appropriate pharmacokinetic properties such that they may be active with regard to the central and/or peripheral nervous system. In some embodiments, the compounds provided herein are used to treat a cardiovascular disease such as atrial and ventricular arrhythmias, including atrial fibrillation, Prinzmetal's (variant) angina, stable angina, unstable angina, ischemia and reperfusion injury in cardiac, kidney, liver and the brain, exercise induced angina, pulmonary hypertension, congestive heart disease including diastolic and systolic heart failure, recurrent ischemia, cerebral ischemia, stroke, renal ischemia, ischemia associated with organ transplant, acute coronary syndrome, peripheral arterial disease, intermittent claudication, and myocardial infarction. In some embodiments, the compounds provided herein may be used in the treatment of diseases affecting the neuromuscular system resulting in itching, seizures, or paralysis, or in the treatment of diabetes or reduced insulin sensitivity, and disease states related to diabetes, such as diabetic peripheral neuropathy. In some embodiments, a disclosed method comprises administering the pharmaceutical composition.

In some embodiments, provided herein is a method of treating a neurological disorder or a psychiatric disorder, wherein the method comprises administering to a subject in need thereof a compound disclosed herein, or a pharmaceutically acceptable salt thereof or a pharmaceutical composition disclosed herein.

Combination Therapy

A compound or composition described herein (e.g., for use in modulating a sodium ion channel, e.g., the late sodium (INaL) current) may be administered in combination with another agent or therapy. A subject to be administered a compound disclosed herein may have a disease, disorder, or condition, or a symptom thereof, that would benefit from treatment with another agent or therapy. These diseases or conditions can relate to epilepsy or an epilepsy syndrome, a neurodevelopmental disorder, pain, or a neuromuscular disorder.

Antiepilepsy Agents

Anti-epilepsy agents include brivaracetam, carbamazepine, clobazam, clonazepam, diazepam, divalproex, eslicarbazepine, ethosuximide, ezogabine, felbamate, gabapentin, lacosamide, lamotrigine, levetiracetam, lorazepam, oxcarbezepine, permpanel, phenobarbital, phenytoin, pregabalin, primidone, rufinamide, tigabine, topiramate, valproic acid, vigabatrin, zonisamide, and cannabidiol.

Cardiovascular Agent Combination Therapy

Cardiovascular related diseases or conditions that can benefit from a combination treatment of the sodium channel blockers of the invention with other therapeutic agents include, without limitation, angina including stable angina, unstable angina (UA), exercised-induced angina, variant angina, arrhythmias, intermittent claudication, myocardial infarction including non-STE myocardial infarction (NSTEMI), pulmonary hypertension including pulmonary arterial hypertension, heart failure including congestive (or chronic) heart failure and diastolic heart failure and heart failure with preserved ejection fraction (diastolic dysfunction), acute heart failure, or recurrent ischemia.

Therapeutic agents suitable for treating cardiovascular related diseases or conditions include anti-anginals, heart failure agents, antithrombotic agents, antiarrhythmic agents, antihypertensive agents, and lipid lowering agents.

The co-administration of the sodium channel blockers of the invention with therapeutic agents suitable for treating cardiovascular related conditions allows enhancement in the standard of care therapy the patient is currently receiving.

Anti-Anginals

Anti-anginals include beta-blockers, calcium channel blockers, and nitrates. Beta blockers reduce the heart's need for oxygen by reducing its workload resulting in a decreased heart rate and less vigorous heart contraction. Examples of beta-blockers include acebutolol (Sectral), atenolol (Tenormin), betaxolol (Kerlone), bisoprolol/hydrochlorothiazide (Ziac), bisoprolol (Zebeta), carteolol (Cartrol), esmolol (Brevibloc), labetalol (Normodyne, Trandate), metoprolol (Lopressor, Toprol XL), nadolol (Corgard), propranolol (Inderal), sotalol (Betapace), and timolol (Blocadren).

Nitrates dilate the arteries and veins thereby increasing coronary blood flow and decreasing blood pressure. Examples of nitrates include nitroglycerin, nitrate patches, isosorbide dinitrate, and isosorbide-5-mononitrate.

Calcium channel blockers prevent the normal flow of calcium into the cells of the heart and blood vessels causing the blood vessels to relax thereby increasing the supply of blood and oxygen to the heart. Examples of calcium channel blockers include amlodipine (Norvasc, Lotrel), bepridil (Vascor), diltiazem (Cardizem, Tiazac), felodipine (Plendil), nifedipine (Adalat, Procardia), nimodipine (Nimotop), nisoldipine (Sular), verapamil (Calan, Isoptin, Verelan), and nicardipine.

Heart Failure Agents

Agents used to treat heart failure include diuretics, ACE inhibitors, vasodilators, and cardiac glycosides. Diuretics eliminate excess fluids in the tissues and circulation thereby relieving many of the symptoms of heart failure. Examples of diuretics include hydrochlorothiazide, metolazone (Zaroxolyn), furosemide (Lasix), bumetanide (Bumex), spironolactone (Aldactone), and eplerenone (Inspra).

Angiotensin converting enzyme (ACE) inhibitors reduce the workload on the heart by expanding the blood vessels and decreasing resistance to blood flow. Examples of ACE inhibitors include benazepril (Lotensin), captopril (Capoten), enalapril (Vasotec), fosinopril (Monopril), lisinopril (Prinivil, Zestril), moexipril (Univasc), perindopril (Aceon), quinapril (Accupril), ramipril (Altace), and trandolapril (Mavik).

Vasodilators reduce pressure on the blood vessels by making them relax and expand. Examples of vasodilators include hydralazine, diazoxide, prazosin, clonidine, and methyldopa. ACE inhibitors, nitrates, potassium channel activators, and calcium channel blockers also act as vasodilators.

Cardiac glycosides are compounds that increase the force of the heart's contractions. These compounds strengthen the pumping capacity of the heart and improve irregular heartbeat activity. Examples of cardiac glycosides include digitalis, digoxin, and digitoxin.

Antithrombotic Agents

Antithrombotics inhibit the clotting ability of the blood. There are three main types of antithrombotics—platelet inhibitors, anticoagulants, and thrombolytic agents.

Platelet inhibitors inhibit the clotting activity of platelets, thereby reducing clotting in the arteries. Examples of platelet inhibitors include acetylsalicylic acid (aspirin), ticlopidine, clopidogrel (plavix), dipyridamole, cilostazol, persantine sulfinpyrazone, dipyridamole, indomethacin, and glycoprotein IIb/IIIa inhibitors, such as abciximab, tirofiban, and eptifibatide (Integrelin). Beta blockers and calcium channel blockers also have a platelet-inhibiting effect.

Anticoagulants prevent blood clots from growing larger and prevent the formation of new clots. Examples of anticoagulants include bivalirudin (Angiomax), warfarin (Coumadin), unfractionated heparin, low molecular weight heparin, danaparoid, lepirudin, and argatroban.

Thrombolytic agents act to break down an existing blood clot. Examples of thrombolytic agents include streptokinase, urokinase, and tenecteplase (TNK), and tissue plasminogen activator (t-PA).

Antiarrhythmic Agents

Antiarrhythmic agents are used to treat disorders of the heart rate and rhythm. Examples of antiarrhythmic agents include amiodarone, dronedarone, quinidine, procainamide, lidocaine, and propafenone. Cardiac glycosides and beta blockers are also used as antiarrhythmic agents.

Combinations with amiodarone and dronedarone are of particular interest given the recently discovered synergistic effects of the sodium channel blocker ranolazine and amioarone and dronedarone.

Antihypertensive Agents

Antihypertensive agents are used to treat hypertension, a condition in which the blood pressure is consistently higher than normal. Hypertension is associated with many aspects of cardiovascular disease, including congestive heart failure, atherosclerosis, and clot for illation. Examples of antihypertensive agents include alpha-1-adrenergic antagonists, such as prazosin (Minipress), doxazosin mesylate (Cardura), prazosin hydrochloride (Minipress), prazosin, polythiazide (Minizide), and terazosin hydrochloride (Hytrin); beta-adrenergic antagonists, such as propranolol (Inderal), nadolol (Corgard), timolol (Blocadren), metoprolol (Lopressor), and pindolol (Visken); central alpha-adrenoceptor agonists, such as clonidine hydrochloride (Catapres), clonidine hydrochloride and chlorthalidone (Clorpres, Combipres), guanabenz Acetate (Wytensin), guanfacine hydrochloride (Tenex), methyldopa (Aldomet), methyldopa and chlorothiazide (Aldoclor), methyldopa and hydrochlorothiazide (Aldoril); combined alpha/beta-adrenergic antagonists, such as labetalol (Normodyne, Trandate), Carvedilol (Coreg); adrenergic neuron blocking agents, such as guanethidine (ismelin), reserpine (Serpasil); central nervous system-acting antihypertensives, such as clonidine (Catapres), methyldopa (Aldomet), guanabenz (Wytensin); anti-angiotensin II agents; ACE inhibitors, such as perindopril (Aceon) captopril (Capoten), enalapril (Vasotec), lisinopril (Prinivil, Zestril); angiotensin-II receptor antagonists, such as Candesartan (Atacand), Eprosartan (Teveten), Irbesartan (Avapro), Losartan (Cozaar), Telmisartan (Micardis), Valsartan (Diovan); calcium channel blockers, such as verapamil (Calan, Isoptin), diltiazem (Cardizem), nifedipine (Adalat, Procardia); diuretics; direct vasodilators, such as nitroprusside (Nipride), diazoxide (Hyperstat IV), hydralazine (Apresoline), minoxidil (Loniten), verapamil; and potassium channel activators, such as aprikalim, bimakalim, cromakalim, emakalim, nicorandil, and pinacidil.

Lipid Lowering Agents

Lipid lowering agents are used to lower the amounts of cholesterol or fatty sugars present in the blood. Examples of lipid lowering agents include bezafibrate (Bezalip), ciprofibrate (Modalim), and statins, such as atorvastatin (Lipitor), fluvastatin (Lescol), lovastatin (Mevacor, Altocor), mevastatin, pitavastatin (Livalo, Pitava) pravastatin (Lipostat), rosuvastatin (Crestor), and simvastatin (Zocor).

In this invention, the patient presenting with an acute coronary disease event often suffers from secondary medical conditions such as one or more of a metabolic disorder, a pulmonary disorder, a peripheral vascular disorder, or a gastrointestinal disorder. Such patients can benefit from treatment of a combination therapy comprising administering to the patient ranolazine in combination with at least one therapeutic agent.

Pulmonary Disorders Combination Therapy

Pulmonary disorder refers to any disease or condition related to the lungs. Examples of pulmonary disorders include, without limitation, asthma, chronic obstructive pulmonary disease (COPD), bronchitis, and emphysema.

Examples of therapeutics agents used to treat pulmonary disorders include bronchodilators including beta2 agonists and anticholinergics, corticosteroids, and electrolyte supplements. Specific examples of therapeutic agents used to treat pulmonary disorders include epinephrine, terbutaline (Brethaire, Bricanyl), albuterol (Proventil), salmeterol (Serevent, Serevent Diskus), theophylline, ipratropium bromide (Atrovent), tiotropium (Spiriva), methylprednisolone (Solu-Medrol, Medrol), magnesium, and potassium.

Metabolic Disorders Combination Therapy

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents, as described in the section "Cardiovascular Agent Combination Therapy" above. Additional therapeutic agents used to treat metabolic disorders include insulin, sulfonylureas, biguanides, alpha-glucosidase inhibitors, and incretin mimetics.

Peripheral Vascular Disorders Combination Therapy

Peripheral vascular disorders are disorders related to the blood vessels (arteries and veins) located outside the heart and brain, including, for example peripheral arterial disease (PAD), a condition that develops when the arteries that supply blood to the internal organs, arms, and legs become completely or partially blocked as a result of atherosclerosis.

Gastrointestinal Disorders Combination Therapy

Gastrointestinal disorders refer to diseases and conditions associated with the gastrointestinal tract. Examples of gastrointestinal disorders include gastroesophageal reflux disease (GERD), inflammatory bowel disease (IBD), gastroenteritis, gastritis and peptic ulcer disease, and pancreatitis.

Examples of therapeutic agents used to treat gastrointestinal disorders include proton pump inhibitors, such as pantoprazole (Protonix), lansoprazole (Prevacid), esomeprazole (Nexium), omeprazole (Prilosec), rabeprazole; H2 blockers, such as cimetidine (Tagamet), ranitidine (Zantac), famotidine (Pepcid), nizatidine (Axid); prostaglandins, such as misoprostoL (Cytotec); sucralfate; and antacids.

Antibiotics, Analgesics, Antidepressants and Anti-Anxiety Agents Combination Therapy Patients presenting with an acute coronary disease event may exhibit conditions that benefit from administration of therapeutic agent or agents that are antibiotics, analgesics, antidepressant and anti-anxiety agents in combination with ranolazine.

Antibiotics

Antibiotics are therapeutic agents that kill, or stop the growth of, microorganisms, including both bacteria and fungi. Example of antibiotic agents include .beta.-Lactam antibiotics, including penicillins (amoxicillin), cephalosporins, such as cefazolin, cefuroxime, cefadroxil (Duricef), cephalexin (Keflex), cephradine (Velosef), cefaclor (Ceclor), cefuroxime axtel (Ceftin), cefprozil (Cefzil), loracarbef (Lorabid), cefixime (Suprax), cefpodoxime proxetil (Vantin), ceftibuten (Cedax), cefdinir (Omnicef), ceftriaxone (Rocephin), carbapenems, and monobactams; tetracyclines, such as tetracycline; macrolide antibiotics, such as erythromycin; aminoglycosides, such as gentamicin, tobramycin, amikacin; quinolones such as ciprofloxacin; cyclic peptides, such as vancomycin, streptogramins, polymyxins; lincosamides, such as clindamycin; oxazolidinoes, such as linezolid; and sulfa antibiotics, such as sulfisoxazole.

Analgesics

Analgesics are therapeutic agents that are used to relieve pain. Examples of analgesics include opiates and morphinomimetics, such as fentanyl and morphine; paracetamol; NSAIDs, and COX-2 inhibitors. Given the ability of the sodium channel blockers of the invention to treat neuropathic pain via inhibition of the Nav 1.7 and 1.8 sodium channels, combination with analgesics are particularly envisioned. See U.S. Patent Application Publication 20090203707.

Antidepressant and Anti-Anxiety Agents

Antidepressant and anti-anxiety agents include those agents used to treat anxiety disorders, depression, and those used as sedatives and tranquillizers. Examples of antidepressant and anti-anxiety agents include benzodiazepines, such as diazepam, lorazepam, and midazolam; benzodiazepines; barbiturates; glutethimide; chloral hydrate; meprobamate; sertraline (Zoloft, Lustral, Apo-Sertral, Asentra, Gladem, Serlift, Stimuloton); escitalopram (Lexapro, Cipralex); fluoxetine (Prozac, Sarafem, Fluctin, Fontex, Prodep, Fludep, Lovan); venlafaxine (Effexor XR, Efexor); citalopram (Celexa, Cipramil, Talohexane); paroxetine (Paxil, Seroxat, Aropax); trazodone (Desyrel); amitriptyline (Elavil); and bupropion (Wellbutrin, Zyban). Antidepressant and anti-anxiety agents may include neuroactive steroid and ketamine and related NMDA receptor antagonists.

Accordingly, one aspect of the invention provides for a composition comprising the sodium channel blockers of the invention and at least one therapeutic agent. In an alternative embodiment, the composition comprises the sodium channel blockers of the invention and at least two therapeutic agents. In further alternative embodiments, the composition comprises the sodium channel blockers of the invention and at least three therapeutic agents, the sodium channel blockers of the invention and at least four therapeutic agents, or the sodium channel blockers of the invention and at least five therapeutic agents.

The methods of combination therapy include co-administration of a single formulation containing the sodium channel blockers of the invention and therapeutic agent or agents, essentially contemporaneous administration of more than one formulation comprising the sodium channel blocker of the invention and therapeutic agent or agents, and consecutive administration of a sodium channel blocker of the invention and therapeutic agent or agents, in any order, wherein preferably there is a time period where the sodium channel blocker of the invention and therapeutic agent or agents simultaneously exert their therapeutic effect.

EXEMPLIFICATION

The representative examples that follow are intended to help illustrate the invention, and are not intended to, nor should they be construed to, limit the scope of the invention.

The compounds provided herein can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimal reaction conditions may vary with the particular reactants or solvent used, but such conditions can be determined by one skilled in the art by routine optimization.

Additionally, as will be apparent to those skilled in the art, conventional protecting groups may be necessary to prevent certain functional groups from undergoing undesired reactions. The choice of a suitable protecting group for a particular functional group as well as suitable conditions for protection and deprotection are well known in the art. For example, numerous protecting groups, and their introduction and removal, are described in T. W. Greene and P. G. M. Wuts, *Protecting Groups in Organic Synthesis*, Second Edition, Wiley, New York, 1991, and references cited therein.

The compounds provided herein may be isolated and purified by known standard procedures. Such procedures include recrystallization, filtration, flash chromatography, trituration, high pressure liquid chromatography (HPLC), or supercritical fluid chromatography (SFC). Note that flash chromatography may either be performed manually or via an automated system. The compounds provided herein may be characterized by known standard procedures, such as nuclear magnetic resonance spectroscopy (NMR) or liquid chromatography mass spectrometry (LCMS). NMR chemical shifts are reported in part per million (ppm) and are generated using methods well known to those of skill in the art.

Exemplary general methods for analytical LCMS include Method A (Xtimate C18 (2.1 mm×30 mm, 3 μm); A=H$_2$O (0.04% TFA) and B=CH$_3$CN (0.02% TFA); 50° C.; 1.2 mL/min; 10-80% B over 0.9 minutes, then 80% B for 0.6 minutes) and Method B (Chromolith Flash RP-18 endcapped C18 (2 mm×25 mm); A=H$_2$O (0.04% TFA) and B=CH$_3$CN (0.02% TFA); 50° C.; 1.5 mL/min; 5-95% B over 0.7 minutes, then 95% B for 0.4 minutes).

List of Abbreviations
Pd(dppf)Cl$_2$ [1,1'-bis(diphenylphosphino)ferrocene]palladium(II) dichloride
Pd(t-Bu$_3$P)$_2$ bis(tri-tert-butylphosphine)palladium(0)
Pd(OAc)$_2$ palladium(II) acetate
SPhos 2-dicyclohexylphosphino-2',6'-dimethoxybiphenyl
Et$_3$N triethylamine
AgOTf silver trifluoromethanesulfonate
DMF N,N-dimethylformamide
MeOH methanol
EtOH ethanol
i-Pr$_2$O diisopropyl ether
THF tetrahydrofuran
DCM dichloromethane
AcN or MeCN acetonitrile
EA or EtOAc ethyl acetate
PE petroleum ether
DMSO dimethyl sulfoxide
AcOH acetic acid
NBS N-bromosuccinimide
NaOMe sodium methoxide
EtONa sodium ethoxide
TsOH p-toluenesulfonic acid
DEA N,N-diethylaniline
DIPEA N,N-diisopropylethylamine
TFA trifluoroacetic acid
KOAc potassium acetate
T3P propanephosphonic acid anhydride Example 1: 3-[cyclopropylmethoxy(difluoro)methyl]-6-[5-fluoro-6-(2,2,2-trifluoroethoxy)-3-pyridy]-[1,2,4]triazolo[4,3-a]pyridine

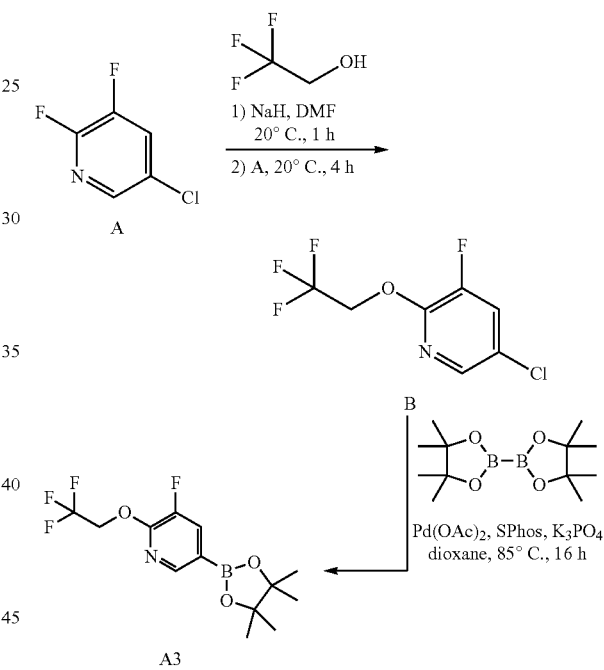

Synthesis of B: To a suspension of NaH (2.94 g, 73.56 mmol) in THF (50 mL) was added 2,2,2-trifluoroethanol (7.36 g, 73.56 mmol) slowly at 20° C., and the mixture was stirred for 1 hour. 5-chloro-2,3-difluoro-pyridine (10 g, 66.88 mmol) was then added, and the mixture was stirred at 20° C. for another 4 hours. The mixture was quenched with sat.NH$_4$Cl (50 mL) and extracted with EtOAc (100 mL×2). The combined organic phase was washed with brine (50 mL), dried over Na$_2$SO$_4$, filtered and concentrated to afford B (15000 mg, 65.34 mmol) as an oil. $^1$H NMR (400 MHz, CDCl$_3$) $\delta_H$=7.83 (d, 1H), 7.38 (dd, 1H), 4.73 (q, 2H).

Synthesis of A3: A mixture of B (8 g, 34.85 mmol), 4,4,5,5-tetramethyl-2-(4,4,5,5-tetramethyl-1,3,2-dioxaborolan-2-yl)-1,3,2-dioxaborolane (26.55 g, 104.55 mmol), K$_3$PO$_4$ (14.79 g, 69.7 mmol), SPhos (4.29 g, 10.45 mmol) and Pd(OAc)$_2$ (782.4 mg, 3.48 mmol) in 1,4-dioxane (250 mL) was stirred at 85° C. for 16 hours. After cooling to room temperature, the mixture was filtered through Celite and eluted with EtOAc (50 mL×2). The filtrate was concentrated and diluted with EtOAc (200 mL), washed with water (100 mL×2) and brine (100 mL), dried over Na$_2$SO$_4$, filtered and concentrated to give the crude product, which was purified by flash chromatography on silica gel (EtOAc in PE=0 to 10% to 40%) to afford the product (3 g, 4.6021 mmol) as an oil. $^1$H NMR (400 MHz, CDCl$_3$) $\delta_H$=8.26 (d, 1H), 7.72 (dd, 1H), 4.87 (q, 2H), 1.35 (s, 12H). LCMS R$_t$=0.94 min using Method B, MS ESI calcd. for C$_{13}$H$_{17}$BF$_4$NO$_3$ [M+H]$^+$ 322.1, found 322.3.

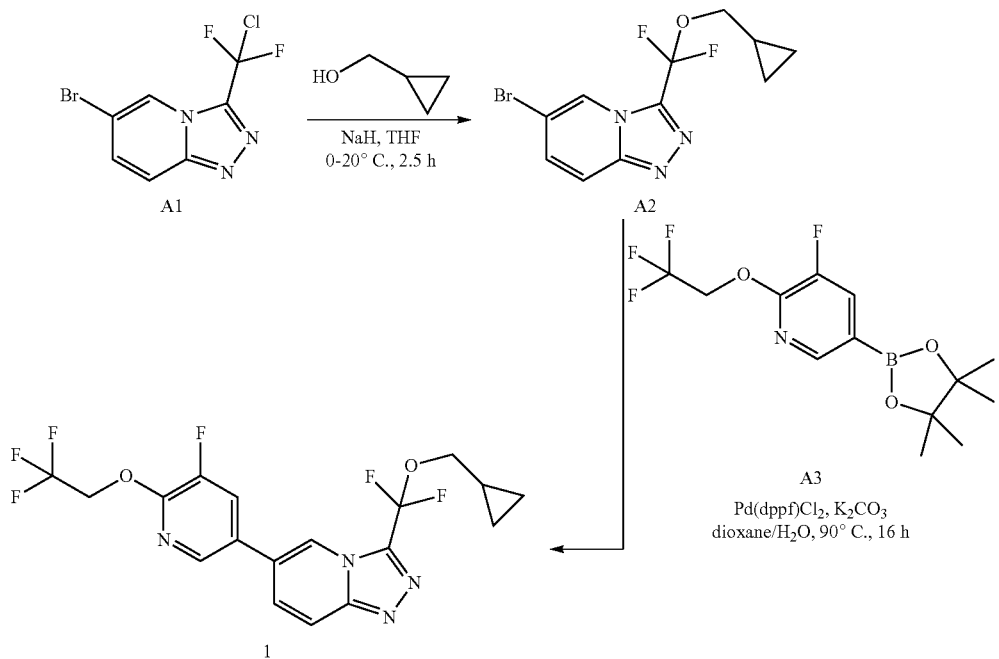

Synthesis of A2: To a mixture of cyclopropylmethanol (382.93 mg, 5.31 mmol) in THF (10 mL) was added NaH (212.41 mg, 5.31 mmol), and the mixture was stirred at 20° C. for 0.5 hour. Then to the mixture was added 6-bromo-3-[chloro(difluoro)methyl]-[1,2,4]triazolo[4,3-a]pyridine (300 mg, 1.06 mmol), and the mixture was stirred at 20° C. for 2 hours. The reaction was quenched with sat.NH$_4$Cl (10 mL), and the mixture was extracted with EtOAc (10 mL×2). The combined organic phase was washed with brine (10 mL), dried over Na$_2$SO$_4$, filtered and concentrated to give the crude product. The crude product was purified by flash chromatography on silica gel (EtOAc in PE=10% to 40%) to give the product (240 mg, 0.73 mmol) as a solid. LCMS Rt=2.29 min in 4 min chromatography.

Synthesis of Compound 1: A mixture of 3-fluoro-5-(4,4,5,5-tetramethyl-1,3,2-dioxaborolan-2-yl)-2-(2,2,2-trifluoroethoxy)pyridine (111.02 mg, 0.35 mmol), Pd(dppf)Cl$_2$ (34.5 mg, 0.05 mmol), 6-bromo-3-[cyclopropylmethoxy(difluoro)methyl]-[1,2,4]triazolo[4,3-a]pyridine (100 mg, 0.31 mmol) and K$_2$CO$_3$ (86.89 mg, 0.63 mmol) in 1,4-Dioxane (5 mL) and Water (1 mL) was stirred at 90° C. for 16 hours under N$_2$. After cooling to room temperature, the mixture was filtered through Celite, and eluted with EtOAc (10 mL×2), and the filtrate was concentrated to give the crude product. The crude product was purified by Prep-HPLC (Waters Xbridge 150 mm×25 mm 5 μm) A=H$_2$O (10 mM NH$_4$HCO$_3$) and B=CH$_3$CN; 50-70% B over 7 minutes) to give the product (100.49 mg, 0.23 mmol) as a solid. $^1$H NMR (400 MHz, DMSO-d$_6$) $\delta_H$=8.75 (s, 1H), 8.46 (d, 1H), 8.34 (dd, 11.2 Hz, 1H), 8.14-8.09 (m, 1H), 7.97 (dd, 1H), 5.18 (q, 2H), 4.09 (d, 2H), 1.31-1.21 (m, 1H), 0.61-0.55 (m, 2H), 0.43-0.37 (m, 2H). LCMS $R_t$=1.31 min in 2.0 min chromatography, MS ESI calcd. for $C_{18}H_{15}F_6N_4O_2$ [M+H]$^+$ 433.1, found 433.0.

Example 2: 3-[difluoro(isobutoxy)methyl]-6-[5-fluoro-6-(2,2,2-trifluoroethoxy)-3-pyridyl]-[1,2,4]triazolo[4,3-a]pyridine

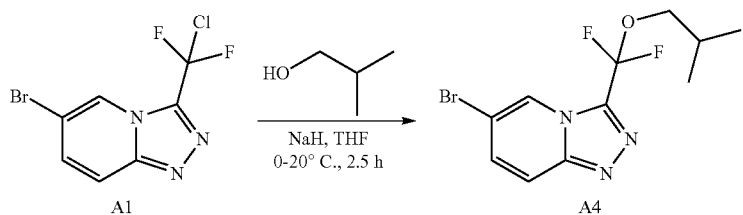

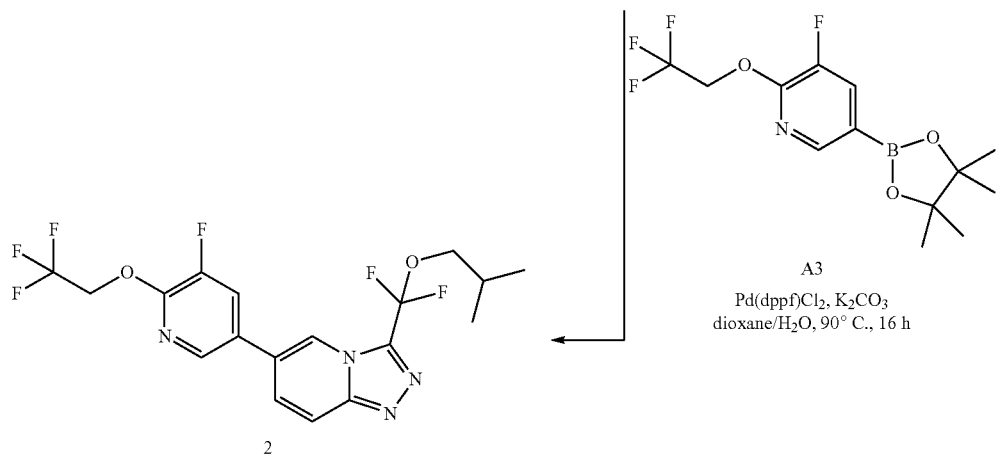

Synthesis of A4: To a mixture of 2-methylpropan-1-ol (393.6 mg, 5.31 mmol) in THF (10 mL) was added NaH (212.41 mg, 5.31 mmol), and the mixture was stirred at 20° C. for 0.5 hour. Then to the mixture was added 6-bromo-3-[chloro(difluoro)methyl]-[1,2,4]triazolo[4,3-a]pyridine (300 mg, 1.06 mmol), and the mixture was stirred at 20° C. for 2 hours. The reaction was quenched with sat.NH$_4$Cl (10 mL), and the mixture was extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=10% to 40%) to give the product (100 mg, 0.30 mmol) as a solid. LCMS Rt=0.86 min in 1.5 min chromatography, MS ESI calcd. $C_{11}H_{13}BrF_2N_3O$ [M+H+2]$^+$ 320.0, found 320.2.

Synthesis of Compound 2: A mixture of 3-fluoro-5-(4,4,5,5-tetramethyl-1,3,2-dioxaborolan-2-yl)-2-(2,2,2-trifluoroethoxy)pyridine (110.33 mg, 0.34 mmol), Pd(dppf)Cl$_2$ (34.28 mg, 0.05 mmol), 6-bromo-3-[difluoro(isobutoxy)methyl]-[1,2,4]triazolo[4,3-a]pyridine (100 mg, 0.31 mmol) and K$_2$CO$_3$ (86.35 mg, 0.62 mmol) in 1,4-Dioxane (5 mL) and Water (1 mL) was stirred at 90° C. for 16 hours under N$_2$. After cooling to room temperature, the mixture was filtered through Celite, and eluted with EtOAc (10 mL×2), and the filtrate was concentrated to give the crude product. The crude product was purified by Prep-HPLC (Waters Xbridge 150 mm×25 mm 5 μm) A=H$_2$O (10 mM NH$_4$HCO$_3$) and B=CH$_3$CN; 50-70% B over 8 minutes) to give the product (53.41 mg, 0.12 mmol) as a solid. $^1$H NMR (400 MHz, DMSO-d$_6$) $\delta_H$=8.70 (s, 1H), 8.44 (d, 1H), 8.33 (dd, 1H), 8.12 (dd, 1H), 7.96 (dd, 1H), 5.18 (q, 2H), 4.02 (d, 2H), 2.09-1.98 (m, 1H), 0.96 (d, 6H). LCMS R$_t$=1.34 min in 2.0 min chromatography, MS ESI calcd. for C$_{18}$H$_{17}$F$_6$N$_4$O$_2$ [M+H]$^+$ 435.1, found 435.1.

Example 3: 3-[ethoxy(difluoro)methyl]-6-[5-fluoro-6-(2,2,2-trifluoroethoxy)-3-pyridyl]-[1,2,4]triazolo[4,3-a]pyridine

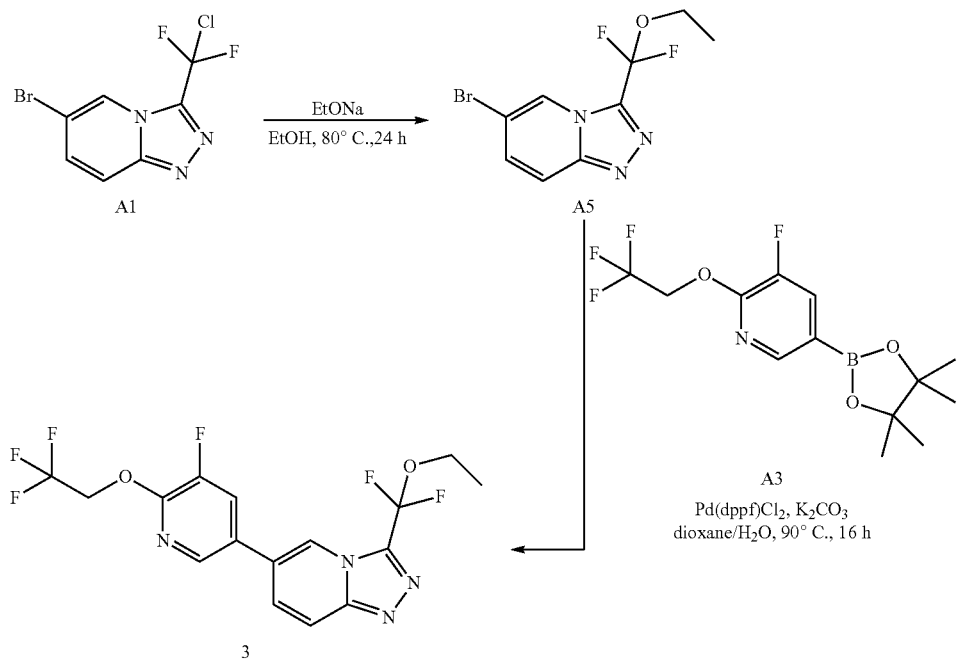

Synthesis of A5: A mixture of 6-bromo-3-[chloro(difluoro)methyl]-[1,2,4]triazolo[4,3-a]pyridine (300 mg, 1.06 mmol) and EtONa (361.37 mg, 5.31 mmol) in Ethanol (10 mL) was stirred at 80° C. for 24 hours. After cooling to room temperature, the reaction was quenched with sat.NH$_4$Cl (10 mL), and the mixture was extracted with EtOAc (20 mL×2). The combined organic phase was washed with brine (10 mL), dried over Na$_2$SO$_4$, filtered and concentrated to give the crude product. The crude product was purified by flash chromatography on silica gel (EtOAc in PE=10% to 40%) to give the product (70 mg, 0.17 mmol) as a solid. LCMS R$_t$=1.97 min in 4 min chromatography, MS ESI calcd. C$_9$H$_9$BrF$_2$N$_3$O [M+H+2]$^+$ 294.0, found 293.8.

Synthesis of Compound 3: A mixture of 3-fluoro-5-(4,4,5,5-tetramethyl-1,3,2-dioxaborolan-2-yl)-2-(2,2,2-trifluoroethoxy)pyridine (84.65 mg, 0.26 mmol), Pd(dppf)Cl$_2$ (26.3 mg, 0.04 mmol), 6-bromo-3-[ethoxy(difluoro)methyl]-[1,2,4]triazolo[4,3-a]pyridine (70 mg, 0.24 mmol) and K$_2$CO$_3$ (66.25 mg, 0.48 mmol) in 1,4-Dioxane (5 mL) and Water (1 mL) was stirred at 90° C. for 16 hours under N$_2$. After cooling to room temperature, the mixture was filtered through Celite, and eluted with EtOAc (10 mL×2), and the filtrate was concentrated to give the crude product. The crude product was purified by Prep-HPLC (Waters Xbridge 150 mm×25 mm 5 μm) A=H$_2$O (10 mM NH$_4$HCO$_3$) and B=CH$_3$CN; 42-62% B over 8 minutes) to give the product (44.33 mg, 0.11 mmol) as a solid. $^1$H NMR (400 MHz, DMSO-d$_6$) δ$_H$=8.73 (s, 1H), 8.46 (d, 1H), 8.35 (br d, 1H), 8.11 (d, 1H), 7.96 (d, 1H), 5.18 (q, 2H), 4.29 (q, 2H), 1.36 (t, 3H) LCMS R$_t$=1.25 min in 2.0 min chromatography, MS ESI calcd. for C$_{16}$H$_{13}$F$_6$N$_4$O$_2$ [M+H]$^+$ 407.1, found 407.0.

Example 4: 3-[difluoro(isopropoxy)methyl]-6-[5-fluoro-6-(2,2,2-trifluoroethoxy)-3-pyridyl]-[1,2,4]triazolo[4,3-a]pyridine

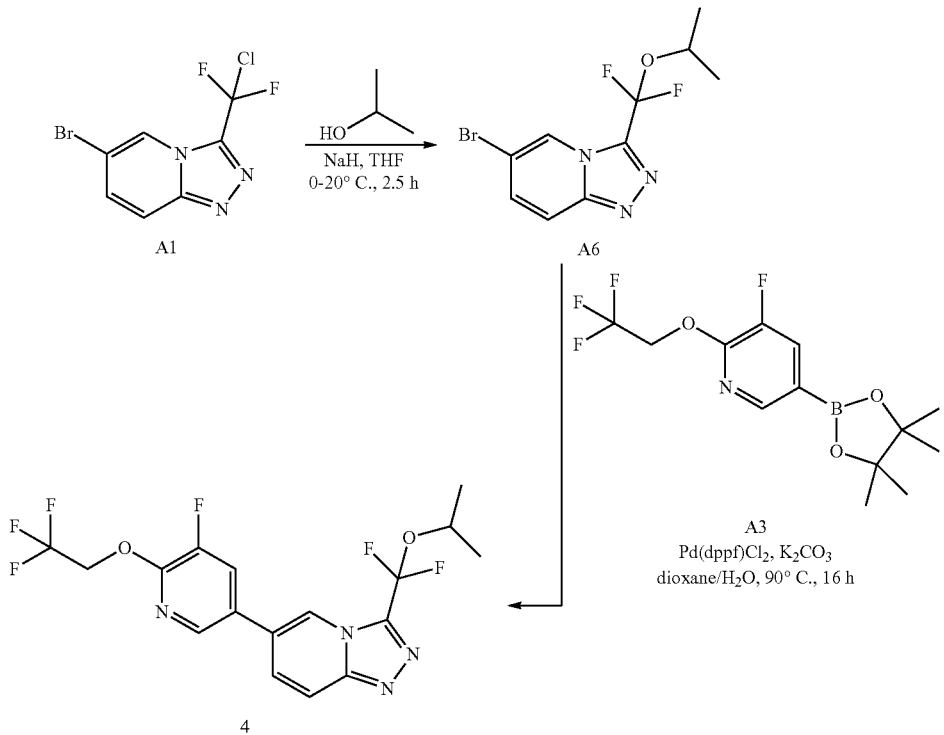

Synthesis of A6: To a mixture of propan-2-ol (319.15 mg, 5.31 mmol) in THF (10 mL) was added NaH (127.45 mg, 3.19 mmol), and the mixture was stirred at 20° C. for 0.5 hour. Then to the mixture was added 6-bromo-3-[chloro(difluoro)methyl]-[1,2,4]triazolo[4,3-a]pyridine (300 mg, 1.06 mmol), and the mixture was stirred at 20° C. for 2 hours. The reaction was quenched with sat.NH$_4$Cl (10 mL), and the mixture was extracted with EtOAc (10 mL×2). The combined organic phase was washed with brine (10 mL), dried over Na$_2$SO$_4$, filtered and concentrated to give the crude product. The crude product was purified by flash chromatography on silica gel (EtOAc in PE=10% to 40%) to give the product (240 mg, 0.72 mmol) as a solid. LCMS Rt=2.18 min in 4 min chromatography, MS ESI calcd. C$_{10}$H$_{11}$BrF$_2$N$_3$O [M+H+2]$^+$ 306.0, found 305.9.

Synthesis of Compound 4: A mixture of 3-fluoro-5-(4,4,5,5-tetramethyl-1,3,2-dioxaborolan-2-yl)-2-(2,2,2-trifluoro-ethoxy)pyridine (115.38 mg, 0.36 mmol), Pd(dppf)Cl$_2$ (35.85 mg, 0.05 mmol), 6-bromo-3-[difluoro(isopropoxy)methyl]-[1,2,4]triazolo[4,3-a]pyridine (100 mg, 0.33 mmol) and K$_2$CO$_3$ (90.3 mg, 0.65 mmol) in 1,4-Dioxane (5 mL) and Water (1 mL) was stirred at 90° C. for 16 hours under N$_2$. After cooling to room temperature, the mixture was filtered through Celite, and eluted with EtOAc (10 mL×2), and the filtrate was concentrated to give the crude product. The crude product was purified by Prep-HPLC (Waters Xbridge 150 mm×25 mm 5 μm) A=H$_2$O (10 mM NH$_4$HCO$_3$) and B=CH$_3$CN; 45-65% B over 8 minutes) to give the product (80.25 mg, 0.19 mmol) as a solid. $^1$H NMR (400 MHz, DMSO-d$_6$) δ$_H$=8.60 (s, 1H), 8.43 (d, 1H), 8.32 (dd, 1H), 8.11 (d, 1H), 7.95 (dd, 1H), 5.17 (q, 2H), 4.90 (spt, 1H), 1.41 (d, 6H). LCMS R$_t$=1.29 min in 2.0 min chromatography, MS ESI calcd. for C$_{17}$H$_{15}$F$_6$N$_4$O$_2$ [M+H]$^+$ 421.1, found 421.0.

Example 5: 3-[difluoro(methoxy)methyl]-6-[5-fluoro-6-(2,2,2-trifluoro-1,1-dimethyl-ethoxy)-3-pyridyl]-[1,2,4]triazolo[4,3-b]pyridazine

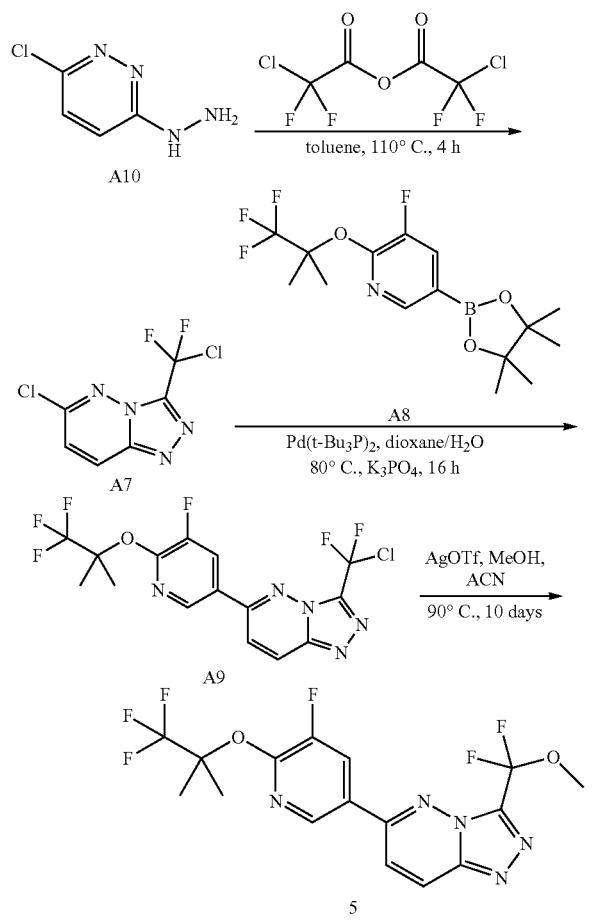

Synthesis of A7: To a mixture of (6-chloropyridazin-3-yl)hydrazine (3 g, 20.75 mmol) in Toluene (40 mL) was added (2-chloro-2,2-difluoro-acetyl) 2-chloro-2,2-difluoro-acetate (5.55 g, 22.83 mmol). The reaction mixture was stirred at 110° C. for 4 hours. After cooling to room temperature, the reaction mixture was concentrated. The residue was diluted with saturated NaHCO$_3$ (50 mL), and the mixture was extracted with EtOAc (50 mL×2). The combined organic phase was washed with brine (20 mL), dried over Na$_2$SO$_4$, filtered and concentrated to give the crude product as a solid. $^1$H NMR (400 MHz, DMSO-d$_6$) δ$_H$=8.67 (d, 1H), 7.78 (d, 1H).

Synthesis of A9: A mixture of 6-chloro-3-[chloro(difluoro)methyl]-[1,2,4]triazolo[4,3-b]pyridazine (200 mg, 0.84 mmol), 3-fluoro-5-(4,4,5,5-tetramethyl-1,3,2-dioxaborolan-2-yl)-2-(2,2,2-trifluoro-1,1-dimethyl-ethoxy)pyridine (350.58 mg, 1 mmol), Pd(t-Bu$_3$P)$_2$ (64.15 mg, 0.13 mmol), and K$_3$PO$_4$ (532.95 mg, 2.51 mmol) in 1,4-Dioxane (2 mL) and Water (0.20 mL) was stirred at 80° C. for 16 hours. After cooling to room temperature, the suspension was diluted with EtOAc (10 mL), filtered through silica gel, eluted with EtOAc (20 mL). The combined filtrates were concentrated to afford crude product. The crude product was purified by flash chromatograph on silica gel (EtOAc in PE=20% to 50% to 80%) to give the product (260 mg, 0.50 mmol) as a solid. LCMS R$_t$=0.96 min in 1.5 min chromatography, MS ESI calcd. for C$_{15}$E$_{11}$ClF$_6$N$_5$O [M+H]$^+$ 426.1, found 425.9.

Synthesis of Compound 5: To a mixture of 3-[chloro(difluoro)methyl]-6-[5-fluoro-6-(2,2,2-trifluoro-1,1-dimethyl-ethoxy)-3-pyridyl]-[1,2,4]triazolo[4,3-b]pyridazine (150 mg, 0.35 mmol) in MeCN (1 mL) was added AgOTf (905.31 mg, 3.52 mmol) and MeOH (8 mL, 0.35 mmol). The mixture was stirred at 90° C. for 10 days. After cooling to room temperature, the mixture was concentrated to give a residue. The residue was diluted with water (30 mL), extracted with EtOAc (30 mL×2). The combined organic phase was washed with water (20 mL×2), brine (30 mL×2), dried over anhydrous Na$_2$SO$_4$, filtered and concentrated to give the crude product. The crude product was purified by Prep-HPLC (Waters Xbridge 150 mm×25 mm, 5 μm), A=H$_2$O (0.05% NH$_4$OH) and B=CH$_3$CN; 57-87% B over 9 minutes) to give the product as a solid. $^1$H NMR (CDCl$_3$, 400 MHz) δ$_H$=8.55 (d, 1H), 8.29 (d, 1H), 8.09 (dd, 1H), 7.65 (d, 1H), 3.94 (s, 3H), 1.90 (s, 6H). LCMS R$_t$=1.32 min in 2.0 min chromatography, MS ESI calcd. for C$_{16}$H$_{14}$F$_6$N$_5$O$_2$ [M+H]$^+$ 422.1, found 422.0.

Example 6: 3-[difluoro(methoxy)methyl]-6-[5-fluoro-6-[(1S)-2,2,2-trifluoro-1-methyl-ethoxy]-3-pyridyl]-[1,2,4]triazolo[4,3-a]pyridine

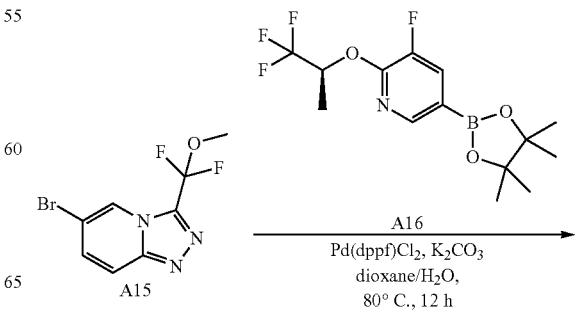

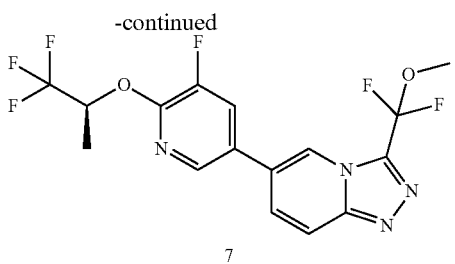

7

A mixture of 6-bromo-3-[difluoro(methoxy)methyl]-[1,2,4]triazolo[4,3-a]pyridine (100 mg, 360 μmol), 3-fluoro-5-(4,4,5,5-tetramethyl-1,3,2-dioxaborolan-2-yl)-2-[(1S)-2,2,2-trifluoro-1-methyl-ethoxy]pyridine (144.62 mg, 430 μmol), K$_2$CO$_3$ (99.41 mg, 720 μmol) and Pd(dppf)Cl$_2$ (39.47 mg, 50 μmol) in 1,4-Dioxane (5 mL) and Water (500 μL) was stirred at 80° C. for 12 hours under N$_2$. After cooling to room temperature, the mixture was diluted with H$_2$O (10 mL), and the mixture was extracted with EtOAc (20 mL×2). The combined organic phase was washed with water (10 mL) and brine (10 mL), dried over Na$_2$SO$_4$, filtered and concentrated to give the crude product. The crude product was purified by Prep-HPLC (Boston Prime C18 (150×30 mm, 5 μm), A=H$_2$O (0.05% NH$_4$OH) and B=CH$_3$CN; 53-83% B over 8 minutes) to give the product as a solid. $^1$H NMR (400 MHz, DMSO-d$_6$) δ$_H$=8.73 (s, 1H), 8.45 (d, 1H), 8.33 (dd, 1H), 8.10 (d, 1H), 7.94 (d, 1H), 6.01 (spt, 1H), 3.89 (s, 3H), 1.54 (d, 3H). LCMS R$_t$=1.27 min in 2.0 min chromatography, MS ESI calcd. C$_{18}$H$_{13}$F$_6$N$_4$O$_2$ [M+H]$^+$ 407.09, found 406.9.

Example 7: 3-[difluoro(methoxy)methyl]-6-[5-fluoro-6-[(1R)-2,2,2-trifluoro-1-methyl-ethoxy]-3-pyridyl]-[1,2,4]triazolo[4,3-a]pyridine

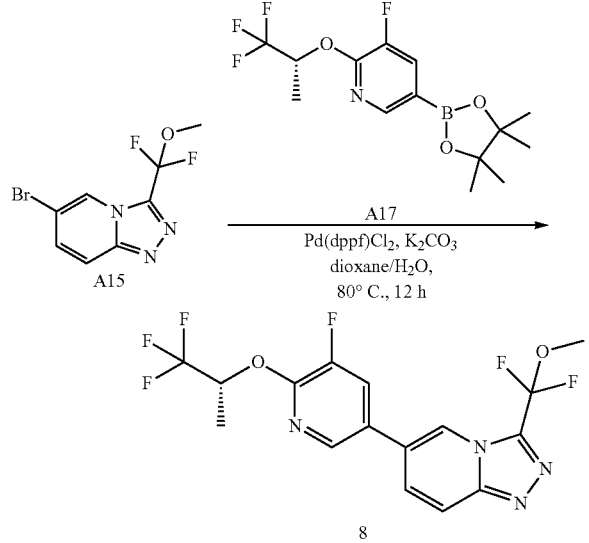

A mixture of 6-bromo-3-[difluoro(methoxy)methyl]-[1,2,4]triazolo[4,3-a]pyridine (100 mg, 360 μmol), 3-fluoro-5-(4,4,5,5-tetramethyl-1,3,2-dioxaborolan-2-yl)-2-[(1R)-2,2,2-trifluoro-1-methyl-ethoxy]pyridine (144.62 mg, 430 μmol), K$_2$CO$_3$ (99.41 mg, 720 μmol) and Pd(dppf)Cl$_2$ (39.47 mg, 50 μmol) in 1,4-Dioxane (5 mL) and Water (500 μL) was stirred at 80° C. for 12 hours under N$_2$. After cooling to room temperature, the mixture was diluted with H$_2$O (10 mL), and the mixture was extracted with EtOAc (20 mL×2). The combined organic phase was washed with water (10 mL) and brine (10 mL), dried over Na$_2$SO$_4$, filtered and concentrated to give the crude product. The crude product was purified by Prep-HPLC (Boston Prime C18 (150 mm×30 mm, 5 μm), A=H$_2$O (0.05% NH$_4$OH) and B=CH$_3$CN; 53-83% B over 8 minutes) to give the product as a solid. $^1$H-NMR (400 MHz, DMSO-d$_6$) δ$_H$=8.74 (s, 1H), 8.46 (d, 1H), 8.35 (dd, 1H), 8.11 (d, 1H), 7.95 (dd, 1H), 6.02 (spt, 1H), 3.95-3.82 (m, 3H), 1.55 (d, 3H). LCMS R$_t$=1.27 min in 2.0 min chromatography, MS ESI calcd. C$_{18}$H$_{13}$F$_6$N$_4$O$_2$ [M+H]$^+$ 407.1, found 406.9.

Example 8: 3-[cyclopropylmethoxy(difluoro)methyl]-6-[5-fluoro-6-(2,2,2-trifluoroethoxy)-3-pyridyl]-[1,2,4]triazolo[4,3-a]pyrazine

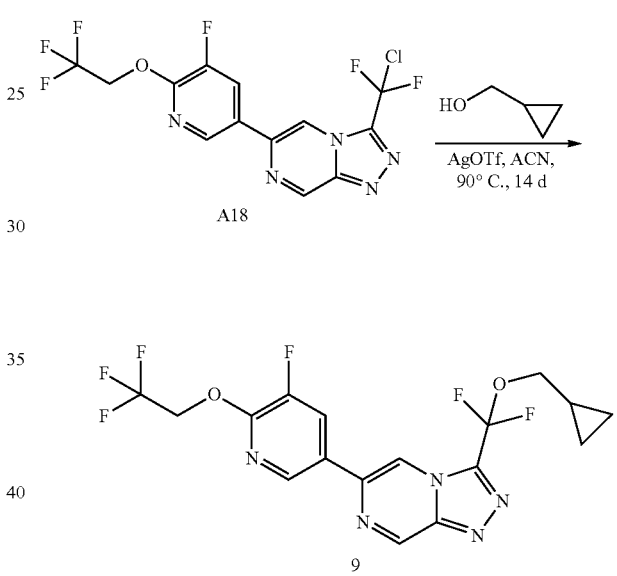

A mixture of 3-[chloro(difluoro)methyl]-6-[5-fluoro-6-(2,2,2-trifluoroethoxy)-3-pyridyl]-[1,2,4]triazolo[4,3-a]pyrazine (300 mg, 0.75 mmol) and AgOTf (1938.39 mg, 7.54 mmol) in cyclopropylmethanol (15 mL, 0.75 mmol) and CH$_3$CN (15 mL) was stirred at 90° C. for 14 days. After cooling to room temperature, the reaction was diluted with EtOAc (40 mL), and to the mixture was added saturated NaCl (40 mL), the mixture was filtered through Celite and eluted with EtOAc (20 mL×2), and the filtrate was concentrated to give the crude product. The crude product was purified by Prep-TLC (EtOAc:PE=1:1) to give the impure product. The impure product was purified by Prep-HPLC (Waters Xbridge 150 mm×25 mm 5 μm) A=H$_2$O (10 mM NH$_4$HCO$_3$) and B=CH$_3$CN; 48-68% B over 8 minutes) to give the product as a solid. $^1$H-NMR (CDCl$_3$, 400 MHz) δ$_H$=9.52 (d, 1H), 8.57 (d, 1H), 8.50 (d, 1H), 8.07 (dd, 1H), 4.93 (q, 2H), 4.13 (d, 2H), 1.40-1.30 (m, 1H), 0.79-0.73 (m, 2H), 0.49-0.42 (m, 2H). LCMS R$_t$=1.33 min in 2.0 min chromatography, MS ESI calcd. for C$_{17}$H$_{14}$F$_6$N$_5$O$_2$ [M+H]$^+$ 434.1, found 434.0.

Example 9: 3-[cyclopropylmethoxy(difluoro)methyl]-6-[5-fluoro-6-(2,2,2-trifluoroethoxy)-3-pyridyl]-[1,2,4]triazolo[4,3-a]pyrazine

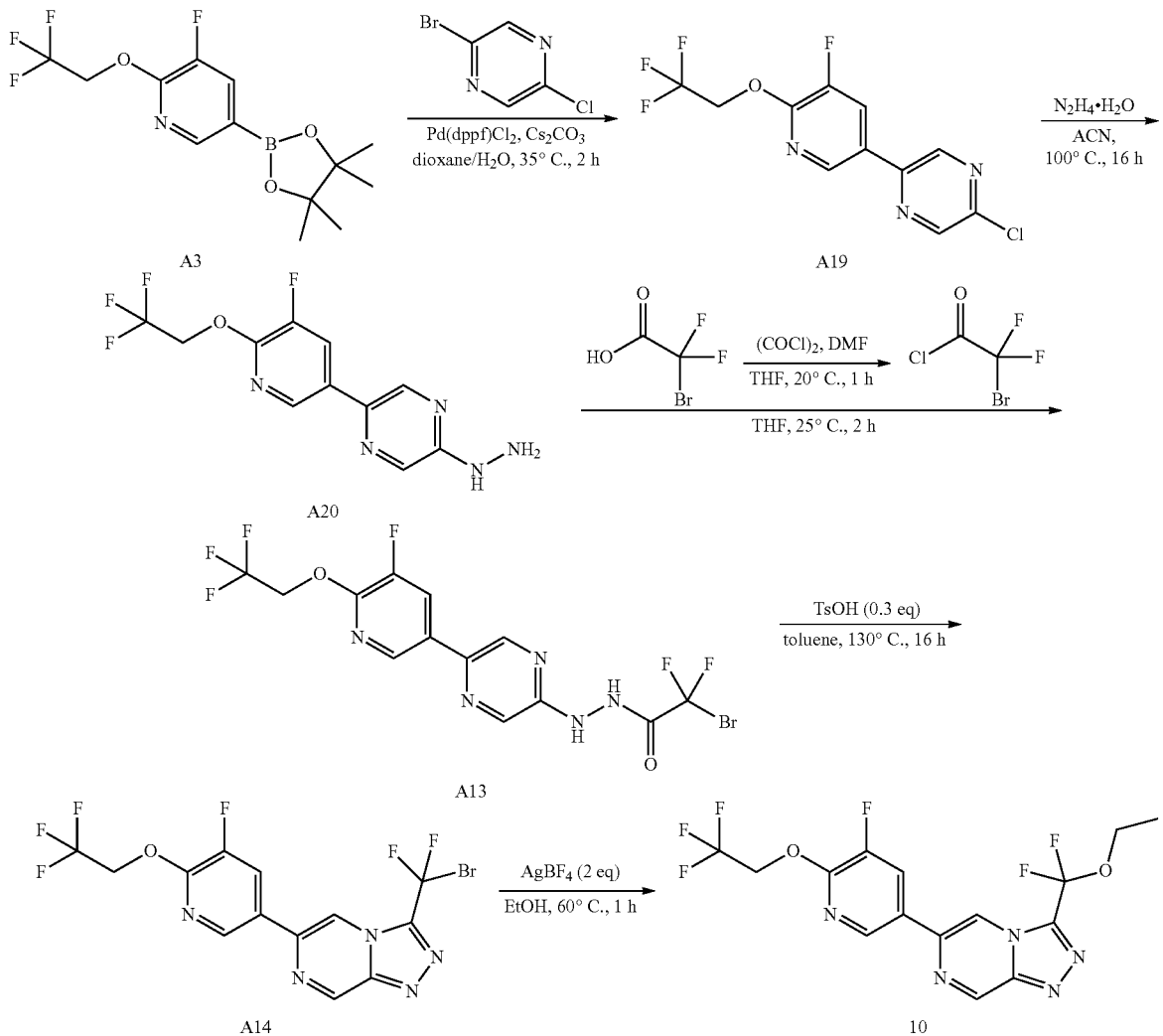

Synthesis of A19: A mixture of Pd(dppf)Cl$_2$ (15.13 g, 20.68 mmol), Cs$_2$CO$_3$ (269.49 g, 827.17 mmol), 3-fluoro-5-(4,4,5,5-tetramethyl-1,3,2-dioxaborolan-2-yl)-2-(2,2,2-trifluoroethoxy)pyridine (141.18 g, 439.69 mmol) and 2-bromo-5-chloro-pyrazine (80 g, 413.59 mmol) in 1,4-Dioxane (1 L) and Water (150 mL) under N$_2$ was stirred at 35° C. for 2 hours. After cooling to room temperature, to the mixture was added water (300 mL) and the mixture was filtered through Celite. After separating, the organic phase was washed with brine (300 mL), dried over anhydrous Na$_2$SO$_4$, filtered and concentrated to give the crude product. The crude product was re-dissolved in EA/PE=1/3 (500 mL) and then filtered through silica gel mat. The cake was washed with EA/PE=1/3 (500 mL). The combined organic phase was concentrated to give a residue as oil. To the oil was added PE (500 mL) slowly and some solid was obtained. The solid was collected and dried in oven to give the product (100 g, 242.4 mmol, 58% yield) as a solid. LCMS R$_t$=1.28 min in 2.0 min chromatography, 10-80AB, MS ESI calcd. for C$_{11}$H$_7$ClF$_4$N$_3$O [M+H]$^+$ 308.0, found 307.9.

Synthesis of A20: A mixture of 2-chloro-5-[5-fluoro-6-(2,2,2-trifluoroethoxy)-3-pyridyl]pyrazine (140 g, 339.36 mmol) and hydrazine; hydrate (169.88 g, 3393.6 mmol) in MeCN (1.4 L) was stirred at 100° C. for 16 hours. After cooling to room temperature, the mixture was poured into water (4.5 L). Some solid was observed and the solid was collected by filtered. The cake was washed with water (500 mL×2). The solid was re-dissolved in EtOAc (3 L), washed with brine (500 mL×2), dried over anhydrous $Na_2SO_4$, filtered and concentrated to give the crude product (100 g, 329.8 mmol, 97% yield) as a solid. LCMS $R_t$=0.74 min in 1.5 min chromatography, 5-95AB, MS ESI calcd. for $C_{11}H_{10}F_4N_5O$ [M+H]$^+$ 304.1, found 303.9.

Synthesis of A13: To a solution of 2-bromo-2,2-difluoro-acetic acid (87 g, 497.34 mmol) in THF (1 L) was added one drop of DMF and (COCl)$_2$ (50.5 mL, 596.81 mmol). The resulting mixture was stirred at 20° C. for 1 hour. The resulting solution was used into next step directly. To the solution of 2-bromo-2,2-difluoro-acetyl chloride (95.66 g, 494.69 mmol) in THF (1 L) was added [5-[5-fluoro-6-(2,2,2-trifluoroethoxy)-3-pyridyl]pyrazin-2-yl]hydrazine (100 g, 329.79 mmol). The resulting mixture was stirred at 20° C. for 2 hours. To the solution was added water (1 L), extracted with EtOAc (1L×2). The combined organic phase was washed with brine (500 mL×2), dried over anhydrous $Na_2SO_4$, filtered and concentrated to give the crude product (150 g, 326.0 mmol, 98% yield, mixture of mono- and bis-alkylated products) as a solid. LCMS $R_t$=0.92 min in 1.5 min chromatography, 5-95AB, MS ESI calcd. for $C_{13}H_9BrF_6N_5O_2$ [M+H]$^+$ 460.1, found 459.8.

Synthesis of A14: A solution of 2-bromo-2,2-difluoro-N'-[5-[5-fluoro-6-(2,2,2-trifluoroethoxy)-3-pyridyl]pyrazin-2-yl]acetohydrazide (150 g, 325.99 mmol) and TsOH (16.84 g, 97.8 mmol) in Toluene (1.5 L) was stirred at 130° C. for 16 hours. After cooling to room temperature, the mixture was poured into water (2 L), extracted with EtOAc (2L×2). The combined organic phase was washed with brine (1 L×2), dried over anhydrous $Na_2SO_4$, filtered and concentrated to give the crude product. The crude product was purified by chromatography flash on siliga gel (EtOAc in PE=0% to 15% to 30%) to give the product (80 g, 181.0 mmol, 55% yield) as oil. $^1$H NMR (CDCl$_3$, 400 MHz) $\delta_H$=9.60 (d, 1H), 8.55 (d, 1H), 8.45 (s, 1H), 8.09 (dd, 1H), 4.93 (q, 2H).

Synthesis of Compound 10: A mixture of 3-[bromo(difluoro)methyl]-6-[5-fluoro-6-(2,2,2-trifluoroethoxy)-3-pyridyl]-[1,2,4]triazolo[4,3-a]pyrazine (76 g, 171.9 mmol) and AgBF$_4$ (66.93 g, 343.81 mmol) in Ethanol (760 mL) was stirred at 60° C. for 1 hour. After cooling to room temperature, the mixture was poured into saturated aqueous NaCl (1 L) and EtOAc (2 L). The mixture was filtered through Celite. After separating, the aqueous layer was extracted with EtOAc (500 mL×2). The combined organic phase was washed with brine (500 mL×2), dried over anhydrous $Na_2SO_4$, filtered and concentrated to give the crude product. The crude product was purified by chromatography flash column on silica gel (EtOAc in PE=0% to 30% to 50%) and then triturated from EtOH (50 mL) to give the product (44.45 g, 109.01 mmol, 63% yield) as a solid. $^1$H NMR (CDCl$_3$ 400 MHz) $\delta_H$=9.52 (d, 1H), 8.49 (dd, 2H), 8.07 (dd, 1H), 4.93 (q, 2H), 4.37 (q, 2H), 1.51 (t, 3H). LCMS $R_t$=1.25 min in 2.0 min chromatography, 10-80AB, MS ESI calcd. for $C_{15}H_{12}F_6N_5O_2$ [M+H]$^+$ 408.1, found 408.0.

Example 10: 3-[difluoro(methoxy)methyl]-6-[5-fluoro-6-[1-(trifluoromethyl)cyclobutoxy]-3-pyridyl]-[1,2,4]triazolo[4,3-a]pyrazine

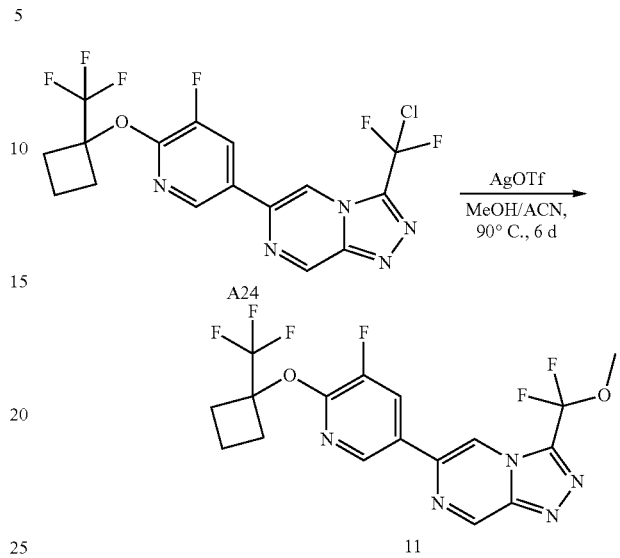

A mixture of 3-[chloro(difluoro)methyl]-6-[5-fluoro-6-[1-(trifluoromethyl)cyclobutoxy]-3-pyridyl]-[1,2,4]triazolo[4,3-a]pyrazine (1.4 g, 3.2 mmol) and AgOTf (8.22 g, 31.98 mmol), in mixed solvent Methanol (14 mL) and DMF (14 mL) was stirred at 90° C. for 24 hours. After cooling to room temperature, the reaction mixture was treated with brine (40 mL), and the precipitate was filtered. The filtrate was extracted with EtOAc (40 mL×2). The combined organic phase was washed with brine (20 mL), dried over $Na_2SO_4$ and concentrated to give a crude product. The crude product was purified by Prep-HPLC (Waters Xbridge (150 mm×25 mm 5 μm) A=H$_2$O (10 mM NH$_4$HCO$_3$) and B=CH$_3$CN; 57-67% B over 8 minutes) to give the product (240 mg). Another batch was started with 1.2 g of A24, and about 110 mg of the product was obtained by Prep-HPLC (Boston Prime C18 (150 mm×30 mm, 5 μm) A=H$_2$O (0.05% NH$_4$OH) and B=CH$_3$CN; 50-80% B over 9 minutes). Two batches of the product were combined and lyophilized to give the product as a solid. $^1$H NMR (CDCl$_3$, 400 MHz) $\delta_H$=9.51 (d, 1H), 8.49 (d, 1H), 8.47 (d, 1H), 8.05 (dd, 1H), 3.98 (s, 3H), 2.98-2.86 (m, 2H), 2.81-2.72 (m, 2H), 2.11-1.93 (m, 2H). LCMS $R_t$=1.30 min in 2 min chromatography, 10-80AB, MS ESI calcd. for $C_{17}H_{14}F_6N_5O_2$ [M+H]$^+$ 434.1, found 433.9.

Example 11: 3-[difluoro(methoxy)methyl]-6-[5-fluoro-6-[(1S)-2,2,2-trifluoro-1-methyl-ethoxy]-3-pyridyl]-[1,2,4]triazolo[4,3-b]pyridazine

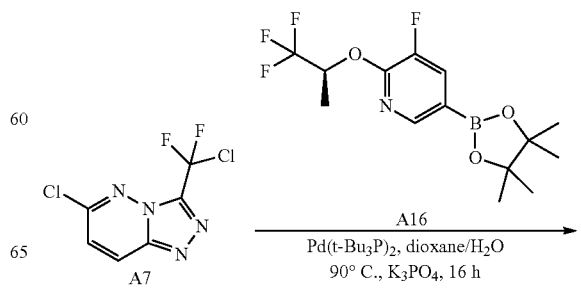

-continued

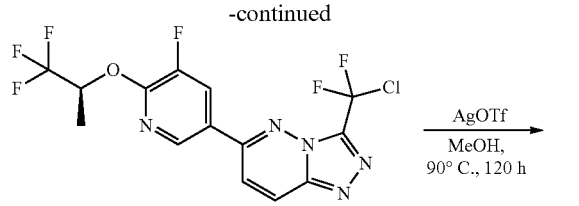

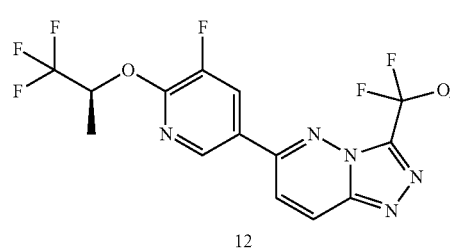

12

Synthesis of A25: A mixture of 6-chloro-3-[chloro(difluoro)methyl]-[1,2,4]triazolo[4,3-b]pyridazine (120 mg, 0.50 mmol), 3-fluoro-5-(4,4,5,5-tetramethyl-1,3,2-dioxaborolan-2-yl)-2-[(1S)-2,2,2-trifluoro-1-methyl-ethoxy]pyridine (201.9 mg, 0.60 mmol), K$_3$PO$_4$ (319.74 mg, 1.51 mmol), Pd(t-Bu$_3$P)$_2$ (25.66 mg, 0.05 mmol) in 1,4-dioxane (12 mL) and H$_2$O (4 mL) was stirred at 90° C. for 16 hours. After cooling to room temperature, the reaction mixture was concentrated, diluted with water (20 mL), and extracted with ethyl acetate (20 mL×2). The combined organic phase was washed with brine (40 mL), dried over Na$_2$SO$_4$ and concentrated to give a residue. The residue was purified by flash chromatography on silica gel (EtOAc in PE=0% to 60%) to give the product (120 mg, 0.29 mmol) as a solid. $^1$1-NMR (CDCl$_3$, 400 MHz) δ$_H$=8.57 (d, 1H), 8.35 (d, 1H), 8.15 (dd, 1H), 7.74 (d, 1H), 5.93 (m, 1H) 1.61 (d, 3H).

Synthesis of Compound 12: A mixture of AgOTf (599.15 mg, 2.33 mmol), 3-[chloro(difluoro)methyl]-6-[5-fluoro-6-[(1S)-2,2,2-trifluoro-1-methyl-ethoxy]-3-pyridyl]-[1,2,4]triazolo[4,3-b]pyridazine (120 mg, 0.29 mmol) in methanol (6 mL) was stirred at 90° C. for 120 hours. After cooling to room temperature, the reaction mixture was treated with brine (20 mL), and the precipitate was filtrated. The filtrate was concentrated, diluted with water (20 mL), and extracted with ethyl acetate (20 mL×2). The combined organic phase was washed with brine (40 mL), dried over Na$_2$SO$_4$ and concentrated to give a residue. The residue was purified by prep-HPLC (Boston Prime C18 150×30 mm 5 μm) A=H$_2$O (0.05% NH$_4$OH) and B=CH$_3$CN; 52-82% B over 8 minutes) to give the product (5.12 mg, 13 μmol). $^1$H-NMR (CDCl$_3$, 400 MHz) δ$_H$=8.55 (d, 1H), 8.30 (d, 1H), 8.14 (dd, 1H), 7.66 (d, 1H), 5.92 (m, 1H), 3.94 (s, 3H), 1.61 (d, 3H). LCMS R$_t$=1.28 min in 2.0 min chromatography, MS ESI calcd. for C$_{15}$H$_{12}$F$_6$N$_5$O$_2$ [M+H]$^+$ 408.1, found 408.0.

Example 12: 3-[difluoro(methoxy)methyl]-6-[5-fluoro-6-[(1R)-2,2,2-trifluoro-1-methyl-ethoxy]-3-pyridyl]-[1,2,4]triazolo[4,3-b]pyridazine

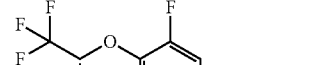

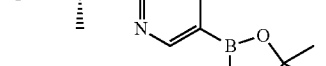
A7

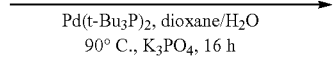
A26

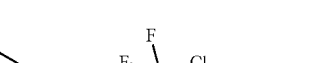
13

Synthesis of A26: A mixture of 6-chloro-3-[chloro(difluoro)methyl]-[1,2,4]triazolo[4,3-b]pyridazine (120 mg, 0.50 mmol), 3-fluoro-5-(4,4,5,5-tetramethyl-1,3,2-dioxaborolan-2-yl)-2-[(1R)-2,2,2-trifluoro-1-methyl-ethoxy]pyridine (201.9 mg, 0.60 mmol), K$_3$PO$_4$ (319.74 mg, 1.51 mmol), Pd(t-Bu$_3$P)$_2$ (25.66 mg, 0.05 mmol) in 1,4-dioxane (12 mL) and H$_2$O (4 mL) at 90° C. for 16 hours. After cooling to room temperature, the reaction mixture was concentrated to remove solvent, diluted with water (20 mL) and extracted with ethyl acetate (20 mL×2). The combined organic phase was washed with brine (40 mL), dried over Na$_2$SO$_4$ and concentrated to give the crude product. The crude product was purified by flash chromatography on silica gel (EtOAc in PE=0% to 60%) to give the product (140 mg, 0.34 mmol) as a solid. $^1$1-NMR (CDCl$_3$, 400 MHz) δ$_H$=8.57 (d, 1H), 8.35 (d, 1H), 8.14 (dd, 1H), 7.74 (d, 1H), 5.93 (m, 1H), 1.61 (d, 3H).

Synthesis of Compound 13: A mixture of 3-[chloro(difluoro)methyl]-6-[5-fluoro-6-[(1R)-2,2,2-trifluoro-1-methyl-ethoxy]-3-pyridyl]-[1,2,4]triazolo[4,3-b]pyridazine (140 mg, 0.34 mmol), AgOTf (699 mg, 2.72 mmol) in methanol (8 mL) and was stirred at 90° C. for 120 hours. After cooling to room temperature, the reaction mixture was treated with brine (20 mL), and the precipitate was filtrated. The filtrate was concentrated and diluted with water (20 mL), then extracted with ethyl acetate (20 mL×2). The combined organic phase was washed with brine (40 mL), dried over Na$_2$SO$_4$ and concentrated to give a residue. The residue was purified by Prep-HPLC (Boston Prime C18 150×30 mm 5 μm) A=H$_2$O (0.05% NH$_4$OH) and B=CH$_3$CN; 52-82% B over 8 minutes) to give the product (5 mg, 12.2 μmol). $^1$H-NMR (CDCl$_3$, 400 MHz) δ$_H$=8.55 (d, 1H), 8.30 (d, 1H), 8.14 (dd, 1H), 7.66 (d, 1H), 5.92 (m, 1H), 3.94 (s, 3H), 1.61 (d, 3H). LCMS $R_f$=1.26 min in 2.0 min chromatography MS ESI calcd. for $C_{15}H_{12}F_6N_5O_2$ [M+H]$^+$ 408.1, found 408.0.

Example 13: 3-[cyclopropylmethoxy(difluoro) methyl]-6-[5-fluoro-6-(2,2,2-trifluoroethoxy)-3-pyridyl]-[1,2,4]triazolo[4,3-b]pyridazine

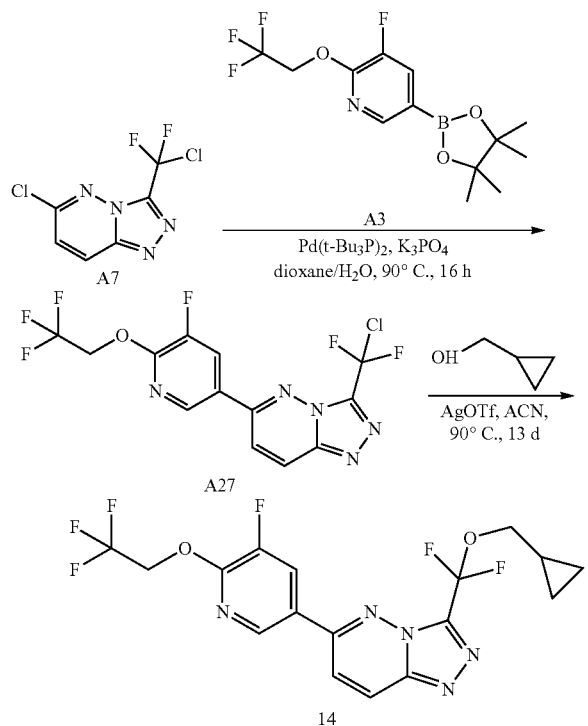

$K_3PO_4$ (888.25 mg, 4.18 mmol) in 1,4-Dioxane (15 mL) and Water (1.5 mL) was stirred at 90° C. for 16 hours under $N_2$. The mixture was filtered through Celite, and eluted with EtOAc (10 mL×2), and the filtrate was concentrated to give the crude product. The crude product was purified by flash chromatography on silica gel (EtOAc in PE=20% to 60%) to give the product (900 mg, 1.90 mmol) as a solid. LCMS Rt=0.85 min in 1.5 min chromatography, MS ESI calcd. $C_{13}H_7ClF_6N_5O$ [M+H]$^+$ 398.0, found 398.0.

Synthesis of Compound 14: A mixture of 3-[chloro(difluoro)methyl]-6-[5-fluoro-6-(2,2,2-trifluoroethoxy)-3-pyridyl]-[1,2,4]triazolo[4,3-b]pyridazine (200 mg, 0.50 mmol) and AgOTf (1292.26 mg, 5.03 mmol) in cyclopropylmethanol (10 mL, 0.50 mmol) and $CH_3CN$ (10 mL) was stirred at 90° C. for 13 days. After cooling to room temperature, the reaction was diluted with EtOAc (40 mL) and brine (40 mL). The mixture was filtered through Celite, eluted with EtOAc (20 mL×2), and the filtrate was concentrated to give the crude product. The crude product was purified by Prep-HPLC (Boston Prime C18 150 mm×30 mm 5 µm) A=$H_2O$ (0.05% $NH_4OH$ v/v) and B=$CH_3CN$; 58-88% B over 8 minutes) to give the impure product. The impure product was triturated from n-hexane/i-$Pr_2O$ (v/v=1:1, 2 mL) to give the product (9.82 mg, 22.2 µmol) as a solid. $^1$H NMR (DMSO-d$_6$, 400 MHz) $\delta_H$=8.83 (d, 1H), 8.67 (d, 1H), 8.45 (dd, 1H), 8.21 (d, 1H), 5.22 (q, 2H), 4.03 (d, 2H), 1.26-1.18 (m, 1H), 0.62-0.54 (m, 2H), 0.43-0.33 (m, 2H). LCMS $R_f$=2.87 min in 4.0 min chromatography, MS ESI calcd. for $C_{17}H_{14}F_6N_5O_2$ [M+H]$^+$ 434.1, found 434.0.

Example 14: 3-[difluoro(methoxy)methyl]-6-[5-fluoro-6-(2,2,2-trifluoro-1,1-dimethyl-ethoxy)-3-pyridyl]-[1,2,4]triazolo[4,3-a]pyrazine

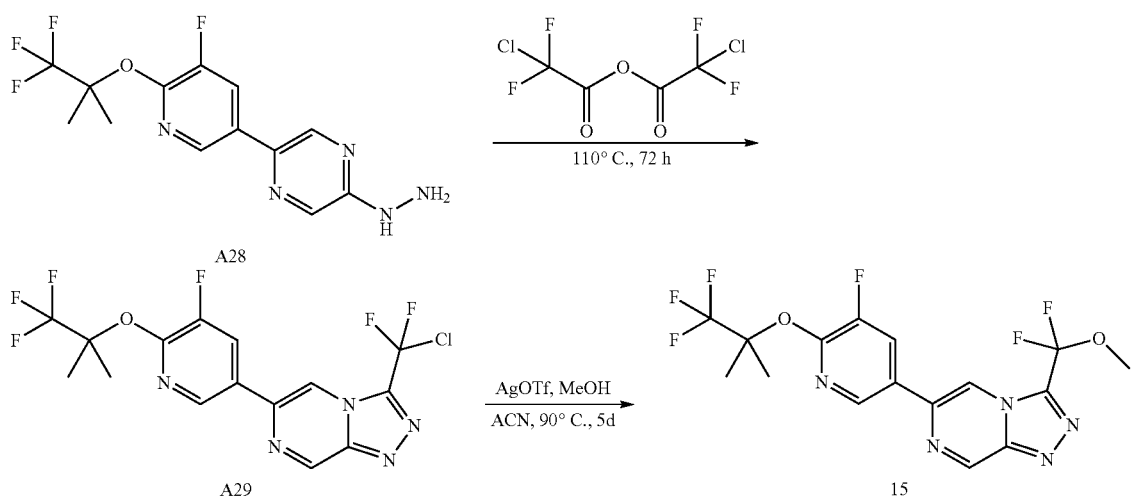

Synthesis of A27: A mixture of 6-chloro-3-[chloro(difluoro)methyl]-[1,2,4]triazolo[4,3-b]pyridazine (500 mg, 2.09 mmol), 3-fluoro-5-(4,4,5,5-tetramethyl-1,3,2-dioxaborolan-2-yl)-2-(2,2,2-trifluoroethoxy)pyridine (2015.06 mg, 6.28 mmol), Pd(t-Bu$_3$P)$_2$ (160.37 mg, 0.31 mmol) and Synthesis of A29: A solution of [5-[5-fluoro-6-(2,2,2-trifluoro-1,1-dimethyl-ethoxy)-3-pyridyl]pyrazin-2-yl]hydrazine (300 mg, 0.91 mmol) and (2-chloro-2,2-difluoroacetyl) 2-chloro-2,2-difluoro-acetate (660.02 mg, 2.72 mmol) in Toluene (30 mL) was stirred at 110° C. for 72 hours. After cooling to room temperature, the mixture was concentrated to give a residue. To the residue was added water (50 mL), and the mixture was extracted with EtOAc (50 mL×2). The combined organic phase was washed with water (50 mL), brine (50 mL×2), dried over anhydrous Na$_2$SO$_4$, filtered and concentrated to give the crude product. The crude product was purified by flash chromatography column on silica gel (EtOAc in PE=0% to 10% to 20%) to give the product (150 mg, 346.3 µmol) as a solid. LCMS R$_t$=3.06 min in 4.0 min chromatography, MS ESI calcd. for C$_{15}$H$_{11}$ClF$_6$N$_5$O [M+H]$^+$ 426.0, found 426.0.

Synthesis of Compound 15: To a solution of 3-[chloro(difluoro)methyl]-6-[5-fluoro-6-(2,2,2-trifluoro-1,1-dimethyl-ethoxy)-3-pyridyl]-[1,2,4]triazolo[4,3-a]pyrazine (150 mg, 0.35 mmol) in Methanol (5 mL) and MeCN (5 mL) was added AgOTf (1.81 g, 7.05 mmol). The resulting mixture was stirred at 90° C. in a sealed tube under N$_2$ for 5 days. The mixture was cooled to room temperature and then brine (20 mL) and EtOAc (30 mL) were added and the mixture was filtered. After the filtrate was separated, the organic phase was washed with water (20 mL×2), brine (20 mL×2), dried over anhydrous Na$_2$SO$_4$, filtered and concentrated to give the crude product. The crude product was purified by Prep-TLC (PE:EtOAc=4:1) to give the product (14.23 mg, 33.2 mmol) as a solid. $^1$H NMR (CDCl$_3$, 400 MHz) δ$_H$=9.52 (d, 1H), 8.51 (d, 1H), 8.45 (d, 1H), 8.02 (dd, 1H), 3.98 (s, 3H), 1.89 (s, 6H). LCMS R$_t$=1.33 min in 2.0 min chromatography, MS ESI calcd. for C$_{16}$H$_{14}$F$_6$N$_5$O$_2$ [M+H]$^+$ 422.1, found 422.0.

Example 15: 3-[ethoxy(difluoro)methyl]-6-[5-fluoro-6-(2,2,2-trifluoroethoxy)-3-pyridyl]-[1,2,4]triazolo[4,3-b]pyridazine

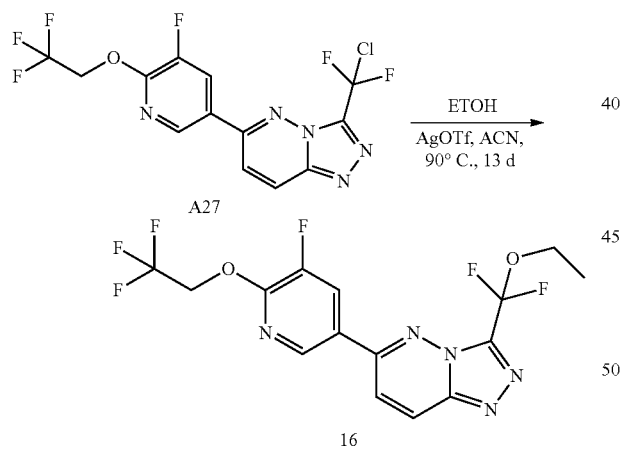

A mixture of 3-[chloro(difluoro)methyl]-6-[5-fluoro-6-(2,2,2-trifluoroethoxy)-3-pyridyl]-[1,2,4]triazolo[4,3-b]pyridazine (200 mg, 0.50 mmol) and AgOTf (1292.26 mg, 5.03 mmol) in ethanol (10 mL, 0.50 mmol) and CH$_3$CN (10 mL) was stirred at 90° C. for 13 days. After cooling to room temperature, the reaction was diluted with EtOAc (40 mL) and brine (40 mL). The mixture was filtered through Celite, eluted with EtOAc (20 mL×2), and the filtrate was concentrated to give the crude product. The crude product was purified by Prep-TLC (EtOAc:DCM:PE=1:1:1) to give the impure product. The impure product was triturated from n-hexane/CH$_2$Cl$_2$ (v/v=1:2, 6 mL) to give the product (15.95 mg, 39.2 mmol) as a solid. $^1$H NMR (DMSO-d$_6$, 400 MHz) δ$_H$=8.81 (d, 1H), 8.68 (d, 1H), 8.43 (dd, 1H), 8.21 (d, 1H), 5.22 (q, 2H), 4.24 (q, 2H), 1.36 (t, 3H). LCMS R$_t$=1.26 min in 2.0 min chromatography, MS ESI calcd. for C$_{15}$H$_{12}$F$_6$N$_5$O$_2$ [M+H]$^+$ 408.1, found 408.0.

Example 16: 3-[difluoro(methoxy)methyl]-6-[5-fluoro-6-[1-(trifluoromethyl)cyclobutoxy]-3-pyridyl]-[1,2,4]triazolo[4,3-b]pyridazine

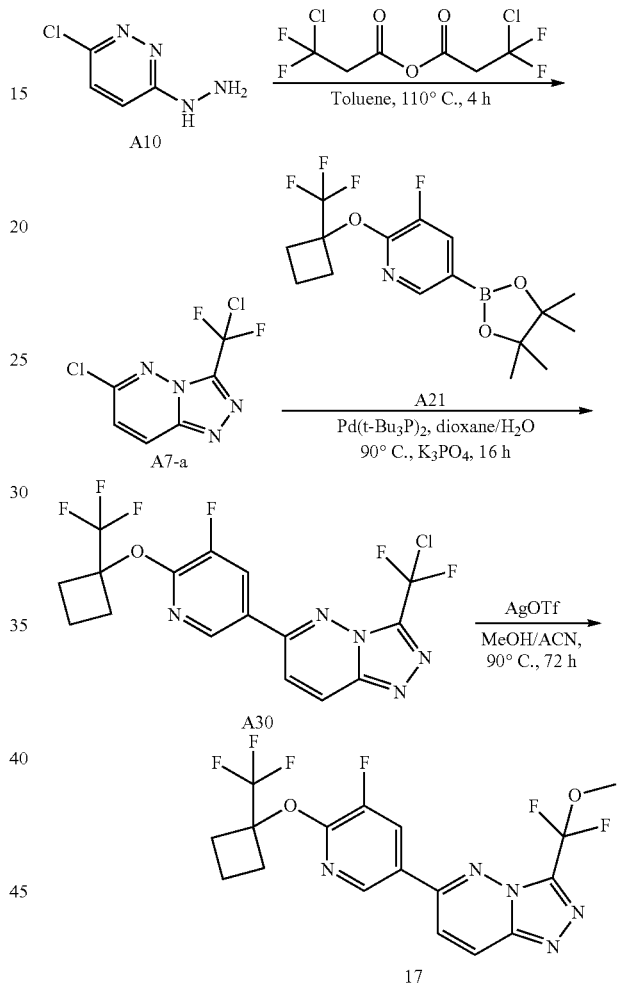

Synthesis of A7-a: To a mixture of (6-chloropyridazin-3-yl)hydrazine (3.0 g, 20.75 mmol) in toluene (40 mL) was added (2-chloro-2,2-difluoro-acetyl)-2-chloro-2,2-difluoro-acetate (7.56 g, 31.13 mmol). The reaction mixture was stirred at 110° C. for 4 hours. After cooling to room temperature, the reaction mixture was concentrated. The residue was diluted with sat. NaHCO$_3$ (50 mL), and the mixture was extracted with EtOAc (50 mL×2). The combined organic phase was washed with brine (20 mL), dried over Na$_2$SO$_4$, filtered and concentrated to give the crude product (4700 mg, 19.66 mmol) as a solid. $^1$H NMR (400MHZ, CDCl$_3$) δ$_H$=7.35 (d, 1H), 8.23 (d, 1H).

Synthesis of A30: A mixture of 6-chloro-3-[chloro(difluoro)methyl]-[1,2,4]triazolo[4,3-b]pyridazine (150 mg, 0.63 mmol), 3-fluoro-5-(4,4,5,5-tetramethyl-1,3,2-dioxaborolan-2-yl)-2-[1-(trifluoromethyl)cyclobutoxy]pyridine (362.64 mg, 1 mmol), K$_3$PO$_4$ (399.65 mg, 1.88 mmol), Bis(tri-tert-butylphosphine) palladium(0) (64.15 mg, 0.1300 mmol) in 1,4-Dioxane (12 mL) and Water (4 mL) was stirred at 80° C. for 16 hours. From TLC, new spot (Rf=0.45, UV) was observed, and no starting material (Rf=0.8, UV) remained. After cooling to room temperature, the reaction mixture was concentrated to remove solvent, diluted with water (20 mL) and extracted with ethyl acetate (20 mL×2). The combined organic phase was washed with brine (40 mL), dried over $Na_2SO_4$ and concentrated to give the crude product. The crude product was purified by flash chromatography on silica gel (EtOAc in PE=0% to 60%) to give the product (120 mg, 0.27 mmol) as a solid. $^1H$ NMR (CDCl$_3$, 400 MHz) $\delta_H$=8.57 (d, 1H), 8.33 (d, 1H), 8.15-8.06 (m, 1H), 7.73 (d, 1H), 2.82-2.96 (m, 2H), 2.78-2.81 (m, 2H), 2.00-2.08 (m, 2H).

Synthesis of Compound 17: A mixture of 3-[chloro(difluoro)methyl]-6-[5-fluoro-6-[1-(trifluoromethyl)cyclobutoxy]-3-pyridyl]-[1,2,4]triazolo[4,3-b]pyridazine (120 mg, 0.27 mmol), silver trifluoromethanesulfonate (0.7 g, 2.74 mmol), in mixed solvent methanol (12 mL) and MeCN (4 mL) was stirred at 80° C. for 72 hours. After cooling to room temperature, the reaction mixture was treated with brine (20 mL) and the precipitate was filtered. The filtrate was concentrated to remove solvent, and diluted with water (20 mL), and extracted with ethyl acetate (20 mL×2). The combined organic phase was washed with brine (40 mL), dried over $Na_2SO_4$ and concentrated to give a residue. The crude product was purified by prep-HPLC (Boston Prime C18 150×30 mm 5 μm) A=H$_2$O (0.05% NH$_4$OH) and B=ACN; 52-82% B over 8 minutes) to give the product (27.93 mg, 64.5 μmol) as a solid. $^1H$ NMR (CDCl$_3$, 400 MHz) $\delta_H$=8.54 (d, 1H), 8.28 (d, 1H), 8.11 (dd, 1H), 7.64 (d, 1H), 3.93 (s, 3H), 2.82-2.96 (m, 2H), 2.76-2.81 (m, 2H), 1.57-2.07 (m, 2H). LCMS R$_t$=1.32 min in 2.0 min chromatography, MS ESI calcd. for C$_{17}$H$_{14}$F$_6$N$_5$O$_2$ [M+H]$^+$434.1, found 434.0.

Example 17: 3-[difluoro(methoxy)methyl]-6-[5-fluoro-6-[1-(trifluoromethyl)cyclobutoxy]-3-pyridyl]-[1,2,4]triazolo[4,3-a]pyridine

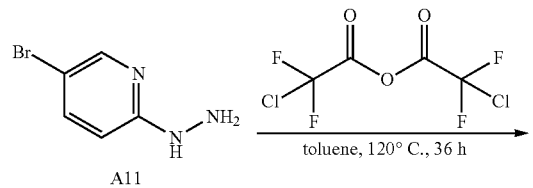

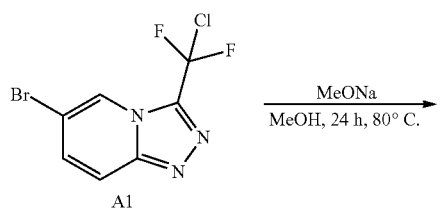

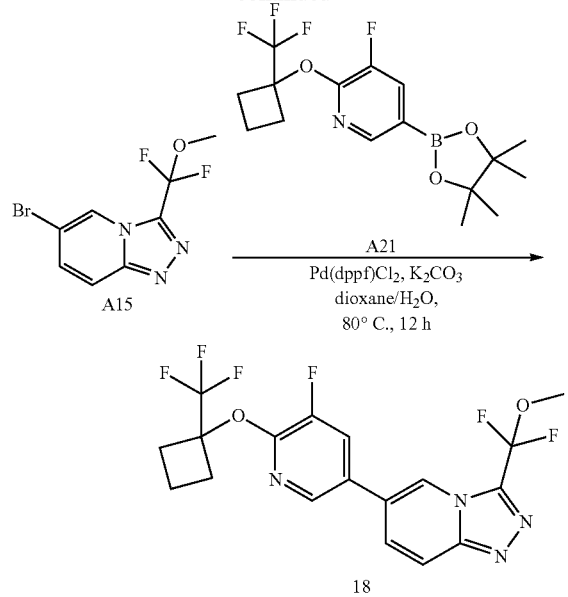

Synthesis of A1: A mixture of (5-bromo-2-pyridyl)hydrazine (2.6 g, 13.83 mmol) and (2-chloro-2,2-difluoro-acetyl) 2-chloro-2,2-difluoro-acetate (5.04 g, 20.74 mmol) in toluene (100 mL) was stirred at 10° C. for 1 hour, and then the mixture was warmed to 120° C. and stirred for 36 hours. After cooling to room temperature, the reaction was quenched with saturated NaHCO$_3$ (50 mL), and the mixture was extracted with EtOAc (50 mL×2). The organic layer was washed with brine (50 mL), drived over Na$_2$SO$_4$, filtered and concentrated to give the crude product. The crude product was purified by flash chromatography on silica gel (EtOAc in PE=0% to 20% to 30%) to give the product (3900 mg, 13.81 mmol) as a solid. $^1H$ NMR (400 MHz, CDCl$_3$) $\delta_H$=8.42 (s, 1H), 7.84 (d, 1H), 7.53 (dd, 1H). LCMS R$_t$=3.19 min in 7.0 min chromatography, MS ESI calcd. for C$_7$H$_4$BrClF$_2$N$_3$ [M+H+2]$^+$283.9, found 283.6.

Synthesis of A15: A mixture of 6-bromo-3-[chloro(difluoro)methyl]-[1,2,4]triazolo[4,3-a]pyridine (1 g, 3.54 mmol) and NaOMe (956.21 mg, 17.7 mmol) in Methanol (20 mL) was stirred at 80° C. for 24 hours. After cooling to room temperature, the reaction was quenched with sat.NH$_4$Cl (50 mL), and the mixture was extracted with EtOAc (50 mL×2). The combine organic layer was washed with brine (50 mL), dried over Na$_2$SO$_4$, filtered and concentrated to give the crude product. The crude product was purified by flash chromatography on silica gel (EtOAc in PE=0% to 30% to 40%) to give the product (380 mg, 127.56 μmol) as a solid. $^1$1-NMR (CDCl$_3$, 400 MHz) $\delta_H$=8.43 (s, 1H), 7.77 (d, 1H), 7.47-7.41 (m, 1H), 3.92 (s, 3H). LCMS R$_t$=2.95 min in 7.0 min chromatography, MS ESI calcd. for C$_8$H$_7$BrF$_2$N$_3$O [M+H+2]$^+$280.0, found 279.7.

Synthesis of Compound 18: A mixture of 6-bromo-3-[difluoro(methoxy)methyl]-[1,2,4]triazolo[4,3-a]pyridine (100 mg, 0.36 mmol), 3-fluoro-5-(4,4,5,5-tetramethyl-1,3,2-dioxaborolan-2-yl)-2-[1-(trifluoromethyl)cyclobutoxy]pyridine (155.86 mg, 0.43 mmol), K$_2$CO$_3$ (99.41 mg, 0.72 mmol) and Pd(dppf)Cl$_2$ (39.47 mg, 0.05 mmol) in 1,4-Dioxane (5 mL) and Water (0.50 mL) was stirred at 80° C. for 12 hours. After cooling to room temperature, the mixture was diluted with H$_2$O (10 mL), and the mixture was extracted with EtOAc (20 mL×2). The combined organic phase was washed with water (30 mL) and brine (10 mL), dried over Na$_2$SO$_4$, filtered and concentrated to give the crude product. The crude product was purified by Prep-HPLC (Boston Prime C18 (150×30 mm, 5 μm), A=H$_2$O (0.05% NH$_4$OH) and B=CH$_3$CN; 58-88% B over 8 minutes) to give the product (66.89 mg, 15.47 μmol) as a solid. $^1$H NMR (DMSO-d$_6$, 400 MHz) δ$_H$=8.75 (s, 1H), 8.46 (d, 1H), 8.33 (dd, 1H), 8.10 (d, 1H), 7.96 (dd, 1H), 3.89 (s, 3H), 2.97-2.85 (m, 2H), 2.72-2.62 (m, 2H), 2.07-1.95 (m, 1H), 1.93-1.81 (m, 1H). LCMS R$_t$=1.32 min in 2.0 min chromatography, MS ESI calcd. C$_{18}$H$_{15}$F$_6$N$_4$O$_2$ [M+H]$^+$ 433.1, found 432.9.

Example 18: Synthesis of 3-[cyclopropylmethoxy (difluoro)methyl]-6-[5-fluoro-6-[(1S)-2,2,2-trifluoro-1-methyl-ethoxy]-3-pyridyl]-[1,2,4]triazolo[4,3-a]pyridine

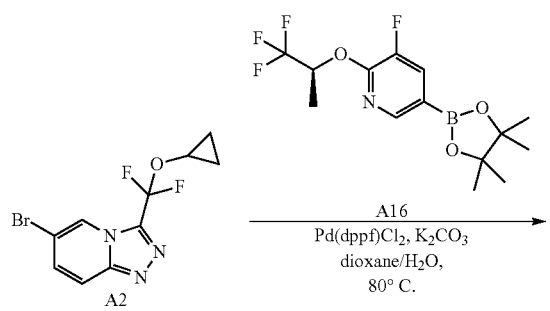

A mixture of 6-bromo-3-[cyclopropylmethoxy(difluoro) methyl]-[1,2,4]triazolo[4,3-a]pyridine (65 mg, 200 μmol), 3-fluoro-5-(4,4,5,5-tetramethyl-1,3,2-dioxaborolan-2-yl)-2-[(1S)-2,2,2-trifluoro-1-methyl-ethoxy]pyridine (82.16 mg, 250 μmol), K$_2$CO$_3$ (56.48 mg, 410 μmol) and Pd(dppf)Cl$_2$ (22.43 mg, 30 μmol) in 1,4-Dioxane (5 mL) and Water (0.50 mL) was stirred at 80° C. for 12 hours under N$_2$. After cooling to room temperature, the mixture was diluted with H$_2$O (10 mL), and the mixture was extracted with EtOAc (20 mL×2). The combined organic phase was washed with water (20 mL) and brine (30 mL), dried over Na$_2$SO$_4$, filtered and concentrated to give the crude product. The crude product was purified by Prep-HPLC (Boston Prime C18 (150×30 mm, 5 μm) A=H$_2$O (0.05% NH$_4$OH) and B=CH$_3$CN; 62-92% B over 8 minutes) yielding the product (43.42 mg, 97.3 μmol, 48% yield) as a solid. $^1$H NMR (DMSO-d$_6$, 400 MHz) δ$_H$=8.74 (s, 1H), 8.44 (d, 1H), 8.32 (dd, 1H), 8.11 (dd, 1H), 7.95 (dd, 1H), 6.02 (spt, 1H), 4.09 (d, 2H), 1.54 (d, 3H), 1.32-1.21 (m, 1H), 0.62-0.52 (m, 2H), 0.44-0.33 (m, 2H). LCMS R$_t$=1.37 min in 2.0 min chromatography, 10-80AB, MS ESI calcd. C$_{19}$H$_{17}$F$_6$N$_4$O$_2$ [M+H]$^+$ 447.1, found 447.0.

Example 19: 3-[difluoro(isopropoxy)methyl]-6-[5-fluoro-6-[(1S)-2,2,2-trifluoro-1-methyl-ethoxy]-3-pyridyl]-[1,2,4]triazolo[4,3-a]pyridine A mixture of 6-bromo-3-[difluoro(isopropoxy)methyl]-[1,2,4]triazolo[4,3-a]pyridine (70 mg, 230 μmol), 3-fluoro-5-(4,4,5,5-tetramethyl-1,3,2-dioxaborolan-2-yl)-2-[(1S)-2,2,2-trifluoro-1-methyl-ethoxy]pyridine (91.96 mg, 270 μmol), K$_2$CO$_3$ (63.21 mg, 460 μmol) and Pd(dppf)Cl$_2$ (25.1 mg, 30 μmol) in 1,4-Dioxane (5 mL) and Water (0.50 mL) was stirred at 80° C. for 12 hours under N$_2$. After cooling to room temperature, the mixture was diluted with H$_2$O (10 mL), and the mixture was extracted with EtOAc (20 mL×2). The combined organic phase was washed with water (20 mL) and brine (30 mL), dried over Na$_2$SO$_4$, filtered and concentrated to give the crude product. The crude product was purified by Prep-HPLC (Boston Prime C18 (150×30 mm, 5 μm), A=H$_2$O (0.05% NH$_4$OH) and B=CH$_3$CN; 60-90% B over 8 minutes) to give the product (33.94 mg, 78.1 μmol, 34% yield) as a solid. $^1$H NMR (DMSO-d$_6$, 400 MHz) δ$_H$=8.61 (s, 1H), 8.43 (d, 1H), 8.31 (dd, 1H), 8.11 (dd, 1H), 7.95 (dd, 1H), 6.02 (spt, 1H), 4.90 (spt, 1H), 1.54 (d, 3H), 1.41 (d, 6H). LCMS R$_t$=1.35 min in 2.0 min chromatography, 10-80AB, MS ESI calcd. C$_{18}$H$_{17}$F$_6$N$_4$O$_2$ [M+H]$^+$ 435.1, found 435.0.

Example 20: 3-[difluoro(isopropoxy)methyl]-6-[5-fluoro-6-[(1R)-2,2,2-trifluoro-1-methyl-ethoxy]-3-pyridyl]-[1,2,4]triazolo[4,3-a]pyridine

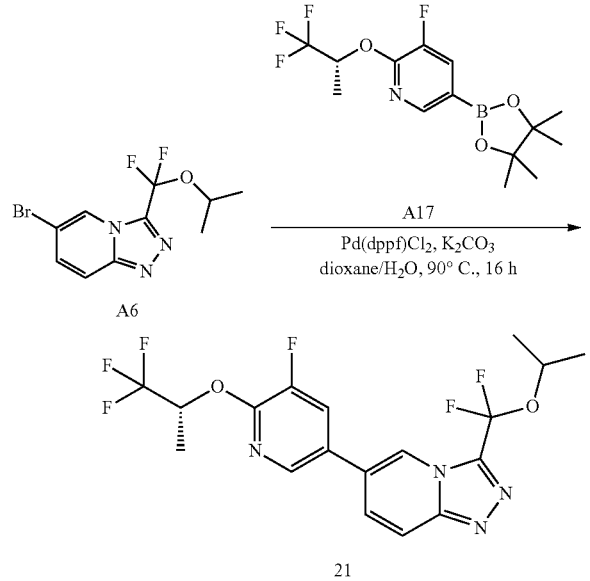

A mixture of 3-fluoro-5-(4,4,5,5-tetramethyl-1,3,2-dioxaborolan-2-yl)-2-[(1R)-2,2,2-trifluoro-1-methyl-ethoxy]pyridine (84.29 mg, 0.25 mmol), Pd(dppf)Cl$_2$ (25.1 mg, 0.03 mmol), 6-bromo-3-[difluoro(isopropoxy)methyl]-[1,2,4]triazolo[4,3-a]pyridine (70 mg, 0.23 mmol) and K$_2$CO$_3$ (63.21 mg, 0.46 mmol) in 1,4-Dioxane (5 mL) and Water (1 mL) was stirred at 90° C. for 16 hours under N$_2$. After cooling to room temperature, the mixture was filtered through Celite, and eluted with EtOAc (10 mL×2), and the filtrate was concentrated to give the crude product. The crude product was purified by Prep-HPLC (Boston Prime C18 (150 mm×30 mm 5 μm) A=H$_2$O (0.05% ammonia hydroxide v/v) and B=CH$_3$CN; 60-90% B over 8 minutes) to give the product (24.78 mg, 57.1 μmol, 25% yield) as a solid. $^1$H NMR (DMSO-d$_6$, 400 MHz) δ$_H$=8.61 (s, 1H), 8.43 (d, 1H), 8.32 (dd, 1H), 8.12 (d, 1H), 7.95 (dd, 1H), 6.03 (spt, 1H), 4.95-4.85 (m, 1H), 1.54 (d, 3H), 1.41 (d, 6H). LCMS R$_t$=1.37 min in 2.0 min chromatography, 10-80AB, MS ESI calcd. for C$_{18}$H$_{17}$F$_6$N$_4$O$_2$ [M+H]$^+$ 435.1, found 435.1.

Example 21: 3-[difluoro(isobutoxy)methyl]-6-[5-fluoro-6-[(1S)-2,2,2-trifluoro-1-methyl-ethoxy]-3-pyridyl]-[1,2,4]triazolo[4,3-a]pyridine

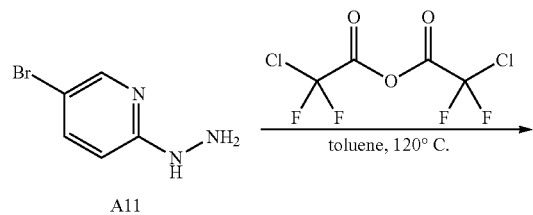

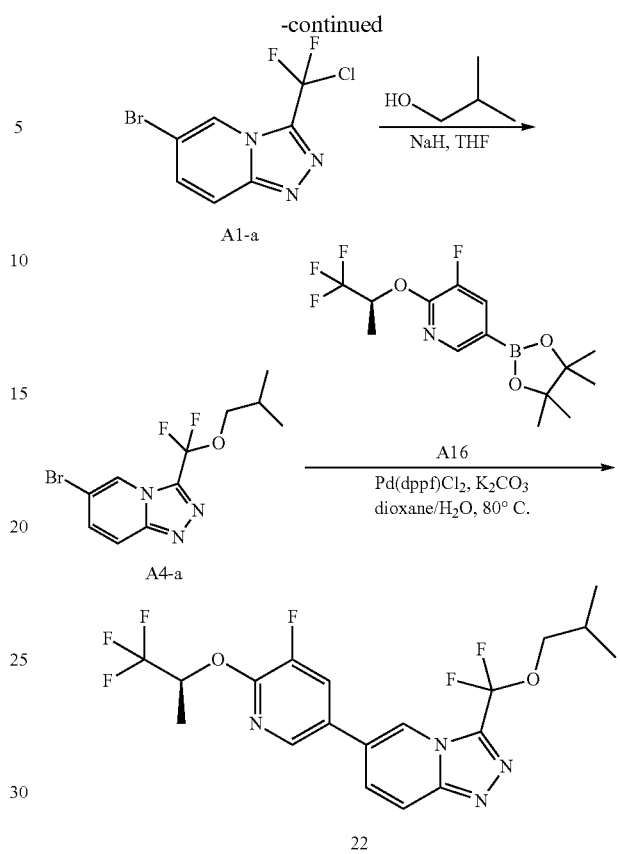

Synthesis of A1-a: A mixture of (5-bromo-2-pyridyl)hydrazine (5 g, 26.59 mmol) and (2-chloro-2,2-difluoro-acetyl) 2-chloro-2,2-difluoro-acetate (9690.21 mg, 39.89 mmol) in Toluene (200 mL) was stirred at 10° C. for 1 hour, and then the mixture was heated at 120° C. for 36 hours. After cooling to room temperature, the reaction was quenched with sat. NaHCO$_3$ (200 mL), then the mixture was extracted with EtOAc (80 mL×2). The organic layer was washed with brine (200 mL), dried over Na$_2$SO$_4$, filtered and concentrated to give the crude product. The crude product was purified by flash chromatography on silica gel (EtOAc in PE=0% to 5% to 20%) to give the product (5700 mg, 20.18 mmol, 76% yield) as a solid. $^1$H NMR (CDCl$_3$, 400 MHz) δ$_H$=8.43 (s, 1H), 7.84 (dd, 1H), 7.54 (dd, 1H).

Synthesis of A4-a: To a mixture of 2-methylpropan-1-ol (1312 mg, 17.7 mmol) in THF (40 mL) was added NaH (708.04 mg, 17.7 mmol), and the mixture was stirred at 20° C. for 0.5 hour. Then to the mixture was added 6-bromo-3-[chloro(difluoro)methyl]-[1,2,4]triazolo[4,3-a]pyridine (1000 mg, 3.54 mmol), and the mixture was stirred at 20° C. for 2 hours. The reaction was quenched with sat. NH$_4$Cl (40 mL), and the mixture was extracted with EtOAc (30 mL×2). The combined organic phase was washed with brine (70 mL), dried over Na$_2$SO$_4$, filtered and concentrated to give the crude product. The crude product was purified by flash chromatography on silica gel (EtOAc in PE=10% to 40%) to give the product (750 mg, 2.34 mmol, 66% yield) as an oil. $^1$H NMR (CDCl$_3$, 400 MHz) δ$_H$=8.44 (s, 1H), 7.77 (d, 1H), 7.44 (dd, 1H), 4.00 (d, 2H), 2.16-2.06 (m, 1H), 1.04 (d, 6H).

Synthesis of Compound 22: A mixture of 6-bromo-3-[difluoro(isobutoxy)methyl]-[1,2,4]triazolo[4,3-a]pyridine (100 mg, 310 μmol), 3-fluoro-5-(4,4,5,5-tetramethyl-1,3,2-dioxaborolan-2-yl)-2-[(1S)-2,2,2-trifluoro-1-methylethoxy]pyridine (125.61 mg, 370 μmol), K$_2$CO$_3$ (86.35 mg, 620 μmol) and Pd(dppf)Cl$_2$ (34.28 mg, 50 μmol) in 1,4-Dioxane (5 mL) and Water (0.50 mL) was stirred at 80° C. for 12 hours under N$_2$. After cooling to room temperature, the mixture was diluted with H$_2$O (10 mL), and then extracted with EtOAc (20 mL×2). The combined organic phase was washed with water (20 mL) and brine (30 mL), dried over Na$_2$SO$_4$, filtered and concentrated to give the crude product. The crude product was purified by Prep-HPLC (Boston Prime C18 (150×30 mm, 5 μm), A=H$_2$O (0.05% NH$_4$OH) and B=CH$_3$CN; 65-95% B over 8 minutes) to give the product (47.11 mg, 105.1 μmol, 34% yield) as a solid. $^1$H NMR (DMSO-d$_6$, 400 MHz) δ$_H$=8.70 (s, 1H), 8.43 (d, 1H), 8.31 (dd, 1H), 8.11 (dd, 1H), 7.95 (dd, 1H), 6.02 (spt, 1H), 4.01 (d, 2H), 2.10-1.95 (m, 1H), 1.54 (d, 3H), 0.96 (d, 6H). LCMS R$_t$=1.41 min in 2.0 min chromatography, 10-80AB, MS ESI calcd. C$_{19}$H$_{19}$F$_6$N$_4$O$_2$ [M+H]$^+$ 449.1, found 449.1.

Example 22: 3-[difluoro(isobutoxy)methyl]-6-[5-fluoro-6-[(1R)-2,2,2-trifluoro-1-methyl-ethoxy]-3-pyridyl]-[1,2,4]triazolo[4,3-a]pyridine

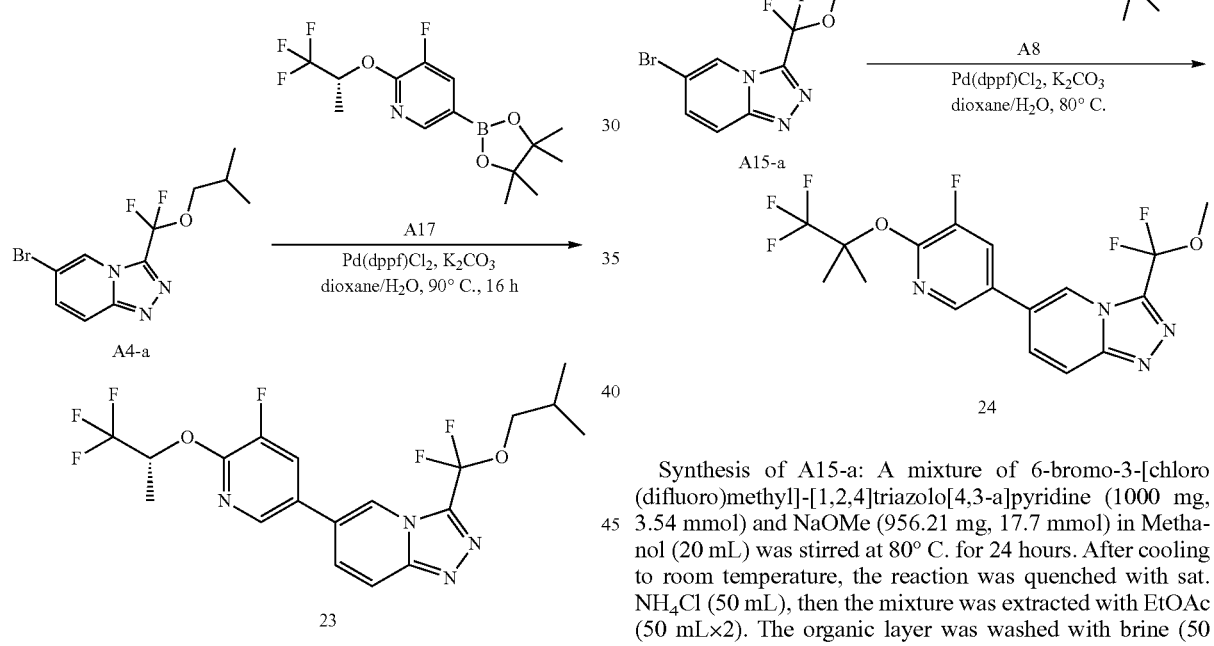

A mixture of 3-fluoro-5-(4,4,5,5-tetramethyl-1,3,2-dioxaborolan-2-yl)-2-[(1R)-2,2,2-trifluoro-1-methyl-ethoxy]pyridine (115.14 mg, 0.34 mmol), Pd(dppf)Cl$_2$ (34.28 mg, 0.05 mmol), 6-bromo-3-[difluoro(isobutoxy)methyl]-[1,2,4]triazolo[4,3-a]pyridine (100 mg, 0.31 mmol) and K$_2$CO$_3$ (86.35 mg, 0.62 mmol) in 1,4-Dioxane (5 mL) and Water (1 mL) was stirred at 90° C. for 16 hours under N$_2$. After cooling to room temperature, the mixture was filtered through Celite, and eluted with EtOAc (10 mL×2), and the filtrate was concentrated to give the crude product. The crude product was purified by Prep-HPLC (Boston Prime C18 150 mm×30 mm 5 μm) A=H$_2$O (0.05% ammonia hydroxide v/v) and B=CH$_3$CN; 61-91% B over 8 minutes) to give the product (68.11 mg, 0.15 mmol, 48% yield) as a solid. $^1$H NMR (DMSO-d$_6$, 400 MHz) δ$_H$=8.70 (s, 1H), 8.43 (d, 1H), 8.31 (dd, 1H), 8.15-8.09 (m, 1H), 7.95 (dd, 1H), 6.08-5.96 (m, 1H), 4.02 (d, 2H), 2.09-1.96 (m, 1H), 1.54 (d, 3H), 0.96 (d, 6H). LCMS R$_t$=1.42 min in 2.0 min chromatography, 10-80ABMS ESI calcd. for C$_{19}$H$_{19}$F$_6$N$_4$O$_2$ [M+H]$^+$ 449.1, found 449.1.

Example 23: 3-[difluoro(methoxy)methyl]-6-[5-fluoro-6-(2,2,2-trifluoro-1,1-dimethyl-ethoxy)-3-pyridyl]-[1,2,4]triazolo[4,3-a]pyridine

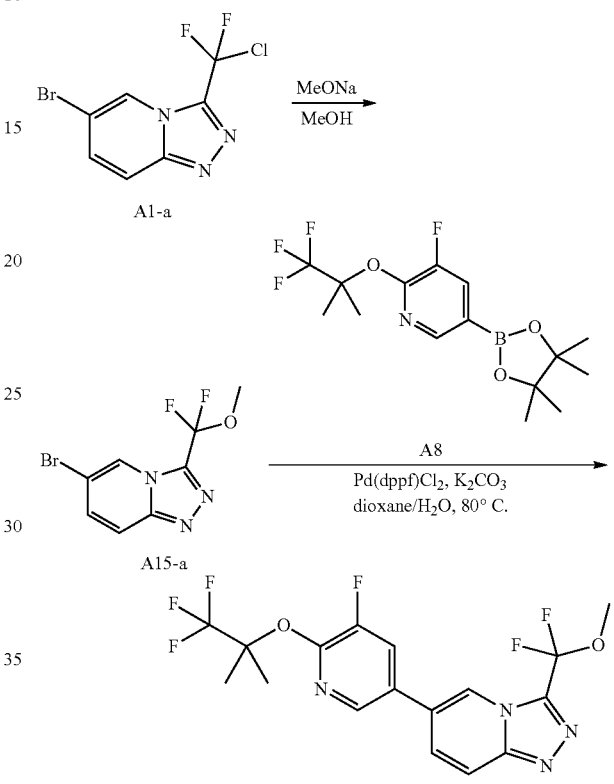

Synthesis of A15-a: A mixture of 6-bromo-3-[chloro(difluoro)methyl]-[1,2,4]triazolo[4,3-a]pyridine (1000 mg, 3.54 mmol) and NaOMe (956.21 mg, 17.7 mmol) in Methanol (20 mL) was stirred at 80° C. for 24 hours. After cooling to room temperature, the reaction was quenched with sat. NH$_4$Cl (50 mL), then the mixture was extracted with EtOAc (50 mL×2). The organic layer was washed with brine (50 mL), dried over Na$_2$SO$_4$, filtered and concentrated to give the crude product. The crude product was purified by flash chromatography on silica gel (EtOAc in PE=0% to 30% to 40%) to give the product (230 mg, 754.3 μmol, 21% yield) as an oil. LCMS R$_t$=1.41 min in 1.5 min chromatography, 5-95AB, MS ESI calcd. C$_8$H$_8$BrF$_2$N$_3$O [M+H+2]$^+$280.0, found 279.9.

Synthesis of Compound 24: A mixture of 6-bromo-3-[difluoro(methoxy)methyl]-[1,2,4]triazolo[4,3-a]pyridine (70 mg, 250 μmol), 3-fluoro-5-(4,4,5,5-tetramethyl-1,3,2-dioxaborolan-2-yl)-2-(2,2,2-trifluoro-1,1-dimethyl-ethoxy)pyridine (105.47 mg, 300 μmol), K$_2$CO$_3$ (69.59 mg, 500 μmol) and Pd(dppf)Cl$_2$ (27.63 mg, 40 μmol) in 1,4-Dioxane (5 mL) and Water (0.50 mL) was stirred at 80° C. for 12 hours under N$_2$. After cooling to room temperature, the mixture was diluted with H$_2$O (20 mL), and the mixture was extracted with EtOAc (20 mL×2). The combined organic phase was washed with water (30 mL) and brine (30 mL), dried over Na₂SO₄, filtered and concentrated to give the crude product. The crude product was purified by Prep-HPLC (Boston Prime C18 (150×30 mm, 5 μm), A=H₂O (0.05% NH₄OH) and B=CH₃CN; 56-86% B over 8 minutes) to give the product (22.72 mg, 54.1 μmol, 21% yield) as a solid. ⁺H NMR (DMSO-d₆, 400 MHz) δ$_H$=8.75 (s, 1H), 8.47 (d, 1H), 8.31 (dd, 1H), 8.14-8.05 (m, 1H), 7.95 (dd, 1H), 3.89 (s, 3H), 1.82 (s, 6H). LCMS R$_t$=1.31 min in 2.0 min chromatography, 10-80AB, MS ESI calcd. C₁₇H₁₅F₆N₄O₂ [M+H]⁺ 421.1, found 421.1.

Example 24: 3-[cyclopropylmethoxy(difluoro) methyl]-6-[5-fluoro-6-[(1R)-2,2,2-trifluoro-1-methyl-ethoxy]-3-pyridyl]-[1,2,4]triazolo[4,3-a]pyridine

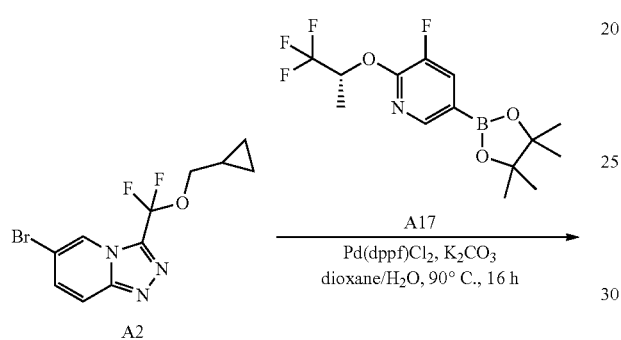

A mixture of 3-fluoro-5-(4,4,5,5-tetramethyl-1,3,2-dioxaborolan-2-yl)-2-[(1R)-2,2,2-trifluoro-1-methyl-ethoxy]pyridine (69.52 mg, 0.21 mmol), Pd(dppf)Cl₂ (20.7 mg, 0.03 mmol), 6-bromo-3-[cyclopropylmethoxy(difluoro)methyl]-[1,2,4]triazolo[4,3-a]pyridine (60 mg, 0.19 mmol) and K₂CO₃ (52.14 mg, 0.38 mmol) in 1,4-Dioxane (5 mL) and Water (1 mL) was stirred at 90° C. for 16 hours under N₂. After cooling to room temperature, the mixture was filtered through Celite, and eluted with EtOAc (10 mL×2), and the filtrate was concentrated to give the crude product. The crude product was purified by Prep-HPLC (Boston Prime C18 150 mm×30 mm 5 μm) A=H₂O (0.05% ammonia hydroxide v/v) and B=CH₃CN; 60-90% B over 8 minutes) to give the product (51.82 mg, 0.12 mmol, 62% yield) as a solid. ¹H NMR (DMSO-d₆, 400 MHz) δ$_H$=8.74 (s, 1H), 8.45 (d, 1H), 8.32 (dd, 1H), 8.11 (dd, 1H), 7.96 (dd, 1H), 6.02 (spt, 1H), 4.09 (d, 2H), 1.54 (d, 3H), 1.32-1.21 (m, 1H), 0.62-0.54 (m, 2H), 0.43-0.36 (m, 2H). LCMS R$_t$=1.39 min in 2.0 min chromatography, 10-80ABMS ESI calcd. for C₁₉H₁₇F₆N₄O₂ [M+H]⁺ 447.1, found 447.1.

Example 25: 3-[ethoxy(difluoro)methyl]-6-[5-fluoro-6-[(1R)-2,2,2-trifluoro-1-methyl-ethoxy]-3-pyridyl]-[1,2,4]triazolo[4,3-a]pyrazine A mixture of 3-[chloro(difluoro)methyl]-6-[5-fluoro-6-[(1R)-2,2,2-trifluoro-1-methyl-ethoxy]-3-pyridyl]-[1,2,4]triazolo[4,3-a]pyrazine (500 mg, 1.21 mmol) and AgOTf (3120.55 mg, 12.15 mmol) in Ethanol (7 mL) and MeCN (7 mL) was stirred at 90° C. for 5 days. The mixture was cooled to room temperature then EtOAc (20 mL) and brine (50 mL) were added to the mixture, the resulting suspension was filtered through Celite. The filtrate was separated and the aqueous phase was extracted with EtOAc (50 mL). The combined organic phase was dried over anhydrous Na₂SO₄, filtered and concentrated to give the crude product. The crude product was purified by chromatography flash on silica gel (EtOAc in PE=10% to 30% to 50%) and then triturated from DCM (3 mL) and n-hexane (4 mL) to give the product (31.35 mg, 74 μmol, 6% yield) as a solid. ¹H NMR (CDCl₃, 400 MHz) δ$_H$=9.52 (d, 1H), 8.48 (dd, 2H), 8.04 (dd, 1H), 5.95-5.87 (m, 1H), 4.37 (q, 2H), 1.60 (d, 3H), 1.51 (t, 3H). LCMS R$_t$=1.35 min in 2 min chromatography, 10-80AB, MS ESI calcd. for C₁₆H₁₄F₆N₅O₂ [M+H]⁺ 422.1, found 422.1.

Example 26: 6-[5-fluoro-6-(2,2,2-trifluoro-1,1-dimethyl-ethoxy)-3-pyridyl]-3-(methoxymethyl)-[1,2,4]triazolo[4,3-b]pyridazine

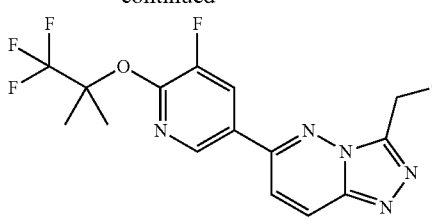

27

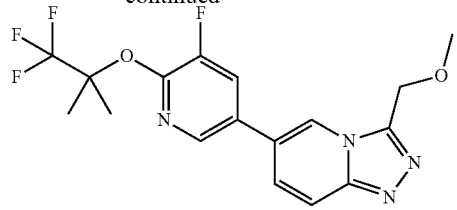

28

A mixture of 6-chloro-3-(methoxymethyl)-[1,2,4]triazolo[4,3-b]pyridazine (100 mg, 0.5 mmol), 3-fluoro-5-(4,4,5,5-tetramethyl-1,3,2-dioxaborolan-2-yl)-2-(2,2,2-trifluoro-1,1-dimethyl-ethoxy)pyridine (210.94 mg, 0.6 mmol), K$_3$PO$_4$ (213.79 mg, 1.01 mmol), Pd(t-Bu$_3$P)$_2$ (38.6 mg, 0.08 mmol) in 1,4-Dioxane (5 mL) and Water (0.5 mL) was stirred at 80° C. for 16 hours under N$_2$. After cooling to room temperature, the mixture was diluted with H$_2$O (10 mL), and the mixture was extracted with EtOAc (20 mL×2). The combined organic phase was washed with water (10 mL) and brine (10 mL), dried over Na$_2$SO$_4$, filtered and concentrated to give the crude product. The crude product was purified by Prep-HPLC (Boston Prime C18 (150 mm×30 mm, 5 µm; mobile phase: [water (0.05% NH$_4$OH)-ACN]; B %: 40-70%, 9 min) to give the product (47.66 mg, 0.12 mmol, 25% yield) as a solid. $^1$H NMR (CDCl$_3$, 400 MHz) δ$_H$=8.54 (d, 1H), 8.24 (d, 1H), 8.09 (dd, 1H), 7.57 (d, 1H), 5.11 (s, 2H), 3.53 (s, 3H), 1.90 (s, 6H). LCMS R$_t$=1.21 min in 2.0 min chromatography, 10-80AB, MS ESI calcd. for C$_{16}$H$_{16}$F$_4$N$_5$O$_2$ [M+H]$^+$ 386.1, found 386.0.

Example 27: 6-[5-fluoro-6-(2,2,2-trifluoro-1,1-dimethyl-ethoxy)-3-pyridyl]-3-(methoxymethyl)-[1,2,4]triazolo[4,3-a]pyridine

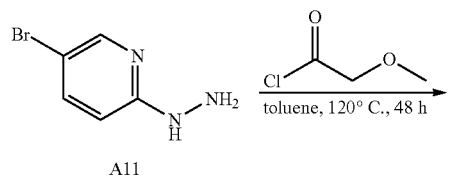

Synthesis of A33: To a solution of (5-bromo-2-pyridyl)hydrazine (8.5 g, 45.21 mmol) in toluene (80 mL), was added 2-methoxyacetyl chloride (5.4 g, 49.73 mmol) dropwise at 25° C. The solution was stirred at 25° C. for 30 min, then refluxed at 120° C. for 48 hours. After cooling to room temperature, the reaction mixture was concentrated to give a residue. The residue was triturated from DCM (100 mL) the yield the product (3.0 g, 10.01 mmol, 22% yield) as a solid. $^1$H NMR (MeOD-d$_4$, 400 MHz) δ=9.15 (s, 1H), 8.19-8.32 (m, 1H), 8.11-7.96 (m, 1H), 5.09 (s, 2H), 3.49 (s, 3H).

Synthesis of Compound 28: A mixture of 6-bromo-3-(methoxymethyl)-[1,2,4]triazolo[4,3-a]pyridine (150 mg, 0.62 mmol), 3-fluoro-5-(4,4,5,5-tetramethyl-1,3,2-dioxaborolan-2-yl)-2-(2,2,2-trifluoro-1,1-dimethyl-ethoxy)pyridine (259.61 mg, 0.74 mmol), K$_2$CO$_3$ (171.29 mg, 1.24 mmol), Pd(dppf)Cl$_2$ (68.01 mg, 0.09 mmol) in mixed solvents 1,4-Dioxane (15 mL) and Water (3 mL) was heated at 85° C. for 16 hours. After cooling to room temperature, the reaction was concentrated and diluted with H$_2$O (20 mL), then extracted with DCM (20 mL×2). The combined organic phase was washed with brine (30 mL), dried over Na$_2$SO$_4$, filtered and concentrated to give the crude product. The crude product was purified using Prep-HPLC (YMC-Actus Triart C18 (100 mm×30 mm, 5 µm) A=H$_2$O (0.05% HCl) and B=CH$_3$CN; 50-75% B over 8 minutes) yielding the product in CH$_3$CN/H$_2$O (~150 mL). The solution was concentrated to remove most of the CH$_3$CN, basified with NaHCO$_3$(solid) to pH-9, then extracted with DCM (50 mL×3). The combined organic phase was concentrated yielding the product (121.16 mg, 0.32 mmol, 51% yield) as a solid. $^1$H NMR (CDCl$_3$, 400 MHz) δ=8.34 (s, 1H), 8.16 (d, 1H), 7.89 (d, 1H), 7.60 (dd, 1H), 7.47 (dd, 1H), 5.08 (s, 2H), 3.42 (s, 3H), 1.87 (s, 6H). LCMS R$_t$=1.25 min in 2.0 min chromatography, 10-80AB, MS ESI calcd. for C$_{17}$H$_{17}$F$_4$N$_4$O$_2$ [M+H]$^+$ 385.1, found 384.9.

Example 28: 6-[5-fluoro-6-(2,2,2-trifluoroethoxy)-3-pyridyl]-3-(methoxymethyl)-[1,2,4]triazolo[4,3-a]pyridine

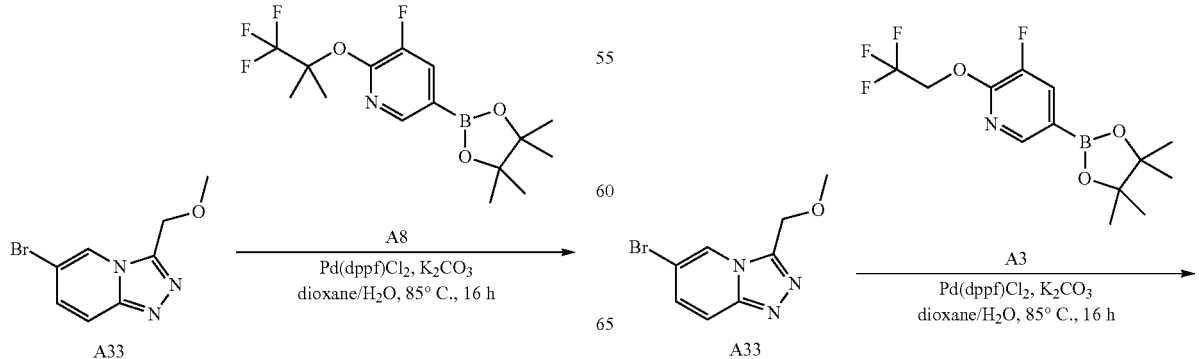

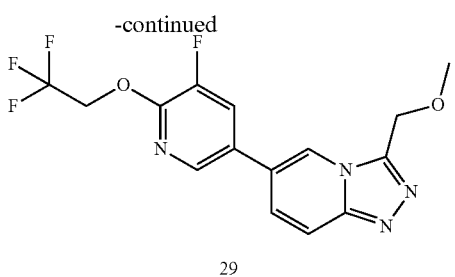

29

A mixture of 6-bromo-3-(methoxymethyl)-[1,2,4]triazolo[4,3-a]pyridine (150 mg, 0.62 mmol), 3-fluoro-5-(4,4,5,5-tetramethyl-1,3,2-dioxaborolan-2-yl)-2-(2,2,2-trifluoroethoxy)pyridine (238.75 mg, 0.74 mmol), $K_2CO_3$ (171.29 mg, 1.24 mmol), Pd(dppf)Cl$_2$ (68.01 mg, 0.09 mmol) in mixed solvents 1,4-Dioxane (15 mL) and Water (3 mL) was stirred at 85° C. for 16 hours. After cooling to room temperature, the reaction was concentrated and diluted with $H_2O$ (20 mL), then extracted with DCM (20 mL×2). The combined organic phase was washed with brine (30 mL), dried over $Na_2SO_4$, filtered and concentrated to give the crude product. The crude product was purified by Prep-HPLC ((Boston Prime C18 (150 mm×30 mm, 5μ.m) A=$H_2O$ (0.05% $NH_4OH$) and B=$CH_3CN$; 40-70% B over 8 minutes) to give the product (141.29 mg, 0.39 mmol, 64% yield) as a solid. $^1$H NMR (CDCl$_3$, 400 MHz) δ=8.35 (s, 1H), 8.17 (d, 1H), 7.90 (d, 1H), 7.65 (dd, 1H), 7.47 (dd, 1H), 5.09 (s, 2H), 4.91 (q, 2H), 3.43 (s, 3H). LCMS R$_t$=1.17 min in 2.0 min chromatography, 10-80AB, MS ESI calcd. for $C_{15}H_{13}F_4N_4O_2$ [M+H]$^+$ 357.1, found 356.9.

Example 29: 3-[difluoro(methoxy)methyl]-6-[5-fluoro-6-(2,2,2-trifluoroethoxy)-3-pyridyl]-[1,2,4]triazolo[4,3-a]pyridine A mixture of 6-bromo-3-[difluoro(methoxy)methyl]-[1,2,4]triazolo[4,3-a]pyridine (70 mg, 250 μmol), 3-fluoro-5-(4,4,5,5-tetramethyl-1,3,2-dioxaborolan-2-yl)-2-(2,2,2-trifluoroethoxy)pyridine (97 mg, 300 μmol), $K_2CO_3$ (69.59 mg, 0.50 mmol) and Pd(dppf)Cl$_2$ (27.63 mg, 0.04 mmol) in 1,4-Dioxane (5 mL) and Water (0.50 mL) was stirred at 80° C. for 12 hours under $N_2$. After cooling to room temperature, the mixture was diluted with $H_2O$ (10 mL), and the mixture was extracted with EtOAc (20 mL×2). The combined organic phase was washed with water (10 mL) and brine (10 mL), dried over $Na_2SO_4$, filtered and concentrated to give the crude product. The crude product was first purified by Prep-HPLC (Boston Prime C18 (150 mm×30 mm, 5 μm), A=$H_2O$ (0.05% $NH_4OH$) and B=$CH_3CN$; 43-73% B over 8 minutes), then followed by Prep-HPLC (Boston Green ODS (150 mm×30 mm, 5 μm), A=$H_2O$ (0.075% TFA) and B=$CH_3CN$; 49-63% B over 10 minutes). The combined fractions were concentrated to remove ACN, and basified with sat. NaHCO$_3$ to pH~8, and the mixture was extracted with EtOAc (30 mL×2). The combined organic phase was washed with brine (40 mL), dried over $Na_2SO_4$, filtered and concentrated to give the product (41.36 mg, 105.4 μmol, 42% yield) as a solid. $^1$H NMR (DMSO-d$_6$, 400 MHz) δ$_H$=8.74 (s, 1H), 8.47 (d, 1H), 8.36 (dd, 1H), 8.11 (dd, 1H), 7.96 (dd, 1H), 5.18 (q, 2H), 3.89 (s, 3H). LCMS R$_t$=1.19 min in 2.0 min chromatography, 10-80AB, MS ESI calcd. $C_{15}H_{11}F_6N_4O_2$ [M+H]$^+$ 393.1, found 393.0.

Example 30: 6-[5-fluoro-6-[(1R)-2,2,2-trifluoro-1-methyl-ethoxy]-3-pyridyl]-3-(methoxymethyl)-[1,2,4]triazolo[4,3-a]pyrazine

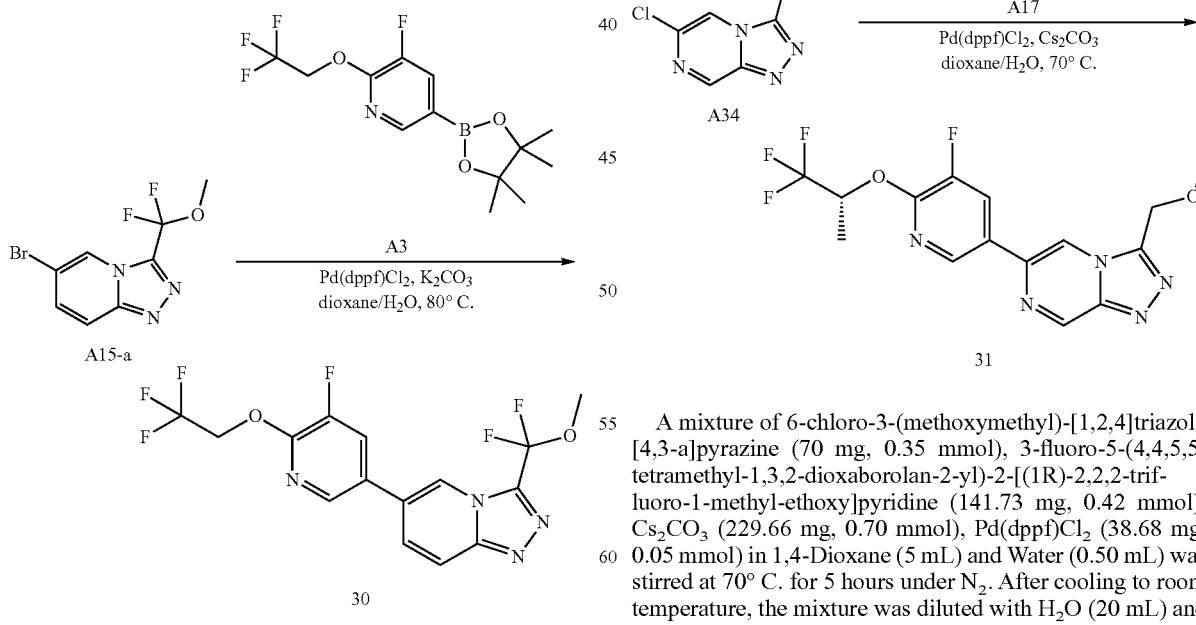

A mixture of 6-chloro-3-(methoxymethyl)-[1,2,4]triazolo[4,3-a]pyrazine (70 mg, 0.35 mmol), 3-fluoro-5-(4,4,5,5-tetramethyl-1,3,2-dioxaborolan-2-yl)-2-[(1R)-2,2,2-trifluoro-1-methyl-ethoxy]pyridine (141.73 mg, 0.42 mmol), Cs$_2$CO$_3$ (229.66 mg, 0.70 mmol), Pd(dppf)Cl$_2$ (38.68 mg, 0.05 mmol) in 1,4-Dioxane (5 mL) and Water (0.50 mL) was stirred at 70° C. for 5 hours under $N_2$. After cooling to room temperature, the mixture was diluted with $H_2O$ (20 mL) and extracted with EtOAc (30 mL×2). The combined organic phase was washed with water (30 mL) and brine (30 mL), dried over $Na_2SO_4$, filtered and concentrated to give the crude product. The crude product was first purified by Prep-TLC (silica gel, PE:EtOAc=1:1). The resulting product was further purified by Prep-HPLC (Boston Prime C18 (150 mm×30 mm, 5 μm),A=H$_2$O (0.05% NH$_4$OH) and B=CH$_3$CN; 38-68% B over 9 minutes), to give the product (4.43 mg, 11.9 μmol, 3% yield) as a solid. $^1$H NMR (CDCl$_3$, 400 MHz) δ$_H$=9.44 (d, 1H), 8.49 (dd, 1H), 8.47 (s, 1H), 8.05 (dd, 1H), 5.95-5.83 (m, 1H), 5.14 (s, 2H), 3.47 (s, 3H), 1.60 (d, 3H). LCMS R$_f$=1.18 min in 2.0 min chromatography, 10-80AB, MS ESI calcd. C$_{15}$H$_{14}$F$_4$N$_5$O$_2$ [M+H]$^+$ 372.1, found 371.9.

Example 31: 3-[ethoxy(difluoro)methyl]-6-[5-fluoro-6-[(1S)-2,2,2-trifluoro-1-methyl-ethoxy]-3-pyridyl]-[1,2,4]triazolo[4,3-a]pyridine

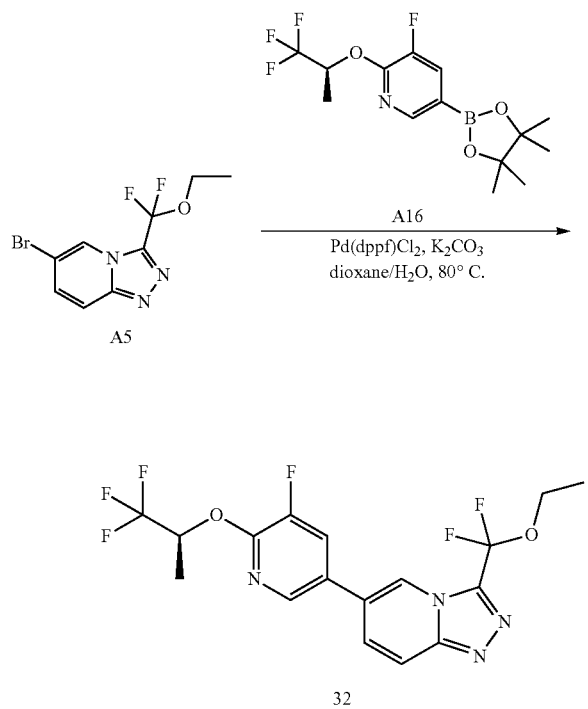

A mixture of 6-bromo-3-[ethoxy(difluoro)methyl]-[1,2,4]triazolo[4,3-a]pyridine (100 mg, 0.34 mmol), 3-fluoro-5-(4,4,5,5-tetramethyl-1,3,2-dioxaborolan-2-yl)-2-[(1S)-2,2,2-trifluoro-1-methyl-ethoxy]pyridine (137.67 mg, 0.41 mmol), K$_2$CO$_3$ (94.64 mg, 0.68 mmol) and Pd(dppf)Cl$_2$ (37.58 mg, 0.05 mmol) in 1,4-Dioxane (5 mL) and Water (0.50 mL) was stirred at 80° C. for 12 hours under N$_2$. After cooling to room temperature, the mixture was diluted with H$_2$O (10 mL), and extracted with EtOAc (20 mL×2). The combined organic phase was washed with water (10 mL) and brine (10 mL), dried over Na$_2$SO$_4$, filtered and concentrated to give the crude product. The crude product was purified by Prep-HPLC (Boston Prime C18 (150 mm×30 mm, 5um), A=H$_2$O (0.05% NH$_4$OH) and B=CH$_3$CN; 60-90% B over 9 minutes) to give the product (39.75 mg, 93.5 μmol, 27% yield) as a solid. $^1$H NMR (DMSO-d$_6$, 400 MHz) δ$_H$=8.72 (s, 1H), 8.44 (d, 1H), 8.33 (dd, 1H), 8.10 (d, 1H), 7.94 (dd, 1H), 6.02 (spt, 1H), 4.29 (q, 2H), 1.54 (d, 3H), 1.36 (t, 3H). LCMS R$_f$=1.28 min in 2.0 min chromatography, 10-80ABMS ESI calcd. C$_{17}$H$_{15}$F$_6$N$_4$O$_2$ [M+H]$^+$ 421.1, found 421.0.

Example 32: 3-[ethoxy(difluoro)methyl]-6-[5-fluoro-6-[(1S)-2,2,2-trifluoro-1-methyl-ethoxy]-3-pyridyl]-[1,2,4]triazolo[4,3-a]pyrazine

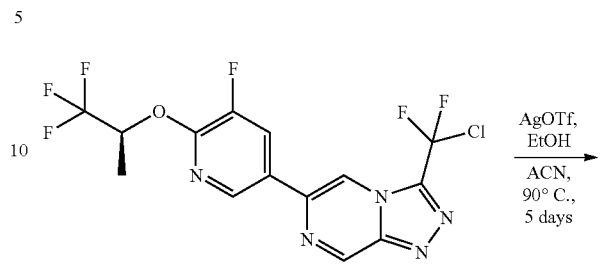

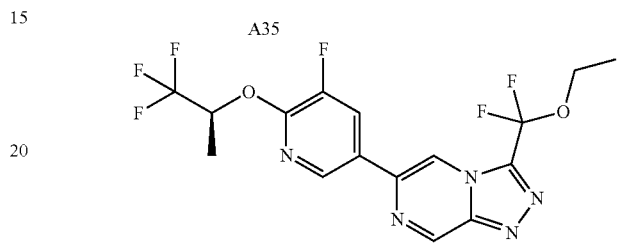

A mixture of 3-[chloro(difluoro)methyl]-6-[5-fluoro-6-[(1S)-2,2,2-trifluoro-1-methyl-ethoxy]-3-pyridyl]-[1,2,4]triazolo[4,3-a]pyrazine (200 mg, 0.49 mmol) and AgOTf (1.25 g, 4.86 mmol) in Ethanol (10 mL) and MeCN (10 mL) was stirred at 90° C. for 5 days. The mixture was cooled to room temperature. EtOAc (50 mL) and brine (50 mL) were added to the mixture, and the mixture was filtered through Celite. The filtrate was separated and the aqueous layer was extracted with EtOAc (50 mL). The combined organic phase was dried over anhydrous Na$_2$SO$_4$, filtered and concentrated to give the crude product. The crude product was purified by flash chromatography on silica gel (EtOAc in PE=10% to 30% to 50%) and then triturated from n-hexane (5 mL) to give the product (41.27 mg, 98.0 μmol, 20% yield) as a solid. $^1$H NMR (CDCl$_3$, 400 MHz) δ$_H$=9.52 (d, 1H), 8.50-8.45 (m, 2H), 8.04 (dd, 1H), 6.00-5.82 (m, 1H), 4.37 (q, 2H), 1.60 (d, 3H), 1.51 (t, 3H). LCMS R$_f$=1.29 min in 2.0 min chromatography, 10-80AB, MS ESI calcd. for C$_{16}$H$_{14}$F$_6$N$_5$O$_2$ [M+H]$^+$ 422.1, found 422.0.

Example 33: 3-[ethoxy(difluoro)methyl]-6-[5-fluoro-6-[(1R)-2,2,2-trifluoro-1-methyl-ethoxy]-3-pyridyl]-[1,2,4]triazolo[4,3-a]pyridine

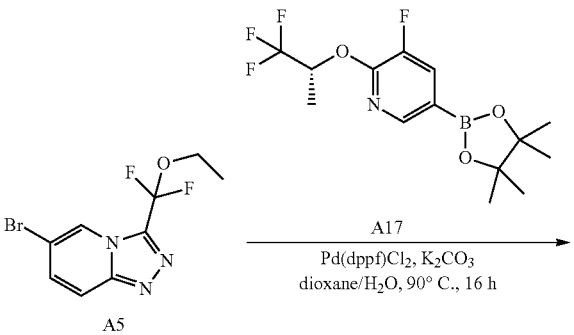

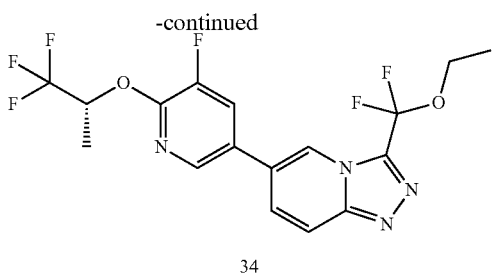

34

A mixture of 3-fluoro-5-(4,4,5,5-tetramethyl-1,3,2-dioxaborolan-2-yl)-2-[(1R)-2,2,2-trifluoro-1-methyl-ethoxy]pyridine (126.2 mg, 0.38 mmol), Pd(dppf)Cl$_2$ (37.58 mg, 0.05 mmol), 6-bromo-3-[ethoxy(difluoro)methyl]-[1,2,4]triazolo[4,3-a]pyridine (100 mg, 0.34 mmol) and K$_2$CO$_3$ (94.64 mg, 0.68 mmol) in 1,4-Dioxane (5 mL) and Water (1 mL) was stirred at 90° C. for 16 hours under N$_2$. After cooling to room temperature, the mixture was filtered through Celite, and eluted with EtOAc (10 mL×2), and the filtrate was concentrated to give the crude product. The crude product was purified by Prep-HPLC (Boston Prime C18 (150 mm×30 mm, 5 μm) A=H$_2$O (0.05% NH$_4$OH) and B=CH$_3$CN; 45-75% B over 9 minutes) to give the product (62.87 mg, 0.15 mmol, 43% yield) as a solid. $^1$H NMR (DMSO-d$_6$, 400 MHz) δ$_H$=8.72 (s, 1H), 8.44 (d, 1H), 8.33 (dd, 1H), 8.14-8.06 (m, 1H), 7.94 (dd, 1H), 6.01 (spt, 1H), 4.28 (q, 2H), 1.54 (d, 3H), 1.36 (t, 3H). LCMS R$_t$=1.26 min in 2.0 min chromatography, 10-80AB, MS ESI calcd. for C$_{17}$H$_{15}$F$_6$N$_4$O$_2$ [M+H]$^+$ 421.1, found 421.0.

Example 34: 6-[5-fluoro-6-(2,2,2-trifluoroethoxy)-3-pyridyl]-3-(methoxymethyl)-[1,2,4]triazolo[4,3-b]pyridazine

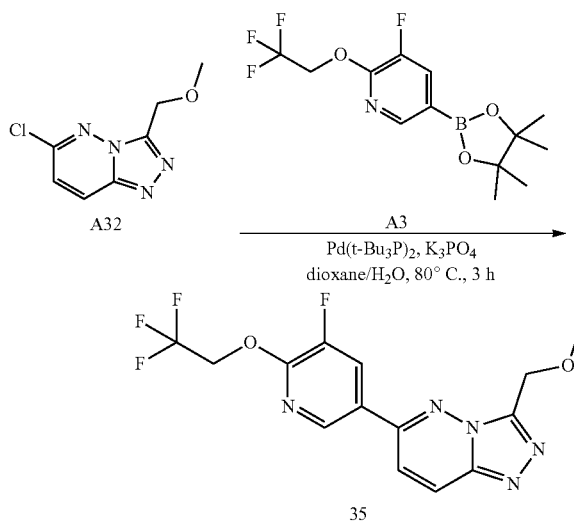

35

A mixture of 6-chloro-3-(methoxymethyl)-[1,2,4]triazolo[4,3-b]pyridazine (100 mg, 0.50 mmol), 3-fluoro-5-(4,4,5,5-tetramethyl-1,3,2-dioxaborolan-2-yl)-2-(2,2,2-trifluoroethoxy)pyridine (194 mg, 0.60 mmol), K$_3$PO$_4$ (213.79 mg, 1.01 mmol) and Pd(t-Bu$_3$P)$_2$ (38.6 mg, 0.08 mmol) in 1,4-Dioxane (10 mL) and Water (1 mL) was stirred at 80° C. under N$_2$ for 3 hours. After cooling to room temperature, water (20 mL) and EtOAc (20 mL) were added to the mixture and the mixture was filtered through Celite. After separating, the organic phase was washed with brine (20 mL), dried over anhydrous Na$_2$SO$_4$, filtered and concentrated to give the crude product. The crude product was purified by Prep-HPLC (Boston Prime C18 (150 mm×30 mm, 5 μm) A=H$_2$O (0.05% NH$_4$OH) and B=CH$_3$CN; 33-63% B over 8 minutes) to give the product (49 mg, 137.2 μmol, 27% yield) as a solid. $^1$H NMR (CDCl$_3$, 400 MHz) δ$_H$=8.54 (d, 1H), 8.25 (d, 1H), 8.17 (dd, 1H), 7.58 (d, 1H), 5.11 (s, 2H), 4.94 (q, 2H), 3.54 (s, 3H). LCMS R$_t$=1.08 min in 2.0 min chromatography, 10-80AB, MS ESI calcd. for C$_{14}$H$_{12}$F$_4$N$_5$O$_2$ [M+H]$^+$ 358.1, found 357.9.

Example 35: 3-[cyclopropoxy(difluoro)methyl]-6-[5-fluoro-6-[(1R)-2,2,2-trifluoro-1-methyl-ethoxy]-3-pyridyl]-[1,2,4]triazolo[4,3-a]pyridine

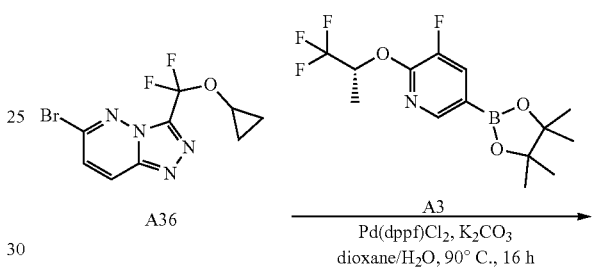

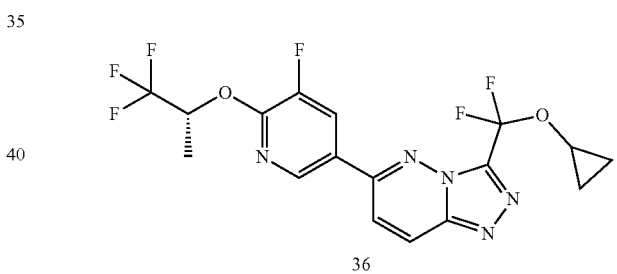

36

A mixture of 3-fluoro-5-(4,4,5,5-tetramethyl-1,3,2-dioxaborolan-2-yl)-2-[(1R)-2,2,2-trifluoro-1-methyl-ethoxy]pyridine (121.22 mg, 0.36 mmol), Pd(dppf)Cl$_2$ (36.09 mg, 0.05 mmol), 6-bromo-3-[cyclopropoxy(difluoro)methyl]-[1,2,4]triazolo[4,3-a]pyridine (100 mg, 0.33 mmol) and K$_2$CO$_3$ (90.9 mg, 0.66 mmol) in 1,4-Dioxane (5 mL) and water (1 mL) was stirred at 90° C. for 16 hours under N$_2$. After cooling to room temperature, the mixture was filtered through Celite, and eluted with EtOAc (10 mL×2), and the filtrate was concentrated to give the crude product. The crude product was purified by Prep-HPLC (Boston Prime C18 (150 mm×30 mm, 5 μm) A=H$_2$O (0.05% NH$_4$OH) and B=CH$_3$CN; 47-77% B over 9 minutes) to give the product (54.98 mg, 0.13 mmol, 39% yield) as a solid. $^1$H NMR (DMSO-d$_6$, 400 MHz) δ$_H$=8.65 (s, 1H), 8.44 (d, 1H), 8.33 (dd, 1H), 8.11 (d, 1H), 7.94 (dd, 1H), 6.07-5.97 (m, 1H), 4.25-4.15 (m, 1H), 1.54 (d, 3H), 0.95-0.86 (m, 2H), 0.77-0.69 (m, 2H). LCMS R$_t$=1.33 min in 2.0 min chromatography, 10-80ABMS ESI calcd. for C$_{18}$H$_{15}$F$_6$N$_4$O$_2$ [M+H]$^+$ 433.1, found 433.1.

Example 36: 3-[cyclopropoxy(difluoro)methyl]-6-[5-fluoro-6-[(1S)-2,2,2-trifluoro-1-methyl-ethoxy]-3-pyridyl]-[1,2,4]triazolo[4,3-a]pyridine

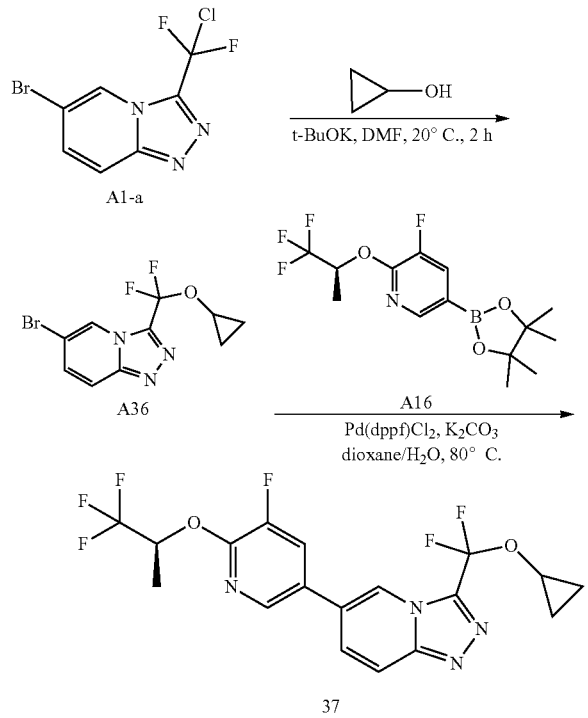

Synthesis of A36: To a mixture of cyclopropanol (246.74 mg, 4.25 mmol), 6-bromo-3-[chloro(difluoro)methyl]-[1,2,4]triazolo[4,3-a]pyridine (600 mg, 2.12 mmol) in DMF (10 mL) was added potassium tert-butoxide (476.69 mg, 4.25 mmol). The reaction mixture was stirred at 20° C. for 2 hours. The reaction was quenched with sat. NH$_4$Cl (40 mL), then the mixture was extracted with EtOAc (50 mL×2). The combined organic phase was washed with water (80 mL) and brine (80 mL), dried over Na$_2$SO$_4$, filtered and concentrated to give the crude product. The crude product was purified by flash chromatography on silica gel (EtOAc in PE=0% to 20% to 40%) to give the product (270 mg, 0.89 mmol, 42% yield) as a solid. LCMS R$_t$=3.74 min in 7.0 min chromatography, 0-60ABMS ESI calcd. C$_{10}$H$_9$BrF$_2$N$_3$O [M+H+2]$^+$306.0, found 305.8.

Synthesis of Compound 37: A mixture of 6-bromo-3-[cyclopropoxy(difluoro)methyl]-[1,2,4]triazolo[4,3-a]pyridine (100 mg, 0.33 mmol), 3-fluoro-5-(4,4,5,5-tetramethyl-1,3,2-dioxaborolan-2-yl)-2-[(1S)-2,2,2-trifluoro-1-methyl-ethoxy]pyridine (132.24 mg, 0.39 mmol), K$_2$CO$_3$ (90.9 mg, 0.66 mmol) and Pd(dppf)Cl$_2$ (36.09 mg, 0.05 mmol) in 1,4-Dioxane (5 mL) and water (0.50 mL) was stirred at 80° C. for 12 hours under N$_2$. After cooling to room temperature, the mixture was diluted with H$_2$O (10 mL), and the mixture was extracted with EtOAc (20 mL×2). The combined organic phase was washed with water (10 mL) and brine (10 mL), dried over Na$_2$SO$_4$, filtered and concentrated to give the crude product. The crude product was purified by Prep-HPLC (Boston Prime C18 (150 mm×30 mm, 5 μm), A=H$_2$O (0.05% NH$_4$OH) and B=CH$_3$CN; 50-70% B over 9 minutes) to give the product (35.99 mg, 83.2 μmol, 25% yield) as a solid. $^1$H NMR (DMSO-d$_6$, 400 MHz) δ$_H$=8.65 (s, 1H), 8.44 (d, 1H), 8.33 (dd, 1H), 8.11 (dd, 1H), 7.94 (dd, 1H), 6.09-5.95 (m, 1H), 4.25-4.14 (m, 1H), 1.54 (d, 3H), 0.95-0.86 (m, 2H), 0.79-0.67 (m, 2H). LCMS R$_t$=1.29 min in 2.0 min chromatography, 10-80AB, MS ESI calcd. C$_{18}$H$_{15}$F$_6$N$_4$O$_2$ [M+H]$^+$ 433.1, found 433.0.

Example 37: 6-[5-fluoro-6-[(1S)-2,2,2-trifluoro-1-methyl-ethoxy]-3-pyridyl]-3-(methoxymethyl)-[1,2,4]triazolo[4,3-a]pyrazine

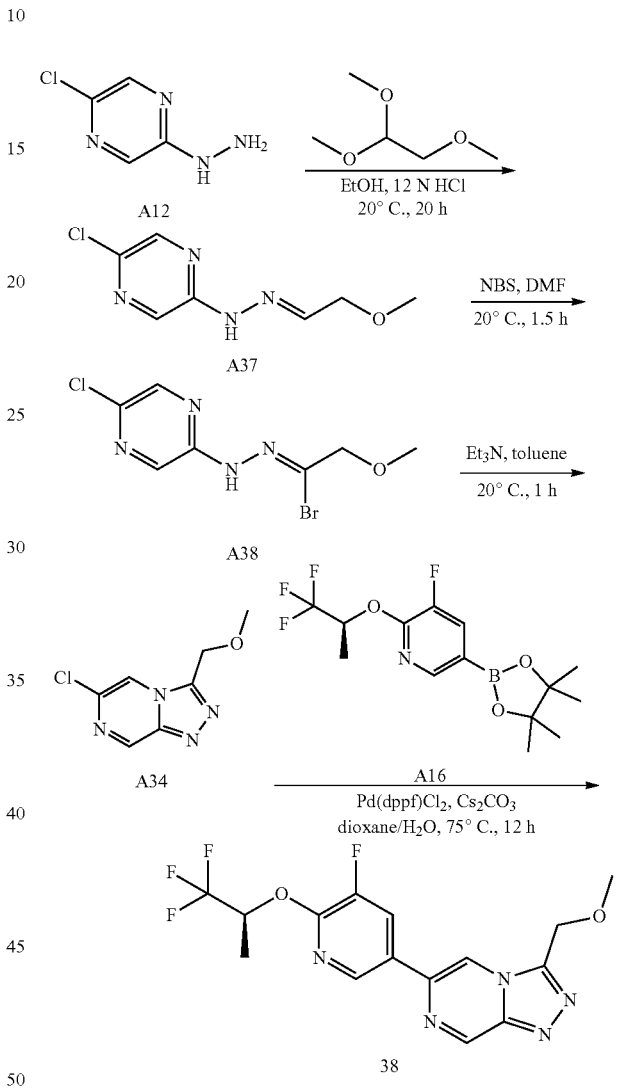

Synthesis of A37: To a mixture of 1,1,2-trimethoxyethane (1.25 g, 10.38 mmol) and (5-chloropyrazin-2-yl)hydrazine (1 g, 6.92 mmol) in Ethanol (20 mL) was added 12N HCl (1.73 mL, 20.75 mmol), then the mixture was stirred at 20° C. for 20 hours. To the mixture was added water (20 mL), then basified with Na$_2$CO$_3$ (solid) to pH 9 and extracted with EtOAc (50 mL×4). The combined organic phase was washed with brine (30 mL), dried over Na$_2$SO$_4$, filtered and concentrated to give the crude product. The crude product was triturated from EtOAc/PE (2/10 mL) and dried in oven, yielding 5-chloro-N-(2-methoxyethylideneamino)pyrazin-2-amine (1050 mg, 3.73 mmol, 54% yield) as a solid. LCMS R$_t$=0.70 min in 1.5 min chromatography, 5-95AB, MS ESI calcd. for C$_7$H$_{10}$ClN$_4$O [M+H]$^+$ 201.0, found 201.0.

Synthesis of A38: To a mixture of 5-chloro-N-(2-methoxyethylideneamino)pyrazin-2-amine (1 g, 4.98 mmol)

in DMF (10 mL) was added a solution of NBS (1.24 g, 6.98 mmol) in DMF (7 mL) dropwise over 0.5 hour, then the mixture was stirred at 20° C. for 1 hour. The mixture was diluted with H₂O (50 mL) and extracted with EtOAc (50 mL×4). The combined organic phase was washed with brine (50 mL), dried over Na₂SO₄, filtered and concentrated to give the crude product (1000 mg, 3.58 mmol, 72% yield) as a solid, which was used directly without any further purification. LCMS $R_t$=0.80 min in 1.5 min chromatography, 5-95AB, MS ESI calcd. for $C_7H_9BrClN_4O$ [M+H+2]⁺ 281.0, found 280.9.

Synthesis of A34: To a mixture of N-(5-chloropyrazin-2-yl)-2-methoxy-ethanehydrazonoyl bromide (1 g, 3.58 mmol) in Toluene (15 mL) was added Et₃N (0.99 mL, 7.16 mmol), then the mixture was stirred at 20° C. for 1 hour. The mixture was diluted with H₂O (30 mL), and extracted with EtOAc (50 mL×2). The combined organic phase was washed with water (20 mL×2) and brine (20 mL), dried over Na₂SO₄, filtered and concentrated to give the crude product. The crude product was purified by flash chromatography on silica gel (EtOAc in PE=0% to 40% to 80%) to give the product (380 mg, 1.87 mmol, 52% yield) as a solid. ¹H NMR (CDCl₃, 400 MHz) $δ_H$=9.21 (d, 1H), 8.28 (d, 1H), 5.07 (s, 2H), 3.45 (s, 3H). LCMS $R_t$=0.30 min in 1.5 min chromatography, 5-95AB, MS ESI calcd. for $C_7H_8ClN_4O$ [M+H]⁺ 199.0, found 199.0.

Synthesis of Compound 38: A mixture of 6-chloro-3-(methoxymethyl)-[1,2,4]triazolo[4,3-a]pyrazine (70 mg, 0.35 mmol), 3-fluoro-5-(4,4,5,5-tetramethyl-1,3,2-dioxaborolan-2-yl)-2-[(1S)-2,2,2-trifluoro-1-methyl-ethoxy]pyridine (177.16 mg, 0.53 mmol), Pd(dppf)Cl₂ (64.47 mg, 88.1 μmol) and Cs₂CO₃ (229.66 mg, 0.70 mmol) in 1,4-Dioxane (8 mL) and Water (0.80 mL) was stirred at 75° C. for 12 hours under N₂. After cooling to room temperature, the mixture was diluted with H₂O (30 mL), and the mixture was extracted with EtOAc (50 mL×2). The combined organic phase was washed with water (20 mL×2) and brine (20 mL), dried over Na₂SO₄, filtered and concentrated to give the crude product. The crude product was first purified by Prep-TLC (silica gel, PE:EtOAc=1:1), followed by prep-HPLC [Boston Prime C18 (150 mm×30 mm, 5 μm) A=H2O (0.05% NH₄OH) and B=CH₃CN; 38-68% B over 9 minutes], to give the product (12.63 mg, 34.0 μmol, 10% yield) as a solid. ¹H NMR (CDCl₃, 400 MHz) $δ_H$=9.44 (d, 1H), 8.50 (d, 1H), 8.47 (d, 1H), 8.05 (dd, 1H), 5.97-5.84 (m, 1H), 5.14 (s, 2H), 3.47 (s, 3H), 1.60 (d, 3H). LCMS $R_t$=1.17 min in 2.0 min chromatography, 10-80ABMS ESI calcd. for $C_{15}H_{14}F_4N_5O_2$ [M+H]⁺ 372.1, found 371.9.

Example 38: 6-[5-fluoro-6-(2,2,2-trifluoroethoxy)-3-pyridyl]-3-(methoxymethyl)-[1,2,4]triazolo[4,3-a]pyrazine

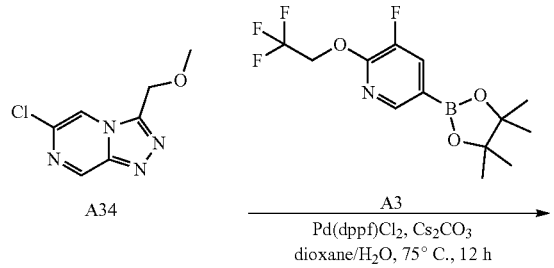

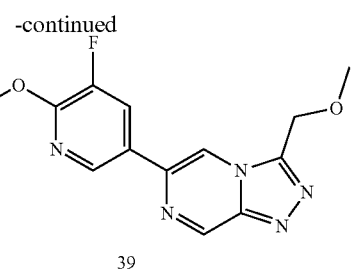

A mixture of 6-chloro-3-(methoxymethyl)-[1,2,4]triazolo[4,3-a]pyrazine (70 mg, 0.35 mmol), 3-fluoro-5-(4,4,5,5-tetramethyl-1,3,2-dioxaborolan-2-yl)-2-(2,2,2-trifluoroethoxy)pyridine (169.75 mg, 0.53 mmol), Pd(dppf)Cl₂ (64.47 mg, 88.1 μmol) and Cs₂CO₃ (229.66 mg, 0.70 mmol) in 1,4-Dioxane (8 mL) and water (0.80 mL) was stirred at 75° C. for 12 hours under N₂. After cooling to room temperature, the mixture was diluted with H₂O (20 mL), and the mixture was extracted with EtOAc (30 mL×2). The combined organic phase was washed with water (20 mL) and brine (20 mL), dried over Na₂SO₄, filtered and concentrated to give the crude product. The crude product was purified by Prep-TLC (silica gel, PE:EtOAc=1:1) to give the product (14.65 mg, 40.7 μmol, 12% yield) as a solid. ¹H NMR (CDCl₃, 400 MHz) $δ_H$=9.44 (d, H), 8.52 (d, 1H), 8.48 (d, 1H), 8.07 (dd, 1H), 5.14 (s, 2H), 4.92 (q, 2H), 3.47 (s, 3H). LCMS $R_t$=1.19 min in 2.0 min chromatography, 10-80ABMS ESI calcd. for $C_{14}H_{12}F_4N_5O_2$ [M+H]⁺ 358.1, found 357.9.

Example 39: 6-[5-fluoro-6-[(1R)-2,2,2-trifluoro-1-methyl-ethoxy]-3-pyridyl]-3-(methoxymethyl)-[1,2,4]triazolo[4,3-a]pyridine

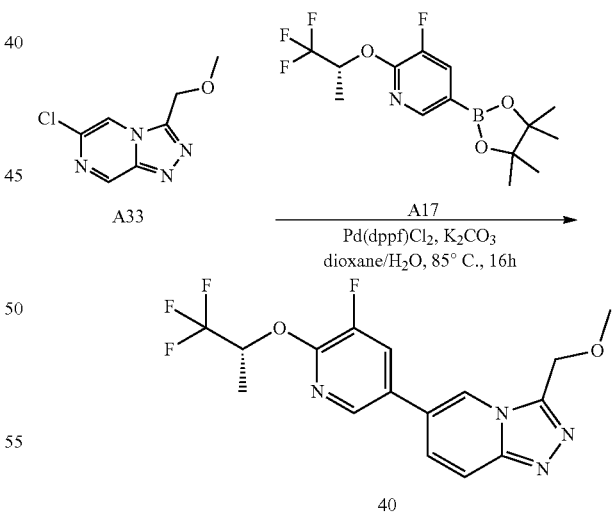

A mixture of 6-bromo-3-(methoxymethyl)-[1,2,4]triazolo[4,3-a]pyridine (200 mg, 0.83 mmol), 3-fluoro-5-(4,4,5,5-tetramethyl-1,3,2-dioxaborolan-2-yl)-2-[(1R)-2,2,2-trifluoro-1-methyl-ethoxy]pyridine (332.23 mg, 0.99 mmol), K₂CO₃ (228.38 mg, 1.65 mmol), Pd(dppf)Cl₂ (90.68 mg, 0.12 mmol) in 1,4-dioxane (15 mL) and Water (5 mL) 85° C. for 16 hours. After cooling to room temperature, the reaction was concentrated and diluted with H₂O (20 mL), then extracted with DCM (20 mL×2). The combined organic phase was washed with brine (30 mL), dried over Na₂SO₄, filtered and concentrated to give the crude product. The crude product was purified using Prep-HPLC (Boston Prime C18 (150 mm×30 mm 5μ.m) A=H₂O (0.05% NH₄OH) and B=CH₃CN; 35-65% B over 9 minutes) to give the product (104.44 mg, 0.28 mmol, 34% yield) as a solid. ¹H NMR (DMSO-d₆, 400 MHz) δ$_H$=8.85 (s, 1H), 8.49 (d, 1H), 8.35 (dd, 1H), 7.89-8.05 (m, 1H), 7.77-7.88 (m, 1H), 6.05-5.87 (m, 1H), 5.02 (s, 2H), 3.35 (s, 3H), 1.55 (d, 3H). LCMS R$_t$=1.150 min in 2.0 min chromatography, 10-80AB, MS ESI calcd. for $C_{16}H_{15}F_4N_4O_2$ [M+H]⁺ 371.1, found 371.1.

Example 40: 3-[ethoxy(difluoro)methyl]-6-[5-fluoro-6-[(1S)-2,2,2-trifluoro-1-methyl-ethoxy]-3-pyridyl]-[1,2,4]triazolo[4,3-b]pyridazine

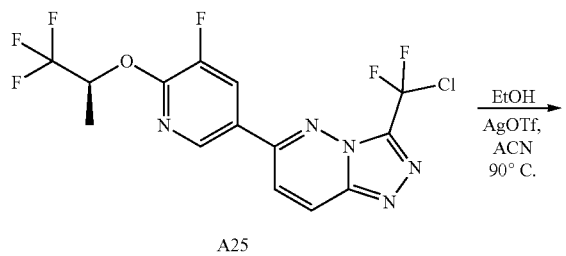

A25

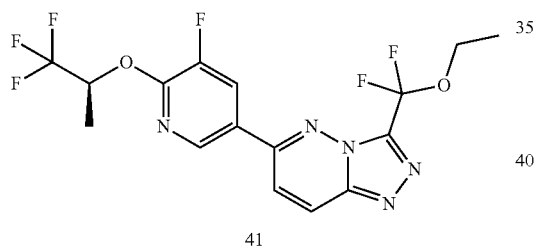

41

A mixture of 3-[chloro(difluoro)methyl]-6-[5-fluoro-6-[(1S)-2,2,2-trifluoro-1-methyl-ethoxy]-3-pyridyl]-[1,2,4]triazolo[4,3-b]pyridazine (300 mg, 0.73 mmol) and AgOTf (1872.33 mg, 7.29 mmol) in ethanol (10 mL) and MeCN (10 mL) was stirred at 90° C. for 9 days. After cooling to room temperature, the reaction was diluted with EtOAc (60 mL), and the mixture was added with brine (20 mL). The mixture was filtered through Celite and extracted with EtOAc (50 mL×2). The combined organic layer was washed with water (50 mL) and brine (50 mL), dried over Na₂SO₄, filtered and concentrated to give the crude product. The crude product was purified by flash chromatography on silica gel (EtOAc in PE=0% to 70. The iproduct was then triturated from n-Hexane (1 mL) and i-Pr₂O (1 mL), to give the product (28.86 mg, 67.3 μmol, 9% yield) as a solid. ¹H NMR (CDCl₃, 400 MHz) δ$_H$=8.54 (d, 1H), 8.29 (d, 1H), 8.13 (dd, 1H), 7.65 (d, 1H), 5.92 (spt, 1H), 4.33 (q, 2H), 1.61 (d, 3H), 1.48 (t, 3H). LCMS R$_t$=1.27 min in 2.0 min chromatography, 10-80AB, MS ESI calcd. $C_{16}H_{14}F_6N_5O_2$ [M+H]⁺ 422.1, found 422.0.

Example 41: 3-[ethoxy(difluoro)methyl]-6-[5-fluoro-6-[(1R)-2,2,2-trifluoro-1-methyl-ethoxy]-3-pyridyl]-[1,2,4]triazolo[4,3-b]pyridazine

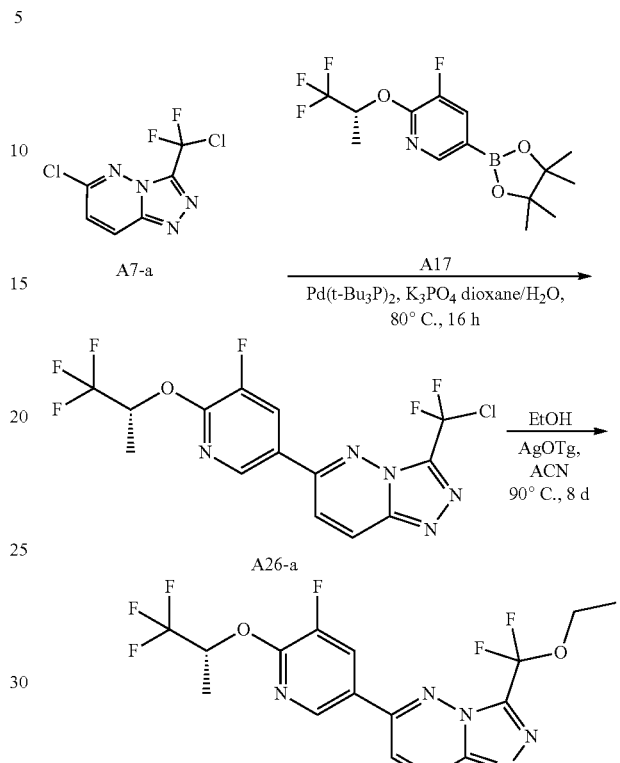

Synthesis of A26-a: A mixture of 3-fluoro-5-(4,4,5,5-tetramethyl-1,3,2-dioxaborolan-2-yl)-2-[(1R)-2,2,2-trifluoro-1-methyl-ethoxy]pyridine (1.54 g, 4.6 mmol), 6-chloro-3-[chloro(difluoro)methyl]-[1,2,4]triazolo[4,3-b]pyridazine (1 g, 4.18 mmol), Pd(t-Bu₃P)₂ (320.73 mg, 0.63 mmol) and K₃PO₄ (1.78 g, 8.37 mmol) in 1,4-Dioxane (20 mL) and water (4 mL) was stirred at 80° C. for 16 hours under N₂. After cooling to room temperature, the mixture was filtered through Celite, and eluted with EtOAc (20 mL×2), and the filtrate was concentrated to give the crude product. The crude product was purified by flash chromatography on silica gel (EtOAc in PE=30% to 60%) to give the product (1000 mg, 2.12 mmol, 51% yield) as a solid. LCMS R$_t$=0.93 min in 1.5 min chromatography, 5-95AB, MS ESI calcd. for $C_{14}H_9ClF_6N_5O$ [M+H]⁺ 412.0, found 412.1.

Synthesis of Compound 42: A mixture of 3-[chloro(difluoro)methyl]-6-[5-fluoro-6-[(1R)-2,2,2-trifluoro-1-methyl-ethoxy]-3-pyridyl]-[1,2,4]triazolo[4,3-b]pyridazine (300 mg, 0.73 mmol) and AgOTf (1872.33 mg, 7.29 mmol) in ethanol (10 mL, 0.73 mmol) and CH₃CN (10 mL) was stirred at 90° C. for 8 days. After cooling to room temperature, the reaction was diluted with EtOAc (40 mL), and the mixture was added to saturated NaCl (40 mL), the mixture was filtered through Celite, and eluted with EtOAc (20 mL×2), and the filtrate was concentrated to give the crude product. The crude product was purified by flash chromatography on silica gel (EtOAc in PE=0% to 50% to 100%). The product was further purified by Prep-HPLC (Boston Prime C18 (150 mm×30 mm 5 μm) A=H₂O (0.05% NH₄OH v/v) and B=CH₃CN; 51-81% B over 9 minutes), to give the product (8.12 mg, 19.3 μmol, 3% yield) as a solid. $^1$H NMR (CDCl$_3$, 400 MHz) $\delta_H$=8.54 (d, 1H), 8.30 (d, 1H), 8.13 (dd, 1H), 7.66 (d, 1H), 5.96-5.88 (m, 1H), 4.33 (q, 2H), 1.62 (s, 3H), 1.48 (t, 3H). LCMS R$_t$=1.29 min in 2.0 min chromatography, 10-80AB, MS ESI calcd. for C$_{16}$H$_{14}$F$_6$N$_5$O$_2$ [M+H]$^+$ 422.1, found 422.0.

Example 42: 6-[5-fluoro-6-[(1S)-2,2,2-trifluoro-1-methyl-ethoxy]-3-pyridyl]-3-(methoxymethyl)-[1,2,4]triazolo[4,3-a]pyridine

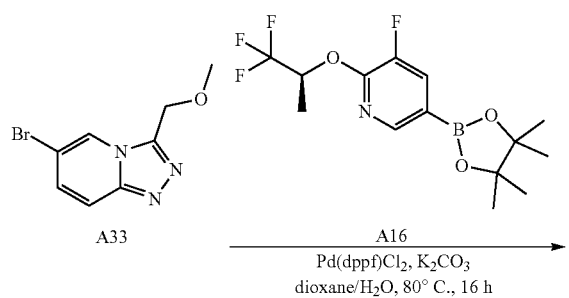

A mixture of 6-bromo-3-(methoxymethyl)-[1,2,4]triazolo[4,3-a]pyridine (100 mg, 0.41 mmol), Pd(dppf)Cl$_2$ (45.34 mg, 0.06 mmol), 3-fluoro-5-(4,4,5,5-tetramethyl-1,3,2-dioxaborolan-2-yl)-2-[(1S)-2,2,2-trifluoro-1-methyl-ethoxy]pyridine (166.12 mg, 0.50 mmol) and K$_2$CO$_3$ (114.19 mg, 0.83 mmol) in 1,4-Dioxane (5 mL) and water (1 mL) was stirred at 80° C. for 16 hours under N$_2$. After cooling to room temperature, the mixture was filtered through Celite, and eluted with EtOAc (10 mL×2), and the filtrate was concentrated to give the crude product. The crude product was purified by flash chromatography on silica gel (EtOAc in PE=50% to 100%). The product was then triturated from n-hexane/DCM (5:1, 10 mL) to give the product (46.5 mg, 0.13 mmol, 30% yield) as a solid. $^1$H NMR (DMSO-d$_6$, 400 MHz) $\delta_H$=8.84 (s, 1H), 8.49 (d, 1H), 8.35 (dd, 1H), 7.97-7.90 (m, 1H), 7.87-7.80 (m, 1H), 6.01 (spt, 1H), 5.01 (s, 2H), 3.34 (s, 3H), 1.54 (d, 3H). LCMS R$_t$=1.13 min in 2.0 min chromatography, 10-80AB, MS ESI calcd. for C$_{16}$H$_{15}$F$_4$N$_4$O$_2$ [M+H]$^+$ 371.1, found 370.9.

Example 43: 6-[5-fluoro-6-[(1S)-2,2,2-trifluoro-1-methyl-ethoxy]-3-pyridyl]-3-(methoxymethyl)-[1,2,4]triazolo[4,3-b]pyridazine

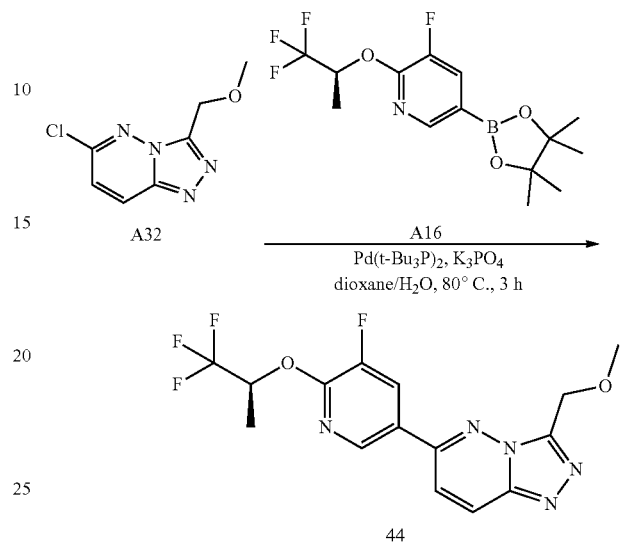

A mixture of 6-chloro-3-(methoxymethyl)-[1,2,4]triazolo[4,3-b]pyridazine (100 mg, 0.50 mmol), 3-fluoro-5-(4,4,5,5-tetramethyl-1,3,2-dioxaborolan-2-yl)-2-[(1S)-2,2,2-trifluoro-1-methyl-ethoxy]pyridine (202.47 mg, 0.60 mmol), K$_3$PO$_4$ (213.79 mg, 1.01 mmol) and Pd(t-Bu$_3$P)$_2$ (38.6 mg, 0.08 mmol) in 1,4-Dioxane (10 mL) and water (1 mL) was stirred at 80° C. under N$_2$ for 3 hours. After cooling to room temperature, water (20 mL) and EtOAc (20 mL) was added to the mixture and filtered through Celite. After separating, the organic phase was washed with brine (20 mL), dried over anhydrous Na$_2$SO$_4$, filtered and concentrated to give the crude product. The crude product was purified by Prep-HPLC (Boston Prime C18 (150 mm×30 mm, 5 μm) A=H$_2$O (0.05% NH$_4$OH) and B=CH$_3$CN; 33-63% B over 8 minutes) to give the product (38 mg, 102.3 μmol, 20% yield) as a solid. $^+$H NMR (CDCl$_3$, 400 MHz) $\delta_H$=8.53 (d, 1H), 8.25 (d, 1H), 8.14 (dd, 1H), 7.57 (d, 1H), 5.98-5.85 (m, 1H), 5.11 (s, 2H), 3.54 (s, 3H), 1.61 (d, 3H). LCMS R$_t$=1.13 min in 2.0 min chromatography, 10-80AB, MS ESI calcd. for C$_{15}$H$_{14}$F$_4$N$_5$O$_2$ [M+H]$^+$ 372.1, found 371.9.

Example 44: 3-[difluoro(isobutoxy)methyl]-6-[5-fluoro-6-[(1S)-2,2,2-trifluoro-1-methyl-ethoxy]-3-pyridyl]-[1,2,4]triazolo[4,3-a]pyrazine

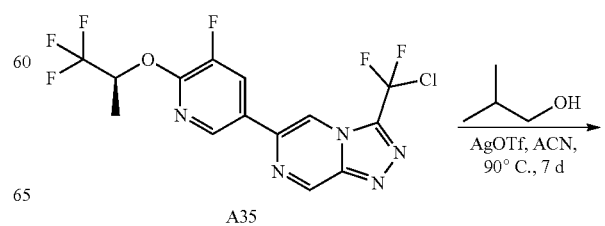

-continued

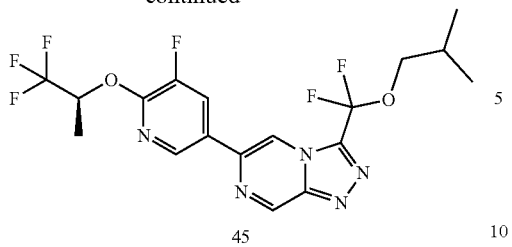

45

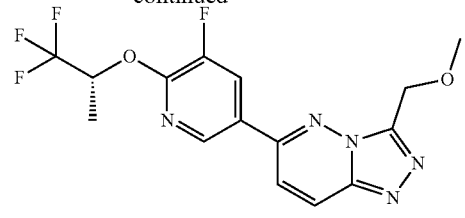

46

A mixture of 3-[chloro(difluoro)methyl]-6-[5-fluoro-6-[(1S)-2,2,2-trifluoro-1-methyl-ethoxy]-3-pyridyl]-[1,2,4]triazolo[4,3-a]pyrazine (200 mg, 0.49 mmol) and AgOTf (1.25 g, 4.86 mmol) in Isobutyl alcohol (10 mL) and MeCN (10 mL) was stirred at 90° C. for 7 days. The EtOAc (50 mL) and brine (50 mL) were added to the mixture and some solid was observed. The mixture was filtered through Celite. The filtrate was separated and the aqueous layer was extracted with EtOAc (50 mL). The combined organic phase was dried over anhydrous $Na_2SO_4$, filtered and concentrated to give the crude product. The crude product was purified by flash chromatography on silica gel (EtOAc in PE=10% to 30% to 50%) to give the product (80 mg) as an oil.

The impure product (80 mg, 0.18 mmol) was purified by Prep-HPLC (Boston Green ODS (150 mm×30 mm, 5 μm) A=$H_2O$ (0.075% TFA) and B=$CH_3CN$; 66-96% B over 8 minutes) and concentrated to give a residue. To the residue was added saturated aqueous $NaHCO_3$ (10 mL), and the mixture was extracted with EtOAc (15 mL×2). The combined organic phase was washed with brine (20 mL), dried over anhydrous $Na_2SO_4$, filtered and concentrated to give the product (55.97 mg, 124.6 μmol, 70% yield) as a solid. $^1$H NMR ($CDCl_3$+$D_2O$, 400 MHz) $\delta_H$=9.52 (d, 1H), 8.53-8.43 (m, 2H), 8.04 (dd, 1H), 5.98-5.84 (m, 1H), 4.06 (d, 2H), 2.21-2.06 (m, 1H), 1.60 (d, 3H), 1.08 (d, 6H). LCMS $R_t$=1.37 min in 2.0 min chromatography, 10-80AB, MS ESI calcd. for $C_{18}H_{18}F_6N_5O_2$ [M+H]$^+$ 450.1, found 450.0.

Example 45: 6-[5-fluoro-6-[(1R)-2,2,2-trifluoro-1-methyl-ethoxy]-3-pyridyl]-3-(methoxymethyl)-[1,2,4]triazolo[4,3-b]pyridazine

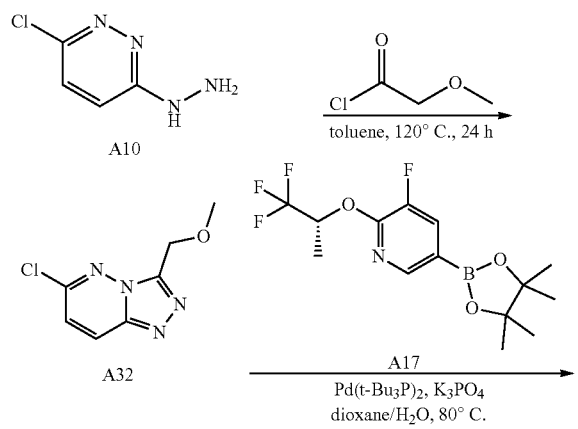

Synthesis of A32: To a solution of (6-chloropyridazin-3-yl)hydrazine (3 g, 20.75 mmol) in Toluene (80 mL) was added 2-methoxyacetyl chloride (2.48 g, 22.83 mmol) dropwise at 25° C. The solution was stirred at 25° C. for 30 min, and refluxed at 120° C. for 24 hours. After cooling to room temperature, the mixture was diluted with $H_2O$ (40 mL) and extracted with EtOAc (40 mL×2). The combined organic phase was washed with brine (40 mL), dried over $Na_2SO_4$, filtered and concentrated to give the crude product. The crude product was triturated from i-$Pr_2O$ (10 mL), to give the product (1500 mg, 7.31 mmol, 35% yield) as a solid. LCMS $R_t$=0.43 min in 1.5 min chromatography, 5-95AB, MS ESI calcd. for $C_7H_8ClN_4O$ [M+H]$^+$ 198.0, found 199.0.

Synthesis of Compound 46: A mixture of 6-chloro-3-(methoxymethyl)-[1,2,4]triazolo[4,3-b]pyridazine (100 mg, 0.5 mmol), 3-fluoro-5-(4,4,5,5-tetramethyl-1,3,2-dioxaborolan-2-yl)-2-[(1R)-2,2,2-trifluoro-1-methyl-ethoxy]pyridine (202.47 mg, 0.6 mmol), $K_3PO_4$ (213.79 mg, 1.01 mmol), Pd(t-$Bu_3P)_2$ (38.6 mg, 0.08 mmol) in 1,4-Dioxane (5 mL) and water (0.5 mL) was stirred at 80° C. for 12 hours under $N_2$. After cooling to room temperature, the mixture was diluted with $H_2O$ (10 mL) and extracted with EtOAc (20 mL×2). The combined organic phase was washed with water (10 mL) and brine (10 mL), dried over $Na_2SO_4$, filtered and concentrated to give the crude product. The crude product was purified by Prep-HPLC (column: Boston Prime (150 mm×30 mm, 5 μm; mobile phase: A=$H_2O$ (0.05% $NH_4OH$); B=$CH_3CN$, 35-65% B over 9 min) to give the product (43.29 mg, 0.12 mmol, 23% yield) as a solid. $^1$H NMR ($CDCl_3$, 400 MHz) $\delta_H$=8.53 (d, 1H), 8.25 (d, 1H), 8.14 (dd, 1H), 7.57 (d, 1H), 5.98-5.5.85 (m, 1H), 5.11 (s, 2H), 3.54 (s, 3H), 1.61 (d, 3H). LCMS $R_t$=1.17 min in 2.0 min chromatography, 10-80AB, MS ESI calcd. for $C_{15}H_{14}F_4N_5O_2$ [M+H]$^+$ 372.1, found 372.1.

Example 46: 3-[difluoro(isobutoxy)methyl]-6-[5-fluoro-6-[(1S)-2,2,2-trifluoro-1-methyl-ethoxy]-3-pyridyl]-[1,2,4]triazolo[4,3-b]pyridazine

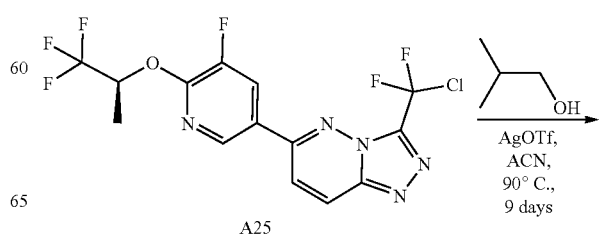

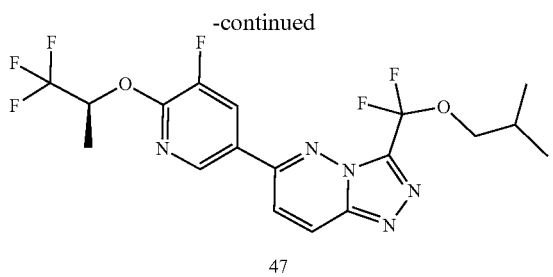

47

A mixture of 3-[chloro(difluoro)methyl]-6-[5-fluoro-6-[(1S)-2,2,2-trifluoro-1-methyl-ethoxy]-3-pyridyl]-[1,2,4]triazolo[4,3-b]pyridazine (300 mg, 0.73 mmol) and AgOTf (1872.33 mg, 7.29 mmol) in 2-methylpropan-1-ol (10 mL, 0.73 mmol) and MeCN (10 mL) was stirred at 90° C. for 9 days. After cooling to room temperature, the reaction was diluted with EtOAc (60 mL) and brine (20 mL), filtered through Celite, and extracted with EtOAc (50 mL×2). The combined organic layer was washed with water (50 mL) and brine (50 mL), dried over Na$_2$SO$_4$, filtered and concentrated to give the crude product. The crude product was purified by flash chromatography on silica gel (EtOAc in PE=0% to 70%) The isolated product was further purified by Prep-HPLC (Boston Prime C18 (150 mm×30 mm, 5 μm), A=H$_2$O (0.05% NH$_4$OH) and B=CH$_3$CN; 60-90% B over 9 minutes) to give the product (7.42 mg, 16.5 μmol, 2% yield) as a solid. $^1$H NMR (CDCl$_3$, 400 MHz) δ$_H$=8.54 (d, 1H), 8.30 (d, 1H), 8.14 (dd, 1H), 7.66 (d, 1H), 5.98-5.85 (m, 1H), 4.01 (d, 2H), 2.15-2.01 (m, 1H), 1.61 (d, 3H), 1.05 (d, 6H). LCMS R$_t$=1.39 min in 2.0 min chromatography, 10-80AB, MS ESI calcd. C$_{18}$H$_{18}$F$_6$N$_5$O$_2$ [M+H]$^+$ 450.1, found 450.1.

Example 47: 3-[ethoxy(difluoro)methyl]-6-[5-fluoro-6-[(1S)-2,2,2-trifluoro-1-methyl-ethoxy]-3-pyridyl]-[1,2,4]triazolo[4,3-b]pyridazine

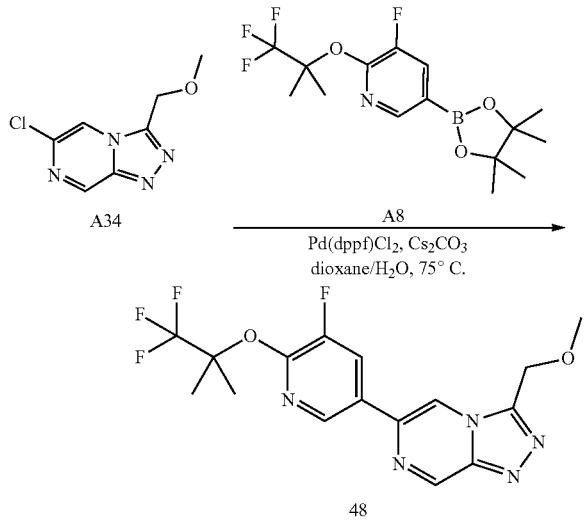

48

A mixture of 6-chloro-3-(methoxymethyl)-[1,2,4]triazolo[4,3-a]pyrazine (150 mg, 0.76 mmol), 3-fluoro-5-(4,4,5,5-tetramethyl-1,3,2-dioxaborolan-2-yl)-2-(2,2,2-trifluoro-1,1-dimethyl-ethoxy)pyridine (527.36 mg, 1.51 mmol), Cs$_2$CO$_3$ (738.18 mg, 2.27 mmol), Pd(dppf)Cl$_2$ (110.52 mg, 0.15 mmol) in 1,4-Dioxane (8 mL) and water (0.80 mL) was stirred at 75° C. for 9 hours under N$_2$. After cooling to room temperature, the mixture was diluted with H$_2$O (20 mL), and the mixture was extracted with EtOAc (30 mL×2). The combined organic phase was washed with water (30 mL×1) and brine (30 mL), dried over Na$_2$SO$_4$, filtered and concentrated to give the crude product. The crude product was purified by Prep-HPLC (Boston Prime C18 (150 mm×30 mm, 5 μm), A=H$_2$O (0.05% NH$_4$OH) and B=CH$_3$CN; 49-59% B over 9 minutes) to give the product (90.56 mg, 235 μmol, 31% yield) as a solid. $^1$H NMR (CDCl$_3$, 400 MHz) δ$_H$=9.43 (s, 1H), 8.57-8.40 (m, 2H), 8.01 (d, 1H), 5.13 (s, 2H), 3.46 (s, 3H), 1.88 (s, 6H). LCMS R$_t$=1.24 min in 2.0 min chromatography, 10-80AB, MS ESI calcd. C$_{16}$H$_{16}$F$_4$N$_5$O$_2$ [M+H]$^+$ 386.1 found 386.1

Example 48: 3-[difluoro(isobutoxy)methyl]-6-[5-fluoro-6-[(1R)-2,2,2-trifluoro-1-methyl-ethoxy]-3-pyridyl]-[1,2,4]triazolo[4,3-b]pyridazine

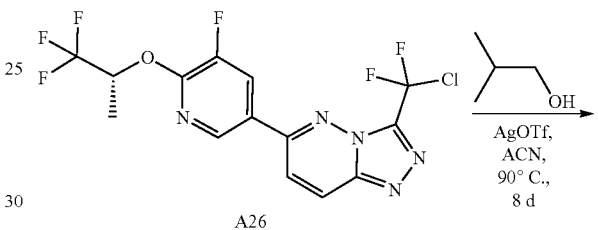

A26

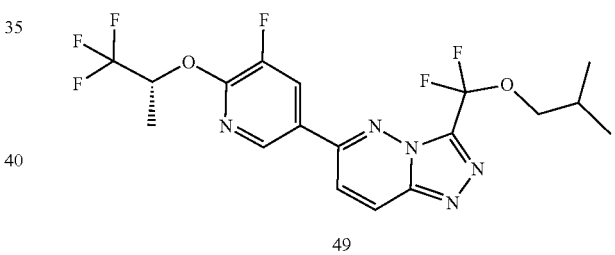

49

A mixture of 3-[chloro(difluoro)methyl]-6-[5-fluoro-6-[(1R)-2,2,2-trifluoro-1-methyl-ethoxy]-3-pyridyl]-[1,2,4]triazolo[4,3-b]pyridazine (500 mg, 1.21 mmol) and AgOTf (3120.6 mg, 12.15 mmol) in 2-methylpropan-1-ol (10 mL, 1.21 mmol) and CH$_3$CN (10 mL) was stirred at 90° C. for 8 days. After cooling to room temperature, the reaction was diluted with EtOAc (40 mL), and the mixture was added with brine (40 mL), the mixture was filtered through Celite, and eluted with EtOAc (20 mL×2), and the filtrate was concentrated to give the crude product. The crude product was purified by flash chromatography on silica gel (EtOAc in PE=0% to 50% to 100%) to give the impure product. The impure product was purified by Prep-HPLC (Waters Xbridge 150 mm×25 mm, 5 μm) A=H$_2$O (10 mM NH$_4$HCO$_3$) and B=CH$_3$CN; 54-84% B over 8 minutes) to give the product (53.85 mg, 0.12 mmol, 10% yield) as a solid. $^1$H NMR (CDCl$_3$, 400 MHz) δ$_H$=8.54 (d, 1H), 8.30 (d, 1H), 8.13 (dd, 1H), 7.66 (d, 1H), 5.92 (spt, 1H), 4.01 (d, 2H), 2.16-2.04 (m, 1H), 1.61 (d, 3H), 1.05 (d, 6H). LCMS R$_t$=1.42 min in 2.0 min chromatography, 10-80AB, MS ESI calcd. for C$_{18}$H$_{18}$F$_6$N$_5$O$_2$ [M+H]$^+$ 450.1, found 450.1.

Example 49: 3-(ethoxymethyl)-6-[5-fluoro-6-[(1S)-2,2,2-trifluoro-1-methyl-ethoxy]-3-pyridyl]-[1,2,4]triazolo[4,3-a]pyrazine

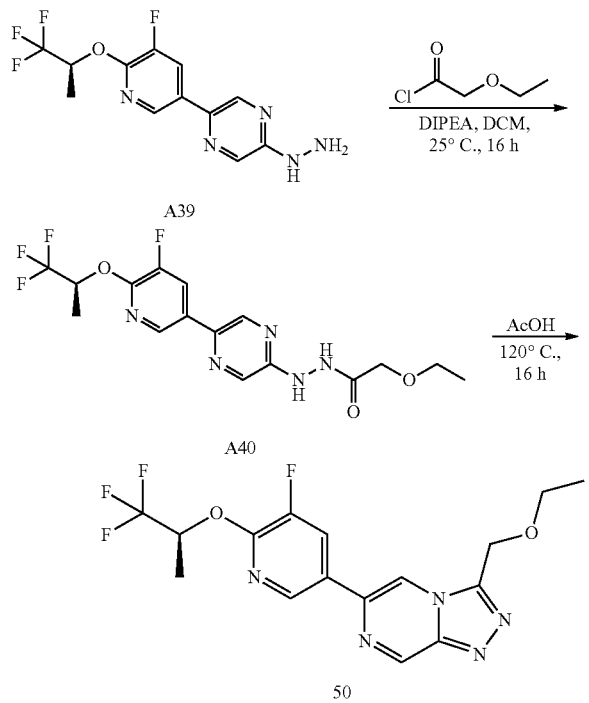

Example 50: 3-[cyclopropoxy(difluoro)methyl]-6-[5-fluoro-6-[(1R)-2,2,2-trifluoro-1-methyl-ethoxy]-3-pyridyl]-[1,2,4]triazolo[4,3-a]pyrazine

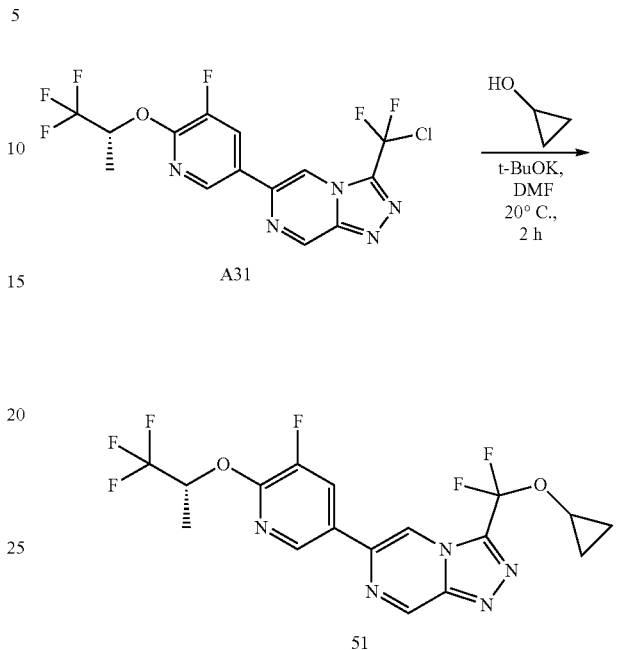

To a mixture of cyclopropanol (28.22 mg, 0.49 mmol), 3-[chloro(difluoro)methyl]-6-[5-fluoro-6-[(1R)-2,2,2-trifluoro-1-methyl-ethoxy]-3-pyridyl]-[1,2,4]triazolo[4,3-a]pyrazine (100 mg, 0.24 mmol) in DMF (2 mL) was added potassium tert-butoxide (54.51 mg, 0.49 mmol) dropwise. The reaction mixture was stirred at 20° C. for 2 hours. The reaction was quenched with saturated NH$_4$Cl (10 mL), and the mixture was extracted with EtOAc (10 mL×2). The combined organic phase was washed with brine (10 mL), dried over Na$_2$SO$_4$, filtered and concentrated to give the crude product. The crude product was purified by Prep-HPLC (Waters Xbridge (150 mm×25 mm, 5 μm) A=H$_2$O (10 mM NH$_4$HCO$_3$) and B=CH$_3$CN; 57-67% B over 8 minutes) to give the product (3.98 mg, 0.01 mmol, 4% yield) as an oil. $^1$H NMR (CD$_3$CN, 400 MHz) δ$_H$=9.46 (s, 1H), 8.67-8.56 (m, 2H), 8.20 (dd, 1H), 6.01-5.92 (m, 1H), 4.21-4.14 (m, 1H), 1.58 (d, 3H), 1.00-0.91 (m, 2H), 0.81-0.73 (m, 2H). LCMS R$_t$=1.31 min in 2 min chromatography, 10-80AB, MS ESI calcd. for C$_{17}$H$_{14}$F$_6$N$_5$O$_2$ [M+H]$^+$ 434.1, found 433.9.

Synthesis of A40: A mixture of [5-[5-fluoro-6-[(1S)-2,2,2-trifluoro-1-methyl-ethoxy]-3-pyridyl]pyrazin-2-yl]hydrazine (200 mg, 0.63 mmol), DIPEA (0.33 mL, 1.89 mmol), and 2-ethoxyacetyl chloride (92.71 mg, 0.76 mmol) in CH$_2$Cl$_2$ (10 mL) was stirred at 25° C. for 16 hours. The mixture was concentrated to the residue, and the residue was re-dissolved in EtOAc (20 mL), washed with water (10 mL×2), brine (10 mL×2), dried over anhydrous Na$_2$SO$_4$, filtered and concentrated to give the product (150 mg, 0.13 mmol, 20% yield) as a solid. LCMS R$_t$=0.84 min in 1.5 min chromatography, 5-95AB, MS ESI calcd. for C$_{16}$H$_{18}$F$_4$N$_5$O$_3$ [M+H]$^+$ 404.1, found 404.2.

Synthesis of Compound 50: To a mixture of 2-ethoxy-N'-[5-[5-fluoro-6-[(1S)-2,2,2-trifluoro-1-methyl-ethoxy]-3-pyridyl]pyrazin-2-yl]acetohydrazide (150 mg, 0.37 mmol) in Acetic acid (15 mL) was stirred at 120° C. for 4 days. After cooling to room temperature, the mixture was concentrated yielding a solid. The solid was re-dissolved in EtOAc (20 mL), basified with sat. Na$_2$CO$_3$ to pH 9, washed with water (10 mL×2), brine (10 mL×2), dried over anhydrous Na$_2$SO$_4$, filtered and concentrated to give the crude product. The crude product was purified by Prep-HPLC (Boston Prime C18 150 mm×30 mm 5 μm) A=H$_2$O (0.05% ammonia hydroxide) and B=CH$_3$CN; 45-75% B over 9 minutes) to give the product (48.08 mg, 0.12 mmol, 34% yield) as a solid. $^1$H NMR (DMSO-d$_6$, 400 MHz) δ$_H$=9.55 (d, 1H), 9.15 (d, 1H), 8.77 (d, 1H), 8.49 (dd, 1H), 6.08-5.98 (m, 1H), 5.08 (s, 2H), 3.61 (q, 2H), 1.55 (d, 3H), 1.15 (t, 3H). LCMS R$_t$=1.23 min in 2.0 min chromatography, 10-80AB, MS ESI calcd. for C$_{16}$H$_{16}$F$_4$N$_5$O$_2$ [M+H]$^+$ 386.1, found 386.0.

Example 51: 3-(ethoxymethyl)-6-[5-fluoro-6-[(1R)-2,2,2-trifluoro-1-methyl-ethoxy]-3-pyridyl]-[1,2,4]triazolo[4,3-a]pyrazine

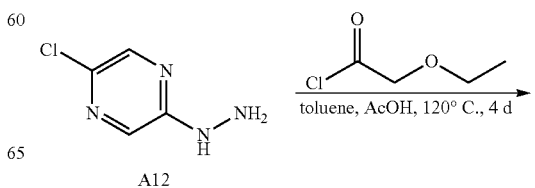

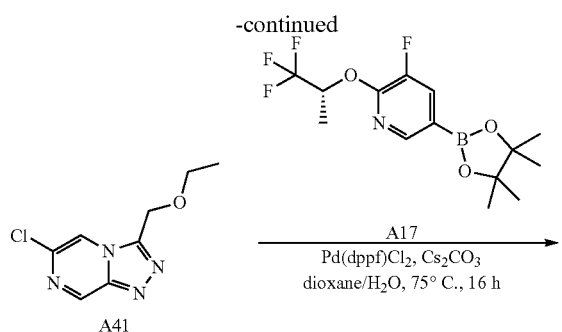

Synthesis of A41: To a mixture of (5-chloropyrazin-2-yl) hydrazine (500 mg, 3.46 mmol) and 2-ethoxyacetyl chloride (551.03 mg, 4.5 mmol) in Toluene (7 mL) was stirred at 20° C. for 2 hours then heated to 130° C. for 3 days. Then most of the toluene was removed, and Acetic acid (40 mL) was added and and stirred at 120° C. for 16 hours. After cooling to room temperature, the mixture was concentrated to give a residue. The residue was re-dissolved in EtOAc (40 mL), basified with saturated $Na_2CO_3$ to pH 9, washed with water (20 mL×2), brine (20 mL×2), dried over anhydrous $Na_2SO_4$, filtered and concentrated to give the crude product. The crude product was purified by flash chromatography on silica gel (EtOAc in PE=40% to 70%), to give the product (240 mg, 1.11 mmol, 32% yield) as a solid. LCMS $R_t$=0.60 min in 1.5 min chromatography, 5-95AB, MS ESI calcd. for $C_8H_{10}ClN_4O$ $[M+H]^+$ 213.0, found 213.0.

Synthesis of Compound 52: A mixture of 3-fluoro-5-(4,4,5,5-tetramethyl-1,3,2-dioxaborolan-2-yl)-2-[(1R)-2,2,2-trifluoro-1-methyl-ethoxy]pyridine (453.86 mg, 1.35 mmol), $Cs_2CO_3$ (1103.16 mg, 3.39 mmol), 6-chloro-3-(ethoxymethyl)-[1,2,4]triazolo[4,3-a]pyrazine (240 mg, 1.13 mmol) and $Pd(dppf)Cl_2$ (123.88 mg, 0.17 mmol) in 1,4-Dioxane (10 mL) and water (2 mL) was stirred at 75° C. for 16 hours under $N_2$. After cooling to room temperature, the mixture was filtered through Celite, and eluted with EtOAc (10 mL×2), and the filtrate was concentrated to give the crude product. The crude product was purified by flash chromatography on silica gel (EtOAc in PE=30% to 60% to 100%) to give the impure product. The impure product was purified by Prep-HPLC (Waters Xbridge 150 mm×25 mm, 5 μm) A=$H_2O$ (10 mM $NH_4HCO_3$) and B=$CH_3CN$; 40-70% B over 8 minutes) to give the product (37.8 mg, 98.1 μmol, 9% yield) as a solid. $^1$H NMR (DMSO-$d_6$, 400 MHz) $\delta_H$=9.56 (d, 1H), 9.15 (d, 1H), 8.77 (d, H), 8.49 (dd, 1H), 6.09-5.97 (m, 1H), 5.08 (s, 2H), 3.61 (q, 2H), 1.55 (d, 3H), 1.14 (t, 3H). LCMS $R_t$=1.24 min in 2.0 min chromatography, 10-80AB, MS ESI calcd. for $C_{16}H_{16}F_4N_5O_2$ $[M+H]^+$ 386.1, found 386.1.

Example 52: 3-[difluoro(methoxy)methyl]-6-[5-fluoro-6-(2,2,2-trifluoroethoxy)-3-pyridyl]-[1,2,4]triazolo[4,3-a]pyrazine

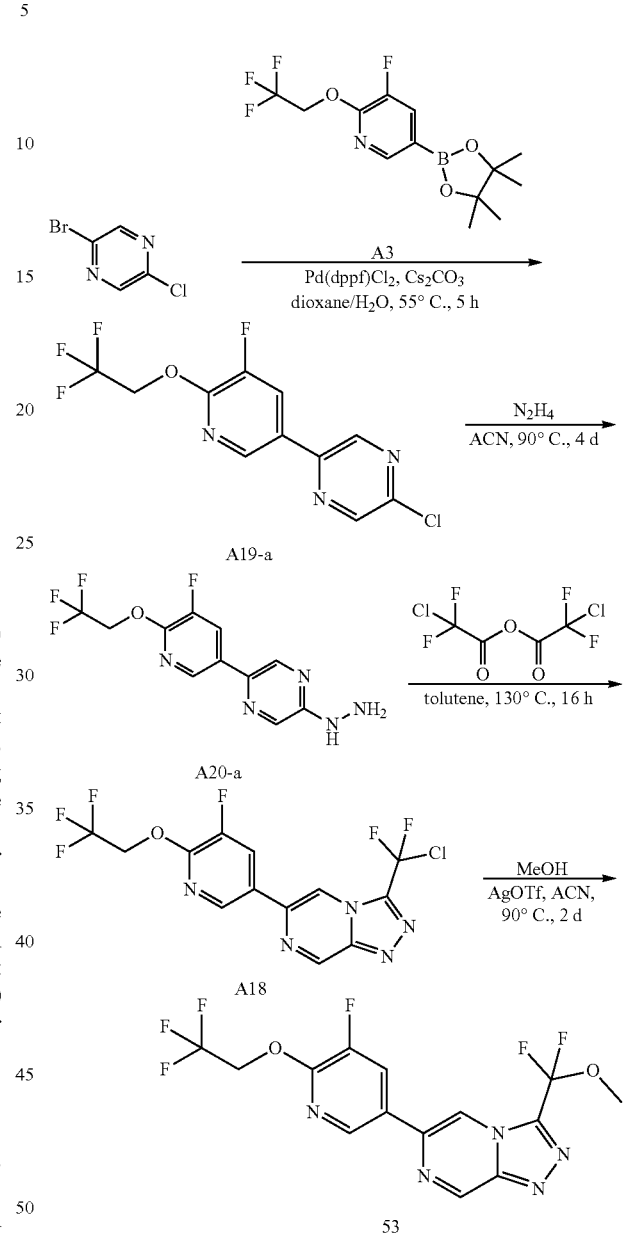

Synthesis of A19-a: A mixture of 2-bromo-5-chloropyrazine (3 g, 15.51 mmol), 3-fluoro-5-(4,4,5,5-tetramethyl-1,3,2-dioxaborolan-2-yl)-2-(2,2,2-trifluoroethoxy)pyridine (4.98 g, 15.51 mmol), $Cs_2CO_3$ (10.11 g, 31.02 mmol) and $Pd(dppf)Cl_2$ (1.7 g, 2.33 mmol) in 1,4-Dioxane (50 mL) and water (5 mL) was stirred at 55° C. under $N_2$ for 5 hours. The reaction was cooled to room temperature and concentrated to give a residue. To the residue was added water (50 mL) and EtOAc (50 mL) and then the mixture was filtered. After separation, the organic phase was washed with brine (50 mL), dried over anhydrous $Na_2SO_4$, filtered and concentrated to give the crude product. The crude product was purified by chromatography flash on silica gel (EtOAc in PE=0% to 5% to 10%) to give the product (3700 mg, 10.69 mmol, 69% yield) as a solid. $^1$H NMR (DMSO-$d_6$, 400 MHz) $\delta_H$=9.19 (d, 1H), 8.88 (d, 1H), 8.80 (d, 1H), 8.49 (dd, 1H), 5.18 (q, 2H). LCMS $R_t$=0.93 min in 1.5 min chromatography, 5-95AB, MS ESI calcd. for $C_{11}H_{17}ClF_4N_3O$ [M+H]$^+$ 308.0, found 308.0.

Synthesis of A20-a: To a mixture of 2-chloro-5-[5-fluoro-6-(2,2,2-trifluoroethoxy)-3-pyridyl]pyrazine (3.7 g, 12.03 mmol) in MeCN (50 mL) was added hydrazine (3.85 g, 120.27 mmol), and the mixture was stirred at 90° C. for 16 hours. The reaction was cooled to room temperature and concentrated to give a residue. Water (30 mL) was added to the residue and extracted with EtOAc (30 mL×2). The combined organic phase was washed with brine (30 mL), dried over anhydrous $Na_2SO_4$, filtered and concentrated to give the crude product (3500 mg, 9.60 mmol, 80% yield) as a solid. $^1$H NMR (DMSO-$d_6$, 400 MHz) $\delta_H$=8.62 (d, 1H), 8.58 (d, 1H), 8.30-8.24 (m, 2H), 8.19 (d, 1H), 5.12 (q, 2H), 4.36 (s, 2H). LCMS $R_t$=0.73 min in 1.5 min chromatography, 5-95AB, MS ESI calcd. for $C_{11}H_{10}F_4N_5O$ [M+1H]$^+$ 304.1, found 304.0.

Synthesis of A18: A solution of [5-[5-fluoro-6-(2,2,2-trifluoroethoxy)-3-pyridyl]pyrazin-2-yl]hydrazine (3 g, 9.89 mmol) and (2-chloro-2,2-difluoro-acetyl) 2-chloro-2,2-difluoro-acetate (7.21 g, 29.68 mmol) in Toluene (60 mL) was stirred at 110° C. for 96 hours, Then to the mixture was added molecular sieves (3 g), and the mixture was stirred at 130° C. for another 16 hours. After cooling to room temperature, the mixture was concentrated to give a residue. To the residue was added water (20 mL), extracted with EtOAc (30 mL×2). The combined organic phase was washed with water (20 mL), brine (20 mL×2), dried over anhydrous $Na_2SO_4$, filtered and concentrated to give the crude product. The crude product was purified by flash chromatography column on silica gel (EtOAc in PE=0% to 10% to 20%) to give the product (1300 mg, 3.24 mmol, 33% yield) as an oil. LCMS $R_t$=2.63 min in 4 min chromatography, 10-80AB, MS ESI calcd. for $C_{13}H_7ClF_6N_5O$ [M+H]$^+$ 398.0, found 397.9.

Synthesis of Compound 53: A mixture of 3-[chloro(difluoro)methyl]-6-[5-fluoro-6-(2,2,2-trifluoroethoxy)-3-pyridyl]-[1,2,4]triazolo[4,3-a]pyrazine (600 mg, 1.51 mmol) and AgOTf (3.88 g, 15.09 mmol), in Methanol (12 mL) and DMF (4 mL) was stirred at 90° C. for 48 hours. After cooling to room temperature, the reaction mixture was treated with brine (20 mL), and the precipitate was filtrated. The filtrate was concentrated and diluted with water (20 mL), then extracted with EtOAc (20 mL×3). The combined organic phase was washed with brine (20 mL), dried over $Na_2SO_4$ and concentrated to give a crude product. The crude product was purified by flash chromatography on silica gel (EtOAc in PE=0% to 10% to 30%) to give the product (247.53 mg, 0.63 mmol, 42% yield) as a solid. $^1$H NMR (CDCl$_3$, 400 MHz) $\delta_H$=9.52 (d, 1H), 8.52 (d, 1H), 8.46 (d, 1H), 8.07 (dd, 1H), 4.93 (q, 2H), 3.98 (s, 3H). LCMS $R_t$=1.23 min in 1.5 min chromatography, 5-95AB, MS ESI calcd. for $C_{14}H_{10}F_6N_5O_2$ [M+H]$^+$ 394.1, found 394.0.

Example 53: 3-[difluoro(methoxy)methyl]-6-[6-(2,2,2-trifluoro-1,1-dimethyl-ethoxy)-3-pyridyl]-[1,2,4]triazolo[4,3-a]pyrazine

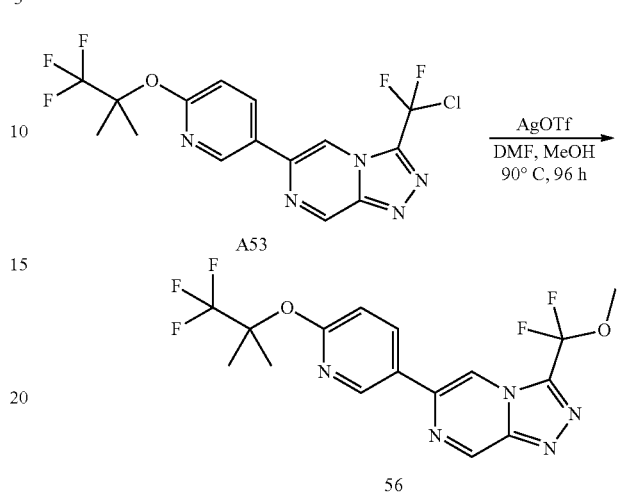

A mixture of 3-[chloro(difluoro)methyl]-6-[6-(2,2,2-trifluoro-1,1-dimethyl-ethoxy)-3-pyridyl]-[1,2,4]triazolo[4,3-a]pyrazine (1.9 g, 4.66 mmol) and AgOTf (11.97 g, 46.59 mmol) in solvents DMF (15 mL) and methanol (15 mL) was stirred at 90° C. for 96 hours. After cooling to room temperature, the reaction mixture was treated with brine (50 mL), and the precipitate was filtrated. The filtrate was concentrated and diluted with water (40 mL), then extracted with EtOAc (50 mL×2). The combined organic phase was washed with brine (50 mL), dried over $Na_2SO_4$ and concentrated to give a crude product. The crude product was purified with flash chromatography on silica gel (EtOAc in PE=0% to 40%) to give the product (170 mg). Another 88 mg of the product was obtained from other batch. Three batches of the product were combined and lyophilized to give the product (193.0 mg, 0.48 mmol) as a solid. $^1$H NMR (400 MHz, CDCl$_3$) $\delta$=9.52 (d, 1H), 8.72 (d, 1H), 8.43 (s, 1H), 8.19 (dd, 1H), 6.94 (d, 1H), 3.98 (s, 3H), 1.87 ppm (s, 6H). LCMS $R_t$=1.235 min in 2.0 min chromatography, 10-80AB, MS ESI calcd. for $C_{16}H_{15}F_5N_5O_2$ [M+H]$^+$ 404.1, found 403.9.

Example 54: 3-[chloro(difluoro)methyl]-6-[6-[1-(trifluoromethyl)cyclobutoxy]-3-pyridyl]-[1,2,4]triazolo[4,3-a]pyrazine

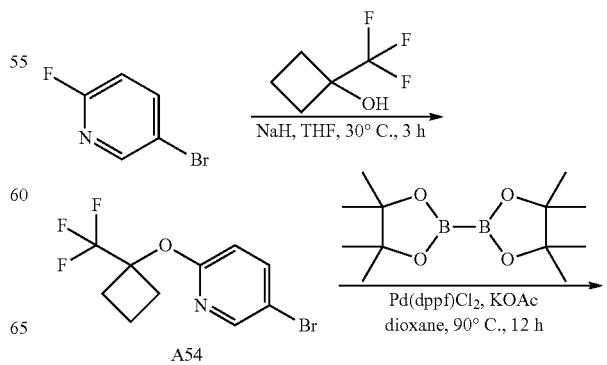

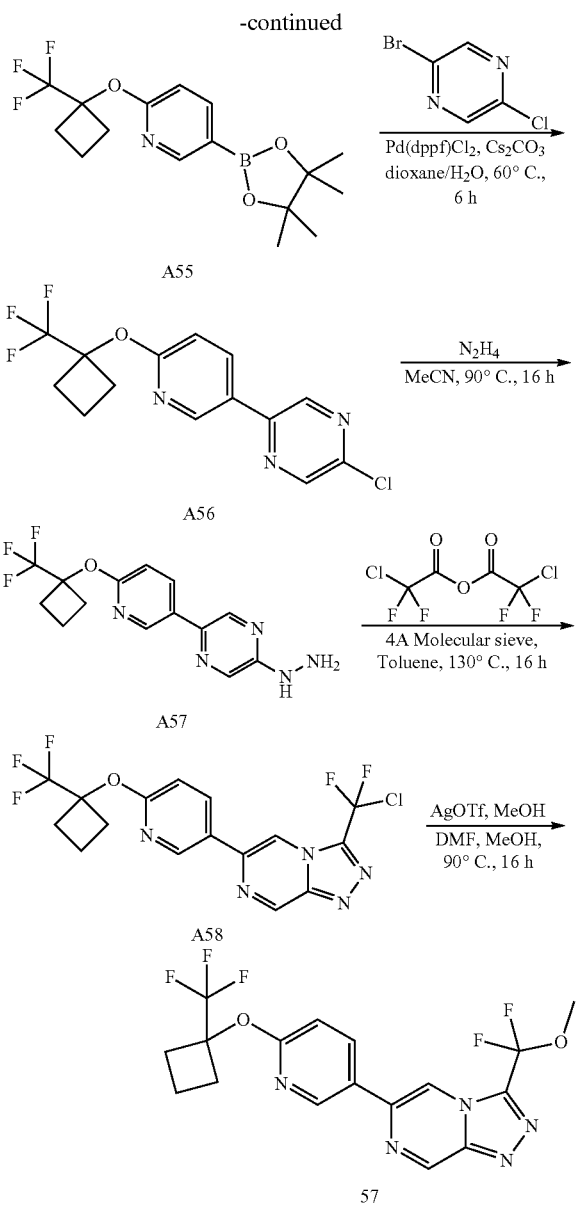

was concentrated to give the residue. The residue was diluted with H₂O (40 mL), and the mixture was extracted with EtOAc (40 mL×2). The combined organic phase was washed with water (40 mL) and brine (40 mL), dried over Na$_2$SO$_4$, filtered and concentrated to give the crude product. The crude product was purified by flash chromatography on silica gel (EtOAc in PE=0% to 1%) to give the crude product (2.65 g, 3.92 mmol, 46% yield) as an oil. $^1$H NMR (CDCl$_3$, 400 MHz) δ$_H$=8.54 (d, 1H), 7.95 (dd, 1H), 6.74 (d, 1H), 2.99-2.81 (m, 2H), 2.75-2.53 (m, 2H), 2.13-1.78 (m, 2H), 1.34 (s, 12H).

Synthesis of A56: A mixture of 5-(4,4,5,5-tetramethyl-1,3,2-dioxaborolan-2-yl)-2-[1-(trifluoromethyl)cyclobutoxy]pyridine (2.1 g, 6.12 mmol), 2-bromo-5-chloro-pyrazine (1.18 g, 6.12 mmol), Pd(dppf)Cl$_2$ (671.68 mg, 0.92 mmol) and Cs$_2$CO$_3$ (3.99 g, 12.24 mmol) in 1,4-Dioxane (20 mL) and Water (2 mL) was stirred at 60° C. for 6 hours under N$_2$. After cooling to room temperature, the mixture was concentrated to give the residue. The residue was diluted with H$_2$O (20 mL), and the mixture was extracted with EtOAc (20 mL×2). The combined organic phase was washed with water (20 mL) and brine (40 mL), dried over Na$_2$SO$_4$, filtered and concentrated to give the crude product. The crude product was purified by flash chromatography on silica gel (EtOAc in PE=0% to 1% to 10%) to give the product (1.5 g, 4.263 mmol, 70% yield) as an oil. $^1$H NMR (CDCl$_3$, 400 MHz) δ$_H$=8.80-8.72 (m, 2H), 8.63 (d, 1H), 8.25 (dd, 1H), 6.91 (d, 1H), 3.01-2.83 (m, 2H), 2.78-2.62 (m, 2H), 2.18-1.84 (m, 2H).

Synthesis of A57: A mixture of 2-chloro-5-[6-[1-(trifluoromethyl)cyclobutoxy]-3-pyridyl]pyrazine (1.2 g, 3.64 mmol) and hydrazine (1.17 g, 36.4 mmol) in MeCN (20 mL) was heated to 90° C. and stirred for 16 hours. After cooling to room temperature, the reaction mixture was concentrated and diluted with H$_2$O (30 mL) and extracted with EtOAc (30 mL×2). The combined organic phase was washed with brine (30 mL), dried over Na$_2$SO$_4$, filtered and concentrated to give crude product (950 mg, 2.48 mmol, 68% yield) as a solid. LCMS R$_t$=0.99 min in 2.0 min chromatography, 10-80AB, MS ESI calcd. for C$_{14}$H$_{15}$F$_3$N$_5$O [M+H]$^+$ 326.1, found 326.0.

Synthesis of A58: A mixture of [5-[6-[1-(trifluoromethyl)cyclobutoxy]-3-pyridyl]pyrazin-2-yl]hydrazine (1.13 g, 3.47 mmol), 4A Molecular sieve (1 g, 3.47 mmol) and (2-chloro-2,2-difluoro-acetyl) 2-chloro-2,2-difluoro-acetate (1.69 g, 6.95 mmol) in Toluene (15 mL) was heated to 130° C. and stirred for 16 hours. After cooling to room temperature, the reaction mixture was filtered and diluted with H$_2$O (50 mL) and extracted with EtOAc (50 mL×2). The combined organic phase was washed with brine (50 mL), dried over Na$_2$SO$_4$, filtered and concentrated to give the crude product (820 mg, 1.13 mmol, 33% yield) as a solid.

LCMS R$_t$=1.38 min in 2.0 min chromatography, 10-80AB, MS ESI calcd. for C$_{16}$H$_{12}$ClF$_5$N$_5$O [M+H]$^+$ 420.1, found 420.0.

Synthesis of Compound 57: A mixture of 3-[chloro(difluoro)methyl]-6-[6-[1-(trifluoromethyl)cyclobutoxy]-3-pyridyl]-[1,2,4]triazolo[4,3-a]pyrazine (600 mg, 1.43 mmol), AgOTf (4.4 g, 17.15 mmol) in DMF (6 mL) and methanol (6 mL, 1.43 mmol) was stirred at 90° C. for 16 hours. After cooling to room temperature, the reaction was quenched with sat. NaCl (30 mL) and extracted with EtOAc (30 mL×2). The organic layer was washed with brine (30 mL), dried over Na$_2$SO$_4$, filtered and concentrated to give the crude product. The crude product was purified by flash chromatography on silica gel (EtOAc in PE=0% to 40% to 70%) to give the product (194.76 mg, 0.47 mmol, 33%

Synthesis of A54: To a solution of 1-(trifluoromethyl)cyclobutanol (5 g, 35.69 mmol) in THF (300 mL) was added NaH (1.86 g, 46.4 mmol) at 0° C. over 20 minutes, and the mixture was stirred at 0° C. for 30 mins. Then to the mixture was added 5-bromo-2-fluoro-pyridine (8.48 g, 48.18 mmol), and the mixture was stirred at 30° C. for 3 hours. The mixture was quenched with sat. NH$_4$Cl (50 mL), then the mixture was extracted with EtOAc (50 mL). The combined organic phase was washed with brine (50 mL×3), dried over Na$_2$SO$_4$, filtered and concentrated to give the crude product (4.8 g, 15.49 mmol, 43% yield) as an oil. LCMS R$_t$=0.99 min in 1.5 min chromatography, 5-95AB, MS ESI calcd. for C$_{10}$H$_{10}$BrF$_3$NO [M+H]$^+$ 295.9, found 296.0.

Synthesis of A55: A mixture of 5-bromo-2-[1-(trifluoromethyl)cyclobutoxy]pyridine (2.5 g, 8.44 mmol), 4,4,5,5-tetramethyl-2-(4,4,5,5-tetramethyl-1,3,2-dioxaborolan-2-yl)-1,3,2-dioxaborolane (3.22 g, 12.67 mmol), KOAc (1.66 g, 16.89 mmol) and Pd(dppf)Cl$_2$ (432.48 mg, 0.59 mmol) in 1,4-Dioxane (50 mL) was stirred at 90° C. for 12 hours under N$_2$. After cooling to room temperature, the mixture yield) as a solid. ¹H NMR (CDCl₃, 400 MHz) δ_H=9.52 (d, 1H), 8.72 (d, 1H), 8.44 (d, 1H), 8.23 (dd, 1H), 7.0-6.89 (m, 1H), 3.97 (s, 3H), 3.00-2.85 (m, 2H), 2.80-2.63 (m, 2H), 2.13-1.89 (m, 2H). LCMS R_t=1.33 min in 2.0 min chromatography, 10-80AB, MS ESI calcd. for $C_{17}H_{15}F_5N_5O_2$ [M+H]⁺ 416.1, found 416.1.

Example 56: 3-[difluoro(methoxy)methyl]-6-[5-fluoro-6-[(1S)-2,2,2-trifluoro-1-methyl-ethoxy]-3-pyridyl]-5-methyl-[1,2,4]triazolo[4,3-a]pyrazine

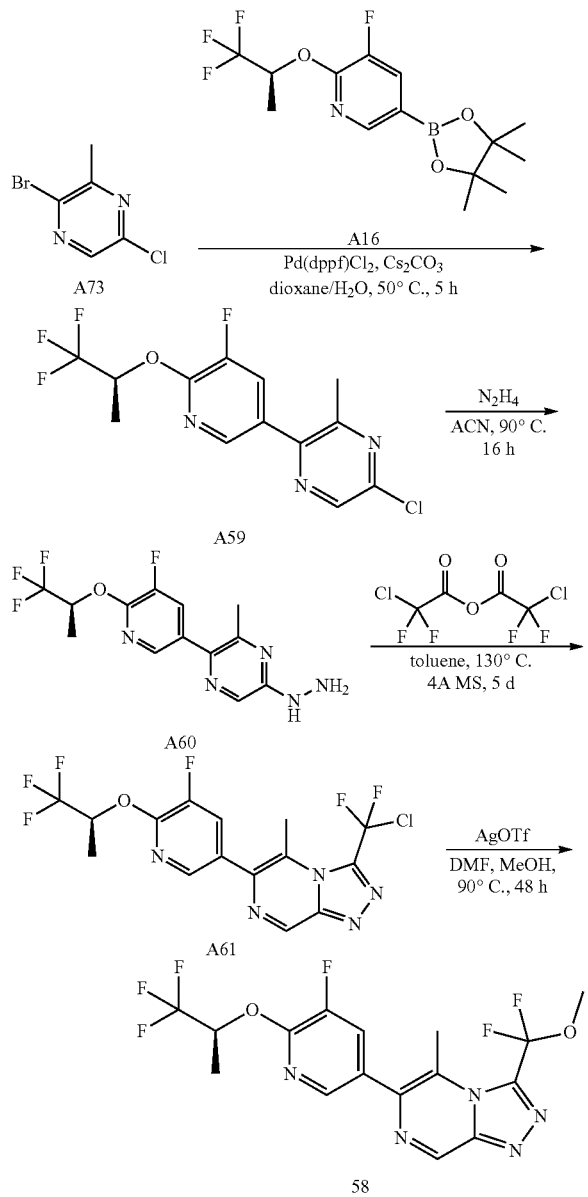

Synthesis of A59: A mixture of 2-bromo-5-chloro-3-methyl-pyrazine (900 mg, 4.34 mmol), 3-fluoro-5-(4,4,5,5-tetramethyl-1,3,2-dioxaborolan-2-yl)-2-[(1S)-2,2,2-trifluoro-1-methyl-ethoxy]pyridine (1.31 g, 3.9 mmol), Pd(dppf)Cl₂ (0.48 g, 0.65 mmol) and Cs₂CO₃ (2.83 g, 8.68 mmol) in 1,4-Dioxane (40 mL) and Water (8 mL) was stirred under N₂ at 50° C. for 5 hours. The mixture was cooled to room temperature, diluted with EtOAc (30 mL), filtered through silica gel and eluted with EtOAc (20 mL), and the filtrate was concentrated to give the crude product. The product was purified by flash chromatography on silica gel (EtOAc in PE=0% to 3%) to give the product (1100 mg, 2.83 mmol, 65% yield) as a solid. LCMS R_t=1.41 min in 1.5 min chromatography, 10-80AB, MS ESI calcd. for $C_{13}H_{11}ClF_4N_3O$ [M+H]⁺ 336.0, found 336.0.

Synthesis of A60: A mixture of 5-chloro-2-[5-fluoro-6-[(1S)-2,2,2-trifluoro-1-methyl-ethoxy]-3-pyridyl]-3-methyl-pyrazine (1.1 g, 3.28 mmol) and hydrazine (1.05 g, 32.83 mmol) in MeCN (20 mL) was heated to 90° C. and stirred for 16 hours. After cooling to room temperature, the reaction mixture was concentrated. The mixture was diluted with H₂O (20 mL), extracted with EtOAc (20 mL×2). The combined organic phase was washed with brine (20 mL), dried over Na₂SO₄, filtered and concentrated to give the crude product. The crude product was triturated from PE (5 mL) to give the product (800 mg, 2.41 mmol, 68% yield) as a solid. The crude product was used into the next step without further purification. LCMS R_t=0.75 min in 1.5 min chromatography, 5-95AB, MS ESI calcd. for $C_{13}H_{14}F_4N_5O$ [M+H]⁺ 332.1, found 332.1.

Synthesis of A61: To a mixture of [5-[5-fluoro-6-[(1S)-2,2,2-trifluoro-1-methyl-ethoxy]-3-pyridyl]-6-methyl-pyrazin-2-yl]hydrazine (500 mg, 1.51 mmol) in Toluene (10 mL) was added (2-chloro-2,2-difluoro-acetyl) 2-chloro-2,2-difluoro-acetate (366.68 mg, 1.51 mmol) and 4A Molecular Sieves (1 g). The reaction mixture was stirred at 110° C. for 5 days. After cooling to room temperature, the reaction mixture was concentrated. The residue was diluted with sat. NaHCO₃ (30 mL), and the mixture was extracted with EtOAc (30 mL×2). The combined organic phase was washed with brine (20 mL), dried over Na₂SO₄, filtered and concentrated to give a residue. The residue was purification by flash column on silica gel (EtOAc in PE=0% to 20%) to give the product (105 mg, 0.16 mmol, 11% yield) as a solid. LCMS R_t=0.92 min in 1.5 min chromatography, 5-95AB, MS ESI calcd. for $C_{15}H_{11}ClF_6N_5O$ [M+H]⁺ 426.0, found 426.2.

Synthesis of Compound 58: A mixture of 3-[chloro(difluoro)methyl]-6-[5-fluoro-6-[(1 S)-2,2,2-trifluoro-1-methyl-ethoxy]-3-pyridyl]-5-methyl-[1,2,4]triazolo[4,3-a]pyrazine (105 mg, 0.25 mmol) and AgOTf (633.7 mg, 2.47 mmol) in mixed solvent Methanol (1 mL) and DMF (1 mL) was stirred at 90° C. for 48 hours. After cooling to room temperature, the reaction mixture was treated with brine (15 mL), and the precipitate was filtered off. The filtrate was extracted with EtOAc (15 mL×2). The combined organic phase was dried over Na₂SO₄ and concentrated to give a crude product. The crude product was purified by flash chromatography on silica gel (EtOAc in PE=0% to 30% to 50%). The e product was then triturated from DCM (0.5 mL) and n-hexane (0.5 mL) to give the product (2.05 mg, 4.90 μmol, 2% yield). ¹H NMR (CDCl₃, 400 MHz) δ_H=9.39 (s, 1H), 8.11 (d, 1H), 7.69 (dd, 1H), 5.94-5.86 (m, 1H), 3.92 (s, 3H), 2.88 (s, 3H), 1.60 (d, 3H). LCMS R_t=1.24 min in 2 min chromatography, 10-80AB, MS ESI calcd. for $C_{16}H_{14}F_6N_5O_2$ [M+H]⁺ 422.1, found 422.0.

Example 57: 3-[difluoro(methoxy)methyl]-6-[6-[(1S)-2,2,2-trifluoro-1-methyl-ethoxy]-3-pyridyl]-[1,2,4]triazolo[4,3-a]pyrazine

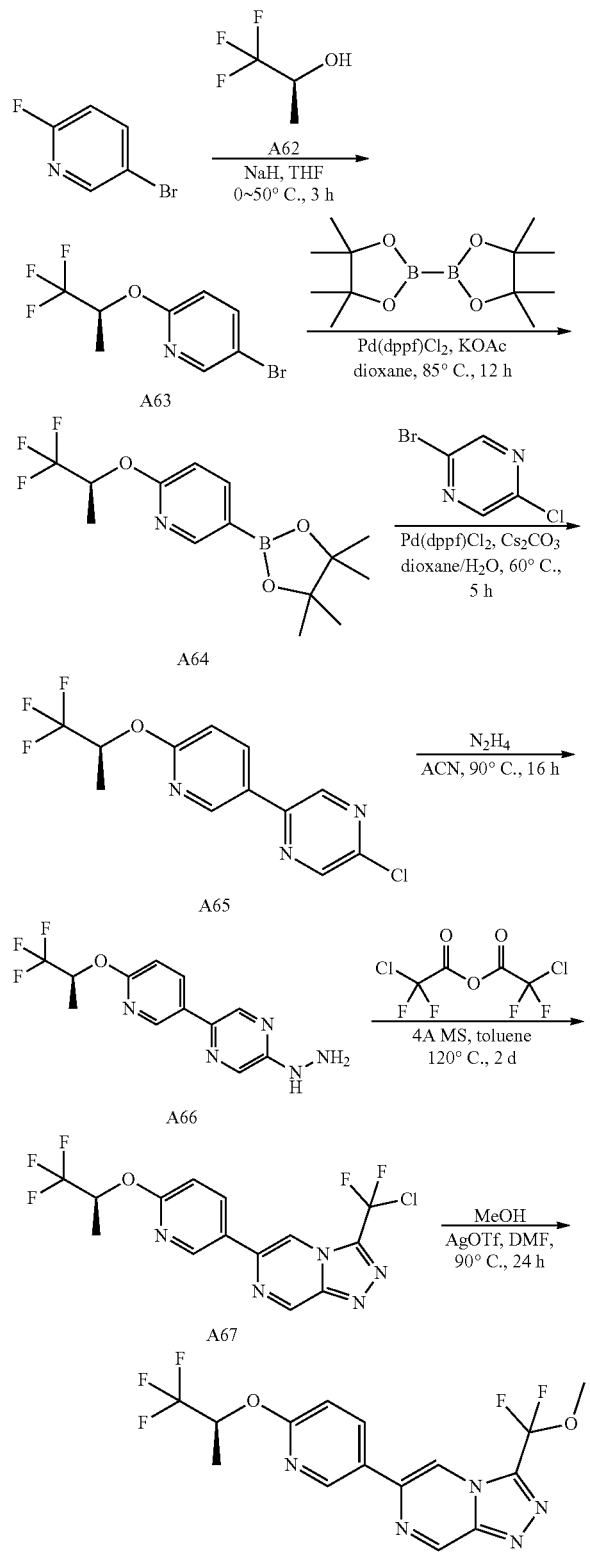

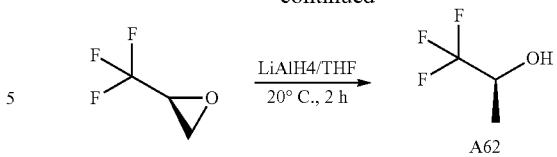

Synthesis of A62: To a mixture of (2S)-2-(trifluoromethyl)oxirane (3 g, 26.77 mmol) in THF (25 mL) was added LiAlH$_4$ (0.5 g, 13.2 mmol) at 0° C. under N$_2$ over 30 minutes, then the mixture was stirred at 20° C. for 2 hours. After cooling to 0° C., the mixture was quenched with water (0.9 g), the mixture was stirred at 35° C. for 30 minutes. The mixture was filtered through Celite, eluted with THF (20 mL×2), the organic phase was washed with brine (20 mL×2) and dried over Na$_2$SO$_4$, filtered to give the crude product of (2S)-1,1,1-trifluoropropan-2-ol (3 g, 26.3 mmol, 98% yield) as a solution in THF, which was used directly without any further purification.

Synthesis of A63: To a solution of (2S)-1,1,1-trifluoropropan-2-ol in THF (50 mL) was added NaH (0.8 g, 19.94 mmol) at 0° C. over 20 minutes, and the mixture was stirred at 0° C. for 40 minutes. Then to the mixture was added 5-bromo-2-fluoro-pyridine (2.7 g, 15.34 mmol), and the mixture was stirred at 50° C. for 2 hours. The mixture was quenched with sat. NH$_4$Cl (40 mL), extracted with EtOAc (60 mL), the combined organic phase was washed with brine (40 mL×2), dried over Na$_2$SO$_4$, filtered and concentrated to give the crude product (3.48 g, 9.29 mmol, 61% yield) as an oil. LCMS R$_t$=0.95 min in 1.5 min chromatography, 5-95AB, MS ESI calcd. for C$_8$H$_8$BrF$_3$NO [M+H]$^+$ 270.0, found 269.9.

Synthesis of A64: A mixture of 5-bromo-2-[(1S)-2,2,2-trifluoro-1-methyl-ethoxy]pyridine (3.48 g, 12.89 mmol), 4,4,5,5-tetramethyl-2-(4,4,5,5-tetramethyl-1,3,2-dioxaborolan-2-yl)-1,3,2-dioxaborolane (4.91 g, 19.33 mmol), KOAc (2.53 g, 25.77 mmol) and Pd(dppf)Cl$_2$ (1.13 g, 1.55 mmol) in 1,4-Dioxane (35 mL) was stirred at 85° C. for 12 hours under N$_2$. After cooling to room temperature, the mixture was concentrated to give a residue. The residue was diluted with H$_2$O (30 mL), and the mixture was extracted with EtOAc (40 mL×2). The combined organic phase was washed with water (40 mL) and brine (40 mL), dried over Na$_2$SO$_4$, filtered and concentrated to give the crude product. The crude product was purified by flash chromatography on silica gel (EtOAc in PE=0% to 1%) to give the product (3 g, 5.72 mmol, 44% yield) as an oil. $^1$H NMR (DMSO-d$_6$, 400 MHz) δ$_H$=8.42 (d, 1H), 7.96 (dd, 1H), 6.93 (d, 1H), 6.00-5.93 (m, 1H), 1.45 (d, 3H), 1.30 (s, 12H). LCMS R$_t$=1.02 min in 1.5 min chromatography, 5-95AB, MS ESI calcd. for C$_{14}$H$_{20}$BF$_3$NO$_3$ [M+H]$^+$ 318.1, found 318.1.

Synthesis of A65: A mixture of 5-(4,4,5,5-tetramethyl-1,3,2-dioxaborolan-2-yl)-2-[(1S)-2,2,2-trifluoro-1-methyl-ethoxy]pyridine (600 mg, 1.89 mmol), 2-bromo-5-chloropyrazine (329.39 mg, 1.7 mmol), Pd(dppf)Cl$_2$ (207.67 mg, 0.28 mmol) and Cs$_2$CO$_3$ (1232.88 mg, 3.78 mmol) in 1,4-Dioxane (15 mL) and Water (1.5 mL) was stirred at 60° C. for 5 hours under N$_2$. After cooling to room temperature, the mixture was concentrated to give the residue. The residue was diluted with H$_2$O (20 mL), and the mixture was extracted with EtOAc (30 mL×2). The combined organic phase was washed with water (20 mL) and brine (20 mL), dried over Na$_2$SO$_4$, filtered and concentrated to give the crude product. The crude product was purified by flash chromatography on silica gel (EtOAc in PE=0% to 3%) to give the product (350 mg, 1.15 mmol, 61% yield) as an oil. LCMS R$_f$=0.95 min in 1.5 min chromatography, 5-95AB, MS ESI calcd. for C$_{12}$H$_{10}$ClF$_3$N$_3$O [M+H]$^+$ 304.0, found 304.1.

Synthesis of A66: A mixture of 2-chloro-5-[6-[(1S)-2,2,2-trifluoro-1-methyl-ethoxy]-3-pyridyl]pyrazine (351.14 mg, 1.16 mmol) and hydrazine (741.21 mg, 23.13 mmol) in CH$_3$CN (5 mL) was stirred at 90° C. for 16 hours. After cooling to room temperature, the reaction was quenched with sat.NH$_4$Cl (30 mL), and the mixture was extracted with EtOAc (20 mL×2). The combined organic phase was washed with brine (30 mL), dried over Na$_2$SO$_4$, filtered and concentrated to give the crude product (350 mg, 1.05 mmol, 91% yield) as a solid. LCMS R$_f$=0.74 min in 1.5 min chromatography, 5-95AB, MS ESI calcd. for C$_{12}$H$_{13}$F$_3$N$_5$O [M+H]$^+$ 300.1, found 300.1.

Synthesis of A67: A mixture of [5-[6-[(1S)-2,2,2-trifluoro-1-methyl-ethoxy]-3-pyridyl]pyrazin-2-yl]hydrazine (350 mg, 1.17 mmol), (2-chloro-2,2-difluoro-acetyl) 2-chloro-2,2-difluoro-acetate (852.42 mg, 3.51 mmol) and 4A Molecular Sieves (500 mg, 1.17 mmol) in Toluene (8 mL) was stirred at 120° C. for 2 days. After cooling to room temperature, the reaction was quenched with saturated NaHCO$_3$ (20 mL), and the mixture was extracted with EtOAc (20 mL×2). The combined organic phase was washed with water (20 mL) and brine (20 mL), dried over Na$_2$SO$_4$, filtered and concentrated to give the product (420 mg, 1.01 mmol, 86% yield) as a solid. LCMS R$_f$=0.92 min in 1.5 min chromatography, 5-95ABMS ESI calcd. for C$_{14}$H$_{10}$ClF$_5$N$_5$O [M+H]$^+$ 394.0, found 394.1.

Synthesis of Compound 59: A mixture of 3-[chloro(difluoro)methyl]-6-[6-[(1S)-2,2,2-trifluoro-1-methyl-ethoxy]-3-pyridyl]-[1,2,4]triazolo[4,3-a]pyrazine (420 mg, 1.07 mmol), AgOTf (3289.25 mg, 12.8 mmol) in DMF (6 mL) and methanol (6 mL, 1.07 mmol) was stirred at 90° C. for 24 hours. After cooling to room temperature, the reaction was diluted with EtOAc (30 mL) and quenched with saturated NaCl (30 mL), and the mixture was filtered through Celite and eluted with EtOAc (10 mL). The filtrate was washed with water (30 mL) and brine (30 mL), dried over Na$_2$SO$_4$, filtered and concentrated to give the crude product. The crude product was purified by flash chromatography on silica gel (EtOAc in PE=0% to 15% to 30%) to give the impure product. The impure product was triturated from n-hexane/DCM (2:1, 6 mL) to give the product (118.39 mg, 0.30 mmol, 29% yield) as a solid. $^1$H NMR (CD$_3$CN, 400 MHz) δ$_H$=9.46 (d, 1H), 8.81 (d, 1H), 8.66 (d, 1H), 8.35 (dd, 1H), 6.99 (d, 1H), 5.99-5.88 (m, 1H), 3.94 (s, 3H), 1.53 (d, 3H). LCMS R$_f$=1.28 min in 2.0 min chromatography, 10-80AB, MS ESI calcd. for C$_{15}$H$_{13}$F$_5$N$_5$O$_2$ [M+H]$^+$ 390.1, found 390.0.

Example 58: 3-[difluoro(methoxy)methyl]-6-[5-fluoro-6-[(1R)-2,2,2-trifluoro-1-methyl-ethoxy]-3-pyridyl]-5-methyl-[1,2,4]triazolo[4,3-a]pyrazine

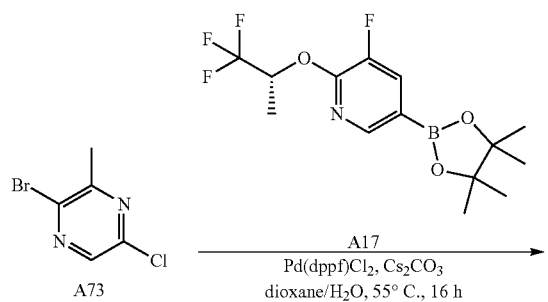

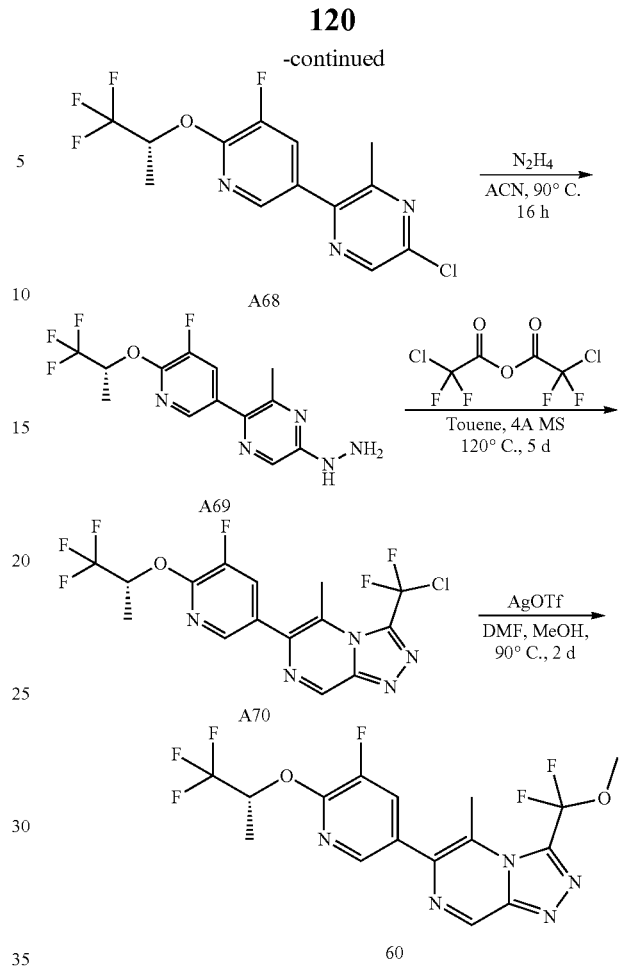

Synthesis of A68: A mixture of 2-bromo-5-chloro-3-methyl-pyrazine (900 mg, 4.34 mmol), 3-fluoro-5-(4,4,5,5-tetramethyl-1,3,2-dioxaborolan-2-yl)-2-[(1R)-2,2,2-trifluoro-1-methyl-ethoxy]pyridine (1.31 g, 3.9 mmol), Pd(dppf)Cl$_2$ (0.48 g, 0.65 mmol) and Cs$_2$CO$_3$ (2.83 g, 8.68 mmol) in 1,4-Dioxane (40 mL) and water (8 mL) was stirred under N$_2$ at 55° C. for 16 hours. The mixture was cooling to room temperature, diluted with EtOAc (50 mL), filtered with silica gel, eluted with EtOAc (20 mL) and concentrated to give the crude product. The product was purified by flash chromatography on silica gel (EtOAc in PE=0% to 20%) yielding the product (930 mg, 2.62 mmol, 60% yield) as a colorless oil. LCMS R$_f$=0.95 min in 1.5 min chromatography, 5-95AB, MS ESI calcd. for C$_{13}$H$_{11}$ClF$_4$N$_3$O [M+H]$^+$ 336.0, found 336.1.

Synthesis of A69: A mixture of hydrazine (1775.89 mg, 55.41 mmol) and 5-chloro-2-[5-fluoro-6-[(1R)-2,2,2-trifluoro-1-methyl-ethoxy]-3-pyridyl]-3-methyl-pyrazine (930 mg, 2.77 mmol) in CH$_3$CN (10 mL) was stirred at 90° C. for 16 hours. After cooling to room temperature, the reaction was quenched with sat.NH$_4$Cl (30 mL), and the mixture was extracted with EtOAc (40 mL×2). The combined organic phase was washed with water (30 mL) and brine (30 mL), dried over Na$_2$SO$_4$, filtered and concentrated to give the crude product (980 mg, 2.45 mmol, 89% yield) as a solid. LCMS R$_f$=0.75 min in 1.5 min chromatography, 5-95AB, MS ESI calcd. for C$_{13}$H$_{14}$F$_4$N$_5$O [M+H]$^+$ 332.1, found 332.2.

Synthesis of A70: A mixture of [5-[5-fluoro-6-[(1R)-2,2,2-trifluoro-1-methyl-ethoxy]-3-pyridyl]-6-methyl-pyrazin- 2-yl]hydrazine (600 mg, 1.81 mmol), (2-chloro-2,2-difluoro-acetyl) 2-chloro-2,2-difluoro-acetate (1320.05 mg, 5.43 mmol) and 4A Molecular Sieves (600 mg, 1.81 mmol) in Toluene (10 mL) was stirred at 120° C. for 5 days. After cooling to room temperature, the reaction was quenched with saturated NaHCO$_3$ (20 mL), and the mixture was extracted with EtOAc (20 mL×2). The combined organic phase was washed with water (20 mL) and brine (20 mL), dried over Na$_2$SO$_4$, filtered and concentrated to give the crude product. The crude product was purified by flash chromatography on silica gel (EtOAc in PE=0% to 40%) to give the product (140 mg, 0.22 mmol, 12% yield) as a solid. LCMS R$_t$=0.92 min in 1.5 min chromatography, 5-95AB, MS ESI calcd. for C$_{15}$H$_{11}$ClF$_6$N$_5$O [M+H]$^+$ 426.0, found 426.1.

Synthesis of Compound 60: A mixture of 3-[chloro(difluoro)methyl]-6-[5-fluoro-6-[(1R)-2,2,2-trifluoro-1-methylethoxy]-3-pyridyl]-5-methyl-[1,2,4]triazolo[4,3-a]pyrazine (140 mg, 0.33 mmol), AgOTf (1267.44 mg, 4.93 mmol) in DMF (2 mL) and methanol (2 mL, 0.33 mmol) was stirred at 90° C. for 2 days. After cooling to room temperature, the reaction was diluted with EtOAc (10 mL) and saturated NaCl (10 mL), and the mixture was filtered through Celite and eluted with EtOAc (10 mL). The combined organic phase was washed with water (10 mL) and brine (10 mL), dried over Na$_2$SO$_4$, filtered and concentrated to give the crude product. The crude product was purified by Prep-TLC (silica gel, PE:EtOAc=2:1) to give the impure product. The impure product was triturated from n-hexane/DCM (2:1, 3 mL) to give the product (11.92 mg, 28.3 μmol, 9% yield) as a solid. $^1$H NMR (CDCl$_3$, 400 MHz) δ$_H$=9.39 (s, 1H), 8.11 (d, 1H), 7.69 (dd, 1H), 5.96-5.85 (m, 1H), 3.92 (s, 3H), 2.88 (s, 3H), 1.60 (d, 3H). LCMS R$_t$=1.28 min in 2.0 min chromatography, 10-80AB, MS ESI calcd. for C$_{16}$H$_{14}$F$_6$N$_5$O$_2$ [M+H]$^+$ 422.1, found 422.2.

Example 59: 3-[difluoro(methoxy)methyl]-6-[5-fluoro-6-(2,2,2-trifluoroethoxy)-3-pyridyl]-5-methyl-[1,2,4]triazolo[4,3-a]pyrazine

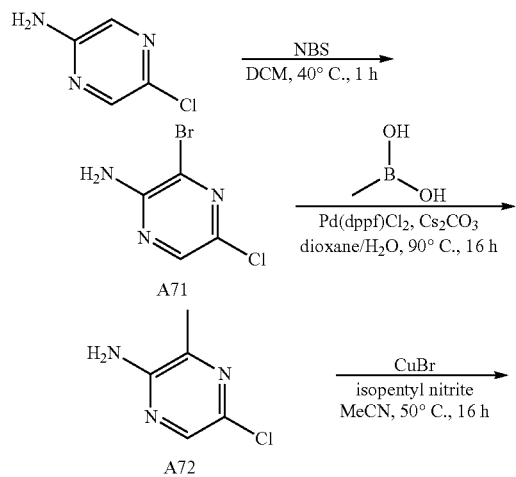

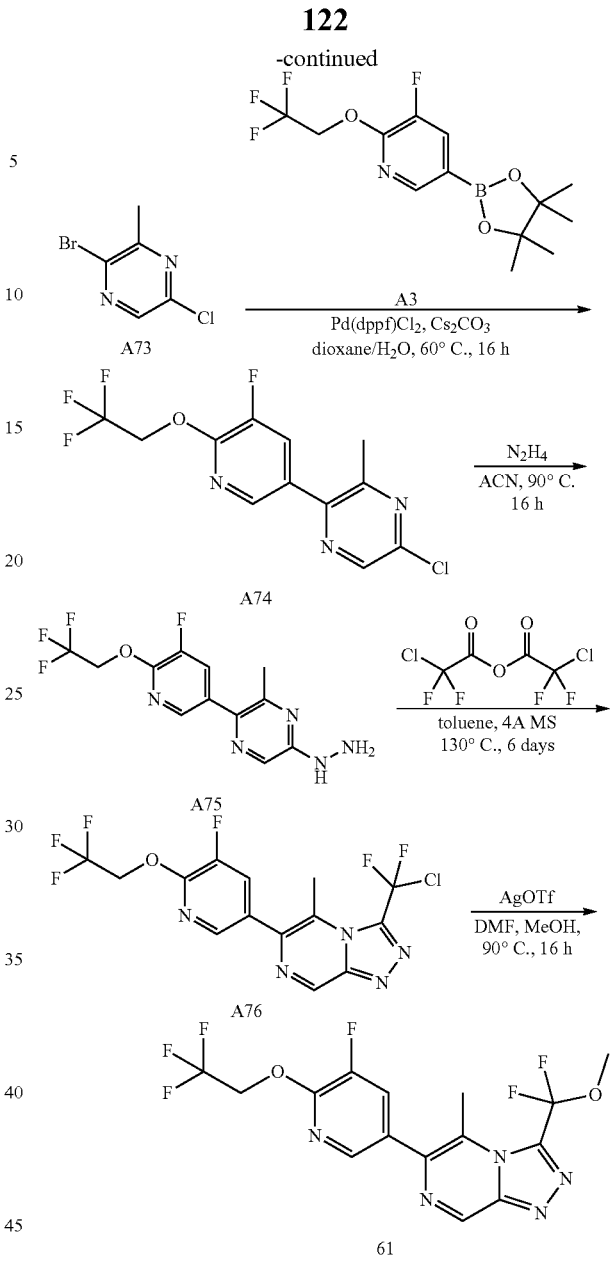

Synthesis of A71: To a solution of 5-chloropyrazin-2-amine (25 g, 192.98 mmol) in DCM (250 mL) was added NBS (34.35 g, 192.98 mmol). The resulting mixture was stirred at 40° C. for 1 hour. After cooling to room temperature and concentrated, water (200 mL) was added to give residue, extracted with EtOAc (150 mL×2). The combined organic phase was washed with brine (150 mL), dried over Na$_2$SO$_4$, filtered and concentrated to give the crude product. The crude product was purified by chromatography column on silica gel (EtOAc in PE=0% to 15% to 30%) to give the product (31 g, 148.72 mmol, 77% yield) as a solid. $^1$H NMR (DMSO-d$_6$, 400 MHz) δ$_H$=8.09 (s, 1H), 6.96 (s, 2H).

Synthesis of A72: A mixture of 3-bromo-5-chloropyrazin-2-amine (31 g, 148.72 mmol), Pd(dppf)Cl$_2$ (16.32 g, 22.31 mmol), methylboronic acid (13.35 g, 223.09 mmol) and Cs$_2$CO$_3$ (96.91 g, 297.45 mmol) in Water (30 mL) and 1,4-Dioxane (300 mL) was stirred at 90° C. for 16 hours. After cooling to room temperature, the mixture was concentrated to give a residue. To the residue was added water (100 mL), extracted with EtOAc (100 mL×2). The combined organic phase was washed with brine (100 mL), dried over anhydrous Na$_2$SO$_4$, filtered and concentrated to give the crude product. The crude product was purified by flash chromatography on silica gel (EtOAc in PE=20% to 40% to 60% to 80%) to give the product (13 g, 90.548 mmol, 61% yield) as a solid. $^1$H NMR (DMSO-d$_6$, 400 MHz) $\delta_H$=7.83 (s, 1H), 6.40 (s, 2H), 2.26 (s, 3H).

Synthesis of A73: A mixture of 5-chloro-3-methyl-pyrazin-2-amine (3 g, 20.9 mmol), isopentyl nitrite (3.67 g, 31.34 mmol) and CuBr (3 g, 20.9 mmol) in MeCN (30 mL) was stirred at 50° C. for 12 hours. The mixture was diluted with H$_2$O (30 mL), and the mixture was extracted with EtOAc (70 mL×2). The combined organic phase was washed with water (30 mL×2) and brine (30 mL), dried over Na$_2$SO$_4$, filtered and concentrated to give the crude product. The crude product was purified by flash column chromatography on silica gel (DCM in PE=0% to 2%) to give the product (1.2 g, 5.78 mmol, 28% yield) as an oil. $^1$H NMR (CDCl$_3$, 400 MHz) $\delta_H$=8.22 (s, 1H), 2.68 (s, 3H). LCMS R$_t$=1.10 min in 2.0 min chromatography, 10-80AB, MS ESI calcd. for C$_5$H$_5$BrClN$_2$ [M+H]$^+$ 208.9, found 208.7.

Synthesis of A74: A mixture of 2-bromo-5-chloro-3-methyl-pyrazine (1.2 g, 5.78 mmol), 3-fluoro-5-(4,4,5,5-tetramethyl-1,3,2-dioxaborolan-2-yl)-2-(2,2,2-trifluoroethoxy)pyridine (1.3 g, 4.05 mmol), Cs$_2$CO$_3$ (3.77 g, 11.57 mmol) and Pd(dppf)Cl$_2$ (634.85 mg, 0.87 mmol) in 1,4-Dioxane (30 mL) and water (3 mL) was stirred at 60° C. under N$_2$ for 16 hours. After cooling to room temperature, water (30 mL) and EtOAc (50 mL) were added to the mixture and the mixture was filtered through Celite. After the filtrate was separated, the organic phase was washed with brine (30 mL), dried over anhydrous Na$_2$SO$_4$, filtered and concentrated to give the crude product. The crude product was purified by flash column chromatography on silica gel (EtOAc in PE=0% to 1% to 2%) to give the product (580 mg, 1.71 mmol, 30% yield) as a solid. $^1$H NMR (CDCl$_3$, 400 MHz) $\delta_H$=8.52 (s, 1H), 8.19 (d, 1H), 7.73 (dd, 1H), 4.91 (q, 2H), 2.69 (s, 3H). LCMS R$_t$=0.93 min in 1.5 min chromatography, 5-95AB, MS ESI calcd. for C$_{12}$H$_9$ClF$_4$N$_3$O [M+H]$^+$ 322.0, found 322.0.

Synthesis of A75: A solution of 5-chloro-2-[5-fluoro-6-(2,2,2-trifluoroethoxy)-3-pyridyl]-3-methyl-pyrazine (640 mg, 1.89 mmol) and hydrazine (605.42 mg, 18.89 mmol) in MeCN (20 mL) was stirred at 90° C. for 16 hours. After cooling to room temperature, the mixture was concentrated, water (20 mL) was added, and the mixture was extracted with EtOAc (20 mL×3). The combined organic phase was washed with brine (20 mL×2), dried over anhydrous Na$_2$SO$_4$, filtered and concentrated to give the crude product (530 mg, 1.30 mmol, 69% yield) as a solid. $^1$H NMR (DMSO-d$_6$, 400 MHz) $\delta_H$=8.18 (d, 1H), 8.08 (s, 1H), 8.06 (s, 1H), 7.97 (dd, 1H), 5.13 (q, 2H), 4.32 (br s, 2H), 2.41 (s, 3H). LCMS R$_t$=0.72 min in 1.5 min chromatography, 5-95AB, MS ESI calcd. for C$_{12}$H$_{12}$F$_4$N$_5$O [M+H]$^+$ 318.1, found 318.1.

Synthesis of A76: A solution of [5-[5-fluoro-6-(2,2,2-trifluoroethoxy)-3-pyridyl]-6-methyl-pyrazin-2-yl]hydrazine (530 mg, 1.67 mmol), (2-chloro-2,2-difluoro-acetyl) 2-chloro-2,2-difluoro-acetate (1.22 g, 5.01 mmol) and 4A Molecular Sieves (3 g) in Toluene (30 mL) was stirred at 120° C. for 6 days. After cooling to room temperature, the mixture was concentrated to give a residue. To the residue was added water (50 mL) then extracted with EtOAc (50 mL×2). The combined organic phase was washed with water (50 mL) and brine (50 mL×2), dried over anhydrous Na$_2$SO$_4$, filtered and concentrated to give the crude product. The crude product was purified by flash chromatography column on silica gel (EtOAc in PE=0% to 15% to 30%) to give the product (180 mg, 426.2 μmol, 26% yield) as an oil. LCMS R$_t$=3.64 min in 7.0 min chromatography, 10-80AB, MS ESI calcd. for C$_{14}$H$_9$ClF$_6$N$_5$O [M+H]$^+$ 412.0, found 412.1.

Synthesis of Compound 61: A solution of 3-[chloro(difluoro)methyl]-6-[5-fluoro-6-(2,2,2-trifluoroethoxy)-3-pyridyl]-5-methyl-[1,2,4]triazolo[4,3-a]pyrazine (180 mg, 0.44 mmol) and AgOTf (1.69 g, 6.56 mmol) in Methanol (5 mL) and DMF (5 mL) was stirred at 90° C. under N$_2$ for 16 hours. After cooling to room temperature, saturated NaCl (50 mL) and EtOAc (50 mL) were added to the mixture and the mixture was filtered through Celite. After separation, the organic phase was washed with brine (30 mL), dried over anhydrous Na$_2$SO$_4$, filtered and concentrated to give the crude product. The crude product was purified by flash column chromatography on silica gel (EtOAc in PE=0% to 15% to 30%) to give the product (38.62 mg, 94.1 μmol, 22% yield) as a solid. $^1$H NMR (CDCl$_3$, 400 MHz) $\delta_H$=9.39 (s, 1H), 8.12 (d, 1H), 7.71 (dd, 1H), 4.93 (q, 2H), 3.92 (s, 3H), 2.88 (s, 3H). LCMS R$_t$=1.20 min in 2.0 min chromatography, 10-80AB, MS ESI calcd. for C$_{15}$H$_{12}$F$_6$N$_5$O$_2$ [M+H]$^+$ 408.1, found 407.9.

Example 60: 3-[difluoro(methoxy)methyl]-6-[6-[(1R)-2,2,2-trifluoro-1-methyl-ethoxy]-3-pyridyl]-[1,2,4]triazolo[4,3-a]pyrazine

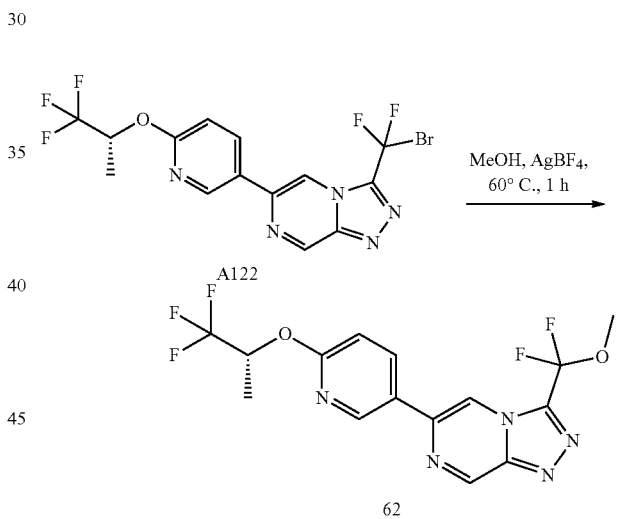

To a suspension of 3-[bromo(difluoro)methyl]-6-[6-[rac-(1R)-2,2,2-trifluoro-1-methyl-ethoxy]-3-pyridyl]-[1,2,4]triazolo[4,3-a]pyrazine (2.9 g, 6.62 mmol) in methanol (30 mL) was added AgBF$_4$ (2.58 g, 13.24 mmol) at 25° C. under N$_2$. The mixture was protected from light and stirred at 60° C. for 1 hour. The solution was added to saturated NaCl (30 mL) and filtered. The filter was extracted with EtOAc (20 mL×2). The combined organic phase was washed with brine (50 mL), dried over Na$_2$SO$_4$, filtered and concentrated. The crude product was purified by chromatography flash column on silica gel (EtOAc in PE=0% to 10% to 20%) to give the product (1.96 g, ee=92.28%) as a solid. Analytical SFC: Analysis by SFC (Chiralpak OJ-3 150×4.6 mm I.D., 3 um Mobile phase: A: CO$_2$, B: ethanol (0.05% DEA); Gradient: from 5% to 40% of B in 5 min and from 40% to 5% of B in 0.5 min, hold 5% of B for 1.5 min; Flow rate: 2.5 mL/min Column temp: 35° C.) showed two peaks at =2.71 min and 2.96 min. The product was separated by SFC (DAICEL CHIRALCEL OJ (250 mm×50 mm, 10 ∞cm); A=CO₂ and B=0.1% NH₃H₂O EtOH; 35° C.; 200 mL/min; 25% B; 8 min run; 100 injections, Rt of peak 1=4.2 min and Peak 2=4.7 min) to give the product (1415.6 mg, 3.64 mmol, 55% yield) as a solid. ¹H NMR (400 MHz, CD₃CN) δ$_H$=9.45 (d, 1H), 8.80 (d, 1H), 8.66 (d, 1H), 8.35 (dd, 1H), 6.99 (d, 1H), 5.97-5.90 (m, 1H), 3.94 (s, 3H), 1.53 (d, 3H). LCMS R$_t$=1.27 min in 2.0 min chromatography, 10-80AB, MS ESI calcd. for C$_{15}$H$_{13}$F$_5$N$_5$O$_2$ [M+H]⁺ 389.1, found 390.0.

Example 61: 3-[cyclopropoxy(difluoro)methyl]-6-[5-fluoro-6-[(1S)-2,2,2-trifluoro-1-methyl-ethoxy]-3-pyridyl]-[1,2,4]triazolo[4,3-a]pyrazine

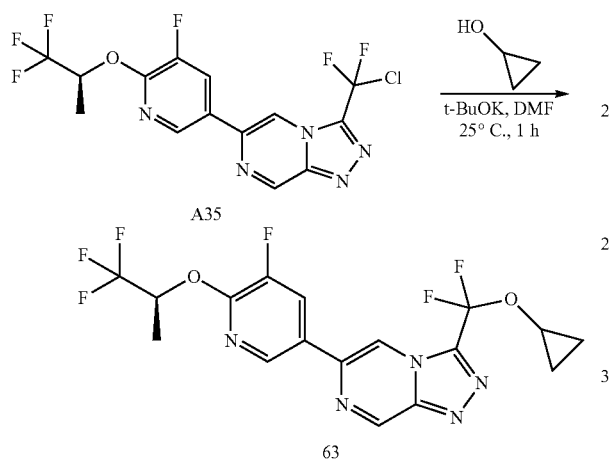

To a mixture of cyclopropanol (84.65 mg, 1.46 mmol), 3-[chloro(difluoro)methyl]-6-[5-fluoro-6-[(1S)-2,2,2-trifluoro-1-methyl-ethoxy]-3-pyridyl]-[1,2,4]triazolo[4,3-a]pyrazine (300 mg, 0.73 mmol) in DMF (5 mL) was added potassium tert-butoxide (163.54 mg, 1.46 mmol). The reaction mixture was stirred at 20° C. for 1 hour. The mixture was diluted with H₂O (10 mL) and extracted with EtOAc (10 mL×2). The combined organic phase was washed with brine (20 mL), dried over Na₂SO₄, filtered and concentrated to give the crude product. The crude product was purified by flash chromatography on silica gel (EtOAc in PE=0% to 30%) to give the impure product. The impure product was triturated from n-hexane/DCM (2:1, 3 mL) to give the product (33.18 mg, 76.6 μmol, 11% yield). ¹H NMR (CDCl₃, 400 MHz) δ$_H$=9.52 (d, 1H), 8.49 (d, 1H), 8.43 (d, 1H), 8.05 (dd, 1H), 5.96-5.86 (m, 1H), 4.21-4.16 (m, 1H), 1.61 (d, 3H), 1.04-0.99 (m, 2H), 0.87-0.81 (m, 2H). LCMS R$_t$=1.34 min in 2.0 min chromatography, 10-80AB. MS ESI calcd. for C$_{17}$H$_{14}$F$_6$N$_5$O$_2$ [M+H]⁺ 434.1, found 434.1.

Example 62: 6-(6-benzyloxy-5-fluoro-3-pyridyl)-3-[ethoxy(difluoro)methyl]-[1,2,4]triazolo[4,3-a]pyrazine

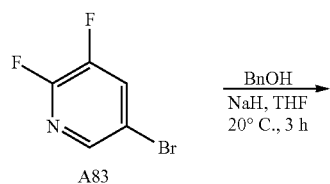

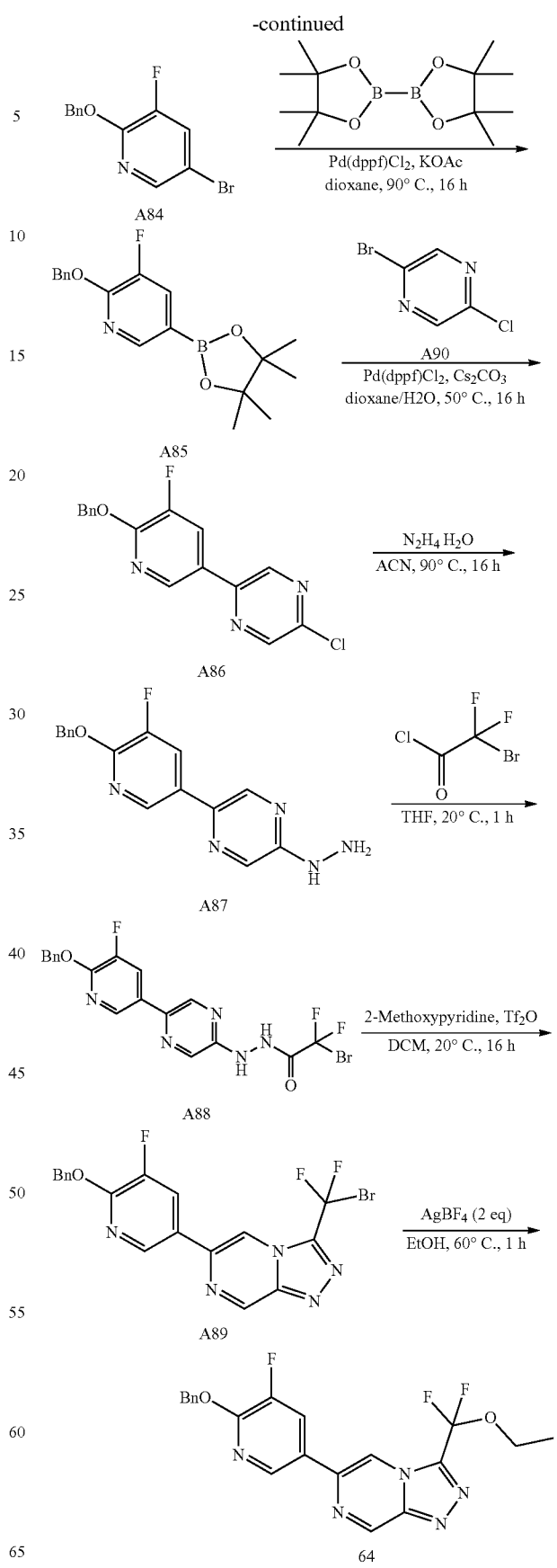

Synthesis of A84: To a solution of phenylmethanol (10.5 g, 97.1 mmol) in THF (100 mL) was added NaH (7 g, 175 mmol) in portions at 0° C. over 0.5 hour. After the addition, the mixture was stirred at 20° C. for another 1 hour. Then 5-bromo-2,3-difluoro-pyridine (18.83 g, 97.1 mmol) was added to the mixture. The resulting mixture was stirred at 20° C. for 3 hours. The mixture was poured into saturated NH$_4$Cl solution (100 mL) and the mixture was extracted with EtOAc (100 mL×2). The combined organic phase was washed with brine (100 mL), dried over anhydrous Na$_2$SO$_4$, filtered and concentrated to give the crude product (27 g, 89.52 mmol) as an oil.

Synthesis of A85: A mixture of 2-benzyloxy-5-bromo-3-fluoro-pyridine (27 g, 95.71 mmol), 4,4,5,5-tetramethyl-2-(4,4,5,5-tetramethyl-1,3,2-dioxaborolan-2-yl)-1,3,2-dioxaborolane (29.16 g, 114.85 mmol), KOAc (18.79 g, 191.41 mmol) and Pd(dppf)Cl$_2$ (10.5 g, 14.36 mmol) in 1,4-dioxane (300 mL) was stirred at 90° C. under N$_2$ for 16 hours. After cooling to room temperature, the mixture was filtered through Celite and the filtrate was concentrated. The crude product was purified by flash chromatography on silica gel (PE) to give the product (20 g, 60.75 mmol, 63% yield) as a solid. $^1$H NMR (400 MHz, CDCl$_3$) $\delta_H$=8.30 (d, 1H), 7.66 (dd, 1H), 7.50 (d, 2H), 7.41-7.31 (m, 3H), 5.52 (s, 2H), 1.35 (s, 12H).

Synthesis of A86: A mixture of 2-bromo-5-chloro-pyrazine (4 g, 20.68 mmol), 2-benzyloxy-3-fluoro-5-(4,4,5,5-tetramethyl-1,3,2-dioxaborolan-2-yl)pyridine (6.81 g, 20.68 mmol), Cs$_2$CO$_3$ (13.47 g, 41.36 mmol) and Pd(dppf)Cl$_2$ (2.27 g, 3.1 mmol) in 1,4-dioxane (30 mL) and water (3 mL) was stirred at 50° C. under N$_2$ for 16 hours. After cooling to room temperature, the mixture was filtered, and the filtrate was concentrated. Water (50 mL) was added and the aqueous layer was extracted with EtOAc (50 mL×2). The combined organic layer was washed with brine (50 mL), dried over anhydrous Na$_2$SO$_4$, filtered and concentrated. The crude product was purified by flash chromatography on silica gel (EtOAc in PE=0% to 15% to 30%) to give the product (5.5 g, 17.42 mmol, 84% yield) as a solid. $^1$H NMR (400 MHz, DMSO-d$_6$) $\delta_H$=9.15 (s, 1H), 8.85 (s, 1H), 8.77 (s, 1H), 8.37 (d, 1H), 7.52-7.46 (m, 2H), 7.44-7.32 (m, 3H), 5.51 (s, 2H).

Synthesis of A87: A mixture of 2-(6-benzyloxy-5-fluoro-3-pyridyl)-5-chloro-pyrazine (4.2 g, 13.3 mmol) and hydrazine (4.26 g, 133.03 mmol) in MeCN (20 mL) was stirred at 90° C. for 16 hours. After cooling to room temperature, the solution was concentrated under reduced pressure. Water (30 mL) was added and the aqueous layer was extracted with EtOAc (30 mL×2). The combined organic phase was washed with brine (30 mL), dried over anhydrous Na$_2$SO$_4$, filtered and concentrated to give the crude product (4 g, 7.38 mmol) as a solid. LCMS R$_t$=0.76 min in 1.5 min chromatography, 5-95AB, MS ESI calcd. for C$_{16}$H$_{15}$FN$_5$O [M+H]$^+$ 312.1, found 311.9.

Synthesis of A88: To the solution of 2-bromo-2,2-difluoro-acetyl chloride (1.65 g, 8.53 mmol) in THF (30 mL) was added [5-(6-benzyloxy-5-fluoro-3-pyridyl)pyrazin-2-yl]hydrazine (2 g, 6.42 mmol). The mixture was stirred at 20° C. for 1 hour. Water (30 mL) was added and the aqueous layer was extracted with EtOAc (30 mL×2). The combined organic phase was washed with brine (30 mL), dried over anhydrous Na$_2$SO$_4$, filtered and concentrated to give the crude product (900 mg, 1.92 mmol) as a solid. $^1$H NMR (400 MHz, DMSO-d$_6$) $\delta_H$=11.40 (s, 1H), 9.52 (s, 1H), 8.78 (d, 1H), 8.63 (d, 1H), 8.24 (dd, 1H), 8.14 (d, 1H), 7.49 (d, 2H), 7.43-7.32 (m, 3H), 5.49 (s, 2H).

Synthesis of A89: To a mixture of N'-[5-(6-benzyloxy-5-fluoro-3-pyridyl)pyrazin-2-yl]-2-bromo-2,2-difluoro-acetohydrazide (450 mg, 0.96 mmol) in DCM (9 mL) was added 2-methoxypyridine (230.74 mg, 2.11 mmol) and Tf$_2$O (0.19 mL, 1.15 mmol). The mixture was stirred at 20° C. for 16 hours. Water (50 mL) was added and the aqueous layer was extracted with EtOAc (50 mL×2). The combined organic phase was washed with saturated NaHCO$_3$ solution (30 mL) and brine (30 mL), dried over anhydrous Na$_2$SO$_4$, filtered and concentrated. The crude product was purified by flash chromatography on silica gel (EtOAc in PE=0% to 30% to 50%) to give the product (240 mg, 533.1 µmol, 55% yield) as a solid. $^1$H NMR (400 MHz, CDCl$_3$) $\delta_H$=9.57 (d, 1H), 8.55 (d, 1H), 8.41 (s, 1H), 8.01 (dd, 1H), 7.52 (d, 2H), 7.44-7.32 (m, 3H), 5.57 (s, 2H).

Synthesis of Compound 64: A mixture of 6-(6-benzyloxy-5-fluoro-3-pyridyl)-3-[bromo(difluoro)methyl]-[1,2,4]triazolo[4,3-a]pyrazine (240 mg, 0.53 mmol) and AgBF$_4$ (207.55 mg, 1.07 mmol) in ethanol (5 mL) was stirred at 60° C. in the dark for 1 hour. After cooling to room temperature, the mixture was filtered through Celite and the filtrate was concentrated. The crude product was purified by flash chromatography on silica gel (EtOAc in PE=0% to 30% to 50%) to give the product (31.09 mg, 74.8 µmol, 14% yield) as a solid. $^1$H NMR (400 MHz, CDCl$_3$) $\delta_H$=9.51 (d, 1H), 8.50 (d, 1H), 8.46 (s, 1H), 8.00 (dd, 1H), 7.55-7.48 (m, 2H), 7.44-7.33 (m, 3H), 5.56 (s, 2H), 4.37 (q, 2H), 1.51 (t, 3H). LCMS R$_t$=1.38 min in 2.0 min chromatography, 10-80AB, MS ESI calcd. for C$_{20}$H$_{17}$F$_3$N$_5$O$_2$ [M+H]$^+$ 416.1, found 416.0.

Example 63: 3-[difluoro(methoxy)methyl]-6-[5-fluoro-6-(2,2,2-trifluoroethoxy)-3-pyridyl]-7-methyl-[1,2,4]triazolo[4,3-b]pyridazine

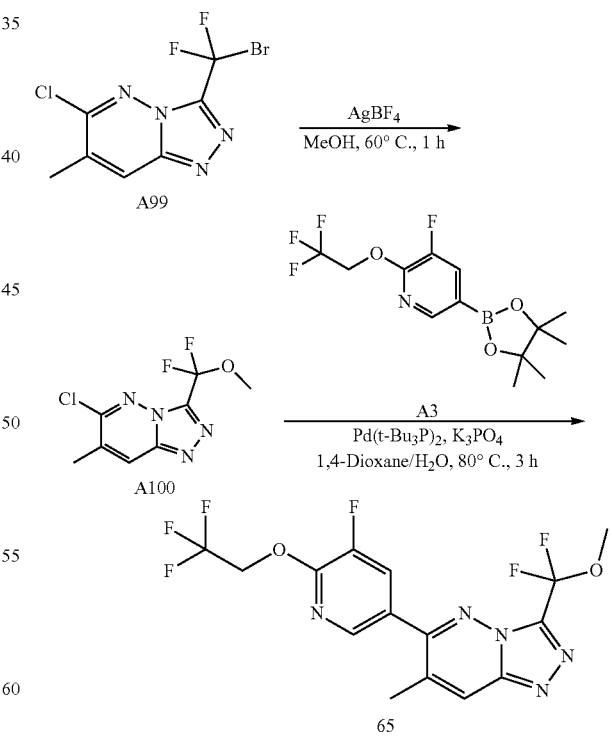

Synthesis of A100: A mixture of 3-[bromo(difluoro)methyl]-6-chloro-7-methyl-[1,2,4]triazolo[4,3-b]pyridazine (900 mg, 3.03 mmol) and AgBF$_4$ (1.17 g, 6.05 mmol) in methanol (10 mL) was stirred at 60° C. under dark for 1 hour. After cooling to room temperature, brine (50 mL) and EtOAc (50 mL) were added to the mixture and the mixture was filtered through Celite. The organic phase was separated and washed with brine (30 mL), dried over anhydrous $Na_2SO_4$, filtered and concentrated. The crude product was purified by flash chromatography on silica gel (EtOAc in PE=0% to 30% to 50%) to give the product (180 mg, 724.0 µmol, 23% yield) as a solid. $^1$H NMR (400 MHz, $CDCl_3$) $\delta_H$=7.99 (s, 1H), 3.90 (s, 3H), 2.53 (s, 3H). LCMS $R_t$=0.78 min in 1.5 min chromatography, 5-95AB, MS ESI calcd. for $C_8H_8ClF_2N_4O$ $[M+H]^+$ 249.0, found 248.9.

Synthesis of Compound 65: A mixture of 6-chloro-3-[difluoro(methoxy)methyl]-7-methyl-[1,2,4]triazolo[4,3-b]pyridazine (100 mg, 0.40 mmol), 3-fluoro-5-(4,4,5,5-tetramethyl-1,3,2-dioxaborolan-2-yl)-2-(2,2,2-trifluoroethoxy)pyridine (193.72 mg, 0.60 mmol), $K_3PO_4$ (170.78 mg, 0.80 mmol) and Pd(t-$Bu_3P)_2$ (30.83 mg, 0.06 mmol) in 1,4-dioxane (5 mL) and water (0.50 mL) was stirred at 80° C. under $N_2$ for 3 hours. After cooling to room temperature, water (20 mL) was added to the mixture and the aqueous layer was extracted with EtOAc (20 mL×2). The combined organic phase was washed with brine (30 mL), dried over anhydrous $Na_2SO_4$, filtered and concentrated. The crude product was purified by flash chromatography on silica gel (EtOAc in PE=0% to 30% to 50%) to give the product (64.84 mg, 158.9 µmol, 39% yield) as a solid. $^1$H NMR (400 MHz, $CDCl_3$) $\delta_H$=8.20 (d, 1H), 8.06 (s, 1H), 7.69 (dd, 1H), 4.94 (q, 2H), 3.88 (s, 3H), 2.48 (s, 3H). LCMS $R_t$=1.18 min in 2.0 min chromatography, 10-80AB, MS ESI calcd. for $C_{15}H_{12}F_6N_5O_2$ $[M+H]^+$ 408.1, found 408.0.

Example 64: 3-[difluoro(methoxy)methyl]-6-[5-fluoro-6-[(1R)-2,2,2-trifluoro-1-methyl-ethoxy]-3-pyridyl]-7-methyl-[1,2,4]triazolo[4,3-b]pyridazine

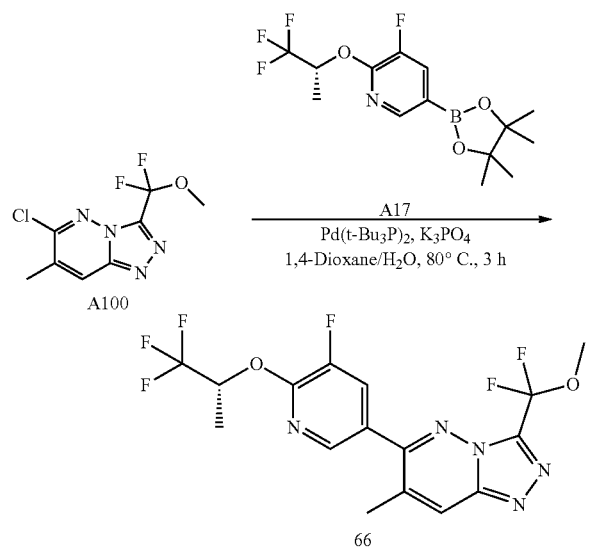

A mixture of 3-fluoro-2-[(1R)-2,2,2-trifluoro-1-methyl-ethoxy]-5-(4,4,5,5-tetramethyl-1,3,2-dioxaborolan-2-yl)pyridine (121.31 mg, 0.36 mmol), 6-chloro-3-[difluoro(methoxy)methyl]-7-methyl-[1,2,4]triazolo[4,3-b]pyridazine (75 mg, 0.3 mmol), Pd(t-$Bu_3P)_2$ (23.13 mg, 0.05 mmol), $K_3PO_4$ (128.09 mg, 0.6 mmol) in 1,4-dioxane (5 mL) and water (0.5 mL) was stirred at 80° C. for 3 hours. After cooling to room temperature, the mixture was concentrated and diluted with $H_2O$ (20 mL). The aqueous layer was extracted with EtOAc (20 mL×2). The combined organic phase was washed with brine (20 mL), dried over anhydrous $Na_2SO_4$, filtered and concentrated. The crude product was purified with flash chromatography on silica gel (EtOAc 100%) to give the product (70.46 mg, 0.17 mmol, 55% yield) as a solid. $^1$H NMR (400 MHz, $CDCl_3$) $\delta_H$=8.18 (d, 1H), 8.06 (d, 1H), 7.67 (dd, 1H), 5.97-5.86 (m, 1H), 3.88 (s, 3H), 2.49 (s, 3H), 1.61 (d, 3H). LCMS Rt=1.24 min in 2 min chromatography, 10-80AB, MS ESI calcd. $C_{16}H_{14}F_6N_5O_2$ $[M+H]^+$ 422.1, found 422.0.

Example 65: 3-[ethoxy(difluoro)methyl]-6-[5-fluoro-6-[(1S)-2,2,2-trifluoro-1-methyl-ethoxy]-3-pyridyl]-5-methyl-[1,2,4]triazolo[4,3-a]pyrazine

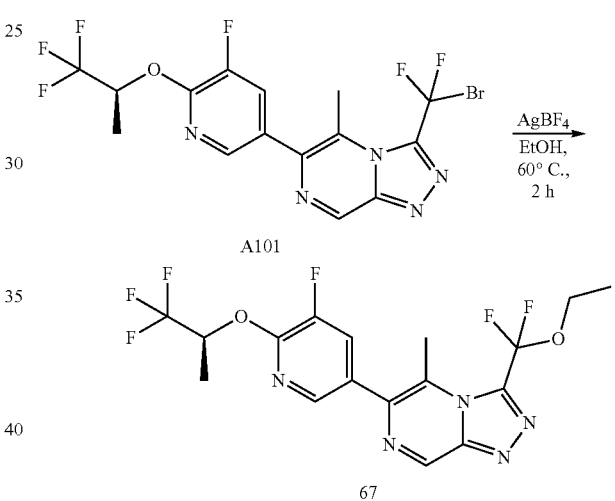

A mixture of 3-[bromo(difluoro)methyl]-6-[5-fluoro-6-[(1S)-2,2,2-trifluoro-1-methyl-ethoxy]-3-pyridyl]-5-methyl-[1,2,4]triazolo[4,3-a]pyrazine (100 mg, 0.21 mmol) and $AgBF_4$ (82.81 mg, 0.43 mmol) in ethanol (1 mL) was stirred at 60° C. in the dark for 1 hour. After cooling to room temperature, EtOAc (30 mL) and saturated aqueous NaCl (30 mL) were added to the mixture. The mixture was filtered through Celite and the phases of the filtrate were separated. The aqueous phase was extracted with EtOAc (20 mL). The combined organic phase was washed with brine (30 mL), dried over anhydrous $Na_2SO_4$, filtered and concentrated. The crude product was purified by flash chromatography on silica gel (EtOAc in PE=0% to 30% to 50%) to give impure product (55 mg) as a solid. The impure product was triturated from EtOH (1 mL) to give the product (19.57 mg, 21% yield) as a solid. $^1$H NMR (400 MHz, $CDCl_3$) $\delta_H$=9.39 (s, 1H), 8.11 (d, 1H), 7.69 (dd, 1H), 5.96-5.85 (m, 1H), 4.32 (q, 2H), 2.90 (s, 3H), 1.60 (d, 3H), 1.45 (t, 3H). LCMS $R_t$=1.34 min in 2.0 min chromatography, 10-80AB, MS ESI calcd. for $C_{17}H_{16}F_6N_5O_2$ $[M+H]^+$ 436.1, found 436.0.

Example 66: 3-[difluoro(methoxy)methyl]-6-[5-fluoro-6-[(1S)-2,2,2-trifluoro-1-methyl-ethoxy]-3-pyridyl]-7-methyl-[1,2,4]triazolo[4,3-b]pyridazine

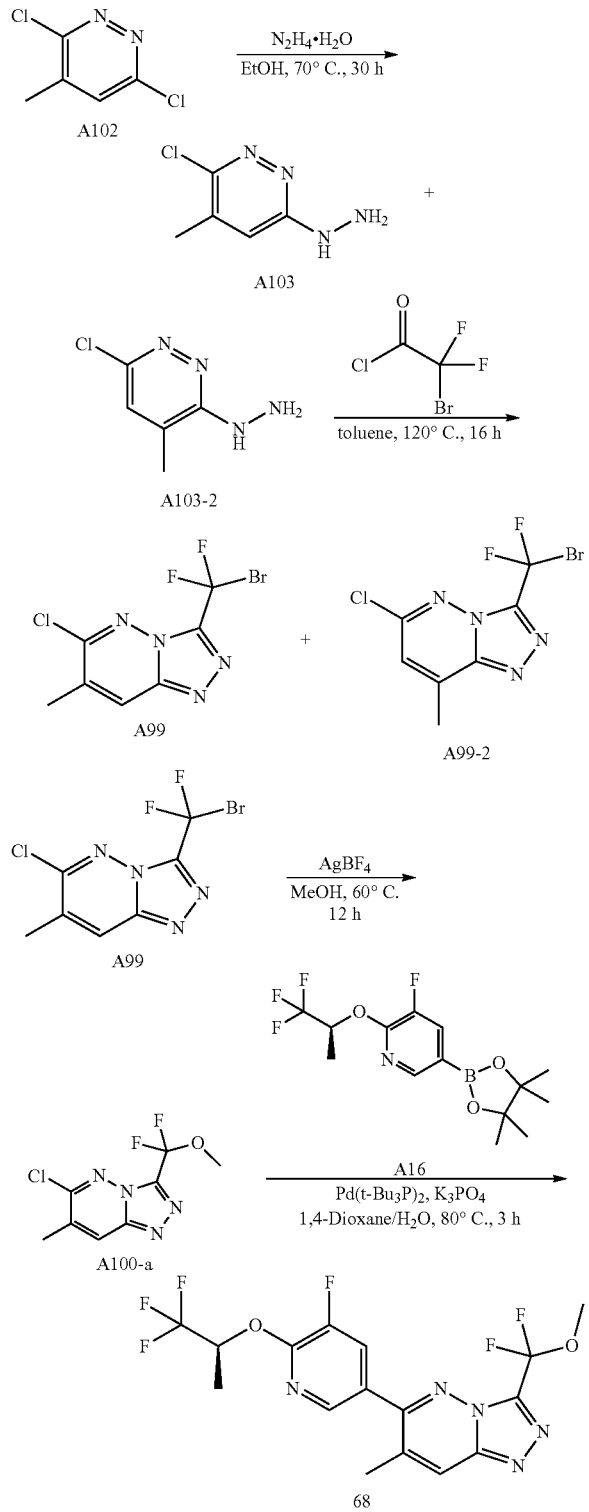

Synthesis of A103: A mixture of 3,6-dichloro-4-methyl-pyridazine (14 g, 85.89 mmol) and N$_2$H$_4$H$_2$O (4.29 g, 85.89 mmol) in ethanol (200 mL) was stirred at 70° C. for 30 hours. After cooling to room temperature, the suspension was filtered. The filter cake was washed with EtOH (50 mL×3) and dried in oven to give the product as a mixture of two regioisomers (A103, A103-2) and in a ratio of approximately 1:1 (determined by $^1$H NMR) (8 g, 50.45 mmol, 58% yield) as a solid.

Synthesis of A99: A mixture of 6-chloro-5-methyl-pyridazin-3-amine (2.0 g, 13.93 mmol), (6-chloro-4-methyl-pyridazin-3-yl)hydrazine and 2-bromo-2,2-difluoro-acetyl chloride (5.4 g, 27.86 mmol) in toluene (80 mL) was stirred at 120° C. for 16 hours. After cooling to room temperature, the mixture was concentrated, and the residue was diluted with H$_2$O (50 mL). The mixture was extracted with EtOAc (100 mL×2). The combined organic phase was washed with brine (30 mL), dried over anhydrous Na$_2$SO$_4$, filtered and concentrated. The crude product was purified by flash chromatography on silica gel (EtOAc in PE=20% to 40% to 60%) to give A99 (400 mg, 1.34 mmol, 10% yield) and A99-2 (600 mg, 2.01 mmol, 14% yield) both as solids. A99 $^1$H NMR (400 MHz, CDCl$_3$) $\delta_H$=8.08 (s, 1H), 2.58 (s, 3H). A99-2 $^1$H NMR (400 MHz, CDCl$_3$) $\delta_H$=7.14 (s, 1H), 2.81 (s, 3H).

Synthesis of A100-a: A mixture of 3-[bromo(difluoro)methyl]-6-chloro-7-methyl-[1,2,4]triazolo[4,3-b]pyridazine (400 mg, 1.34 mmol) and AgBF$_4$ (523.5 mg, 2.69 mmol) in methanol (5 mL) was stirred at 55° C. in the dark for 12 hours. After cooling to room temperature, aqueous saturated NaCl solution (30 mL) and EtOAc (30 mL) were added. The mixture was filtered through Celite and the filtrate was extracted with EtOAc (30 mL). The combined organic phase was washed with brine (20 mL), dried over anhydrous Na$_2$SO$_4$, filtered and concentrated. The crude product was purified by flash chromatography on silica gel (EtOAc in PE=0% to 30% to 50%) to give the product (230 mg, 0.93 mmol, 68% yield) as a solid. $^1$H NMR (400 MHz, CDCl$_3$) $\delta_H$=7.98 (d, 1H), 3.89 (s, 3H), 2.53 (s, 3H). LCMS Rt=0.73 min in 1.5 min chromatography, 10-80AB, MS ESI calcd. C$_8$H$_8$ClF$_2$N$_4$O [M+H]$^+$ 249.0, found 248.8.

Synthesis of Compound 68: A mixture of 6-chloro-3-[difluoro(methoxy)methyl]-7-methyl-[1,2,4]triazolo[4,3-b]pyridazine (70 mg, 0.28 mmol), 3-fluoro-2-(1S)-2,2,2-trifluoro-1-methyl-ethoxy]-5-(4,4,5,5-tetramethyl-1,3,2-dioxaborolan-2-yl)pyridine (113.22 mg, 0.34 mmol), K$_3$PO$_4$ (119.55 mg, 0.56 mmol) and Pd(t-Bu$_3$P)$_2$ (21.58 mg, 0.04 mmol) in 1,4-dioxane (5 mL) and water (0.5 mL) was stirred at 80° C. under N$_2$ for 3 hours. After cooling to room temperature, the mixture was filtered through Celite and the filtrate was concentrated. Water (20 mL) was added and the mixture was extracted with EtOAc (20 mL×2). The combined organic phase was washed with brine (30 mL), dried over anhydrous Na$_2$SO$_4$, filtered and concentrated. The crude product was purified by prep-TLC (silica gel, EtOAc) to give the product (65 mg, 154.3 μmol, 54% yield) as a solid. $^1$H NMR (400 MHz, CDCl$_3$) $\delta_H$=8.18 (d, 1H), 8.06 (d, 1H), 7.67 (dd, 1H), 5.96-5.87 (m, 1H), 3.88 (s, 3H), 2.49 (s, 3H), 1.61 (d, 3H). LCMS R$_t$=1.31 min in 2.0 min chromatography, 10-80AB, MS ESI calcd. for C$_{16}$H$_{14}$F$_6$N$_5$O$_2$ [M+H]$^+$ 422.1, found 422.2.

Example 67: 6-[5-fluoro-6-(2,2,2-trifluoro-1,1-dimethyl-ethoxy)-3-pyridyl]-3-(methoxymethyl)-7-methyl-[1,2,4]-triazolo[4,3-b]pyridazine

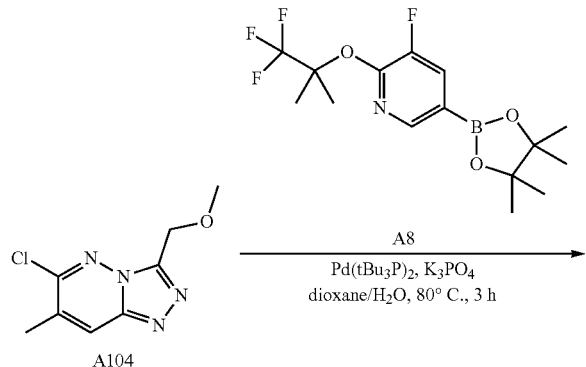

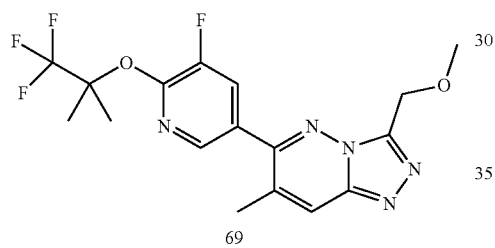

Example 68: 6-[5-fluoro-6-[(1S)-2,2,2-trifluoro-1-methyl-ethoxy]-3-pyridyl]-3-(methoxymethyl)-7-methyl-[1,2,4]triazolo[4,3-b]pyridazine

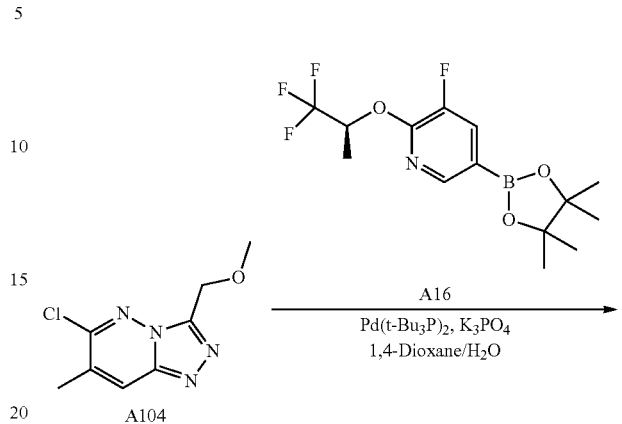

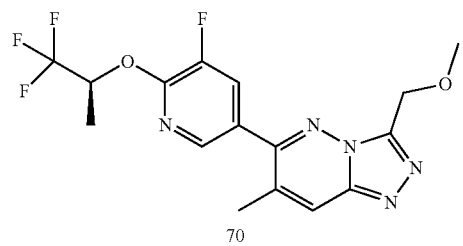

A mixture of 6-chloro-3-(methoxymethyl)-7-methyl-[1,2,4]triazolo[4,3-b]pyridazine (80 mg, 0.38 mmol), 3-fluoro-5-(4,4,5,5-tetramethyl-1,3,2-dioxaborolan-2-yl)-2-(2,2,2-trifluoro-1,1-dimethyl-ethoxy)pyridine (197.03 mg, 0.56 mmol), $K_3PO_4$ (159.74 mg, 0.75 mmol) and $Pd(t-Bu_3P)_2$ (28.84 mg, 0.06 mmol) in 1,4-dioxane (5 mL) and $H_2O$ (0.5 mL) was stirred at 80° C. under $N_2$ for 3 hours. After cooling to 25° C., the mixture was filtered through Celite and the filtrate was concentrated. Water (20 mL) was added and the mixture was extracted with EtOAc (20 mL×2). The combined organic phase was washed with brine (30 mL), dried over anhydrous $Na_2SO_4$, filtered and concentrated. The crude product was purified by prep-HPLC (Waters XBridge BEH C18 (150 mm×25 mm, 5 μm) A=$H_2O$ (0.075% $NH_4HCO_3$) and B=$CH_3CN$; 50-60% B over 9.5 min) to give the product (21.64 mg, 0.05 mmol, 14% yield) as a solid. $^1H$ NMR (400 MHz, $CDCl_3$) $\delta_H$=8.15 (d, 1H), 8.00 (d, 1H), 7.62 (dd, 1H), 5.04 (s, 2H), 3.48 (s, 3H), 2.45 (s, 3H), 1.90 (s, 6H). LCMS $R_t$=1.28 min in 2.0 min chromatography, 10-80AB, MS ESI calcd. for $C_{17}H_{18}F_4N_5O_2$ [M+H]$^+$ 400.1, found 400.1.

A mixture of 6-chloro-3-(methoxymethyl)-7-methyl-[1,2,4]triazolo[4,3-b]pyridazine (70 mg, 0.33 mmol), 3-fluoro-2-[(1S)-2,2,2-trifluoro-1-methyl-ethoxy]-5-(4,4,5,5-tetramethyl-1,3,2-dioxaborolan-2-yl)pyridine (132.38 mg, 0.40 mmol), $K_3PO_4$ (139.78 mg, 0.66 mmol) and $Pd(t-Bu_3P)_2$ (25.24 mg, 0.05 mmol) in 1,4-dioxane (5 mL) and water (0.5 mL) was stirred at 80° C. under $N_2$ for 3 hours. After cooling to 25° C., the mixture was filtered through Celite and the filtrate was concentrated. Water (20 mL) was added and the aqueous layer was extracted with EtOAc (20 mL×2). The combined organic phase was washed with brine (30 mL), dried over anhydrous $Na_2SO_4$, filtered and concentrated. The crude product was purified by flash chromatography on silica gel (EtOAc in PE=10% to 20%) to give the product (33.02 mg, 0.09 mmol, 26% yield) as a solid. $^1H$ NMR (400 MHz, $CDCl_3$) $\delta_H$=8.16 (d, 1H), 8.00 (d, 1H), 7.65 (dd, 1H), 5.96-5.86 (m, 1H), 5.04 (s, 2H), 3.49 (s, 3H), 2.46 (s, 3H), 1.61 (d, 3H). LCMS $R_t$=1.24 min in 2.0 min chromatography, 10-80AB, MS ESI calcd. for $C_{16}H_{16}F_4N_5O_2$ [M+H]$^+$ 386.1, found 385.9.

Example 69: 6-[5-fluoro-6-(2,2,2-trifluoroethoxy)-3-pyridyl]-3-(methoxymethyl)-7-methyl-[1,2,4]triazolo[4,3-b]pyridazine

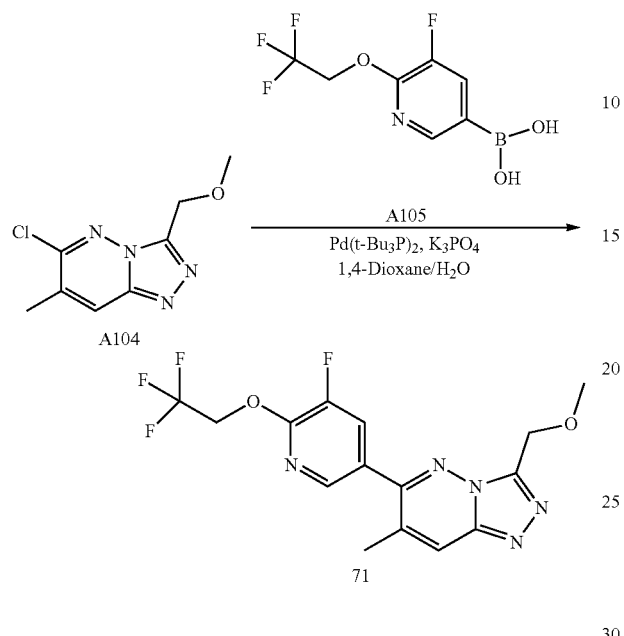

Synthesis of A105: The corresponding pinacol ester was dissolved in MeCN and aqueous HCl was added. The mixture was stirred for 2 hours at room temperature and then concentrated to give A105, which was used crude.

Synthesis of Compound 71: A mixture of 6-chloro-3-(methoxymethyl)-7-methyl-[1,2,4]triazolo[4,3-b]pyridazine (70 mg, 0.33 mmol), [5-fluoro-6-(2,2,2-trifluoroethoxy)-3-pyridyl]boronic acid (94.39 mg, 0.40 mmol), $K_3PO_4$ (139.78 mg, 0.66 mmol) and $Pd(t-Bu_3P)_2$ (25.24 mg, 0.05 mmol) in 1,4-dioxane (5 mL) and water (0.5 mL) was stirred at 80° C. under $N_2$ for 3 hours. After cooling to room temperature, the mixture was filtered through Celite and the filtrate was concentrated. Water (20 mL) was added and the aqueous layer was extracted with EtOAc (20 mL×2). The combined organic phase was washed with brine (30 mL), dried over anhydrous $Na_2SO_4$, filtered and concentrated. The crude product was purified by prep-TLC (silica gel, EtOAc) to give the product (9.8 mg, 0.03 mmol, 8% yield) as a solid. $^1$H NMR (400 MHz, CDCl$_3$) $\delta_H$=8.17 (d, 1H), 8.01 (s, 1H), 7.68 (dd, 1H), 5.04 (s, 2H), 4.93 (q, 2H), 3.49 (s, 3H), 2.45 (s, 3H). LCMS $R_t$=1.19 min in 2.0 min chromatography, 10-80AB, MS ESI calcd. for $C_{15}H_{14}F_4N_5O_2$ [M+H]$^+$ 372.1, found 372.0.

Example 70: 6-[5-fluoro-6-[(1R)-2,2,2-trifluoro-1-methyl-ethoxy]-3-pyridyl]-3-(methoxymethyl)-7-methyl-[1,2,4]triazolo[4,3-b]pyridazine

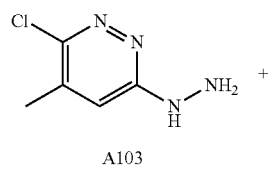

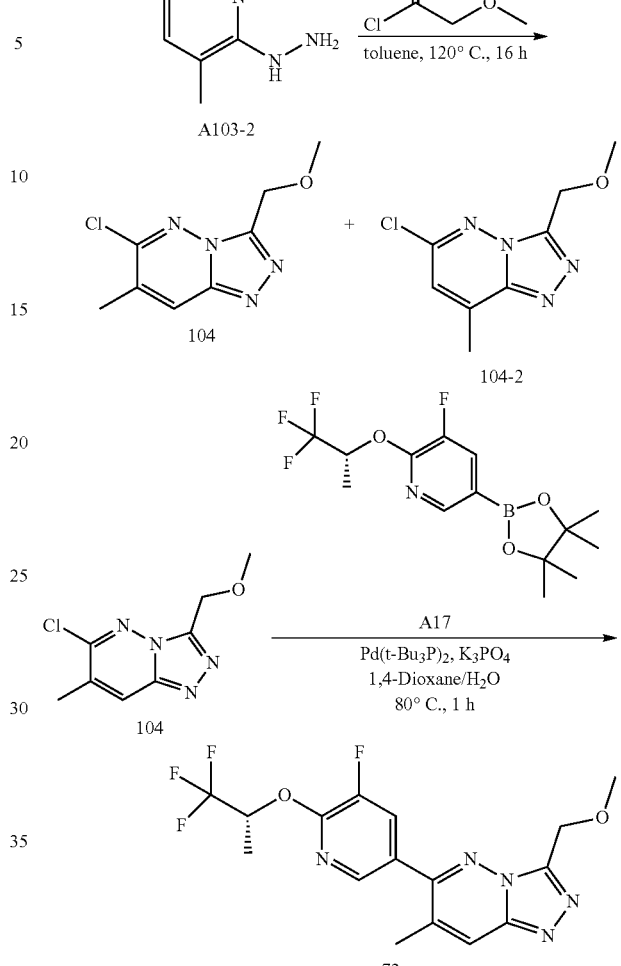

Synthesis of A104: To a solution of a mixture of (6-chloro-5-methyl-pyridazin-3-yl)hydrazine and (6-chloro-4-methyl-pyridazin-3-yl)hydrazine) (2 g, 12.61 mol) in toluene (30 mL) was added 2-methoxyacetyl chloride (2737.12 mg, 25.22 mmol) at 25° C. The mixture was heated to 120° C. and stirred for 16 hours. After cooling to room temperature, the mixture was concentrated, and the residue was diluted with $H_2O$ (30 mL). The mixture was extracted with EtOAc (50 mL×2). The combined organic phase was washed with brine (10 mL), dried over anhydrous $Na_2SO_4$, filtered and concentrated. The crude product was purified by flash chromatography on silica gel (EtOAc) for 3 times to give the A104 (250 mg, 1.17 mmol, 9% yield) and A104-2 (500 mg, 2.35 mmol, 19% yield) both as solids. $^1$H NMR (400 MHz, CDCl$_3$) $\delta_H$=7.94 (d, 1H), 5.02 (s, 2H), 3.50 (s, 3H), 2.51 (s, 3H).

Synthesis of Compound 72: A mixture of 6-chloro-3-(methoxymethyl)-7-methyl-[1,2,4]triazolo[4,3-b]pyridazine (60 mg, 0.28 mmol), 3-fluoro-2-[(1R)-2,2,2-trifluoro-1-methyl-ethoxy]-5-(4,4,5,5-tetramethyl-1,3,2-dioxaborolan-2-yl)pyridine (113.47 mg, 0.34 mmol), $K_3PO_4$ (119.81 mg, 0.56 mmol) and $Pd(t-Bu_3P)_2$ (21.63 mg, 0.04 mmol) in 1,4-dioxane (5 mL) and $H_2O$ (0.5 mL) was stirred at 80° C. under $N_2$ for 1 hours. After cooling to room temperature, the mixture was filtered through Celite and the filtrate was concentrated. Water (20 mL) was added and the mixture was extracted with EtOAc (20 mL×2). The combined organic phase was washed with brine (30 mL), dried over anhydrous $Na_2SO_4$, filtered and concentrated. The crude product was purified by prep-TLC (silica gel, EtOAc) to give the product (23.22 mg, 59.2 μmol, 21% yield) as a solid. $^1$H NMR (400 MHz, $CDCl_3$) $\delta_H$=8.16 (d, 1H), 8.01 (s, 1H), 7.65 (dd, 1H), 5.96-5.85 (m, 1H), 5.04 (s, 2H), 3.49 (s, 3H), 2.45 (s, 3H), 1.61 (d, 3H). LCMS $R_t$=1.24 min in 2.0 min chromatography, 10-80AB, MS ESI calcd. for $C_{16}H_{16}F_4N_5O_2$ [M+H]$^+$ 386.1, found 386.1.

Example 71: 3-(difluoro(methoxy)methyl)-6-(6-(3,3-difluorocyclobutoxy)pyridin-3-yl)-[1,2,4]triazolo[4,3-a]pyrazine

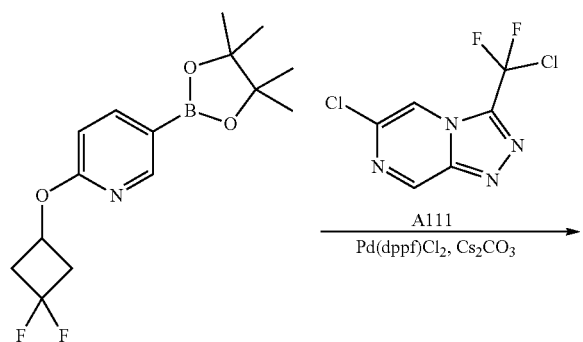

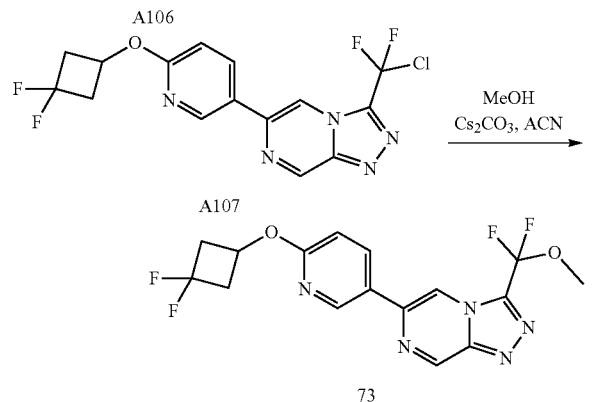

Synthesis of A107: To a stirred solution of 6-chloro-3-[chloro(difluoro)methyl]-[1,2,4]triazolo[4,3-c]pyrazine (1.0 g, 4.18 mmol) and 2-(3,3-difluorocyclobutoxy)-5-(4,4,5,5-tetramethyl-1,3,2-dioxaborolan-2-yl)pyridine (1.43 g, 4.6 mmol) in 1,4-dioxane (27.0 mL) was added water (3.0 mL) and $Cs_2CO_3$ (2.73 g, 8.37 mmol). Pd(dppf)$Cl_2$.DCM (0.34 g, 0.42 mmol) was added to the reaction mixture under nitrogen atmosphere and heated at 80° C. for 16 hours. The reaction mixture was cooled to room temperature, filtered through Celite and concentrated under reduced pressure. The crude product was purified by column chromatography on silica gel with 25% ethyl acetate/PE to afford the product (430 mg, 1.11 mmol, 26% yield). LCMS: 388.1 (M+H), Rt 2.4 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of Compound 73: To a stirred solution of 3-(chlorodifluoromethyl)-6-(6-(3,3-difluorocyclobutoxy) pyridin-3-yl)-[1,2,4]triazolo[4,3-c]pyrazine (100 mg, 0.26 mmol) in MeCN (4.5 mL) was added $Cs_2CO_3$ (515 mg, 1.58 mmol) and methanol (0.21 mL, 5.2 mmol). The reaction was stirred for 1 h at room temperature. The reaction mixture was treated with water (20.0 mL) and extracted with ethyl acetate (2×20 mL). The organic layer was washed with brine (15 mL), dried over anhydrous $Na_2SO_4$ and concentrated. The crude compound was purified by preparative HPLC to afford a solid (32 mg, 0.08 mmol, 32% yield). Prep-HPLC method: Rt=16.1; Column: XBridge C8 (150×19 mm), 5.0 μm; Mobile phase: 0.1% TFA in water/acetonitrile; Flow Rate: 15.0 mL/min. HPLC: Rt 4.49 min, Column: XBridge C8 (50×4.6) mm, 3.5 μm Mobile phase: A: 0.1% TFA in water, B: 0.1% TFA in ACN; Flow Rate: 2.0 mL/min. LCMS: 384.1 (M+H), Rt 2.22 min, Column: ZORBAX XDB C-18 (50×4.6 mm), 3.5 μm Mobile Phase: A: 0.1% HCOOH in water:ACN (95:5), B: ACN; Flow Rate: 1.5 mL/min. $^1$H NMR (400 MHz, $CD_3OD$): δ 9.54 (d, 1H), 8.86 (d, 1H), 8.78 (s, 1H), 8.39 (dd, 1H), 6.99 (d, 1H), 5.25-5.22 (m, 1H), 3.99 (s, 3H), 3.23-3.13 (m, 2H), 2.82-2.70 (m, 2H).

Example 72: 3-(cyclopropoxydifluoromethyl)-6-(6-(2,2,2-trifluoroethoxy)pyridin-3-yl)-[1,2,4]triazolo[4,3-a]pyrazine

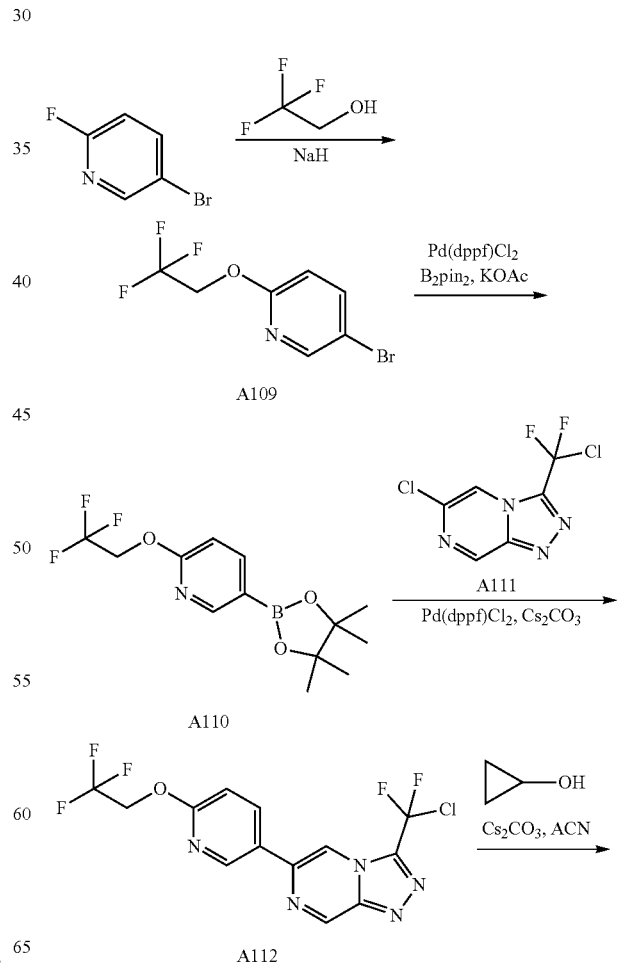

-continued

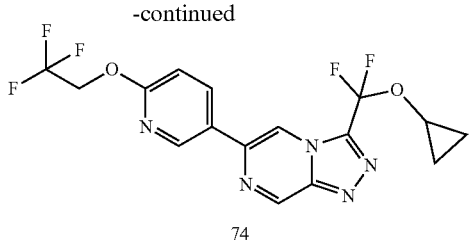

74

Synthesis of A109: To a stirred solution of 2,2,2-trifluoroethanol (3.12 g, 31.25 mmol) in THF (25 mL) at 0° C. was added NaH (60% in mineral oil, 1.25 g, 31.25 mmol) in small portions. The reaction mixture was slowly warmed to room temperature and stirred for 15 min. 5-bromo-2-fluoropyridine (5.0 g, 28.41 mmol) was added drop-wise to the reaction mixture and stirred for 2 hours. The reaction mixture was cooled to 10° C. and treated with ice water (50 mL). The reaction mixture was extracted with ethyl acetate (2×60 mL). The organic layer was washed with brine (50 mL), dried over anhydrous $Na_2SO_4$ and concentrated. The crude compound was purified by column chromatography on silica gel with 5% ethyl acetate/PE to afford the product (5.0 g, 19.5 mmol, 68% yield) LCMS: 256.0 (M+H) and 258 (M+2+H), Rt 2.59 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A110: To a stirred solution of 5-bromo-2-(2,2,2-trifluoroethoxy)pyridine (5.0 g, 19.53 mmol) and bis(pinacolato)diboron (6.45 g, 25.39 mmol) in 1,4-dioxane (50.0 mL) was added potassium acetate (3.83 g, 39.0 mmol). Pd(dppf)Cl$_2$.DCM (1.59 g, 1.95 mmol) was added to the reaction mixture under nitrogen atmosphere and heated at 80° C. for 12 hours. The reaction mixture was cooled to room temperature, filtered through Celite and concentrated under reduced pressure. The crude compound was purified by column chromatography on silica gel with 5% ethyl acetate/PE to afford the product (4.32 g, 14.3 mmol, 73% yield). LCMS: 304.1 (M+H), Rt 2.85 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A112: To a stirred solution of 6-chloro-3-[chloro(difluoro)methyl]-[1,2,4]triazolo[4,3-a]pyrazine (1.3 g, 5.44 mmol) and 5-(4,4,5,5-tetramethyl-1,3,2-dioxaborolan-2-yl)-2-(2,2,2-trifluoroethoxy) pyridine (1.5 g, 4.95 mmol) in 1,4-dioxane (25.0 mL) was added water (2.5 mL) and Cs$_2$CO$_3$ (3.22 g, 9.9 mmol). Pd(dppf)Cl$_2$.DCM (0.4 g, 0.49 mmol) was added to the reaction mixture under nitrogen atmosphere and heated at 80° C. for 12 hours. The reaction mixture was cooled to room temperature, filtered through Celite and concentrated under reduced pressure. The crude product was purified by column chromatography on silica gel with 30% ethyl acetate/PE to afford the product (500 mg, 1.3 mmol, 26% yield). LCMS: 380.0 (M+H), Rt 2.45 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of Compound 74: To a stirred solution of 3-(chlorodifluoromethyl)-6-(6-(2,2,2-trifluoroethoxy)pyridin-3-yl)-[1,2,4]triazolo[4,3-c]pyrazine (100 mg, 0.26 mmol) in MeCN (10 mL) was added Cs$_2$CO$_3$ (514 mg, 1.58 mmol) and cyclopropanol (0.21 mL, 3.29 mmol). The reaction was stirred for 1 hour at room temperature. The reaction mixture was treated with water (15.0 mL) and extracted with ethyl acetate (2×20 mL). The organic layer was washed with brine (15 mL), dried over anhydrous $Na_2SO_4$ and concentrated. The crude compound was purified by preparative HPLC to afford a solid (10 mg, 0.024 mmol, 9% yield). Prep-HPLC method: Rt=14.2; Column: XBridge C8 (150× 19 mm), 5.0 μm; Mobile phase: 0.1% TFA in water/acetonitrile; Flow Rate: 15.0 mL/min. HPLC: Rt 5.01 min, Column: XBridge C8 (50×4.6) mm, 3.5 μm Mobile phase: A: 0.1% TFA in water, B: 0.1% TFA in ACN; Flow Rate: 2.0 mL/min LCMS: 402.1 (M+H), Rt 2.30 min, Column: XBridge C8 (50×4.6 mm), 3.5 μm Mobile Phase: A: 0.1% TFA in water:ACN (95:5), B: 0.1% TFA in ACN; Flow Rate: 1.5 mL/min. $^1$H NMR (400 MHz, CD$_3$OD): δ 9.55 (d, 1H), 8.89 (d, 1H), 8.75 (s, 1H), 8.43 (dd, 1H), 7.09 (d, 1H), 4.98 (q, 2H), 4.26-4.23 (m, 1H), 0.99 (m, 2H), 0.85-0.81 (m, 2H).

Example 73: 3-(cyclopropoxydifluoromethyl)-6-(5-fluoro-6-(2,2,2-trifluoroethoxy)pyridin-3-yl)-[1,2,4]triazolo[4,3-a]pyrazine

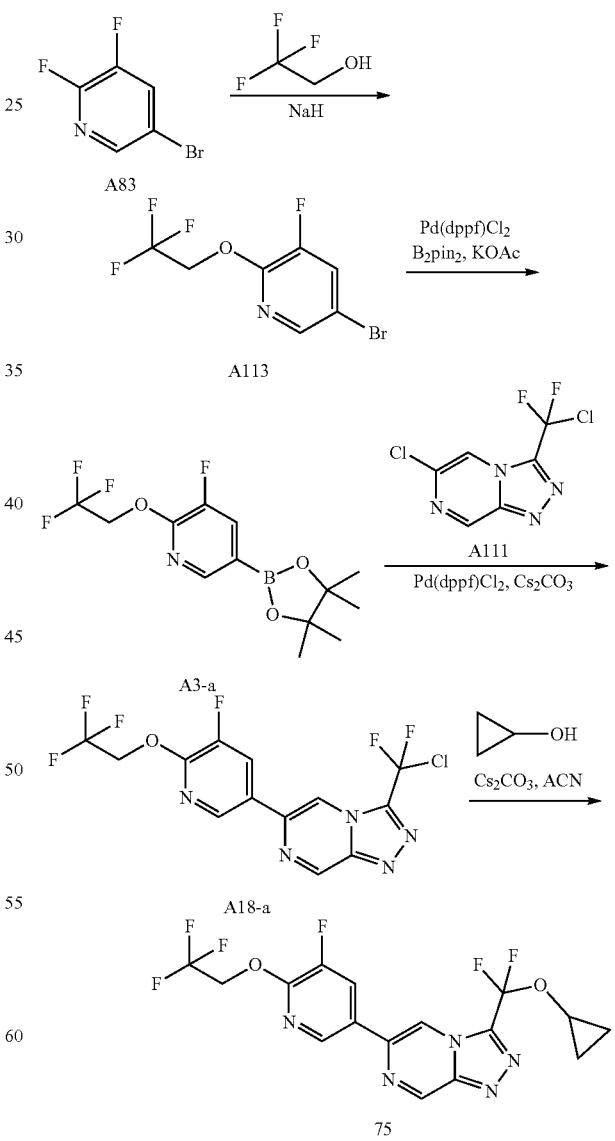

Synthesis of A113: To a stirred solution of 2,2,2-trifluoroethanol (5.67 g, 56.71 mmol) in THF (200 mL) at 0° C.

was added NaH (60% in mineral oil, 2.26 g, 56.71 mmol) in small portions. The reaction mixture was stirred for 15 min and 5-bromo-2,3-difluoro-pyridine (10.0 g, 51.55 mmol) was added drop-wise. The reaction mixture was slowly warmed to room temperature and stirred for 2 hours. The reaction mixture was cooled to 10° C. and treated with ice water (100 mL). The reaction mixture was extracted with ethyl acetate (2×100 mL). The organic layer was washed with brine (80 mL), dried over anhydrous $Na_2SO_4$ and concentrated. The crude compound was purified by column chromatography on silica gel with 2% ethyl acetate/PE to afford the product (10.5 g, 38.1 mmol, 73% yield). LCMS: 273.9 (M+H) and 276.0 (M+2+H), Rt 2.53 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A3-a: To a stirred solution of 5-bromo-3-fluoro-2-(2,2,2-trifluoroethoxy)pyridine (3.0 g, 10.95 mmol) and bis(pinacolato)diboron (3.61 g, 14.23 mmol) in 1,4-dioxane (30.0 mL) was added potassium acetate (2.15 g, 21.9 mmol). $Pd(dppf)Cl_2DCM$ (0.89 g, 1.09 mmol) was added to the reaction mixture under nitrogen atmosphere and heated at 80° C. for 12 hours. The reaction mixture was cooled to room temperature, filtered through Celite and concentrated under reduced pressure. The crude compound was purified by column chromatography on silica gel with 15% ethyl acetate/PE to afford the product (2.0 g, 6.2 mmol, 56% yield). LCMS: 322.1 (M+H), Rt 2.97 min Column: Atlantis dC18 (50×4.6 mm), 5 μm Mobile Phase: A: 0.1% HCOOH in water:ACN (95:5), B: ACN; Flow Rate: 1.5 mL/min.

Synthesis of A18-a: To a stirred solution of 6-chloro-3-[chloro(difluoro)methyl]-[1,2,4]triazolo[4,3-c]pyrazine (2.0 g, 8.37 mmol) and 3-fluoro-5-(4,4,5,5-tetramethyl-1,3,2-dioxaborolan-2-yl)-2-(2,2,2-trifluoroethoxy)pyridine (2.96 g, 9.2 mmol) in 1,4-dioxane (26.0 mL) was added water (4.0 mL) and $K_2CO_3$ (2.31 g, 16.74 mmol). $PdCl_2(PPh_3)_2$ (0.59 g, 0.84 mmol) was added to the reaction mixture under nitrogen atmosphere and heated at 90° C. for 12 hours. The reaction mixture was cooled to room temperature, filtered through Celite and concentrated under reduced pressure. The crude product was purified by column chromatography on silica gel with 30% ethyl acetate/PE to afford the product (1.35 g, 3.4 mmol, 40% yield). LCMS: 398.0 (M+H), Rt 2.51 min Column: Atlantis dC-18 (50×4.6 mm), 3.5 μm Mobile Phase: A: 0.1% HCOOH in water:ACN (95:5), B: ACN; Flow Rate: 1.5 mL/min. $^1$H NMR (400 MHz, DMSO-$d_6$): δ 9.77 (d, 1H), 9.14 (s, 1H), 8.84 (d, 1H), 8.66 (dd, 1H), 5.20 (q, 2H).

Synthesis of Compound 75: To a stirred solution of 3-(chlorodifluoromethyl)-6-(5-fluoro-6-(2,2,2-trifluoroethoxy)pyridin-3-yl)-[1,2,4]triazolo[4,3-a]pyrazine (150.0 mg, 0.38 mmol) in MeCN (8.0 mL) was added $Cs_2CO_3$ (737 mg, 2.26 mmol) and cyclopropanol (0.48 mL, 7.54 mmol). The reaction mixture was stirred for 6 hours at room temperature. The reaction mixture was treated with water (15.0 mL) and extracted with ethyl acetate (2×20 mL). The organic layer was washed with brine (15 mL), dried over anhydrous $Na_2SO_4$ and concentrated. The crude compound was purified by preparative HPLC to afford a solid (15 mg, 0.035 mmol, 9% yield). Prep. HPLC method: Rt 14.8; Column) (Bridge C-18 (150×19 mm), 5.0 μm; Mobile phase: 0.1% TFA in water/acetonitrile; Flow Rate: 15.0 mL/min. HPLC: Rt 5.16 min, Column: XBridge C8 (50×4.6) mm, 3.5 μm Mobile phase: A: 0.1% TFA in water, B: 0.1% TFA in ACN; Flow Rate: 2.0 mL/min. LCMS: 420.0 (M+H), Rt 2.64 min, Column: Atlantis dC18 (50×4.6 mm), 3.5 μm Mobile Phase: A: 0.1% HCOOH in water, B: ACN; Flow Rate: 1.5 mL/min. $^1$H NMR (400 MHz, DMSO-$d_6$): δ 9.71 (d, 1H), 8.93 (d, 1H), 8.78 (d, 1H), 8.56 (dd, 1H), 5.19 (q, 2H), 4.24-4.20 (m, 1H), 0.96-0.92 (m, 2H), 0.77-0.72 (m, 2H).

Example 74: 3-(difluoro(methoxy)methyl)-6-(6-(3,3-difluorocyclobutoxy)-5-fluoropyridin-3-yl)-[1,2,4]triazolo[4,3-a]pyrazine

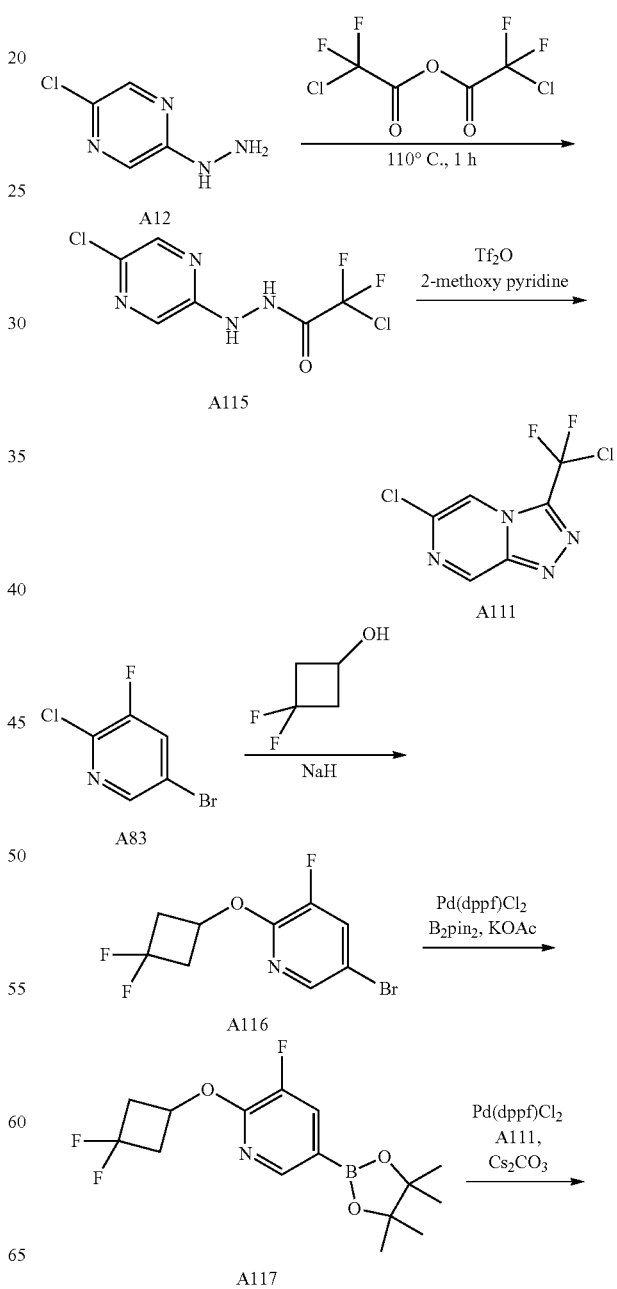

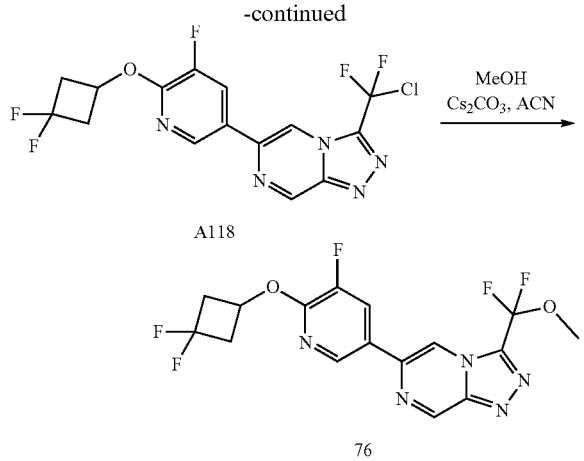

Synthesis of A115: To stirred solution of 2-chloro-5-hydrazineylpyrazine (5.0 g, 33.99 mmol) in toluene (50 mL) was added chlorodifluoroacetic anhydride (6.54 mL, 37.39 mmol) at 0° C. The reaction mixture was heated at 110° C. for 1 hour. The reaction mixture was cooled to room temperature and concentrated. The crude reaction mixture was treated with water (50 mL) and extracted with ethyl acetate (2×50 mL). The organic layer was washed with brine (30 mL), dried over $Na_2SO_4$ and concentrated to a solid (6 g). It was used for the next step without further purification.

Synthesis of A111: To a stirred solution of 2-chloro-N'-(5-chloropyrazin-2-yl)-2,2-difluoroacetohydrazide (6.0 mg, 23.34 mmol) in DCM (120 mL) was added trifluoromethanesulfonic anhydride (4.73 mL, 28.01 mmol) and 2-methoxypridine (4.91 mL, 46.69 mmol) at 0° C. The reaction mixture was slowly warmed to room temperature and stirred for 2 hours. The reaction mixture was treated with 10% sodium bicarbonate solution (50 mL) and extracted with ethyl acetate (2×50 mL). The organic layer was washed with brine (50 mL), dried over $Na_2SO_4$ and concentrated. The crude product was purified by column chromatography on silica gel with 15% EtOAc/PE to afford the product (4.0 g, 16.5 mmol, 71% yield) as a solid. LCMS: 239.0 (M+H), Rt 1.66 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A116: To a stirred solution of 3,3-difluorocyclobutanol (500 mg, 4.63 mmol) in THF (10 mL) at 0° C. was added NaH (60% in mineral oil, 204 mg, 5.09 mmol) in small portions. The reaction mixture was slowly warmed to room temperature and stirred for 15 min. 5-Bromo-2,3-difluoro-pyridine (0.9 g, 4.63 mmol) was then added dropwise to the reaction mixture and stirred for 4 hours. The reaction mixture was cooled to 10° C. and treated with ice water (30 mL). The reaction mixture was extracted with ethyl acetate (2×30 mL). The organic layer was washed with brine (50 mL), dried over anhydrous $Na_2SO_4$ and concentrated. The crude compound was purified by column chromatography on silica gel with 10% ethyl acetate/PE to afford the product (1.0 g, 3.57 mmol, 77% yield). LCMS: 282.0 (M+H) and 284.0 (M+2+H), Rt 2.66 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A117: To a stirred solution of 5-bromo-2-(3,3-difluorocyclobutoxy)-3-fluoropyridine (1.1 g, 3.91 mmol) and bis(pinacolato)diboron (1.29 g, 5.09 mmol) in 1,4-dioxane (20.0 mL) was added potassium acetate (0.77 g, 7.83 mmol). Pd(dppf)$Cl_2$.DCM (0.32 g, 0.39 mmol) was added to the reaction mixture under nitrogen atmosphere and heated at 90° C. for 16 hours. The reaction mixture was cooled to room temperature, filtered through Celite and concentrated under reduced pressure. The crude compound was purified by column chromatography on silica gel with 5% ethyl acetate/PE to afford the product (1.2 g, 3.6 mmol, 93% yield). LCMS: 330.1 (M+H), Rt 2.97 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A118: To a stirred solution of 6-chloro-3-(chlorodifluoromethyl)-[1,2,4]triazolo[4,3-c]pyrazine (0.91 g, 3.83 mmol) and 2-(3,3-difluorocyclobutoxy)-3-fluoro-5-(4,4,5,5-tetramethyl-1,3,2-dioxaborolan-2-yl)pyridine (1.17 g, 3.55 mmol) in 1,4-dioxane (15.0 mL) was added water (3.0 mL) and $Cs_2CO_3$ (2.31 g, 7.13 mmol). Pd(dppf)$Cl_2$.DCM (0.29 g, 0.36 mmol) was added to the reaction mixture under nitrogen atmosphere and heated at 80° C. for 8 hours. The reaction mixture was cooled to room temperature, filtered through Celite and concentrated under reduced pressure. The crude product was purified by column chromatography on silica gel with 30% ethyl acetate/PE to afford the product (1.11 g, 2.75 mmol, 77% yield). LCMS: 405.9 (M+H), Rt 2.30 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of Compound 76: To a stirred solution of 3-(chlorodifluoromethyl)-6-(6-(3,3-difluorocyclobutoxy)-5-fluoropyridin-3-yl)-[1,2,4]triazolo[4,3-a]pyrazine (140 mg, 0.34 mmol) in MeCN (7.5 mL) was added $Cs_2CO_3$ (668 mg, 2.06 mmol) and methanol (0.14 mL, 3.4 mmol). The reaction was stirred for 1 h at room temperature. The reaction mixture was treated with water (20.0 mL) and extracted with ethyl acetate (2×20 mL). The organic layer was washed with brine (15 mL), dried over anhydrous $Na_2SO_4$ and concentrated. The crude compound was purified by preparative HPLC to afford a solid 08 mg, 0.04 mmol, 13% yield.). Prep. HPLC method: Rt 12.9; Column: YMC Phenyl (150×19 mm), 5.0 μm; Mobile phase: 0.1% TFA in water/acetonitrile; Flow Rate: 15.0 mL/min. HPLC: Rt 5.01 min, 97.3% Column: XBridge C8 (50×4.6) mm, 3.5 μm Mobile phase: A: 0.1% TFA in water, B: 0.1% TFA in ACN; Flow Rate: 2.0 mL/min. LCMS: 402.0 (M+H), Rt 2.48 min, Column: Atlantis dC18 (50×4.6 mm), 5.0 μm Mobile Phase: A: 0.1% HCOOH in water:ACN (95:5), B: ACN; Flow Rate: 1.5 mL/min. $^1$H NMR (400 MHz, DMSO-$d_6$): δ 9.70 (d, 1H), 8.97 (s, 1H), 8.77 (d, 1H), 8.49 (dd, 1H), 5.30-5.26 (m, 1H), 3.92 (s, 3H), 3.26-3.19 (m, 2H), 2.89-2.84 (m, 2H).

Example 75: 6-(6-(3,3-difluorocyclobutoxy)-5-fluoropyridin-3-yl)-3-(ethoxydifluoromethyl)-[1,2,4]triazolo[4,3-a]pyrazine

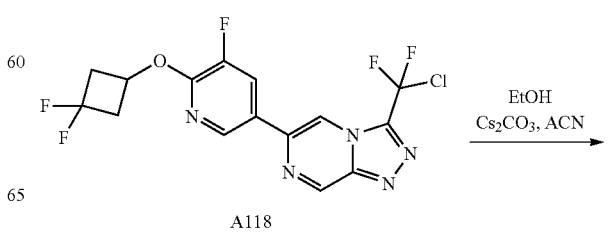

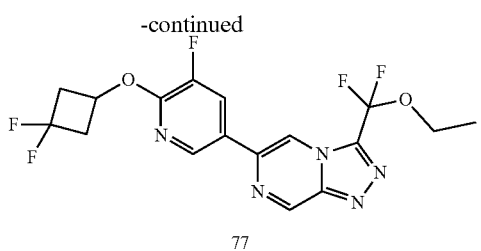

77

To a stirred solution of 3-(chlorodifluoromethyl)-6-(6-(3,3-difluorocyclobutoxy)-5-fluoropyridin-3-yl)-[1,2,4]triazolo[4,3-a]pyrazine (150 mg, 0.34 mmol)) in MeCN (7.5 mL) was added $Cs_2CO_3$ (668 mg, 2.06 mmol) and ethanol (0.2 mL, 3.4 mmol). The reaction mixture was stirred for 1 h at room temperature. The reaction mixture was treated with water (20.0 mL) and extracted with ethyl acetate (2×25 mL). The organic layer was washed with brine (20 mL), dried over anhydrous $Na_2SO_4$ and concentrated. The crude compound was purified by preparative HPLC to afford a solid (22 mg, 0.05 mmol, 15% yield). Prep. HPLC method: Rt 13.1; Column: XBridge C-18 (150×19 mm), 5.0 µm; Mobile phase: 0.1% TFA in water/acetonitrile; Flow Rate: 15.0 mL/min. HPLC: Rt 5.08 min, 94.8% Column: XBridge C8 (50×4.6) mm, 3.5 µm Mobile phase: A: 0.1% TFA in water, B: 0.1% TFA in ACN; Flow Rate: 2.0 mL/min. LCMS: 416.1 (M+H), Rt 2.44 min, Column: ZORBAX XDB C-18 (50×4.6 mm), 3.5 µm Mobile Phase: A: 0.1% HCOOH in water:ACN (95:5), B: ACN; Flow Rate: 1.5 mL/min. $^1$H NMR (400 MHz, $CD_3OD$): δ 9.54 (d, 1H), 8.83 (d, 1H), 8.67 (d, 1H), 8.26 (dd, 1H), 5.32-5.30 (m, 1H), 4.40 (q, 2H), 3.25-3.15 (m, 2H), 2.90-2.77 (m, 2H), 1.49 (t, 3H).

Example 76: 3-(cyclopropoxydifluoromethyl)-6-(6-(3,3-difluorocyclobutoxy)pyridin-3-yl)-[1,2,4]triazolo[4,3-a]pyrazine

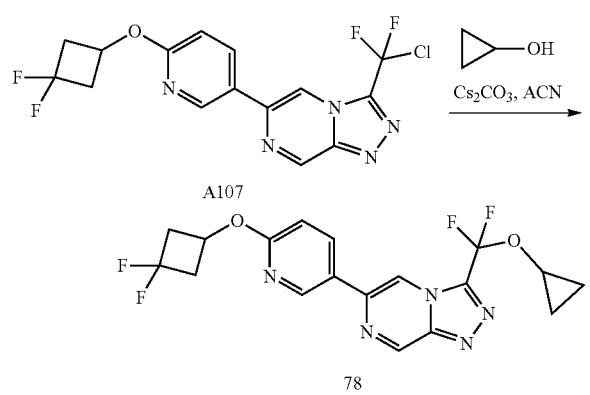

To a stirred solution of 3-(chlorodifluoromethyl)-6-(6-(3,3-difluorocyclobutoxy)pyridin-3-yl)-[1,2,4]triazolo[4,3-a]pyrazine (100 mg, 0.26 mmol) in MeCN (9.0 mL) was added $Cs_2CO_3$ (504 mg, 1.55 mmol) and cyclopropanol (0.33 mL, 5.16 mmol). The reaction mixture was stirred for 4 h at room temperature. The reaction mixture was treated with water (20.0 mL) and extracted with ethyl acetate (2×20 mL). The organic layer was washed with brine (20 mL), dried over anhydrous $Na_2SO_4$ and concentrated. The crude compound was purified by preparative HPLC to afford a solid (14 mg, 0.034 mmol, 13% yield.). Prep. HPLC method: Rt 10.67; Column: Sunfire C-18 (150×19 mm), 5.0 µm; Mobile phase: 0.1% TFA in water/acetonitrile; Flow Rate: 15.0 mL/min. HPLC: Rt 5.19 min, Column: XBridge C8 (50×4.6) mm, 3.5 µm Mobile phase: A: 0.1% TFA in water, B: 0.1% TFA in ACN; Flow Rate: 2.0 mL/min. LCMS: 410.1 (M+H), Rt 2.36 min, Column: XBridge C8 (50×4.6 mm), 3.5 µm Mobile Phase: A: 0.1% TFA in water:ACN (95:5), B: 0.1% TFA in ACN; Flow Rate: 1.5 mL/min. $^1$H NMR (400 MHz, $CD_3OD$): δ 9.54 (d, 1H), 8.84 (d, 1H), 8.71 (s, 1H), 8.37 (dd, 1H), 7.00 (d, 1H), 5.25 (m, 1H), 4.26-4.23 (m, 1H), 3.23-3.13 (m, 2H), 2.82-2.70 (m, 2H), 0.99 (m, 2H), 0.84-0.79 (m, 2H).

Example 77: 3-(ethoxymethyl)-6-(5-fluoro-6-((1,1,1-trifluoro-2-methylpropan-2-yl)oxy)pyridin-3-yl)-[1,2,4]triazolo[4,3-a]pyrazine

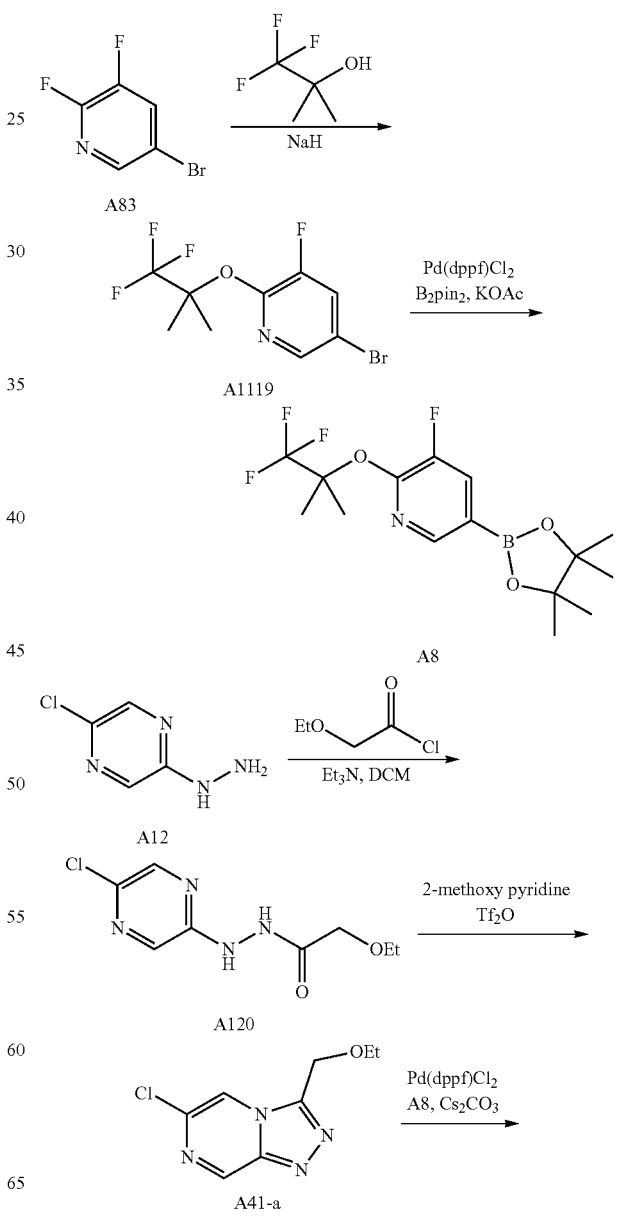

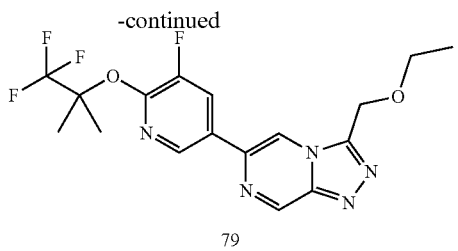

79

Synthesis of A119: To a stirred solution of 1,1,1-trifluoro-2-methylpropan-2-ol (0.57 g, 4.43 mmol) in THF (20 mL) at 0° C. was added NaH (60% in mineral oil, 0.23 g, 5.67 mmol) in small portions. The reaction mixture was slowly warmed to room temperature and stirred for 15 min. 5-bromo-2,3-difluoro-pyridine (1.0 g, 5.16 mmol) was added drop-wise to the reaction mixture and stirred for 16 hours. The reaction mixture was cooled to 10° C. and treated with ice water (30 mL). The reaction mixture was extracted with ethyl acetate (2×50 mL). The organic layer was washed with brine (30 mL), dried over anhydrous $Na_2SO_4$ and concentrated. The crude compound was purified by column chromatography on silica gel with 2% ethyl acetate/PE to afford the product (765 mg, 2.54 mmol, 49% yield). $^+$H NMR (400 MHz, $CDCl_3$): δ 7.99 (d, 1H), 7.54 (dd, 1H), 1.80 (s, 6H).

Synthesis of A8: To a stirred solution of 5-bromo-3-fluoro-2-((1,1,1-trifluoro-2-methylpropan-2-yl)oxy)pyridine (765 mg, 2.54 mmol) and bis(pinacolato)diboron (0.71 g, 2.79 mmol) in 1,4-dioxane (20.0 mL) was added potassium acetate (497 mg, 5.07 mmol). $Pd(dppf)Cl_2 \cdot DCM$ (0.21 g, 0.25 mmol) was added to the reaction mixture under nitrogen atmosphere and heated at 80° C. for 16 hours. The reaction mixture was cooled to room temperature, filtered through Celite and concentrated under reduced pressure. The crude compound was purified by column chromatography on silica gel with 30% ethyl acetate/PE to afford the product_(300 mg, 0.86 mmol, 33% yield). LCMS: 350.1 (M+H), Rt 3.31 min Column: Atlantis dC18 (50×4.6 mm), 3.5 μm Mobile Phase: A: 0.1% HCOOH in water:ACN (95:5), B: ACN; Flow Rate: 1.5 mL/min.

Synthesis of A120: To a stirred solution of (5-chloropyrazin-2-yl)hydrazine (2.0 g, 13.53 mmol) in DCM (15 mL) was added $Et_3N$ (3.78 mL, 27.07 mmol) followed by 2-ethoxyacetyl chloride (2.36 mL, 13.53 mmol) at 0° C. The reaction mixture was slowly warmed to room temperature and stirred for 16 hours. The reaction mixture was treated with saturated ammonium chloride solution (25 mL) and extracted with ethyl acetate (2×25 mL). The organic layer was washed with brine (20 mL), dried over $Na_2SO_4$ and concentrated. The crude product was purified by column chromatography on silica gel with 22% EtOAc/PE to afford the product (0.8 g, 3.47 mmol, 25% yield). LCMS: 231.1 (M+H), Rt 1.07 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A41-a: To a stirred solution of N'-(5-chloropyrazin-2-yl)-2-ethoxyacetohydrazide (400 mg, 1.73 mmol) in DCM (15.0 mL) was added trifluoromethanesulfonic anhydride (0.38 mL, 2.25 mmol) and 2-methoxypridine (377 mg, 3.46 mmol) at 0° C. The reaction mixture was slowly warmed to room temperature and stirred for 16 hours. The reaction mixture was treated with 10% sodium bicarbonate solution (20 mL) and extracted with ethyl acetate (2×25 mL). The organic layer was washed with brine (20 mL), dried over $Na_2SO_4$ and concentrated. The crude product was purified by column chromatography on silica gel with 35% EtOAc/PE to afford the product (100 mg, 0.47 mmol, 27% yield). LCMS: 213.1 (M+H), Rt 1.46 min Column: Atlantis dC18 (50×4.6 mm), 5.0 μm Mobile Phase: A: 0.1% HCOOH in water:ACN (95:5), B: ACN; Flow Rate: 1.5 mL/min.

Synthesis of Compound 79: To a stirred solution of 6-chloro-3-(ethoxymethyl)-[1,2,4]triazolo[4,3-c]pyrazine (150 mg, 0.71 mmol) and 3-fluoro-5-(4,4,5,5-tetramethyl-1,3,2-dioxaborolan-2-yl)-2-((1,1,1-trifluoro-2-methylpropan-2-yl)oxy)pyridine (271 mg, 0.78 mmol) in 1,4-dioxane (10.0 mL) was added water (1.0 mL) and $Cs_2CO_3$ (460 mg, 1.41 mmol). $Pd(dppf)Cl_2 \cdot DCM$ (57 mg, 0.07 mmol) was added to the reaction mixture under nitrogen atmosphere and heated at 80° C. for 16 hours. The reaction mixture was cooled to room temperature, filtered through Celite and concentrated under reduced pressure. The crude compound was purified by preparative HPLC to afford a solid 1105 mg, 0.26 mmol, 36% yield). Prep. HPLC method: Rt 12.75; Column: X-Select (150×19 mm), 5.0 μm; Mobile phase: 0.1% TFA in water/acetonitrile; Flow Rate: 15.0 mL/min. HPLC: Rt 4.95 min, Column: XBridge C8 (50×4.6) mm, 3.5 μm Mobile phase: A: 0.1% TFA in water, B: 0.1% TFA in ACN; Flow Rate: 2.0 mL/min. LCMS: 400.3 (M+H), Rt 2.41 min, Column: ZORBAX XDB C-18 (50×4.6 mm), 3.5 μm Mobile Phase: A: 0.1% HCOOH in water:ACN (95:5), B: ACN; Flow Rate: 1.5 mL/min. $^1$H NMR (400 MHz, DMSO-$d_6$): δ 9.56 (d, 1H), 9.17 (d, 1H), 8.78 (d, 1H), 8.45 (dd, 1H), 5.09 (s, 2H), 3.61 (q, 2H), 1.83 (s, 6H), 1.15 (t, 3H).

Example 79: 3-(ethoxydifluoromethyl)-6-(6-(2,2,2-trifluoroethoxy)pyridin-3-yl)-[1,2,4]triazolo[4,3-a]pyrazine

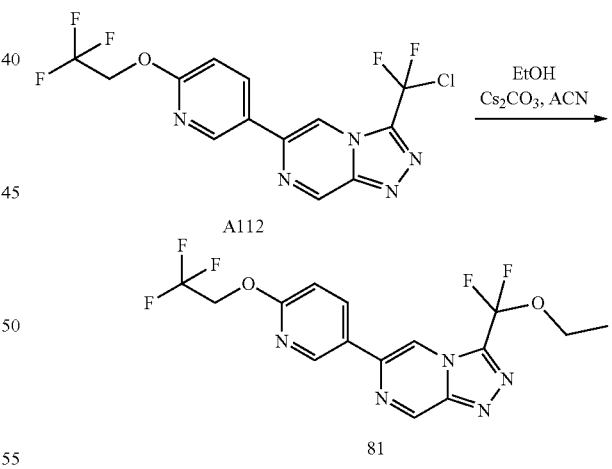

To a stirred solution of 3-(chlorodifluoromethyl)-6-(6-(2,2,2-trifluoroethoxy)pyridin-3-yl)-[1,2,4]triazolo[4,3-a]pyrazine (190 mg, 0.50 mmol)) in MeCN (10.0 mL) was added $Cs_2CO_3$ (978 mg, 3.0 mmol) and ethanol (0.58 mL, 10 mmol) at room temperature and stirred for 3 hours. The reaction mixture was treated with water (15 mL) and extracted with ethyl acetate (2×20 mL). The organic layer was washed with brine (15 mL), dried over anhydrous $Na_2SO_4$ and concentrated. The crude compound was purified by preparative HPLC to afford a solid (10 mg, 0.025 mmol, 5.1% yield). Prep-HPLC method: Rt 9.35; Column:

XBridge (150×19 mm), 5.0 μm; 0.1% TFA in water/acetonitrile; Flow Rate: 15.0 mL/min. HPLC: Rt 4.89 min, Column: XBridge C8 (50×4.6) mm, 3.5 μm Mobile phase: A: 0.1% TFA in water, B: 0.1% TFA in ACN; Flow Rate: 2.0 mL/min. LCMS: 390.0 (M+H), Rt 2.70 min, Column: Atlantis dC-18 (50×4.6 mm), 5 μm Mobile Phase: A: 0.1% HCOOH in water:ACN (95:5), B: ACN; Flow Rate: 1.5 mL/min. $^1$H NMR (400 MHz, CDCl$_3$): δ 9.54 (d, 1H), 8.74 (d, 1H), 8.48 (d, 1H), 8.26 (dd, 1H), 7.06 (d, 1H), 4.87 (q, 2H), 4.38 (q, 2H), 1.52 (t, 3H).

Example 80: 3-(difluoro(isobutoxy)methyl)-6-(5-fluoro-6-(2,2,2-trifluoroethoxy)pyridin-3-yl)-[1,2,4]triazolo[4,3-a]pyrazine

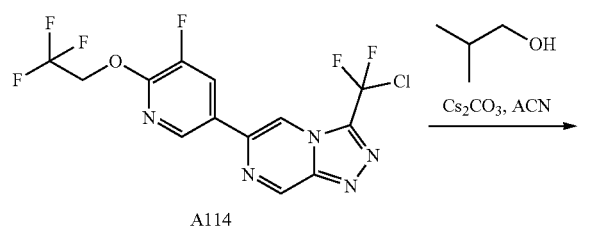

To a stirred solution of 2-methylpropan-1-ol (4.65 mL, 50.29 mmol) in MeCN (20 mL) was added Cs$_2$CO$_3$ (4.92 g, 15.09 mmol) and reaction mixture heated at 70° C. for 20 min. The reaction mixture was cooled to room temperature and 3-(chlorodifluoromethyl)-6-(5-fluoro-6-(2,2,2-trifluoroethoxy)pyridin-3-yl)-[1,2,4]triazolo[4,3-c]pyrazine (1.0 g, 2.51 mmol) was added. The reaction mixture was stirred for 4 h at room temperature and treated with water (30 mL). The reaction mixture was extracted with ethyl acetate (2×30 mL), washed with brine (20 mL), dried over Na$_2$SO$_4$ and concentrated. The crude compound was purified by preparative HPLC to afford a solid (35 mg, 0.08 mmol, 3% yield.). Prep-HPLC method: Rt 9.37; Column: XBridge C8 (150×19 mm), 5.0 μm; 0.1% TFA in water/acetonitrile; Flow Rate: 15.0 mL/min. HPLC: Rt 5.60 min, Column: XBridge C8 (50×4.6) mm, 3.5 μm Mobile phase: A: 0.1% TFA in water, B: 0.1% TFA in ACN; Flow Rate: 2.0 mL/min. LCMS: 436.1 (M+H), Rt 2.63 min, Column: XBridge C8 (50×4.6 mm), 3.5 μm Mobile Phase: A: 0.1% TFA in water:ACN (95:5), B: 0.1% TFA in ACN; Flow Rate: 1.5 mL/min. $^1$H NMR (400 MHz, DMSO-d$_6$): δ 9.72 (d, 1H), 8.97 (d, 1H), 8.77 (d, 1H), 8.54 (dd, 1H), 5.19 (q, 2H), 4.04 (d, 2H), 2.10-2.02 (m, 1H), 0.98 (d, 6H).

Example 81: 5-[3-[difluoro(methoxy)methyl]-[1,2,4]triazolo[4,3-a]pyrazin-6-yl]pyridin-2-ol and 6-(6-benzyloxy-5-fluoro-3-pyridyl)-3-[ethoxy(difluoro)methyl]-[1,2,4]triazolo[4,3-a]pyrazine

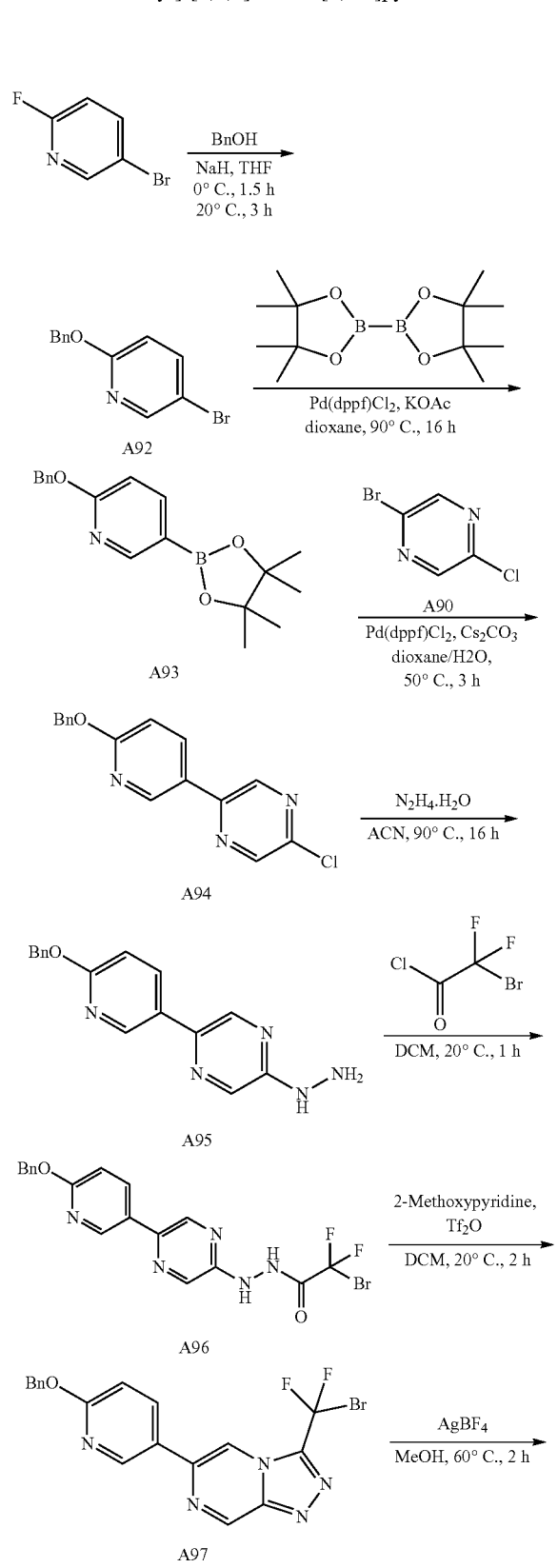

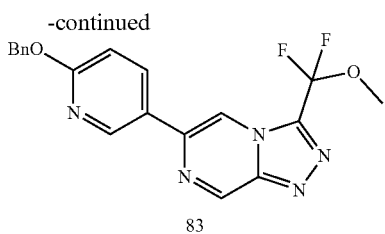

83

Synthesis of A92: To a solution of phenylmethanol (12 g, 110.97 mmol) in THF (100 mL) was added NaH (4.88 g, 122.06 mmol) in portions at 0° C. over 0.5 hour. After the addition, the mixture was stirred at 20° C. for another 1 hour. Then 5-bromo-2-fluoro-pyridine (18.55 g, 105.4 2 mmol) was added to the mixture. The resulting mixture was stirred at 20° C. for 3 hours. The mixture was poured into saturated aqueous $NH_4$ (150 mL) and extracted with EtOAc (200 mL×2). The combined organic phase was washed with brine (100 mL), dried over anhydrous $Na_2SO_4$, filtered and concentrated to give the crude product (27 g, 95.62 mmol, 86% yield) as an oil. LCMS $R_t$=0.96 min in 1.5 min chromatography, 5-95AB, MS ESI calcd. for $C_{12}H_{11}BrNO[M+H+2]^+$ 266.0, found 265.8.

Synthesis of A93: A mixture of 2-benzyloxy-5-bromo-pyridine (27 g, 102.23 mmol), 4,4,5,5-tetramethyl-2-(4,4,5,5-tetramethyl-1,3,2-dioxaborolan-2-yl)-1,3,2-dioxaborolane (31.15 g, 122.67 mmol), KOAc (20.06 g, 204.45 mmol) and $Pd(dppf)Cl_2$ (7.48 g, 10.22 mmol) in 1,4-dioxane (300 mL) was stirred at 90° C. under $N_2$ for 16 hours. After cooling to room temperature, the mixture was filtered through Celite and concentrated to give the crude product. The crude product was filtered through silica gel (50 g) and eluted with PE/EtOAc (5:1, 150 mL×5), and the filtrate was concentrated to give the impure product. The impure product was triturated from i-$Pr_2O$ (100 mL) to give the product (20 g, 64.27 mmol, 63% yield) as a solid.

LCMS $R_t$=0.74 min in 1.5 min chromatography, 5-95AB, MS ESI calcd. for $C_{12}H_{13}BNO_3[M-C_6H_{10}+H]^+$ 230.1, found 230.0.

Synthesis of A94: A mixture of 2-bromo-5-chloro-pyrazine (4 g, 20.68 mmol), 2-benzyloxy-5-(4,4,5,5-tetramethyl-1,3,2-dioxaborolan-2-yl)pyridine (7.08 g, 22.75 mmol), $Cs_2CO_3$ (13.47 g, 41.36 mmol) and $Pd(dppf)Cl_2$ (1.51 g, 2.07 mmol) in 1,4-dioxane (50 mL) and water (10 mL) was stirred at 50° C. under $N_2$ for 3 hours. After cooling to room temperature, the mixture was filtered and concentrated to give a residue. To the residue was added water (100 mL), extracted with EtOAc (150 mL×2). The combined organic phase was washed with brine (50 mL), dried over anhydrous $Na_2SO_4$, filtered and concentrated to give the crude product. The crude product was filtered through silica gel (50 g) and eluted with DCM (150 mL×3). The filtrate was concentrated to give the impure product. The impure product was triturated from i-$Pr_2O$ (15 mL) to give the product of (4 g, 13.44 mmol, 65% yield) as a solid. LCMS $R_t$=1.03 min in 1.5 min chromatography, 5-95AB, MS ESI calcd. for $C_{16}H_{13}ClN_3O$ $[M+H]^+$ 298.1, found 297.9.

Synthesis of A95: A mixture of 2-(6-benzyloxy-3-pyridyl)-5-chloro-pyrazine (4 g, 13.43 mmol) and $N_2H_4·H_2O$ (8.61 g) in MeCN (20 mL) was stirred at 90° C. for 16 hours. After cooling to room temperature, the solution was concentrated to give a residue. To the residue was added water (30 mL), extracted with EtOAc (50 mL×3). The combined organic phase was washed with brine (30 mL), dried over anhydrous $Na_2SO_4$, filtered and concentrated to give the product (4 g, 7.84 mmol, 58% yield) as a solid. LCMS $R_t$=0.74 min in 1.5 min chromatography, 5-95AB, MS ESI calcd. for $C_{16}H_{16}N_5O$ $[M+H]^+$ 294.1, found 293.9.

Synthesis of A96: To a solution of 2-bromo-2,2-difluoro-acetyl chloride (1.78 g, 9.2 mmol) in DCM (20 mL) was added [5-(6-benzyloxy-3-pyridyl)pyrazin-2-yl]hydrazine (1.8 g, 6.14 mmol), and the suspension was stirred at 20° C. for 2 hours. The mixture was diluted with $H_2O$ (20 mL) and extracted with EtOAc (100 mL×2). The combined organic phase was washed with brine (30 mL), dried over $Na_2SO_4$, filtered and concentrated to give the product. The crude product was purified by flash chromatography on silica gel (EtOAc in PE=20% to 40% to 60% to 80%) to give the product of (1.5 g, 3.33 mmol, 54% yield) as a solid. LCMS $R_t$=0.88 min in 1.5 min chromatography, 10-80AB, MS ESI calcd. for $C_{18}H_{15}F_2N_5O_2$ $[M+H]^+$ 450.0, found 449.9.

Synthesis of A97: To a mixture of N'-[5-(6-benzyloxy-3-pyridyl)pyrazin-2-yl]-2-bromo-2,2-difluoro-acetohydrazide (1.3 g, 2.89 mmol) in DCM (10 mL) was added 2-methoxy-pyridine (0.67 mL, 6.35 mmol) and $Tf_2O$ (0.59 mL, 3.46 mmol), and the mixture was stirred at 20° C. for 2 hours. To the mixture was added water (20 mL), extracted with DCM (50 mL×2). The combined organic phase was washed with saturated aqueous $NaHCO_3$ (30 mL) and brine (30 mL), dried over $Na_2SO_4$, filtered and concentrated to give the crude product. The crude product was purified by chromatography flash column on silica gel (EtOAc in PE=0% to 30% to 50%) to give the product (400 mg, 0.93 mmol, 32% yield) as a solid. LCMS $R_t$=0.93 min in 1.5 min chromatography, 10-80AB, MS ESI calcd. for $C_{18}H_{13}BrF_2N_5O$ $[M+H+2]^+$ 434.0, found 434.0.

Synthesis of 83: A mixture of 6-(6-benzyloxy-3-pyridyl)-3-[bromo(difluoro)methyl]-[1,2,4]triazolo[4,3-a]pyrazine (400 mg, 0.93 mmol) and $AgBF_4$ (900.79 mg, 4.63 mmol) in methanol (4 mL) was stirred at 60° C. under dark for 2 hours. After cooling to room temperature, saturated aqueous NaCl (10 mL) was added to the mixture followed by EtOAc (30 mL), and the mixture was filtered through Celite. After the phases of the filtrate were separated, the organic phase was washed with brine (30 mL), dried over $Na_2SO_4$, filtered and concentrated to give the crude product. The crude product was purified by flash chromatography on silica gel (EtOAc in PE=20% to 40%) to give the impure product (150 mg), which was triturated from i-$Pr_2O$ (2 mL) to give the pure product (130 mg). The product (39.76 mg, 0.10 mmol, 11% yield) was obtained as a solid. $^1$H NMR (400 MHz, $CDCl_3$) $δ_H$=9.52 (d, 1H), 8.76 (d, 1H), 8.42 (d, 1H), 8.19 (dd, 1H), 7.53-7.47 (m, 2H), 7.45-7.32 (m, 3H), 6.98 (d, 1H), 5.48 (s, 2H), 3.97 (s, 3H). LCMS $R_t$=1.26 min in 2.0 min chromatography, 10-80AB, MS ESI calcd. for $C_{19}H_{16}F_2N_5O_2$ $[M+H]^+$ 384.1, found 384.1.

Example 82: 3-(difluoro(methoxy)methyl)-6-(6-(3,3-difluorocyclobutoxy)-5-fluoropyridin-3-yl)-[1,2,4]triazolo[4,3-a]pyridine

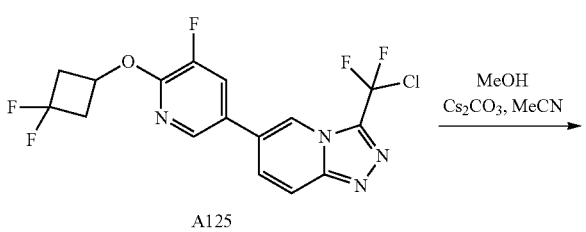

A125

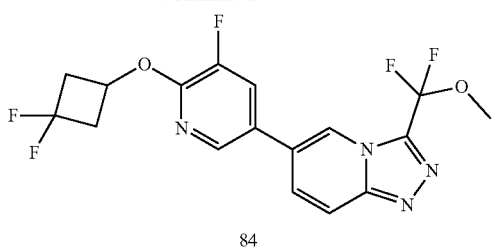

84

To a suspension of Cs₂CO₃ (928 mg, 2.85 mmol) in CH₃CN (2.0 mL) was added methanol (0.23 mL, 5.7 mmol) at room temperature. The reaction mixture was stirred at room temperature for 10 min. and a solution of 3-(chlorodifluoromethyl)-6-(6-(3,3-difluorocyclobutoxy)-5-fluoropyridin-3-yl)-[1,2,4]triazolo[4,3-a]pyridine (190 mg, 0.47 mmol) in CH₃CN (10.0 mL) was added dropwise. The reaction mixture was stirred for 2 hours at room temperature. The reaction mixture was diluted with water (20 mL) and extracted with ethyl acetate (2×25 mL). The organic layer was washed with brine (20 mL), dried over Na₂SO₄ and concentrated. The crude product was purified by preparative HPLC to afford the product (50 mg, 0.12 mmol, 26% yield) as a solid. Prep. HPLC method: Rt 11.75; Column: X-Bridge (150×19 mm), 5.0 µm; Mobile phase: 0.1% TFA in water/acetonitrile; Flow Rate: 15.0 mL/min. HPLC: Rt 4.64 min, 99.8% Column: X-Bridge C8 (50×4.6) mm, 3.5 µm Mobile phase: A: 0.1% TFA in water, B: 0.1% TFA in ACN; Flow Rate: 2.0 mL/min. LCMS: 401.1 (M+H), Rt 2.22 min, 99.6% Column: ZORBAX XDB C-18 (50×4.6 mm), 3.5 µm Mobile Phase: A: 0.1% HCOOH in water:ACN (95:5), B: ACN; Flow Rate: 1.5 mL/min. ¹H NMR (400 MHz, CD₃OD): δ 8.65 (s, 1H), 8.31 (d, 1H), 8.00-7.97 (m, 2H), 7.90 (dd, 1H), 5.32-5.28 (m, 1H), 3.96 (s, 3H), 3.26-3.15 (m, 2H), 2.89-2.77 (m, 2H).

Example 83: 6-(6-(3,3-difluorocyclobutoxy)-5-fluoropyridin-3-yl)-3-(ethoxydifluoromethyl)-[1,2,4]triazolo[4,3-a]pyridine

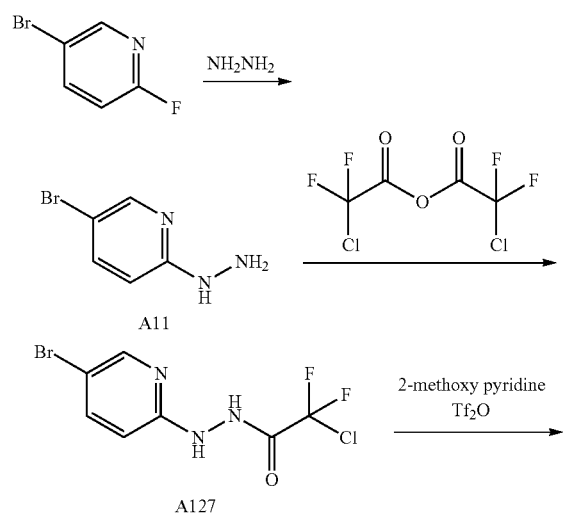

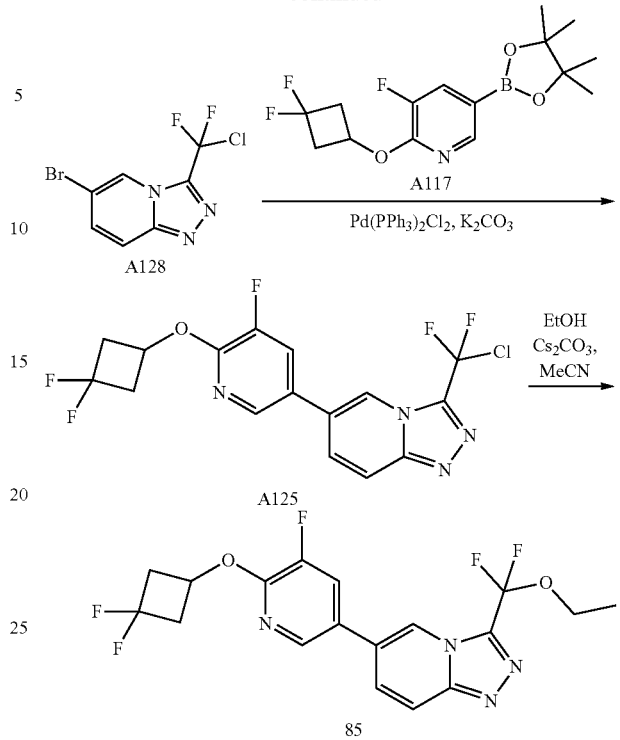

Synthesis A11: To a stirred solution of 5-bromo-2-fluoropyridine (10.0 g, 56.82 mmol) in ethanol (120 mL) was added hydrazine hydrate (11.38 g, 227 mmol) and heated to 80° C. for 12 hours The reaction mixture was cooled to room temperature and treated with ice water (200 mL). The precipitated solid was filtered, washed with water and dried to get the product (10.7 g) as a solid. It was used for the next step without further purification.

Synthesis of A127: To a stirred solution of A11 (2.0 g, 10.6 mmol) in toluene (25 mL) was added 2-chloro-2,2-difluoroacetic anhydride (2.84 g, 11.7 mmol) at 0° C. The reaction mixture was heated at 100° C. for 1 hour. The reaction mixture was cooled to room temperature and concentrated. The crude reaction mixture was treated with water (50 mL) and extracted with ethyl acetate (2×50 mL). The organic layer was washed with sat NaHCO₃ solution (20 mL) followed by brine (30 mL), dried over Na₂SO₄ and concentrated to afford the product (2.7 g) as a solid. It was used for the next step without further purification.

Synthesis of A128: To a stirred solution of A127 (2.7 g, 8.99 mmol) in DCM (30 mL) was added trifluoromethanesulfonic anhydride (1.66 mL, 9.88 mmol) and 2-methoxypridine (1.96 g, 17.97 mmol) at 0° C. The reaction mixture was slowly warmed to room temperature and stirred for 1 hour The reaction mixture was treated with 10% sodium bicarbonate solution (50 mL) and extracted with DCM (2×50 mL). The organic layer was washed with brine (50 mL), dried over Na₂SO₄ and concentrated. The crude product was purified by column chromatography on silica gel with 20% EtOAc/PE to afford the product (1.1 g, 3.9 mmol, 43% yield). LCMS: 282.0 (M+H) and 284.0 (M+2+H), Rt 1.72 min Column: ZORBAX XDB C-18 (50×4.6 mm), 3.5 µm Mobile Phase: A: 0.1% HCOOH in water:ACN (95:5), B: ACN; Flow Rate: 1.5 mL/min.

Synthesis of A125: To a stirred solution of A128 (1.0 g, 3.54 mmol) and 2-(3,3-difluorocyclobutoxy)-3-fluoro-5-(4,4,5,5-tetramethyl-1,3,2-dioxaborolan-2-yl)pyridine (1.28 g, 3.89 mmol) in 1,4-dioxane (20.0 mL) was added water (4.0 mL) and K$_2$CO$_3$ (0.98 g, 7.08 mmol). Pd(PPh$_3$)$_2$Cl$_2$ (0.25 g, 0.35 mmol) was added to the reaction mixture under nitrogen atmosphere and heated at 80° C. for 16 hours The reaction mixture was cooled to room temperature and filtered through Celite. The crude reaction mixture was treated with water (30 mL) and extracted with ethyl acetate (2×30 mL). The organic layer was washed with brine (30 mL), dried over anhydrous Na$_2$SO$_4$ and concentrated. The crude compound was purified by column chromatography on silica gel with 40% ethyl acetate/PE to afford the compound (1.1 g, 2.7 mmol, 76% yield) as a solid. LCMS: 405.0 (M+H), Rt 2.68 min Column: Atlantis dC-18 (50×4.6 mm), 5.0 μm Mobile Phase: A: 0.1% HCOOH in water:ACN (95:5), B: ACN; Flow Rate: 1.5 mL/min.

Synthesis of Compound 85: To a suspension of Cs$_2$CO$_3$ (966 mg, 2.97 mmol) in CH$_3$CN (2.0 mL) was added ethanol (0.35 mL, 5.93 mmol) at room temperature. The reaction mixture was stirred at room temperature for 10 min. and a solution of A125 (200 mg, 0.49 mmol) in CH$_3$CN (10.0 mL) was added dropwise. The reaction mixture was stirred for 1 h and ethanol (0.35 mL, 5.93 mmol) was added at room temperature. The reaction mixture was stirred for another 1 h at room temperature. The reaction mixture was treated with water (20 mL) and extracted with ethyl acetate (2×25 mL). The organic layer was washed with brine (20 mL), dried over Na$_2$SO$_4$ and concentrated. The crude product was purified by column chromatography on silica gel with 22% EtOAc/PE to afford the product (30 mg, 0.07 mmol, 14% yield) as a solid. HPLC: Rt 4.92 min, 99.9% Column: X-Bridge C8 (50×4.6) mm, 3.5 μm Mobile phase: A: 0.1% TFA in water, B: 0.1% TFA in ACN; Flow Rate: 2.0 mL/min. LCMS: 415.1 (M+H), Rt 2.53 min, 99.8% Column: Atlantis dC-18 (50×4.6 mm), 5.0 μm. Mobile Phase: A: 0.1% HCOOH in water:ACN (95:5), B: ACN; Flow Rate: 1.5 mL/min. $^1$H NMR (400 MHz, CD$_3$OD): δ 8.65 (s, 1H), 8.30 (d, 1H), 8.00-7.96 (m, 2H), 7.89 (dd, 1H), 5.32-5.29 (m, 1H), 4.36 (q, 2H), 3.26-3.16 (m, 2H), 2.89-2.78 (m, 2H), 1.47 (t, 3H).

Example 84: (R)-3-(ethoxydifluoromethyl)-6-(6-((1,1,1-trifluoropropan-2-yl)oxy)pyridin-3-yl)-[1,2,4]triazolo[4,3-a]pyrazine

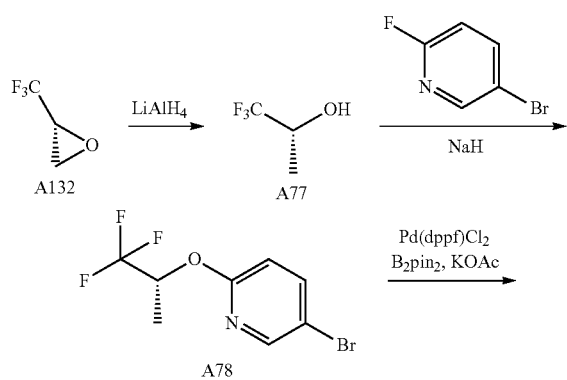

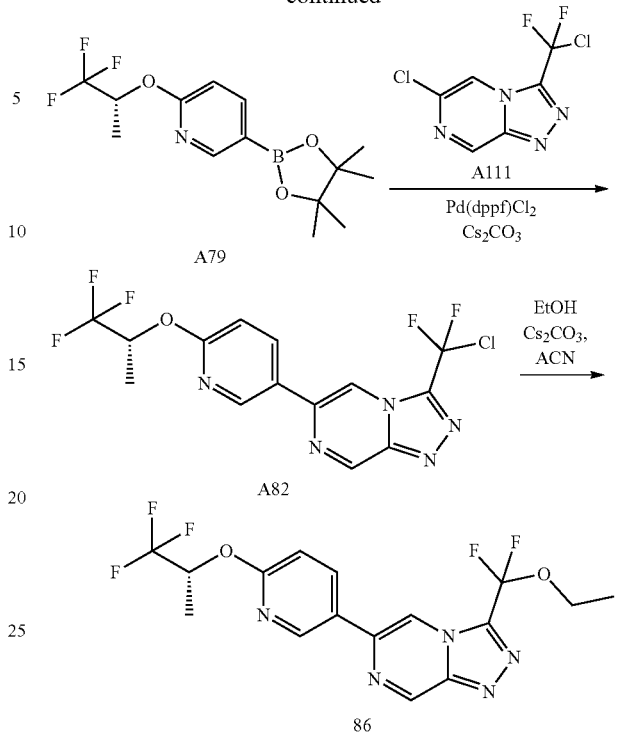

Synthesis of A77: To a solution of A132 (2.2 g, 19.63 mmol) in THF (20.0 mL) was added LiAlH$_4$ (2.0 M in THF, 4.91 mL, 9.82 mmol) dropwise at 0° C. The reaction mixture was slowly warmed to room temperature and stirred for 3 hours. The reaction mixture was cooled to 0° C. and treated with sat Na$_2$SO$_4$ solution (2.0 mL). The reaction mixture was filtered through Celite, the filtrate was dried over Na$_2$SO$_4$ and used for the next step as a solution in THF.

Synthesis of A78: To a solution of A77 (30.68 mmol) in THF was added NaH (1.84 g, 46 mmol) portion wise at 0° C. and stirred for 30 min. 5-bromo-2-fluoro-pyridine (4.32 g, 24.55 mmol) was added to the reaction mixture slowly at 0° C. The reaction mixture was slowly warmed to room temperature and stirred for 3 hours. The reaction mixture was cooled to 10° C., treated with ice water (10 mL) and extracted with ethyl acetate (2×50 mL). The organic layer was washed with brine (40 mL), dried over Na$_2$SO$_4$ and concentrated. The crude product was purified by column chromatography on silica gel with 20% EtOAc/PE to afford the product (3.1 g, 11.5 mmol, 37% yield) as a colourless liquid. LCMS: 270.0 (M+H) and 272.0 (M+2+H), Rt 2.78 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A79: To a stirred solution of A78 (3.1 g, 11.5 mmol) and bis(pinacolato)diboron (3.79 g, 14.92 mmol) in 1,4-dioxane (35.0 mL) was added potassium acetate (2.25 g, 22.96 mmol). Pd(dppf)Cl$_2$.DCM (1.41 g, 1.72 mmol) was added to the reaction mixture under nitrogen atmosphere and heated at 90° C. for 12 hours. The reaction mixture was cooled to room temperature, filtered through Celite and concentrated under reduced pressure. The crude compound was purified by column chromatography on silica gel with 6% ethyl acetate/PE to afford the product (2.8 g, 8.83 mmol, 76% yield) as a solid. LCMS: 318.0 (M+H), Rt 4.04 min Column: ZORBAX Extend (50×4.6 mm), 5 μm Mobile Phase: A: 10 mM Ammonium acetate in water, B: ACN; Flow Rate: 1.2 mL/min.

Synthesis of A82: To a stirred solution of A79 (0.5 g, 1.58 mmol) and 6-chloro-3-(chlorodifluoromethyl)-[1,2,4]triazolo[4,3-a]pyrazine (0.45 g, 1.89 mmol) in 1,4-dioxane (12.0 mL) was added water (2.0 mL) and $Cs_2CO_3$ (1.03 g, 3.15 mmol). $Pd(dppf)Cl_2 \cdot DCM$ (0.11 g, 0.16 mmol) was added to the reaction mixture under nitrogen atmosphere and heated at 90° C. for 16 hours. The reaction mixture was cooled to room temperature, filtered through Celite and concentrated under reduced pressure. The crude compound was purified by column chromatography on silica gel with 15% ethyl acetate/PE to afford the product (350 mg, 0.89 mmol, 56% yield) as a solid. LCMS: 394.1 (M+H), Rt 2.54 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of Compound 86: To a stirred suspension of $Cs_2CO_3$ (993 mg, 3.05 mmol) in MeCN (5.0 mL) was added ethanol (0.36 mL, 6.1 mmol) at room temperature and stirred for 30 min. To the reaction mixture A82 (200 mg, 0.51 mmol) in MeCN (5.0 mL) was added dropwise and stirred for 2 hours. The reaction mixture was treated with water (30 mL) and extracted with ethyl acetate (2×30 mL). The organic layer was washed with brine (20 mL), dried over $Na_2SO_4$ and concentrated The crude compound was purified by column chromatography on silica gel with 18% ethyl acetate/PE to afford the product (35 mg, 0.08 mmol, 17% yield) as a solid. HPLC: Rt 5.22 min, 97.6% Column: X-Bridge C8 (50×4.6) mm, 3.5 μm Mobile phase: A: 0.1% TFA in water, B: 0.1% TFA in ACN; Flow Rate: 2.0 mL/min. LCMS: 404.1 (M+H), Rt 2.53 min, 96.7% Column: ZORBAX Extend C-18 (50×4.6 mm), 5.0 μm Mobile Phase: A: 10 mM Ammonium acetate in water, B: ACN; Flow Rate: 1.2 mL/min. Chiral method: Rt 1.54 min, SFC column: Chiralcel OJ-H; mobile phase: 60:40 (A: B), A=liquid $CO_2$, B=0.5% isopropyl amine in methanol; flow rate: 3.0 mL/min; wave length: 254 nm. $^1$H NMR (400 MHz, $CD_3OD$): δ 9.55 (d, 1H), 8.88-8.87 (m, 1H), 8.80 (d, 1H), 8.42 (dd, 1H), 7.03 (dd, 1H), 6.00-5.93 (m, 1H), 4.39 (q, 2H), 1.55-1.48 (m, 6H).

Example 84: 3-(methoxymethyl)-6-(64 (1,1,1-trifluoro-2-methylpropan-2-yl)oxy)pyridin-3-yl)-[1,2,4]triazolo[4,3-a]pyridine

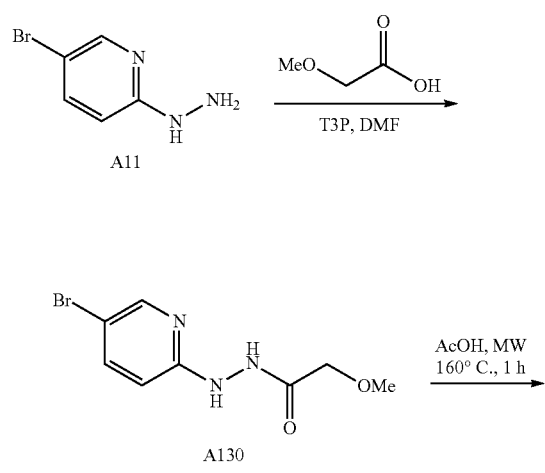

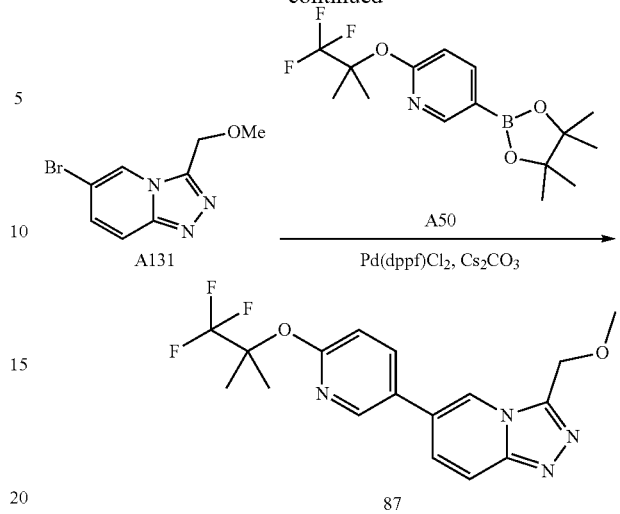

Synthesis of A130: To a stirred solution of methoxyacetic acid (958 mg, 10.64 mmol) in DMF (30.0 mL) was added $Et_3N$ (2.97 mL, 21.27 mmol) followed by T3P (50% in ethyl acetate, 0.43 mL, 21.27 mmol) and 5-bromo-2-hydrazinneylpyridine (2.0 g, 10.64 mmol). The reaction mixture was stirred at room temperature for 4 hours The reaction mixture was treated with water (30 mL) and extracted with ethyl acetate (2×30 mL). The organic layer was washed with brine (40 mL), dried over anhydrous $Na_2SO_4$ and concentrated. The crude compound was purified by column chromatography on silica gel with 20% ethyl acetate/PE to afford the product (900 mg, 3.47 mmol, 32% yield). LCMS: 260.1 (M+H) and 262.1 (M+2+H), Rt 1.10 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A131: To a stirred solution of A130 (250 mg, 0.96 mmol) in acetic acid (4.0 mL) was irradiated in microwave at 160° C. for 1 hour The reaction mixture was cooled to room temperature and treated with 10% sodium bicarbonate solution (20 mL). The reaction mixture was extracted with ethyl acetate (2×25 mL). The organic layer was washed with brine (2×20 mL), dried over $Na_2SO_4$ and concentrated. The crude product was purified by column chromatography on silica gel with 35% EtOAc/PE to afford the product (110 mg, 0.45 mmol, 47% yield). LCMS: 242.1 (M+H) and 244.1 (M+2+H), Rt 1.18 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of Compound 87: To a stirred solution of 5-(4,4,5,5-tetramethyl-1,3,2-dioxaborolan-2-yl)-2-((1,1,1-trifluoro-2-methylpropan-2-yl)oxy)pyridine (250 mg, 0.75 mmol) and A131 (200 mg, 0.83 mmol) in 1,4-dioxane (5.0 mL) was added water (1.0 mL) and $Cs_2CO_3$ (491 mg, 1.51 mmol). $Pd(dppf)Cl_2 \cdot DCM$ (65 mg, 0.08 mmol) was added to the reaction mixture under nitrogen atmosphere and heated at 80° C. for 16 hours The reaction mixture was cooled to room temperature, filtered through Celite and concentrated under reduced pressure. The crude compound was purified by preparative HPLC to afford the product (90 mg, 0.24 mmol, 32% yield) as a solid. Prep-HPLC method: Rt 8.37; Column: X-Bridge C-18 (150×19 mm), 5.0 μm; 0.1% TFA in water/acetonitrile; Flow Rate: 15.0 mL/min. HPLC: Rt 4.18 min, Column: X-Bridge C8 (50×4.6) mm, 3.5 μm Mobile phase: A: 0.1% TFA in water, B: 0.1% TFA in ACN; Flow Rate: 2.0 mL/min. LCMS: 367.1 (M+H), Rt 2.12 min, Column: ZORBAX XDB C-18 (50×4.6 mm), 3.5 μm Mobile Phase: A: 0.1% HCOOH in water:ACN (95:5), B: ACN; Flow Rate: 1.5 mL/min. $^1$H NMR (400 MHz, DMSO-$d_6$): δ 8.79-8.78 (m, 1H), 8.63 (d, 1H), 8.20 (dd, 1H), 7.92 (dd, 1H), 7.81 (dd, 1H), 7.04 (d, 1H), 5.02 (s, 2H), 3.34 (s, 3H), 1.82 (s, 6H).

Example 86: 3-(ethoxydifluoromethyl)-6-(6-((1,1,1-trifluoro-2-methylpropan-2-yl)oxy)pyridin-3-yl)-[1,2,4]triazolo[4,3-a]pyrazine

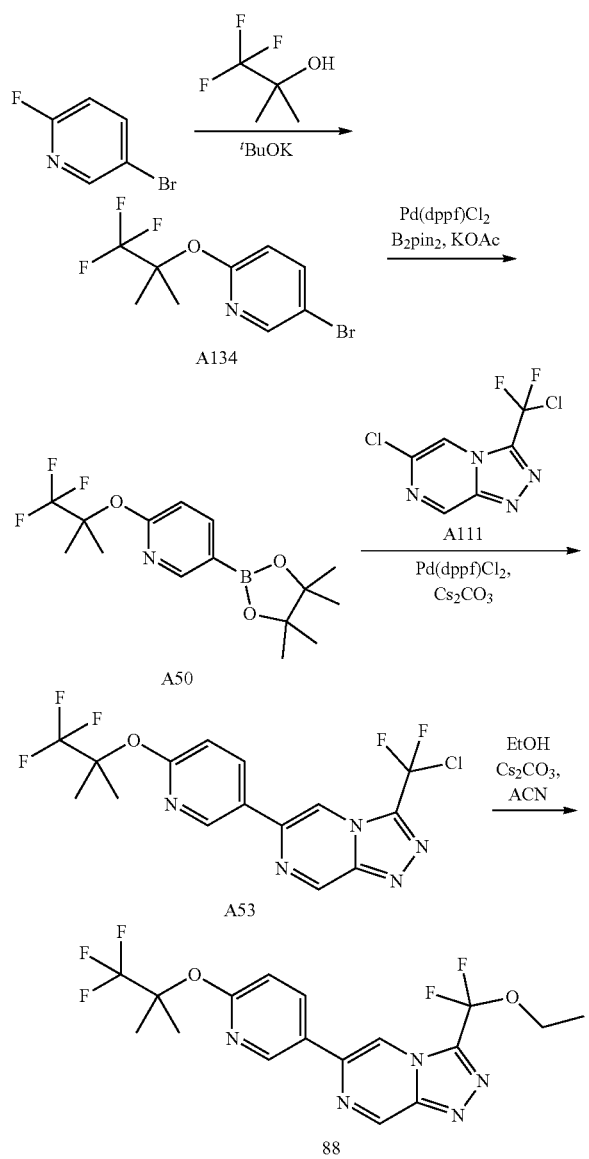

Synthesis of A134: To a stirred solution of 1,1,1-trifluoro-2-methyl-propan-2-ol (5.0 g, 39.04 mmol) in THF (60.0 mL) at 0° C. was added potassium tert-butoxide (6.57 g, 58.55 mmol) in small portions. The reaction mixture was slowly warmed to room temperature and stirred for 15 min. 5-bromo-2-fluoro-pyridine (6.87 g, 39.04 mmol) was added drop-wise to the reaction mixture and stirred for 2 hours. The reaction mixture was cooled to 10° C. and treated with ice water (50 mL). The reaction mixture was extracted with ethyl acetate (2×60 mL). The organic layer was washed with brine (50 mL), dried over anhydrous $Na_2SO_4$ and concentrated. The crude compound was purified by column chromatography on silica gel with 5% ethyl acetate/PE to afford the product (2.3 g, 8.1 mmol, 20% yield). LCMS: 284.0 (M+H) and 286.0 (M+2+H), Rt 2.96 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis A50: To a stirred solution of A134 (2.3 g, 8.1 mmol) and bis(pinacolato)diboron (2.26 g, 8.91 mmol) in 1,4-dioxane (40.0 mL) was added potassium acetate (1.59 g, 16.19 mmol). $Pd(dppf)Cl_2$.DCM (0.66 g, 0.81 mmol) was added to the reaction mixture under nitrogen atmosphere and heated at 80° C. for 12 hours. The reaction mixture was cooled to room temperature, filtered through Celite and concentrated under reduced pressure. The crude compound was purified by column chromatography on silica gel with 5% ethyl acetate/PE to afford the product (1.8 g, 5.4 mmol, 66% yield). LCMS: 332.1 (M+H), Rt 3.21 min Column: ATLANTIS dC-18 (50×4.6 mm), 3.5 μm Mobile Phase: A: 0.1% HCOOH in water:ACN (95:5), B: ACN; Flow Rate: 1.5 mL/min.

Synthesis of A53: To a stirred solution of A50 (1.2 g, 3.62 mmol) and 6-chloro-3-(chlorodifluoromethyl)-[1,2,4]triazolo[4,3-a]pyrazine (0.95 g, 3.99 mmol) in 1,4-dioxane (20.0 mL) was added water (2.0 mL) and $Cs_2CO_3$ (2.36 g, 7.25 mmol). $Pd(dppf)Cl_2$.DCM (0.3 g, 0.36 mmol) was added to the reaction mixture under nitrogen atmosphere and heated at 80° C. for 12 hours. The reaction mixture was cooled to room temperature, filtered through Celite and concentrated under reduced pressure. The crude product was purified by column chromatography on silica gel with 30% ethyl acetate/PE to afford the product (0.75 g, 1.84 mmol, 50% yield). LCMS: 408.0 (M+H), Rt 2.68 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of Compound 88: To a stirred suspension of $Cs_2CO_3$ (1.43 g, 4.41 mmol) in MeCN (3.0 mL) was added ethanol (0.52 mL, 8.83 mmol) at room temperature and stirred for 15 min. To the reaction mixture A53 (300 mg, 0.74 mmol) in MeCN (3.0 mL) was added dropwise and stirred for 6 hours. The reaction mixture was treated with water (50 mL) and extracted with ethyl acetate (2×25 mL). The organic layer was washed with brine (2×20 mL), dried over $Na_2SO_4$ and concentrated. The crude product was purified by column chromatography on silica gel with 15% EtOAc/PE to afford the product (20 mg, 0.047 mmol, 6% yield) as a solid. HPLC: Rt 5.50 min, 98.5% Column: X-Bridge C8 (50×4.6) mm, 3.5 μm Mobile phase: A: 0.1% TFA in water, B: 0.1% TFA in ACN; Flow Rate: 2.0 mL/min. LCMS: 418.1 (M+H), Rt 2.68 min, 97.8% Column: ZORBAX XDB C-18 (50×4.6 mm), 3.5 μm Mobile Phase: A: 0.1% HCOOH in water:ACN (95:5), B: ACN; Flow Rate: 1.5 mL/min. $^1$H NMR (400 MHz, DMSO-$d_6$): δ 9.70 (d, 1H), 8.91 (d, 2H), 8.46 (dd, 1H), 7.04 (d, 1H), 4.32 (q, 2H), 1.83 (s, 6H), 1.39 (t, 3H).

Example 87: Synthesis of Compound 89

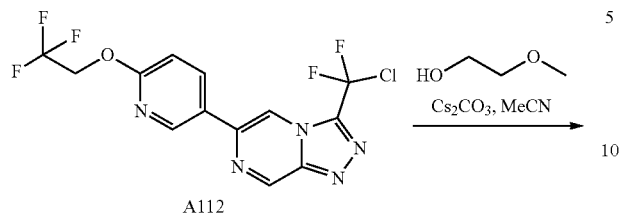

A112

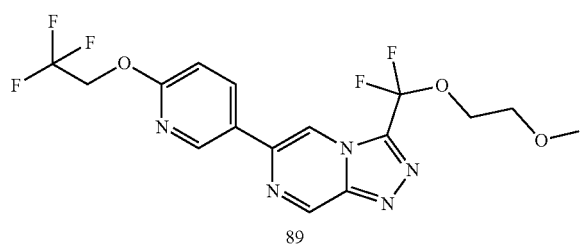

89

To a stirred solution of 3-(chlorodifluoromethyl)-6-(6-(2,2,2-trifluoroethoxy)pyridin-3-yl)-[1,2,4]triazolo[4,3-a]pyrazine (146 mg, 0.38 mmol) in MeCN (5.0 mL) was added Cs$_2$CO$_3$ (751 mg, 2.3 mmol) and 2-methoxyethanol (0.38 mL, 4.8 mmol) at room temperature. The reaction mixture was stirred for 3 h. The reaction mixture was treated water (15 mL) and extracted with ethyl acetate (2×15 mL). The organic layer was washed with brine (20 mL), dried over Na$_2$SO$_4$ and concentrated. The crude compound was purified by preparative HPLC to afford the product (15 mg, 0.03 mmol, 9% yield) as a solid. Prep-HPLC method: Rt 11.3; Column: X-Bridge C8 (150×19 mm), 5.0 μm; 0.1% TFA in water/acetonitrile; Flow Rate: 15.0 mL/min. HPLC: Rt 4.69 min, Column: X-Bridge C8 (50×4.6) mm, 3.5 μm Mobile phase: A: 0.1% TFA in water, B: 0.1% TFA in ACN; Flow Rate: 2.0 mL/min. LCMS: 420.0 (M+H), Rt 2.33 min, Column: X-Bridge C8 (50×4.6 mm), 3.5 μm Mobile Phase: A: 0.1% TFA in water:ACN (95:5), B: 0.1% TFA in ACN; Flow Rate: 1.5 mL/min. $^1$H NMR (400 MHz, DMSO-d$_6$): δ 9.72 (d, 1H), 8.93 (d, 1H), 8.89 (d, 1H), 8.44 (dd, 1H), 7.21 (d, 1H), 5.10 (q, 2H), 4.39 (t, 2H), 3.72 (t, 2H), 3.32 (s, 3H).

Example 88: 3-[difluoro(methoxy)methyl]-6-[5-fluoro-6-[rac-(1R)-2,2,2-trifluoro-1-methyl-ethoxy]-3-pyridyl]-[1,2,4]triazolo[4,3-a]pyrazine

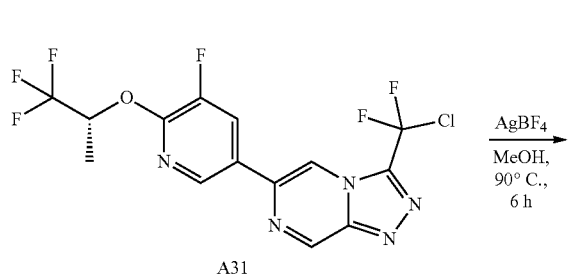

A31

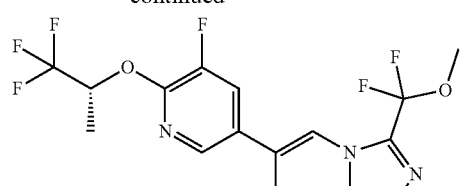

6A

A mixture of 3-[chloro(difluoro)methyl]-6-[5-fluoro-6-[rac-(1R)-2,2,2-trifluoro-1-methyl-ethoxy]-3-pyridyl]-[1,2,4]triazolo[4,3-a]pyrazine (500 mg, 1.21 mmol) and AgBF$_4$ (2.36 g, 12.15 mmol) in Methanol (5 mL) was stirred at 90° C. for 6 hours in a seal tube. After cooling to 25° C., the mixture was quenched with brine (20 mL), diluted with EtOAc (20 mL) and filtered through Celite. The filtrate was extracted with EtOAc (20 mL×3), and the combined organic phase was washed with brine (20 mL), dried over Na$_2$SO$_4$, filtered and concentrated. The residue was purified by flash chromatography on silica gel (EtOAc in PE=0% to 10% to 30%) to give the product (290 mg) as an oil. The impure product was purified by prep-HPLC (Xtimate C18 (150 mm×25 mm, 5 μm) A=H$_2$O (0.075% NH$_4$OH) and B=CH$_3$CN; 51-81% B over 11 minutes) to give the product (256.79 mg, 0.63 mmol) as a solid. $^1$H NMR (400 MHz CDCl$_3$) δ$_H$=9.52 (d, 1H), 8.50 (d, 1H), 8.45 (d, 1H), 8.05 (dd, 1H), 5.95-5.85 (m, 1H), 3.98 (s, 3H), 1.60 (d, 3H). LCMS Rt=1.33 min in 2 min chromatography, 10-80AB, MS ESI calcd. for C$_{15}$H$_{12}$F$_6$N$_5$O$_2$ [M+H]+ 407.9, found 407.9.

Example 89: 3-[difluoro(methoxy)methyl]-6-[5-fluoro-6-[(1S)-2,2,2-trifluoro-1-methyl-ethoxy]-3-pyridyl]-[1,2,4]triazolo[4,3-a]pyrazine

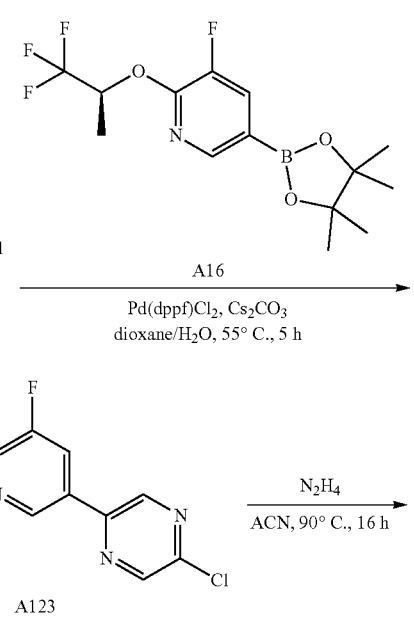

A123

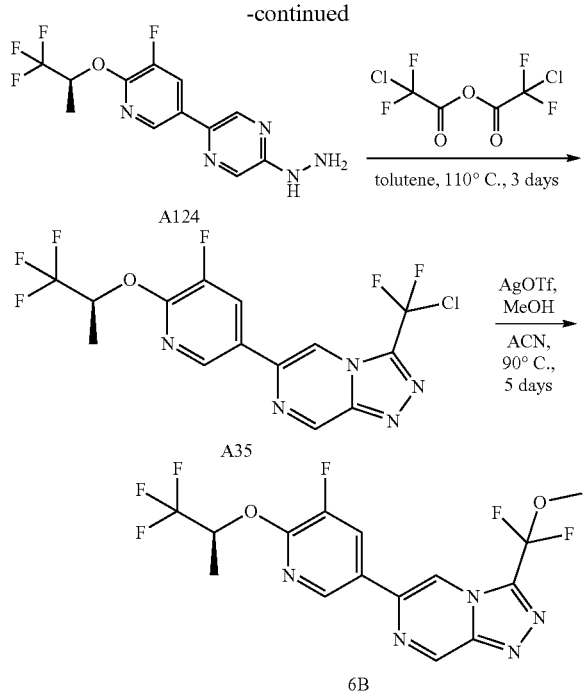

A124

A35

6B

Synthesis of A123: A mixture of 2-bromo-5-chloro-pyrazine (1 g, 5.17 mmol), 3-fluoro-5-(4,4,5,5-tetramethyl-1,3,2-dioxaborolan-2-yl)-2-[(1S)-2,2,2-trifluoro-1-methyl-ethoxy]pyridine (1.73 g, 5.17 mmol), $Cs_2CO_3$ (3.37 g, 10.34 mmol) and Pd(dppf)$Cl_2$ (567.41 mg, 0.78 mmol) in 1,4-Dioxane (100 mL) and Water (10 mL) was stirred at 55° C. under $N_2$ for 5 hours. From LCMS, desired MS was observed and no starting material was remained. The solution was cooled to room temperature and concentrated to give a residue. To the residue was added water (50 mL), extracted with EtOAc (50 mL×2). The combined organic phase was washed with water (50 mL), brine (50 mL×2), dried over anhydrous $Na_2SO_4$, filtered and concentrated to give the crude product. The crude product was purified by flash chromatography column on silica gel (EtOAc in PE=0% to 5%) to give the product (1.4 g, 4.35 mmol, 84% yield) as a solid. $^1H$ NMR (DMSO-$d_6$, 400 MHz) $\delta_H$=9.18 (s, 1H), 8.91-8.74 (m, 2H), 8.46 (dd, 1H), 6.05-5.99 (m, 1H), 1.53 (d, 3H).

Synthesis of A124: A solution of 2-chloro-5-[5-fluoro-6-[(1S)-2,2,2-trifluoro-1-methyl-ethoxy]-3-pyridyl]pyrazine (1.4 g, 4.35 mmol) and hydrazine (697.48 mg, 21.76 mmol) in MeCN (100 mL) was stirred at 90° C. for 16 hours to give a colorless solution. After cooling to room temperature, the solution was concentrated to give a residue. To the residue was added water (50 mL), extracted with EtOAc (50 mL×2). The combined organic phase was washed with brine (50 mL), dried over anhydrous $Na_2SO_4$, filtered and concentrated to give the crude product (1.3 g, 4.10 mmol) as a solid which was used in the next step directly. LCMS $R_t$=0.72 min in 1.5 min chromatography, 5-95AB, MS ESI calcd. for $C_{12}H_{12}F_4N_5O$ [M+H]$^+$ 318.1, found 318.1.

Synthesis of A35: A mixture of [5-[5-fluoro-6-[(1S)-2,2,2-trifluoro-1-methyl-ethoxy]-3-pyridyl]pyrazin-2-yl]hydrazine (1.3 g, 4.1 mmol) and (2-chloro-2,2-difluoro-acetyl) 2-chloro-2,2-difluoro-acetate (2.99 g, 12.29 mmol) in Toluene (50 mL) was stirred at 110° C. for 3 days. After cooling to room temperature and concentrated to give a residue. To the residue was added water (50 mL), extracted with EtOAc (50 mL×2). The combined organic phase was washed with brine (50 mL), dried over anhydrous $Na_2SO_4$, filtered and concentrated to give the crude product. The crude product was purified by chromatography flash column on silica gel (EtOAc in PE=0% to 10% to 30%) to give the product (1.2 g, 2.91 mmol, 71% yield) as an oil. LCMS $R_t$=2.98 min in 4.0 min chromatography, 10-80AB, MS ESI calcd. for $C_{14}H_9ClF_6N_5O$ [M+H]$^+$ 412.0, found 411.9.

Synthesis of Compound 6B: A mixture of 3-[chloro(difluoro)methyl]-6-[5-fluoro-6-[(1S)-2,2,2-trifluoro-1-methyl-ethoxy]-3-pyridyl]-[1,2,4]triazolo[4,3-a]pyrazine (1.2 g, 2.91 mmol) and AgOTf (7.49 g, 29.15 mmol) in MeCN (24 mL) and Methanol (24 mL) was stirred at 90° C. for 5 days. Then EtOAc (50 mL) and brine (50 mL) was added to the mixture, some solid was observed and the mixture was filtered through Celite. The filtrate was separated and the aqueous layer was extracted with EtOAc (50 mL). The combined organic phase was dried over anhydrous $Na_2SO_4$, filtered and concentrated to give the crude product. The crude product was purified by chromatography flash on silica gel (EtOAc in PE=10% to 30% to 50%) and then by Prep-TLC (PE:EA=2:1) to give the product (160 mg, 389.5 μmol, 13% yield) as a solid. $^1H$ NMR (CDCl$_3$+D$_2$O, 400 MHz) $\delta_H$=9.52 (s, 1H), 8.50 (s, 1H), 8.45 (s, 1H), 8.04 (d, 1H), 5.93-5.87 (m, 1H), 3.98 (s, 3H), 1.60 (d, 3H). LCMS $R_t$=1.30 min in 2.0 min chromatography, 10-80AB, MS ESI calcd. for $C_{15}H_{12}F_6N_5O_2$ [M+H]$^+$ 408.1, found 407.9.

Example 90: 2-chloro-5-hydrazineylpyrazine

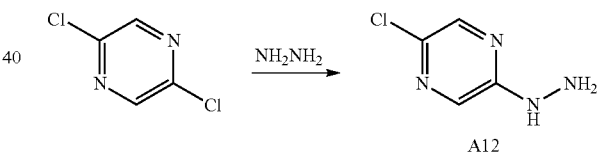

A12

Synthesis of A12: To a stirred solution of 2,5-dichloro-pyrazine (20.0 g, 134.2 mmol) in ethanol (200 mL) was added hydrazine hydrate (20.16 g, 402.74 mmol) and heated to 80° C. for 12 hours. The reaction mixture was cooled to room temperature and treated with ice water. The precipitated solid was filtered, washed with water and dried to get the product (16.0 g) as a solid.

Example 91: 2-(3,3-difluorocyclobutoxy)-5-(4,4,5,5-tetramethyl-1,3,2-dioxaborolan-2-yl)pyridine

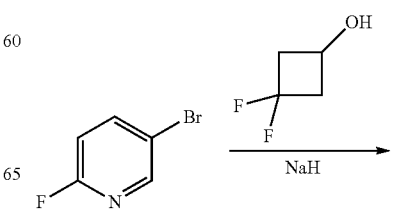

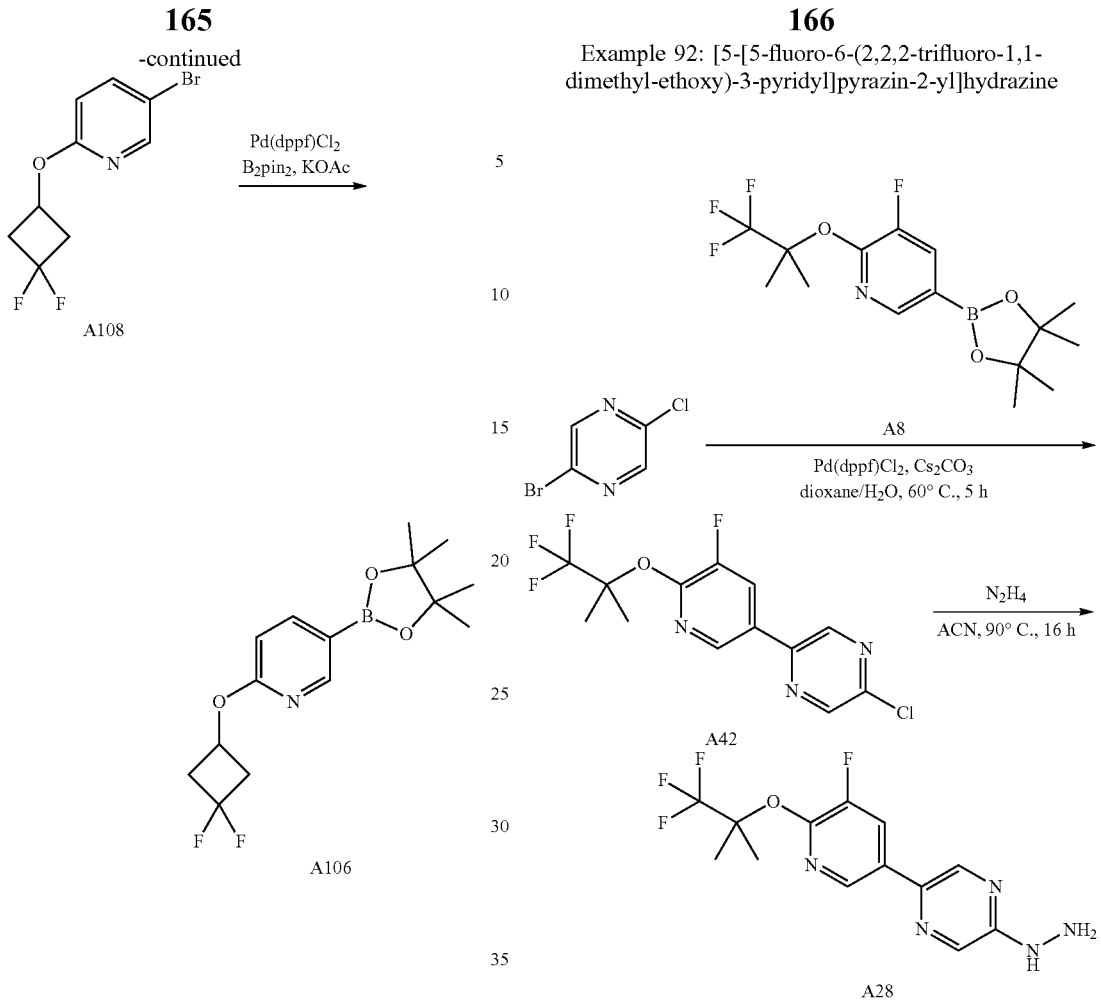

Example 92: [5-[5-fluoro-6-(2,2,2-trifluoro-1,1-dimethyl-ethoxy)-3-pyridyl]pyrazin-2-yl]hydrazine Synthesis of A108: To a stirred solution of 3,3-difluorocyclobutanol (1.2 g, 11.1 mmol) and 5-bromo-2-fluoropyridine (1.5 g, 8.52 mmol) in 1,4-dioxane (15 mL) at 0° C. was added KO$^t$Bu (1.9 g, 17.05 mmol) in small portions. The reaction mixture was slowly warmed to room temperature and stirred for 6 hours. The reaction mixture was treated with ice water (30 mL) and extracted with ethyl acetate (2×30 mL). The organic layer was washed with brine (30 mL), dried over anhydrous $Na_2SO_4$ and concentrated to afford the product (1.6 g) which was used for the next step without further purification. LCMS: 264.0 (M+H) and 266.0 (M+2+H), Rt 2.63 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A106: To a stirred solution of 5-bromo-2-(3,3-difluorocyclobutoxy)pyridine (1.6 g, 6.06 mmol) and bis(pinacolato)diboron (2.0 g, 7.88 mmol) in 1,4-dioxane (32.0 mL) was added potassium acetate (1.78 g, 18.2 mmol). Pd(dppf)Cl$_2$.DCM (0.49 g, 0.61 mmol) was added to the reaction mixture under nitrogen atmosphere and heated at 80° C. for 12 hours. The reaction mixture was cooled to room temperature, filtered through Celite and concentrated under reduced pressure. The crude compound was purified by column chromatography on silica gel with 5% ethyl acetate/PE to afford the product (1.82 g, 5.8 mmol, 96% yield). LCMS: 312.2 (M+H), Rt 2.87 min Column: ZORBAX XDB C-18 (50×4.6 mm), 3.5 μm Mobile Phase: A: 0.1% HCOOH in water:ACN (95:5), B: ACN; Flow Rate: 1.5 mL/min.

Synthesis of A42: A mixture of 2-bromo-5-chloro-pyrazine (2 g, 10.34 mmol), 3-fluoro-5-(4,4,5,5-tetramethyl-1,3,2-dioxaborolan-2-yl)-2-(2,2,2-trifluoro-1,1-dimethyl-ethoxy)pyridine (3.61 g, 10.34 mmol), $Cs_2CO_3$ (6.74 g, 20.68 mmol) and Pd(dppf)Cl$_2$ (1.13 g, 1.55 mmol) in 1,4-Dioxane (80 mL) and Water (8 mL) was stirred at 55° C. under $N_2$ for 5 hours. The mixture was cooled to room temperature and concentrated to give a residue. To the residue was added water (50 mL) and extracted with EtOAc (50 mL×2). The combined organic phase was washed with water (50 mL), brine (50 mL×2), dried over anhydrous $Na_2SO_4$, filtered and concentrated to give the crude product. The crude product was purified by flash chromatography column on silica gel (EtOAc in PE=0% to 5% to 10%) to give the product (2.3 g, 5.45 mmol) as a solid. $^1$H NMR (400 MHz, CDCl$_3$) $\delta_H$=8.77 (d, 1H), 8.64 (d, 1H), 8.53 (d, 1H), 8.05 (dd, 1H), 1.88 (s, 6H). LCMS R$_t$=0.96 min in 1.5 min chromatography, MS ESI calcd. for $C_{13}H_{11}ClF_4N_3O$ [M+H]$^+$ 336.0, found 335.9.

Synthesis of A28: A solution of 2-chloro-5-[5-fluoro-6-(2,2,2-trifluoro-1,1-dimethyl-ethoxy)-3-pyridyl]pyrazine (2.3 g, 6.85 mmol) and hydrazine (2.20 g, 68.52 mmol) in MeCN (50 mL) was stirred at 90° C. under $N_2$ for 16 hours to give a solution. After cooling to room temperature, the solution was concentrated to give a residue. To the residue was added water (50 mL) and extracted with EtOAc (50 mL×2). The combined organic phase was washed with brine (50 mL×2), dried over anhydrous $Na_2SO_4$, filtered and concentrated to give the product (2.1 g, 6.34 mmol, 92.52% yield) as a solid. $^1$H NMR (400 MHz, CDCl$_3$) $\delta_H$=8.42 (d, 2H), 8.29 (s, 1H), 7.94 (d, 1H), 6.12 (s, 1H), 3.92 (s, 2H), 1.84 (s, 6H). LCMS R$_t$=0.77 min in 1.5 min chromatography, MS ESI calcd. for C$_{13}$H$_{14}$F$_4$N$_5$O [M+H]$^+$ 332.1, found 331.9.

Example 93: 3-[chloro(difluoro)methyl]-6-[5-fluoro-6-[1-(trifluoromethyl)cyclobutoxy]-3-pyridyl]-[1,2,4]triazolo[4,3-a]pyrazine

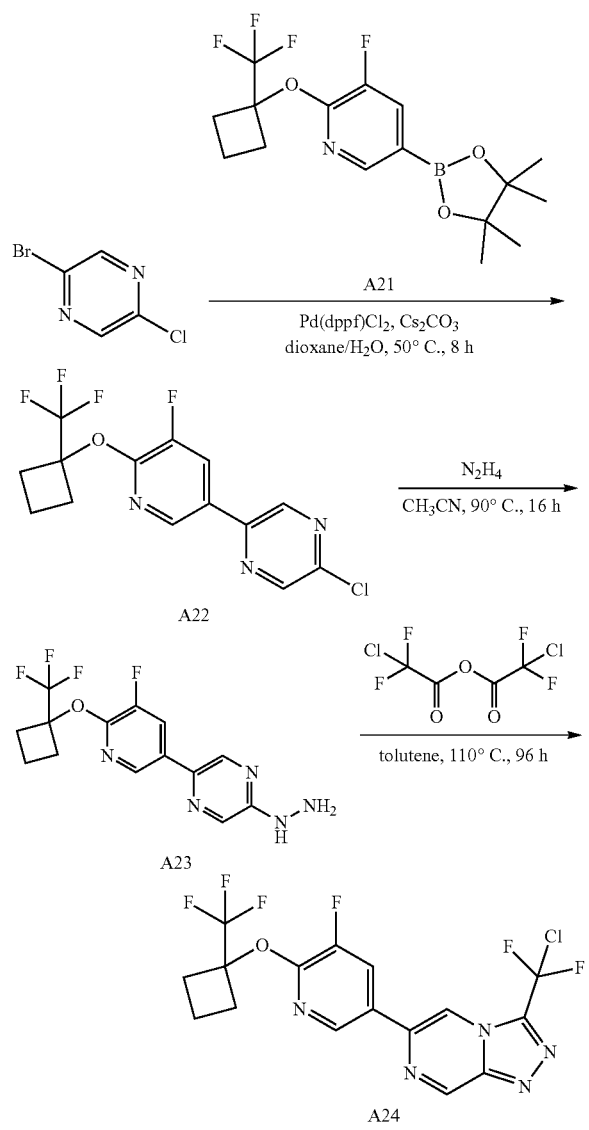

Synthesis of A22: A mixture of 2-bromo-5-chloro-pyrazine (800 mg, 4.14 mmol), 3-fluoro-5-(4,4,5,5-tetramethyl-1,3,2-dioxaborolan-2-yl)-2-[1-(trifluoromethyl)cyclobutoxy]pyridine (1642.99 mg, 4.55 mmol), Cs$_2$CO$_3$ (4042.64 mg, 12.41 mmol), Pd(dppf)Cl$_2$ (60.52 mg, 0.08 mmol) in 1,4-dioxane (12 mL) and H$_2$O (4 mL) was stirred at 50° C. for 8 hours. After cooling to room temperature, the reaction mixture was concentrated to remove solvent, diluted with water (20 mL), and extracted with EtOAc (20 mL×2). The combined organic phase was washed with brine (40 mL), dried over Na$_2$SO$_4$ and concentrated to give a crude product.

The crude product was purified by flash chromatography on silica gel (EtOAc in PE=0% to 10%) to give the product as a solid, which was confirmed by LCMS R$_t$=1.01 min in 1.5 min chromatography, MS ESI calcd. for C$_{14}$H$_{11}$ClF$_4$N$_3$O [M+H]$^+$ 348.1, found 347.9.

Synthesis of A23: A mixture of 2-chloro-5-[5-fluoro-6-[1-(trifluoromethyl)cyclobutoxy]-3-pyridyl]pyrazine (0.8 g, 2.3 mmol) and hydrazine (0.74 g, 23.01 mmol) in MeCN (20 mL) was heated to 90° C. and stirred for 16 hours. After cooling to room temperature, the reaction mixture was concentrated to give crude product as a solid. LCMS R$_t$=1.04 min in 2.0 min chromatography, MS ESI calcd. for C$_{14}$H$_{14}$F$_4$N$_5$O [M+H]$^+$ 344.1, found 344.0.

Synthesis of A24: To a mixture of [5-[5-fluoro-6-[1-(trifluoromethyl)cyclobutoxy]-3-pyridyl]pyrazin-2-yl]hydrazine (0.6 g, 1.75 mmol) in toluene (40 mL) was added (2-chloro-2,2-difluoro-acetyl) 2-chloro-2,2-difluoro-acetate (0.64 g, 2.62 mmol). The reaction mixture was stirred at 110° C. for 96 hours. After cooling to room temperature, the reaction mixture was concentrated to give a residue. The residue was diluted with sat.NaHCO$_3$ (50 mL), and extracted with EtOAc (50 mL×2). The combined organic phase was washed with brine (20 mL), dried over Na$_2$SO$_4$, filtered and concentrated to give a residue. The residue was purified by flash column on silica gel (EtOAc in PE=0% to 20%) to give the product as a solid. $^1$H NMR (CDCl$_3$, 400 MHz) $\delta_H$=9.60 (d, 1H), 8.51 (d, 1H), 8.45 (s, 1H), 8.06 (dd, 1H), 2.87-2.97 (m, 2H), 2.73-2.81 (m, 2H), 1.91-2.04 (m, 2H).

Example 94. 3-[chloro(difluoro)methyl]-6-[5-fluoro-6-[(1R)-2,2,2-trifluoro-1-methyl-ethoxy]-3-pyridyl]-[1,2,4]triazolo[4,3-a]pyrazine

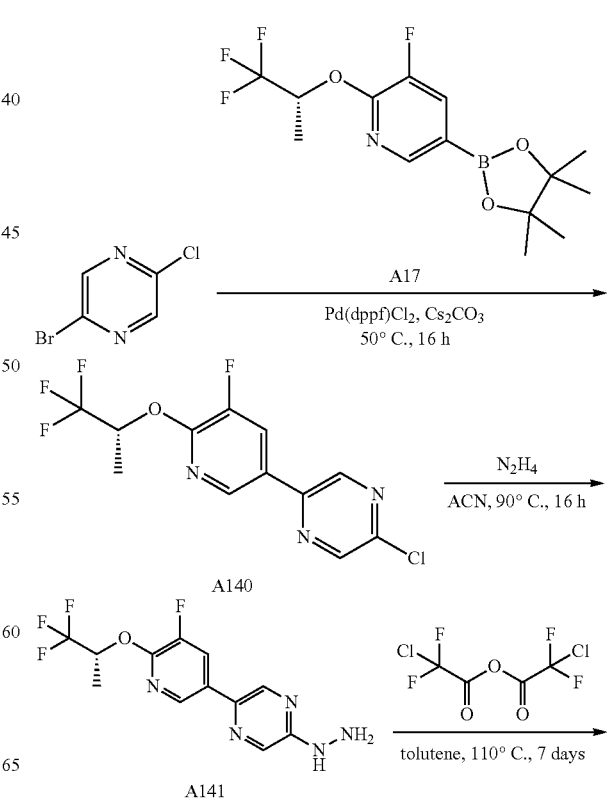

-continued

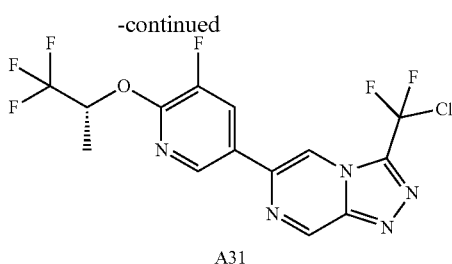

A31

Synthesis of A140: A mixture of 2-bromo-5-chloro-pyrazine (2 g, 10.34 mmol), 3-fluoro-5-(4,4,5,5-tetramethyl-1,3,2-dioxaborolan-2-yl)-2-[(1R)-2,2,2-trifluoro-1-methyl-ethoxy]pyridine (3.12 g, 9.31 mmol), Pd(dppf)Cl$_2$ (1.13 g, 1.55 mmol) and Cs$_2$CO$_3$ (6.74 g, 20.68 mmol) in 1,4-dioxane (100 mL) and water (10 mL) was stirred under N$_2$ at 50° C. for 5 hours. After cooling to room temperature, the mixture was diluted with EtOAc (10 mL), filtered with silica gel, eluted with EtOAc (20 mL) and concentrated to give the crude product. The crude product was purified by flash chromatography on silica gel (EtOAc in PE=0% to 20%) to give the product (2500 mg, 7.21 mmol, 70% yield) as a solid. $^1$H NMR (400 MHz, CDCl$_3$) $\delta_H$=8.77 (d, 1H), 8.64 (d, 1H), 8.53 (d, 1H), 8.08 (dd, 1H), 6.00-5.83 (m, 1H), 1.59 (d, 3H).

Synthesis of A141: A mixture of 2-chloro-5-[5-fluoro-6-[(1R)-2,2,2-trifluoro-1-methyl-ethoxy]-3-pyridyl]pyrazine (2 g, 6.22 mmol) and hydrazine (1.99 g, 62.18 mmol) in MeCN (20 mL) was heated to 90° C. and stirred for 16 hours. After cooling to room temperature, the reaction mixture was concentrated to remove most of the MeCN, then diluted with H$_2$O (100 mL). The mixture was extracted with EtOAc (150 mL×2). The combined organic phase was washed with brine (100 mL), dried over anhydrous Na$_2$SO$_4$, filtered and concentrated to give the crude product (2000 mg, 6.30 mmol) as an oil. $^1$H NMR (400 MHz, DMSO-d$_6$) $\delta_H$=8.62 (d, 1H), 8.58 (d, 1H), 8.29-8.24 (m, 2H), 8.19 (s, 1H), 6.05-5.92 (m, 1H), 4.37 (brs, 2H), 1.51 (d, 3H).

Synthesis of A31: A solution of [5-[5-fluoro-6-[(1R)-2,2,2-trifluoro-1-methyl-ethoxy]-3-pyridyl]pyrazin-2-yl]hydrazine (250 mg, 0.79 mmol) and (2-chloro-2,2-difluoro-acetyl) 2-chloro-2,2-difluoro-acetate (0.21 mL, 1.18 mmol) in toluene (20 mL) was stirred at 110° C. for 7 days. The mixture was concentrated. The residue was diluted with EtOAc (30 mL), basified with saturated NaHCO$_3$ to pH 7-8 and washed with H$_2$O (30 mL×2) and brine (20 mL). The combined organic phase was dried over anhydrous Na$_2$SO$_4$, filtered and concentrated. The crude product was purified by flash chromatography on silica gel (EtOAc in PE=5% to 20% to 50%) to give the product (240 mg, 0.58 mmol, 74% yield) as an oil. $^1$H NMR (400 MHz, DMSO-d$_6$) $\delta_H$=9.77 (d, 1H), 9.13 (d, 1H), 8.83 (d, 1H), 8.65 (dd, 1H), 6.10-5.95 (m, 1H), 1.55 (d, 3H).

Example 95: 3-[bromo(difluoro)methyl]-6-[6-[(1R)-2,2,2-trifluoro-1-methyl-ethoxy]-3-pyridyl]-[1,2,4]triazolo[4,3-a]pyrazine

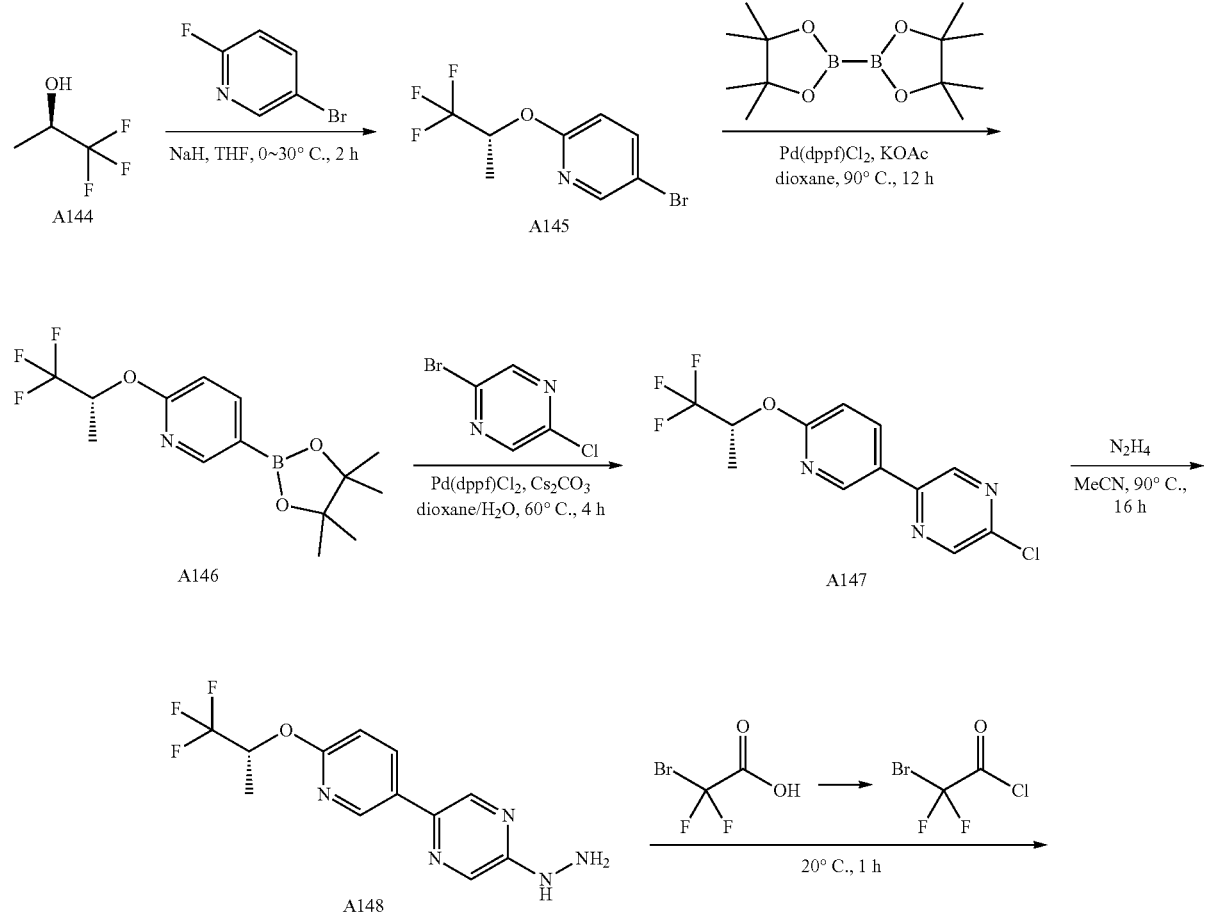

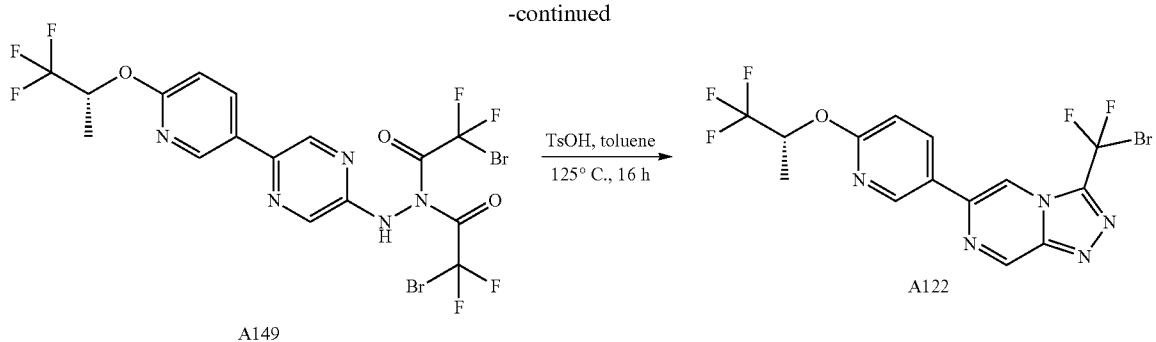

Synthesis of A145: To a solution of (2R)-1,1,1-trifluoro-propan-2-ol (139 g, 1.22 mol) in THF (1570 mL) was added NaH (73.11 g, 1.83 mol, 60% in oil) at 0° C. over 1 hour. The mixture was stirred at 0° C. for 30 mins. Then 5-bromo-2-fluoro-pyridine (193.01 g, 1.10 mol) was added and the mixture was stirred at 30° C. for 4 hours. The mixture was quenched with sat. NH$_4$Cl (1000 mL). The mixture was extracted with EtOAc (1000 mL). The combined organic phase was washed with brine (500 mL×2), dried over anhydrous Na$_2$SO$_4$, filtered and concentrated to give the product (240 g, 888.72 mmol) as an oil. $^1$H NMR (400 MHz, CDCl$_3$) $\delta_H$=8.18 (d, 1H), 7.71 (dd, 1H), 6.74 (d, 1H), 5.78-5.64 (m, 1H), 1.49 (d, 3H).

Synthesis of A146: A mixture of 5-bromo-2-[(1R)-2,2,2-trifluoro-1-methyl-ethoxy]pyridine (240 g, 888.7 mmol), 4,4,5,5-tetramethyl-2-(4,4,5,5-tetramethyl-1,3,2-dioxaborolan-2-yl)-1,3,2-dioxaborolane (270.82 g, 1.07 mol), KOAc (174.44 g, 1.78 mol) and Pd(dppf)Cl$_2$ (26.01 g, 35.55 mmol) in 1,4-dioxane (2000 mL) was stirred at 90° C. for 12 hours under N$_2$. The mixture was cooled then concentrated and the crude product was purified by flash chromatography on silica gel (EtOAc in PE=0 to 1% to 3% to 10%) to give the product (200 g, 630.7 mmol, 71% yield) as an oil. $^1$H NMR (400 MHz, CDCl$_3$) $\delta_H$=8.51 (d, 1H), 7.98 (dd, 1H), 6.79 (d, 1H), 5.90-5.80 (m, 1H), 1.49 (d, 3H), 1.35 (s, 12H).

Synthesis of A147: A mixture of 5-(4,4,5,5-tetramethyl-1,3,2-dioxaborolan-2-yl)-2-[(1R)-2,2,2-trifluoro-1-methyl-1-ethoxy]pyridine (200 g, 630.7 mmol), 2-bromo-5-chloro-pyrazine (122 g, 630.7 mmol), Pd(dppf)Cl$_2$ (46.15 g, 63.07 mmol) and Cs$_2$CO$_3$ (513.7 g, 1.58 mol) in 1,4-dioxane (2000 mL) and water (500 mL) was stirred at 50° C. for 2 hours under N$_2$. After cooling to 25° C., the mixture was separated and the organic phase was concentrated to remove most of dioxane. The residue was poured into water (1 L) and the mixture was extracted with EtOAc (800 mL×2). The combined organic phase was washed with water (500 mL) and brine (500 mL), dried over anhydrous Na$_2$SO$_4$, filtered and concentrated. The crude product was purified by flash chromatography on silica gel (EtOAc in PE=0% to 1% to 3% to 20%) to give the product (122 g, 401.75 mmol, 64% yield) as a solid. $^1$H NMR (400 MHz, CDCl$_3$) $\delta_H$=8.77-8.73 (m, 2H), 8.63 (d, 1H), 8.26 (dd, 1H), 6.96 (d, 1H), 5.93-5.82 (m, 1H), 1.54 (d, 3H).

Synthesis of A148: To a solution of 2-chloro-5-[6-[(1R)-2,2,2-trifluoro-1-methyl-ethoxy]-3-pyridyl]pyrazine (122 g, 401.75 mmol) in MeCN (1000 mL) was added hydrazine (128.76 g, 4.02 mol) at 25° C. The mixture was stirred at 90° C. for 16 hours. After cooling to 25° C., the reaction was poured into water (2 L) and the solid was collected by filtration and washed with water (500 mL×2). The solid was dissolved in EtOAc (1500 mL) and the mixture was washed with brine (500 mL), dried over anhydrous Na$_2$SO$_4$, filtered and concentrated to give the crude product (120 g, 401 mmol) as a solid. LCMS Rt=0.96 min in 2 min chromatography, 10-80AB, MS ESI calcd. For C$_{12}$H$_{13}$F$_3$N$_5$O [M+H]$^+$ 300.1, found 299.9.

Synthesis of A149: To a solution of 2-bromo-2,2-difluoro-acetic acid (91 g, 520.21 mmol) in THF (1000 mL) was added one drop DMF and (COCl)$_2$ (52.82 mL, 624.25 mmol). The mixture was stirred at 20° C. for 30 mins. Then [5-[6-[(1R)-2,2,2-trifluoro-1-methyl-ethoxy]-3-pyridyl]pyrazin-2-yl]hydrazine (120 g, 401 mmol) was added to the solution. The mixture was stirred at 20° C. for 1 hour. The mixture was poured in to water (2 L) and the aqueous layer was extracted with EtOAc (2 L×2). The combined organic phase was washed with brine (1L×2), dried over anhydrous Na$_2$SO$_4$, filtered and concentrated to give the product (180 g, 293.6 mmol) as a solid.

Synthesis of A122: To a solution of 2-bromo-2,2-difluoro-N'-[5-[6-[(1R)-2,2,2-trifluoro-1-methyl-ethoxy]-3-pyridyl]pyrazin-2-yl]acetohydrazide (180 g, 293.6 mmol) in toluene (1500 mL) was added TsOH (5.18 g, 30.07 mmol). The mixture was stirred at 125° C. for 16 hours. After cooling to room temperature, the mixture was poured in to water (1.5 L) and the aqueous layer was extracted with EtOAc (1.5 L×2). The combined organic phase was washed with brine (500 mL×2), dried over anhydrous Na$_2$SO$_4$, filtered and concentrated. The crude product was purified by flash chromatography on silica gel (EtOAc in PE=10% to 20%) to give the product (55 g, 125.57 mmol, 31% yield) as a solid. $^1$H NMR (400 MHz, CDCl$_3$) $\delta_H$=9.59 (d, 1H), 8.76 (d, 1H), 8.41 (d, 1H), 8.25 (dd, 1H), 7.01 (d, 1H), 5.96-5.80 (m, 1H), 1.56 (d, 3H).

Example 96: 3-[bromo(difluoro)methyl]-6-[5-fluoro-6-[(1S)-2,2,2-trifluoro-1-methyl-ethoxy]-3-pyridyl]-5-methyl-[1,2,4]triazolo[4,3-a]pyrazine

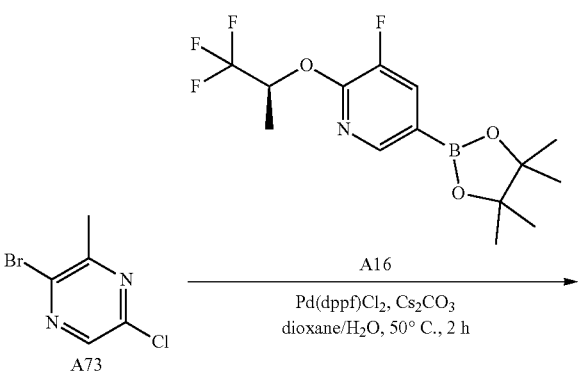

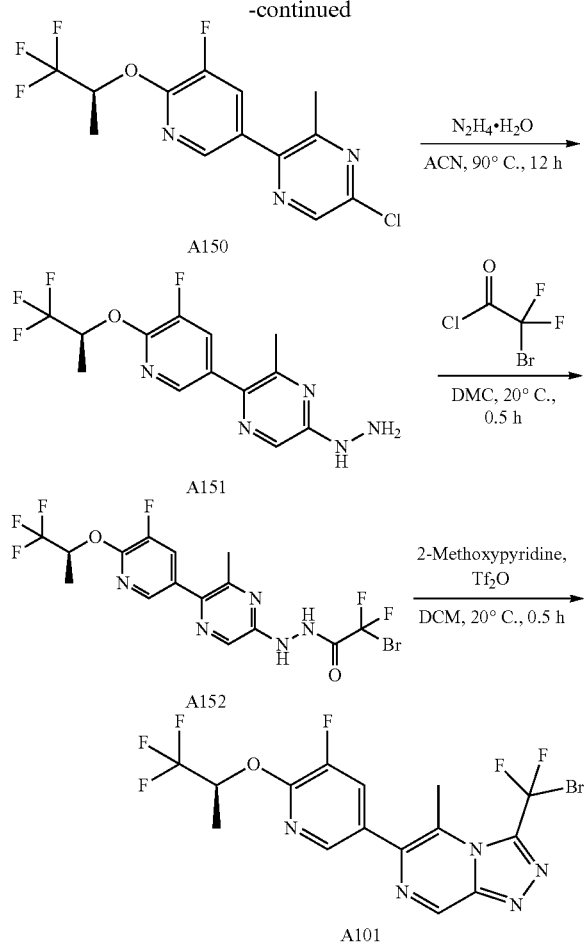

Synthesis of A152: A mixture of [5-[5-fluoro-6-[(1S)-2,2,2-trifluoro-1-methyl-ethoxy]-3-pyridyl]-6-methyl-pyrazin-2-yl]hydrazine (1.3 g, 3.92 mmol) and 2-bromo-2,2-difluoro-acetyl chloride (1.1 g, 5.69 mmol) in DCM (15 mL) was stirred at 20° C. for 0.5 hour. Water (20 mL) was added and the aqueous layer was extracted with EtOAc (30 mL×2). The combined organic phase was washed with brine (30 mL), dried over anhydrous $Na_2SO_4$, filtered and concentrated. The crude product was purified by flash chromatography on silica gel (EtOAc in PE=0% to 30% to 50%) to give the product (1.4 g, 2.86 mmol, 73% yield) as a solid. $^1$H NMR (400 MHz, DMSO-$d_6$) $\delta_H$=11.39 (s, 1H), 9.40 (s, 1H), 8.24 (d, 1H), 8.04 (dd, 1H), 7.97 (s, 1H), 6.08-5.95 (m, 1H), 2.47 (s, 3H), 1.53 (d, 3H).

Synthesis of A101: To a mixture of 2-bromo-2,2-difluoro-N'-[5-[5-fluoro-6-[(1S)-2,2,2-trifluoro-1-methyl-ethoxy]-3-pyridyl]-6-methyl-pyrazin-2-yl]acetohydrazide (1.44 g, 2.89 mmol) and 2-Methoxypyridine (0.77 mL, 7.23 mmol) in DCM (15 mL) was added $Tf_2O$ (897.7 mg, 3.18 mmol). The resulting mixture stirred at 20° C. for 0.5 hour. Water (20 mL) was added and the aqueous layer was extracted with EtOAc (20 mL×2). The combined organic phase was washed with brine (30 mL), dried over anhydrous $Na_2SO_4$, filtered and concentrated. The crude product was purified by flash chromatography on silica gel (EtOAc in PE=0% to 30% to 50%) to give the product (390 mg, 711.9 μmol, 24% yield) as an oil. LCMS $R_t$=1.32 min in 2.0 min chromatography, 10-80AB, MS ESI calcd. for $C_{15}H_{11}BrF_6N_5O$ [M+H]$^+$ 472.0, found 471.8.

Example 97: 3-[chloro(difluoro)methyl]-6-[5-fluoro-6-(2,2,2-trifluoroethoxy)-3-pyridyl]-[1,2,4]triazolo[4,3-a]pyrazine

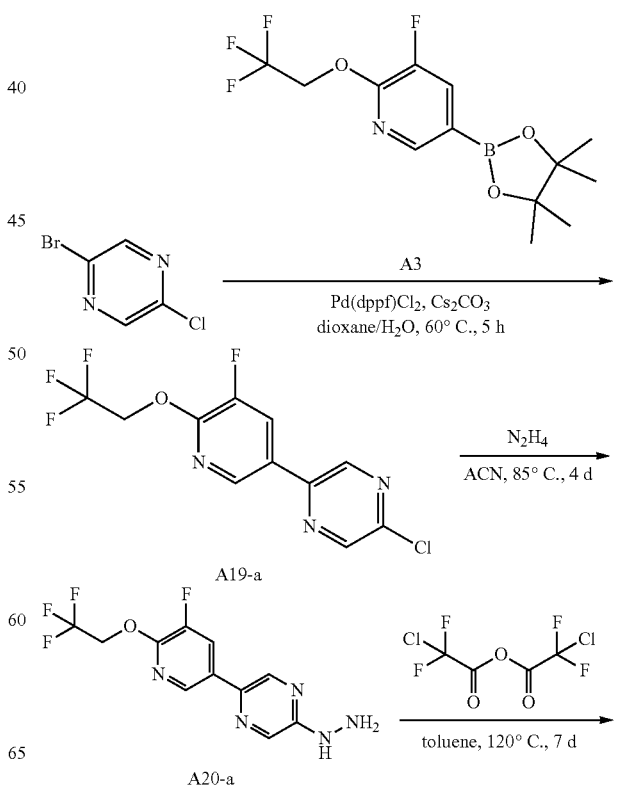

Synthesis of A150: A mixture of 2-bromo-5-chloro-3-methyl-pyrazine (2.47 g, 11.91 mmol), 3-fluoro-2-[(1S)-2,2,2-trifluoro-1-methyl-ethoxy]-5-(4,4,5,5-tetramethyl-1,3,2-dioxaborolan-2-yl)pyridine (3.9 g, 11.64 mmol), $Cs_2CO_3$ (7.76 g, 23.81 mmol) and Pd(dppf)$Cl_2$ (1.31 g, 1.79 mmol) in 1,4-dioxane (15 mL) and water (1.5 mL) was stirred at 50° C. under $N_2$ for 2 hours. After cooling to room temperature, water (20 mL) and EtOAc (30 mL) were added and the mixture was filtered through Celite. After separating, the organic phase was washed with brine (30 mL), dried over anhydrous $Na_2SO_4$, filtered and concentrated. The crude product was purified by flash chromatography on silica gel (EtOAc in PE=0% to 3%) to give the product (2.57 g, 7.65 mmol, 64% yield) as an oil. $^1$H NMR (400 MHz, CDCl$_3$) $\delta_H$=8.51 (s, 1H), 8.18 (s, 1H), 7.71 (d, 1H), 5.95-5.82 (m, 1H), 2.69 (s, 3H), 1.59 (d, 3H).

Synthesis of A151: A solution of 5-chloro-2-[5-fluoro-6-[(1S)-2,2,2-trifluoro-1-methyl-ethoxy]-3-pyridyl]-3-methyl-pyrazine (2.57 g, 7.66 mmol) and hydrazine hydrate (5.75 g, 114.84 mmol) in MeCN (25 mL) was stirred at 90° C. for 12 hours. After cooling to room temperature, the solution was concentrated. Water (20 mL) was added and the aqueous layer was extracted with EtOAc (30 mL×2). The combined organic phase was washed with brine (30 mL), dried over anhydrous $Na_2SO_4$, filtered and concentrated to give the crude product (2.3 g, 6.9 mmol) as a solid. $^1$H NMR (400 MHz, DMSO-$d_6$) $\delta_H$=8.18 (d, 1H), 8.09 (s, 1H), 8.06 (s, 1H), 7.96 (dd, 1H), 6.07-5.90 (m, 1H), 4.33 (s, 2H), 2.41 (s, 3H), 1.52 (d, 3H).

-continued

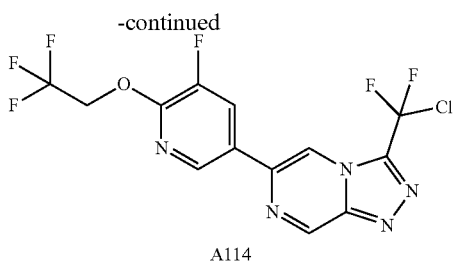

A114

Synthesis of A19-a: A mixture of 2-bromo-5-chloropyrazine (2 g, 10.34 mmol), 3-fluoro-5-(4,4,5,5-tetramethyl-1,3,2-dioxaborolan-2-yl)-2-(2,2,2-trifluoroethoxy)pyridine (3983.83 mg, 12.41 mmol), Pd(dppf)Cl$_2$ (1134.83 mg, 1.55 mmol) and Cs$_2$CO$_3$ (6737.32 mg, 20.68 mmol) in 1,4-dioxane (30 mL) and water (3 mL) was stirred at 60° C. for 5 hours under N$_2$. The mixture was filtered through Celite, and eluted with EtOAc (30 mL×2). The filtrate was concentrated and the crude product was purified by flash chromatography on silica gel (EtOAc in PE=0% to 20%) to give the product (2500 mg, 7.83 mmol, 77% yield) as a solid. LCMS Rt=0.88 min in 1.5 min chromatography, 5-95AB, MS ESI calcd. C$_{11}$H$_7$ClF$_4$N$_3$O [M+H]$^+$ 308.0, found 308.1.

Synthesis of A20-a: A mixture of 2-chloro-5-[5-fluoro-6-(2,2,2-trifluoroethoxy)-3-pyridyl]pyrazine (2.5 g, 8.13 mmol) and hydrazine (2.6 g, 81.27 mmol) in CH$_3$CN (60 mL) was stirred at 85° C. for 4 days. After cooling to room temperature, the reaction was quenched with sat.NH$_4$Cl (50 mL) and the mixture was extracted with EtOAc (40 mL×2). The combined organic phase was washed with brine (50 mL), dried over anhydrous Na$_2$SO$_4$, filtered and concentrated to give the crude product (2400 mg, 5.79 mmol) as a solid. LCMS Rt=0.69 min in 1.5 min chromatography, 5-95AB, MS ESI calcd. C$_{11}$H$_{10}$F$_4$N$_5$O [M+H]$^+$ 304.1, found 304.1.

Synthesis of A114: A mixture of [5-[5-fluoro-6-(2,2,2-trifluoroethoxy)-3-pyridyl]pyrazin-2-yl]hydrazine (2.4 g, 7.92 mmol) and (2-chloro-2,2-difluoro-acetyl)2-chloro-2,2-difluoro-acetate (5.77 g, 23.75 mmol) in toluene (50 mL) was stirred at 120° C. for 7 days. After cooling to room temperature, the reaction was quenched with sat.NaHCO$_3$ (50 mL) and the mixture was extracted with EtOAc (50 mL×2). The combined organic phase was washed with brine (50 mL), dried over anhydrous Na$_2$SO$_4$, filtered and concentrated. The crude product was purified by flash chromatography on silica gel (EtOAc in PE=0% to 30%) to give the product (2500 mg, 5.13 mmol, 65% yield) as an oil. LCMS Rt=2.70 min in 4 min chromatography, 10-80AB, MS ESI calcd. C$_{13}$H$_7$ClF$_6$N$_5$O [M+H]$^+$ 398.0, found 398.0.

Details for the synthesis of certain intermediates and starting materials may be found in PCT/US2017/063533 and PCT/US2018/000224, the contents of which are incorporated herein by reference.

Example 98. Efficacy of Exemplary Compounds in the Modulation of Late Sodium Current (INaL)

Functional characterization of exemplary compounds to modulate INaL expressed by the NaV1.6 voltage-gated sodium channel was accomplished using the PatchXpress™ high throughput electrophysiology platform (Molecular Devices, Sunnyvale, Calif.). HEK-293 cells expressing recombinant, human NaV1.6 (hNaV1.6) were grown in DMEM/high-glucose Dulbecco's modified, 10% FBS, 2 mM sodium pyruvate, 10 mM HEPES and 400 µg/mL G418. Cells were grown to 50% 80% confluency prior to harvesting. Trypsinized cells were washed, allowed to recover for 1 hour and then resuspended in extracellular recording solution at a concentration of 1×106 cells/ml. The onboard liquid handling facility of the PatchXpress was used for dispensing cells and applying test compounds. NaV late currents were evoked by the application of 300 nM ATX-II. INaL was evoked by depolarizing pulses to 0 mV for 200 ms from a non-inactivating holding potential (e.g., −120 mV) at a frequency of 0.1 Hz. INaL amplitude and stability were determined by analyzing the mean current amplitude over the final 20 ms of the test pulse. Following steady state block with exemplary compounds (e.g., as described herein), a Na+ free solution containing an impermeant cation (e.g., Choline or NDMG) was added to confirm the identify of the sodium current. Percent steady-state inhibition of INaL was calculated as: [(INaL_compound)/(INaL_control)]*100, where INaL_compound and INaL control represent INaL recorded in the presence or absence of compound, respectively.

Results from this assay relating to percent inhibition of INaL at hNaV1.6 (measured using a procedure similar to described above but using HEK-293 cells expressing recombinant, human NaV 1.6 (h NaV 1.6) at 1 µM are summarized in Table 1 below. Similarly, results from an assay relating to percent inhibition of INaL at hNaV1.2 (measured using a procedure similar to described above but using HEK-293 cells expressing recombinant, human NaV 1.2 (h NaV 1.2) at 1 µM are summarized in Table 2 below. In this table, "A" indicates inhibition of less than 30%; "B" indicates inhibition of between about 30% to about 70%; and "C" indicates inhibition of greater than 70%.

TABLE 1

| No. | NaV 1.6 Assay Data |
| --- | --- |
| 1 | C |
| 2 | C |
| 3 | C |
| 4 | C |
| 5 | C |
| 6A | C |
| 6B | C |
| 7 | C |
| 8 | C |
| 9 | C |
| 10 | C |
| 11 | C |
| 12 | C |
| 13 | C |
| 14 | C |
| 15 | C |
| 16 | C |
| 17 | C |
| 18 | C |
| 19 | C |
| 20 | C |
| 21 | C |
| 22 | C |
| 23 | C |
| 24 | C |
| 25 | C |
| 26 | C |
| 27 | C |
| 28 | C |
| 29 | A |
| 30 | C |
| 31 | A |
| 32 | C |
| 33 | C |
| 34 | C |
| 35 | A |
| 36 | C |

TABLE 1-continued

| No. | NaV 1.6 Assay Data |
|---|---|
| 37 | C |
| 38 | B |
| 39 | A |
| 40 | A |
| 41 | C |
| 42 | C |
| 43 | B |
| 44 | B |
| 45 | C |
| 46 | B |
| 47 | C |
| 48 | C |
| 49 | C |
| 50 | C |
| 51 | C |
| 52 | B |
| 53 | C |
| 56 | C |
| 57 | C |
| 58 | C |
| 59 | C |
| 60 | B |
| 61 | B |
| 62 | C |
| 63 | C |
| 64 | C |
| 65 | B |
| 66 | C |
| 67 | C |
| 68 | C |
| 69 | B |
| 70 | A |
| 71 | A |
| 72 | A |
| 73 | C |
| 74 | C |
| 75 | C |
| 76 | C |
| 77 | C |
| 78 | C |
| 79 | C |
| 81 | C |
| 82 | C |
| 83 | B |
| 84 | C |
| 85 | C |
| 86 | C |
| 87 | B |
| 88 | C |
| 89 | B |

TABLE 2

| No. | NaV 1.2 Assay Data |
|---|---|
| 16 | C |
| 10 | C |
| 53 | C |
| 56 | C |
| 59 | C |
| 62 | C |

Example 99. Crystallinity Analyses of Compounds by X-Ray Powder Diffractometer and Differential Scanning Calorimetry X-ray powder diffraction (XRPD) data were collected using a Bruker D8 Advance powder diffractometer. The samples were irradiated with copper K-alpha X-rays ($\lambda=1.54179$ Å) with the generator operating at 40 kV/40 mA. The samples were scanned in continuous mode from 3° to 40° (2θ) with a sample rotation speed of 15 rpm and a scanning rate of 10°/min.

Differential scanning calorimetry (DSC) data were collected using a TA Q2000. For each sample analyzed, approximately 1 mg of sample was placed inside a hermetically sealed aluminum pan, containing a pinhole, and heated at a rate of 10° C./min from 25° C. to 300° C.

FIGS. 1A-9A show XRPD patterns of compounds 10, 62, 6B, 56, 3, 11, 53, 59, and 48 raw materials, respectively. FIGS. 1B-9B show DSC of compounds 10, 62, 6B, 56, 3, 11, 53, 59, and 48 respectively. Tables 3-11 show XRPD prominent peaks corresponding to FIGS. 1A-9A, respectively.

TABLE 3

Compound 10 - XRPD prominent peaks corresponding to FIG. 1A

| 2-Theta | I % |
|---|---|
| 9.3 | 100 |
| 12.0 | 23 |
| 13.0 | 8.3 |
| 16.1 | 54.6 |
| 17.7 | 15.5 |
| 18.8 | 98.5 |
| 19.2 | 8.8 |
| 21.1 | 56.2 |
| 21.4 | 59.5 |
| 21.6 | 45.9 |
| 21.9 | 10.2 |
| 22.6 | 38.9 |
| 23.9 | 31.6 |
| 25.2 | 17 |
| 25.4 | 13.9 |
| 26.0 | 28.6 |
| 26.4 | 30.6 |
| 27.8 | 6.3 |
| 28.5 | 9.8 |
| 29.4 | 17.7 |
| 29.6 | 8.2 |
| 30.3 | 24.6 |
| 32.0 | 3.4 |
| 33.1 | 4.6 |
| 33.8 | 1.9 |
| 35.6 | 4.1 |
| 36.2 | 4.8 |
| 39.4 | 6.1 |

TABLE 4

Compound 62 - XRPD prominent peaks corresponding to FIG. 2A

| 2-Theta | I % |
|---|---|
| 6.9 | 100 |
| 7.5 | 0.6 |
| 11.2 | 6.4 |
| 13.7 | 4.3 |
| 13.9 | 25.5 |
| 16.5 | 27.2 |
| 17.4 | 4.2 |
| 18.1 | 7 |
| 19.1 | 4.5 |
| 19.5 | 25.5 |
| 20.8 | 41 |
| 26.8 | 1.6 |
| 29.1 | 0.9 |
| 29.3 | 7 |
| 33.2 | 3.6 |
| 35.0 | 3.5 |
| 36.2 | 3.1 |
| 38.7 | 1.3 |

TABLE 5

Compound 6B - XRPD prominent peaks corresponding to FIG. 3A

| 2-Theta | I % |
|---|---|
| 7.2 | 52.7 |
| 10.4 | 7.3 |
| 12.8 | 11.1 |
| 14.1 | 15.6 |
| 14.4 | 41.4 |
| 15.5 | 8 |
| 15.9 | 12.3 |
| 16.2 | 10.2 |
| 16.7 | 58.2 |
| 17.9 | 28.8 |
| 18.5 | 23.9 |
| 19.0 | 100 |
| 20.4 | 58.9 |
| 20.8 | 27.4 |
| 21.8 | 12.8 |
| 23.2 | 41.6 |
| 24.0 | 24.8 |
| 24.5 | 18.4 |
| 24.9 | 6.9 |
| 25.3 | 9.5 |
| 25.7 | 48.5 |
| 26.5 | 12.1 |
| 28.0 | 38.8 |
| 28.8 | 9.7 |
| 29.2 | 13 |
| 29.6 | 21.7 |
| 30.3 | 7.8 |
| 31.8 | 10.6 |
| 32.4 | 6.4 |

TABLE 6

Compound 56 - XRPD prominent peaks corresponding to FIG. 4A

| 2-Theta | I % |
|---|---|
| 7.3 | 100 |
| 13.7 | 4.7 |
| 14.5 | 34.8 |
| 16.0 | 1.9 |
| 17.9 | 15.7 |
| 19.0 | 16.3 |
| 20.3 | 7.6 |
| 21.9 | 20.8 |
| 24.7 | 6 |
| 25.4 | 5.7 |
| 28.9 | 4 |
| 32.5 | 1.9 |
| 36.8 | 2.2 |

TABLE 7

Compound 3 - XRPD prominent peaks corresponding to FIG. 5A

| 2-Theta | I % |
|---|---|
| 3.2 | 5.9 |
| 8.4 | 13.4 |
| 9.0 | 4.9 |
| 10.7 | 30.5 |
| 12.3 | 31.5 |
| 12.6 | 57 |
| 14.7 | 5.6 |
| 14.9 | 20.3 |
| 15.8 | 37 |
| 16.6 | 26 |
| 16.8 | 24.3 |
| 18.1 | 2.2 |
| 18.3 | 7.9 |
| 18.6 | 100 |
| 19.6 | 2.8 |

TABLE 7-continued

Compound 3 - XRPD prominent peaks corresponding to FIG. 5A

| 2-Theta | I % |
|---|---|
| 20.6 | 13.2 |
| 21.0 | 24.5 |
| 21.4 | 8.3 |
| 22.4 | 7.4 |
| 22.6 | 36.4 |
| 23.8 | 7.6 |
| 24.7 | 7.5 |
| 25.3 | 23.3 |
| 26.9 | 5.9 |
| 27.2 | 6.6 |
| 27.9 | 4.2 |
| 28.1 | 9.3 |
| 29.5 | 6.2 |
| 29.7 | 5.2 |
| 31.1 | 2.7 |
| 32.8 | 2.8 |
| 33.2 | 2.5 |
| 35.9 | 2.8 |
| 37.5 | 5.8 |

TABLE 8

Compound 11 - XPRD prominent peaks corresponding to FIG. 6A

| 2-Theta | I % |
|---|---|
| 5.8 | 100 |
| 9.9 | 4.1 |
| 11.6 | 13.7 |
| 12.0 | 10.5 |
| 14.5 | 15.3 |
| 15.3 | 16.1 |
| 16.0 | 4.9 |
| 16.8 | 8.6 |
| 17.5 | 8.6 |
| 18.7 | 6.7 |
| 19.1 | 9.2 |
| 19.7 | 19.7 |
| 20.7 | 6.8 |
| 21.0 | 33.1 |
| 21.7 | 2.9 |
| 22.4 | 9.8 |
| 23.4 | 5.7 |
| 24.2 | 19.5 |
| 26.4 | 14.8 |
| 27.4 | 22.9 |
| 27.9 | 3.1 |
| 29.5 | 8.5 |
| 29.7 | 4.3 |
| 32.1 | 12 |
| 32.6 | 4.9 |
| 34.3 | 2.7 |
| 35.4 | 13.8 |
| 35.9 | 2.7 |
| 37.6 | 3.2 |

TABLE 9

Compound 53 - XRPD prominent peaks corresponding to FIG. 7A

| 2-Theta | I % |
|---|---|
| 7.3 | 53.8 |
| 10.8 | 10.6 |
| 12.3 | 4.7 |
| 12.6 | 13 |
| 13.8 | 10.9 |
| 14.6 | 6.4 |
| 15.0 | 5.2 |
| 16.6 | 51 |
| 17.8 | 10.9 |

TABLE 9-continued

Compound 53 - XRPD prominent peaks corresponding to FIG. 7A

| 2-Theta | I % |
| --- | --- |
| 18.4 | 100 |
| 19.5 | 8.1 |
| 19.7 | 4.3 |
| 20.3 | 18.5 |
| 20.6 | 4.7 |
| 21.2 | 9.9 |
| 21.6 | 4.7 |
| 22.0 | 5.7 |
| 23.4 | 7.1 |
| 23.6 | 4 |
| 24.3 | 38.5 |
| 25.3 | 6.1 |
| 25.9 | 7.3 |
| 26.6 | 11.1 |
| 27.0 | 3 |
| 28.0 | 17.1 |
| 29.5 | 4.3 |
| 31.2 | 6.8 |
| 32.7 | 2 |
| 33.0 | 2.2 |
| 37.3 | 3.2 |

TABLE 10

Compound 59 - XRPD prominent peaks corresponding to FIG. 8A

| 2-Theta | I % |
| --- | --- |
| 6.9 | 100 |
| 9.5 | 6 |
| 11.2 | 28.8 |
| 13.6 | 13.9 |
| 13.9 | 19.4 |
| 15.0 | 10 |
| 16.4 | 72.1 |
| 16.9 | 6.3 |
| 17.4 | 46.6 |
| 18.0 | 33.3 |
| 19.1 | 28.5 |
| 19.5 | 56.5 |
| 20.8 | 30.4 |
| 21.2 | 8.2 |
| 22.2 | 1.7 |
| 22.5 | 3.6 |
| 22.6 | 3.4 |
| 23.3 | 3.7 |
| 24.5 | 5.2 |
| 24.8 | 10.1 |
| 26.3 | 3.1 |
| 26.7 | 14.3 |
| 26.9 | 8.1 |
| 27.6 | 8.4 |
| 28.4 | 3.4 |
| 28.7 | 3 |
| 29.0 | 5.5 |
| 29.3 | 10.5 |
| 30.1 | 3.4 |
| 33.2 | 9 |
| 35.0 | 2 |
| 36.1 | 3.3 |
| 38.7 | 2.9 |

TABLE 11

Compound 48 - XRPD prominent peaks corresponding to FIG. 9A

| 2-Theta | I % |
| --- | --- |
| 7.3 | 23.6 |
| 9.9 | 97.6 |
| 11.0 | 7.3 |

TABLE 11-continued

Compound 48 - XRPD prominent peaks corresponding to FIG. 9A

| 2-Theta | I % |
| --- | --- |
| 12.3 | 74 |
| 13.8 | 26.2 |
| 14.1 | 70.7 |
| 14.6 | 11.8 |
| 15.2 | 7.8 |
| 15.7 | 21 |
| 16.5 | 42.1 |
| 17.2 | 35.2 |
| 17.4 | 16.3 |
| 18.8 | 44.7 |
| 19.5 | 16.1 |
| 19.8 | 100 |
| 20.3 | 28.4 |
| 20.7 | 68.8 |
| 21.5 | 11.1 |
| 22.3 | 17 |
| 22.5 | 10.6 |
| 23.7 | 74 |
| 24.8 | 63.6 |
| 26.1 | 10.6 |
| 27.7 | 51.5 |
| 28.7 | 18.2 |
| 29.1 | 48.2 |
| 29.7 | 11.1 |
| 30.1 | 7.8 |
| 31.2 | 11.8 |
| 31.7 | 12.3 |
| 33.5 | 5.4 |
| 35.7 | 8.7 |

Example 100. In Vitro Assay Data Peak and Ramp

Functional characterization of exemplary compounds to modulate INa expressed by various human isoforms and disease-causing mutant voltage-gated sodium channels was accomplished using the PatchXpress high throughput electrophysiology platform (Molecular Devices, Sunnyvale, Calif.). HEK-293 cells expressing a recombinant, human NaV1.X sodium channel (either hNaV1.6-WT, hNaV1.6-R223G, hNaV1.6-N984K, hNaV1.6-N1768D, hNaV1.1-WT, hNaV1.2-WT, hNaV1.5-WT, hNaV1.7-WT, or hNaV1.8-WT) were grown in DMEM/high-glucose Dulbecco's modified, 10% FBS, 2 mM sodium pyruvate, 10 mM HEPES and 400 μg/mL G418. Cells were grown to 50% 80% confluency prior to harvesting. Trypsinized cells were washed, allowed to recover for 1 hour and then resuspended in extracellular recording solution at a concentration of $1 \times 10^6$ cells/ml. The onboard liquid handling facility of the PatchXpress was used for dispensing cells and applying test compounds. INa amplitude and stability were determined by analyzing the peak current amplitude.

Voltage Step Activated Sodium Current

Peak INa was evoked by depolarizing steps to 0 mV for 20 ms from a holding potential which evoked half-inactivation (e.g., −60 mV) at a frequency of 0.1 Hz. The voltage of half-inactivation was determined for each cell using a 5 sec prepulse to membrane potentials between −120 mV and −20 mV followed immediately by a voltage step to a fully activating membrane voltage (e.g., 0 mV). Following steady state block with exemplary compounds (e.g., as described herein), the degree of inhibition was measured using the average of three consecutive voltage steps. Percent steady-state inhibition of INa was calculated as: [(INa_compound)/(INa_control)]*100, where INa_compound and INa_control represent INa recorded in the presence or absence of compound, respectively.

Results from this assay relating to percent inhibition measured at 1 are summarized in Table 18 below. In this table, "A" indicates inhibition between less than 0% to 50% and "B" indicates inhibition of greater than 50% and N/A indicates the compound was not tested.

Voltage Ramp Activated Sodium Current

The Nav1.6 mutant channels (hNaV1.6-R223G, hNaV1.6-N984K, hNaV1.6-N1768D) express an enhanced sodium current in response to a ramp voltage depolarization when compared to the wild-type hNaV1.6-WT. This enhanced, depolarizing ramp current is thought to contribute to enhanced neuronal excitability. The degree of block with exemplary compounds (e.g., as described herein) was measured using a +600 mv/sec voltage ramp from −100 mV to +20 mV. The ramp current was defined as the area of the current measured between −55 mV and +15 mV. Following steady state block with exemplary compounds (e.g., as described herein) at 1 µM, a Na$^+$ free solution containing an impermeant cation (e.g., Choline or NMDG) was added for determination of the baseline current level for offline subtraction. Percent inhibition of enhanced ramp current was calculated as (compound−baseline)/(control−baseline)*100, where control represents the ramp current recorded in the absence of compound. Results from this assay are summarized in Table 19 below. In this table, "A" indicates inhibition between less than 0% to 50% and "B" indicates inhibition of greater than 50% and N/A indicates the compound was not tested.

TABLE 18

| Compound | hNav1.1 Peak INa | hNav1.2 Peak INa | hNav1.5 Peak INa | hNav1.6 Peak INa | hNav1.7 Peak INa | hNav1.8 Peak INa |
|---|---|---|---|---|---|---|
| 6B | B | B | B | B | B | B |
| 3 | B | N/A | B | B | B | B |
| 10 | B | A | B | B | B | B |
| 11 | B | N/A | B | B | B | B |
| 48 | N/A | N/A | B | B | B | B |
| 53 | B | A | B | B | B | B |
| 56 | B | B | B | B | B | B |
| 59 | B | B | B | B | B | B |
| 62 | B | B | B | B | B | B |

TABLE 19

| Compound | hNav1.6-R223G Ramp INa | hNav1.6-N984K Ramp INa | hNav1.6-N1768D Ramp INa |
|---|---|---|---|
| 6B | B | B | B |
| 3 | B | B | B |
| 10 | B | A | B |
| 11 | A | B | B |
| 48 | A | A | B |
| 53 | A | A | B |
| 56 | A | B | B |
| 59 | B | B | B |
| 62 | A | B | B |

Example 101. Mouse MES Protocol

Methods:

Male CD-1 mice, weighing 25-35 g were assessed in the Maximal Electroshock induced Seizure (IVIES) assay. Briefly, mice were dosed with compound (n=12/group) according to the dosing parameters in Table 20 and the latency to induce tonic hind limb extension following transauricular electrical stimulation (50 Hz, 50 mA, 0.8 sec duration, pulse width of 10 ms) was recorded up to 60 seconds post stimulus. Mean latency to tonic extension data for all compounds are presented in Table 21.

TABLE 20

Mouse MES dosing parameters.

| Compound | Vehicle | Dose route | Pre-treatment time (min) |
|---|---|---|---|
| 10 | 35% HPCD | PO | 30 |
| 6B | 35% HPCD | PO | 120 |
| 53 | 35% HPCD | PO | 30 |
| 62 | 35% HPCD | PO | 30 |
| 48 | 35% HPCD | PO | 30 |
| 3 | 35% HPCD | PO | 30 |

Results:

TABLE 21

Mean latency to tonic hind limb extension in the MES assay

| | Mean latency to tonic extension (s) | | |
|---|---|---|---|
| Compound | 1 mg/kg | 3 mg/kg | 10 mg/kg |
| 10 | 7.9 | 36.3 | 55.2 |
| 6B | 17.3 | 50.5 | |
| 53 | 36.4 | 60 | 60 |
| 62 | 17.6 | 46.1 | |
| 48 | | 42.5 | 60 |
| 3 | | 60 | 60 |

Example 102. Bile-Metabolite Study

Bile samples are collected (0-4, 4-8, and 8-24 hours post dose) from three male Sprague-Dawley rats following a single intravenous (IV) bolus administration of test compounds, for example, compound 3, 10, 15, 56, 62, or 65, administered at 1 mg/kg to bile duct cannulated rats. The bile samples are pooled in a volume proportional manner to give one 0-24 hour sample. This sample is quenched with two volumes of acetonitrile, vortexed, centrifuged and the supernatant transferred to a 96-well plate and partially dried under nitrogen.

The 0-24 hour bile sample for each rat is analyzed by ultra-high performance liquid chromatography coupled to high resolution mass spectrometry (UPLC-HRMS) and the full scan data processed using manual and automated methods including, for example, Masslynx or Metabolynx, to identify the presence of both expected and unanticipated metabolites. The UPLC-HRMS full scan data are used to define the masses of the parent and metabolites. A separate UPLC-HRMS/MS acquisition is conducted to generate product ion spectra for each metabolite. The metabolite structures are proposed by comparison of the metabolite high resolution product ion spectra with the high resolution product ion spectrum of the test compound. Bile samples from rats receiving compound treatment will display altered metabolite levels and metabolic pathway activation.

Example 103: Evaluation of Effects on Seizures and Survival in the SCN2A$^{Q54}$ Transgenic Mouse Model To evaluate the effect on seizures and survival in a mouse model of increased persistent sodium current, the compounds disclosed in the present application, for example, compound 3, 6B, 10, 11, 53, 56, 59, or 62, may be evaluated in the SCN2A$^{Q54}$ transgenic mouse model (Kearney J. A. et al. A gain-of-function mutation in the sodium channel gene Scn2a results in seizures and behavioral abnormalities. Neuroscience, 102(2), 307-317 (2001)). SCN2A$^{Q54}$ transgenic mice express a transgene with three mutations in the sodium channel NaV1.2 (G879Q, A880Q, L881Q), which leads to an increase in neuronal persistent sodium current. Increased persistent sodium current in these mice is correlated with an epilepsy phenotype and premature death. The compounds (for example, compound 3, 6B, 10, 11, 53, 56, 59, or 62) may be dosed systemically (e.g. by oral gavage, by subcutaneous or intraperitoneal injection, etc) once or twice daily to achieve appropriate plasma levels. In some instances, the compound may be provided in the chow fed ad libitum. For evaluation of acute anticonvulsant effects of compound seizures may be recorded by continuous video recording and/or electroencephalography (EEG) using indwelling electrodes. Anticonvulsant activity may be evaluated by comparing the number of spontaneous behavioral seizures (tonic deviation of the head and body accompanied by forelimb clonus) or spontaneous seizures recorded using EEG, during a 30 60 minute pretreatment period with the number of seizures occurring during a 30 60 minute post treatment period. Administration of the compound may result in a decreased number of seizures compared to baseline (pretreatment). To evaluate compound effects on survival, compounds may be dosed chronically for several weeks, starting, for example, at 3 weeks of age until, for example, 16 weeks of age. Administration of compound may result in reduction of the number of premature deaths. For detailed methods see Anderson L. L. et al. Antiepileptic activity of preferential inhibitors of persistent sodium current. Epilepsia, 55(8), 1274-1283 (2014).

Example 104: Evaluation of Effects on Seizures and Survival in Transgenic Mouse Models with Pathogenic Gain of Function Mutations in SCN2A and SCN8A (Scn2a (R1882Q) Mouse Model and Scn8a$^{N1768D/+}$ Mouse Model)

To evaluate the effect on seizures and survival in mouse models of epileptic encephalopathy, mouse models carrying pathogenic gain of function mutations may be used, for example the Scn2a (R1882Q) mouse model, carrying a gain of function mutation in NaV1.2 (Petrou et al. Antisense oligonucleotide therapy for SCN2A gain-of-function epilepsies (Abst. 1.466), American Epilepsy Society. 2018) and the SC118a$^{N1768D/+}$ mouse model carrying a gain of function mutation in NaV1.6 (Wagnon J. L. et al. Convulsive seizures and SUDEP in a mous mouse model of SCN8A epileptic encephalopathy. *Human Molecular Genetics*, 24(2), 506-515 (2015)). The compounds disclosed in the present application (for example, compound 3, 6B, 10, 11, 53, 56, 59, or 62) may be dosed systemically (e.g. by oral gavage, by subcutaneous or intraperitoneal injection, etc) once or twice daily to achieve appropriate plasma levels. In some instances, the compound may be provided in the chow fed ad libitum. As the phenotype of these models can be severe, treatment may begin with a very young age (e.g. before weaning and as early as postnatal day 5) or by treatment of the dam to achieve appropriate plasma levels in nursing pups. For evaluation of compound effects on spontaneous seizures, seizures may be recorded over one or more days by continuous video recording and/or EEG recording and counted by a reviewer of the video and/or EEG data. The number of spontaneous seizures per hour after treatment may be compared to the number of spontaneous seizures in vehicle treated animals over the same time period. Administration of the compound may result in a decreased number of seizures per hour compared to vehicle treated animals. To evaluate compound effects on survival, compounds may be dosed chronically for several weeks until for example at least 50% of animals have died in the control group. Dosing start may be for example as early as postnatal day 10 in the SCN2A R1882Q model, postnatal day 30-40 in Scn8a$^{N1768D/+}$ mice (heterozygous N1768D mice), or postnatal day 5 in Scn8a$^{D/D}$ mice (homozygous N1768d mice). Administration of compound may result in reduction of the number of premature deaths compared to vehicle treated mice. For detailed methods see e.g. Baker E. M. et al. The novel sodium channel modulator GS-458967 (GS967) in an effective treatment in a mouse model of SCN8A encephalopathy. Epilepsia. 59(6), 1166-76 (2018).

Example 105: Evaluation of Effects on Seizures and Survival in a Mouse Model of Dravet Syndrome To evaluate the effect on seizures and survival in a mouse model of Dravet syndrome, the compounds disclosed in the present application, for example, compound 3, 6B, 10, 11, 53, 56, 59, or 62, may be evaluated in the Scn1a$^{+/-}$ mouse model. The compounds (for example, compound 3, 6B, 10, 11, 53, 56, 59, or 62) may be dosed systemically (e.g. by oral gavage, by subcutaneous or intraperitoneal injection, etc) once or twice daily to achieve appropriate plasma levels. In some instances, compound may be provided in the chow fed ad libitum. As the phenotype of these models can be severe, treatment might begin with treatment of pups before weaning or treatment of the dam to achieve appropriate plasma levels in nursing pups. To increase the severity of the phenotype of this mouse model, Scn1a$^{+/-}$ mice might be exposed to elevated temperature for a short period of time of up to 42 degrees Celsius to induce a short hyperthermia-induced seizure around the time of weaning. For evaluation of compound effects on spontaneous seizures, seizures may be recorded for example for one or more days by continuous video recording and/or EEG recording and counted by a reviewer of the video and/or EEG data. The number of spontaneous seizures per hour after compound treatment may be compared to the number of spontaneous seizures per hour in vehicle treated animals over the same time period. Administration of the compound may result in a decreased number of seizures per hour compared to vehicle treated animals. To evaluate compound effects on survival, compounds may be dosed chronically for several weeks until at least 50% of animals have died in the control group. Dosing would start for example on postnatal day 18. Administration of compound may result in reduction of the number of premature deaths compared to vehicle treated mice. For detailed methods see Anderson L. L. et al. Unexpected efficacy of a novel sodium channel modulator in Dravel syndrome. *Sci. Rep.* 10: 7(1), 1682 (2017).

Example 106: Evaluation of Effects on Seizures, Survival and Other Endpoints in Transgenic Mice of Epileptic Encephalopathy Such as a KCNT1 Mouse Model Carrying the Mouse Equivalent of a Human Pathogenic Mutation (e.g. P924L)

Homozygous mice carrying the mouse equivalent of the human P924L mutation (P905L), exhibit spontaneous seizures, interictal discharges, impaired nesting behavior, and a shortened life span (Burbano L. et al Characterization of a Novel Knock-in Mouse Model of KCNT1 Epileptic Encephalopathy (P2.273). *Neurology* April 2018, 90 (15 Supplement) P2.273). The compounds disclosed in the present application, for example, compound 3, 6B, 10, 11, 53, 56, 59, or 62 may be dosed systemically (e.g. by oral gavage, by subcutaneous or intraperitoneal injection, etc.) once or twice daily to achieve appropriate plasma levels. In some instances, the compound may be provided in the chow fed ad libitum. As the phenotype of these models can be severe, treatment may begin with treatment of pups before weaning or treatment of the dam to achieve appropriate plasma levels in nursing pups. For evaluation of compound effects on spontaneous seizures, seizures may be recorded for example for one or more days by continuous video recording and/or EEG recording as described in the previous example. The number of spontaneous seizures after treatment may be compared to the number of spontaneous seizures in vehicle treated animals over the same time period. Administration of the compound may result in a decreased number of seizures compared to vehicle treated animals. For evaluation of compound effects on interictal discharges, interictal discharges may be recorded by EEG over 1 or more days and counted by a reviewer. The number of interictal discharges per hour after treatment may be compared to the number of interictal discharges per hour in vehicle treated animals over the same time period. Administration of the compound may result in a decrease in the number of interictal discharge compared to vehicle treated animals. For evaluation of compound effects on nest building behavior, mice may be presented with nest building material (e.g. tissue paper) and ability to build nests compared to vehicle treated animal will be assessed. Administration of the compound may result in increased ability to build nests compared to vehicle treated animals. To evaluate compound effects on survival, compounds may be dosed chronically for several weeks until at least 50% of animals have died in the control group. Dosing may start, for example, on postnatal day 18. Administration of the compound may result in reduction of the number of premature deaths compared to vehicle treated mice.

Example 107: Post-Surgical Pain

The analgesic efficacy of the compounds disclosed in the present application, for example, compound 3, 6B, 10, 11, 53, 56, 59, or 62, may be assessed in the post-incision model in rats. Rats may be anesthetized and receive an incision in one hindpaw. The following day, rats may be administered test compound (e.g., compound 3, 6B, 10, 11, 53, 56, 59, or 62) by a systemic route of administration (e.g., oral gavage, subcutaneous injection, intravenous, etc.) to achieve appropriate plasma exposure. Between 30 and 120 min later, mechanical allodynia may be assessed using the Up-down method with von Frey hairs (Chaplan, S. R., Bach, F. W., Pogrel, J. W., Chung, J. M. & Yaksh, T. L. Quantitative assessment of tactile allodynia in the rat paw. *J Neurosci Meth* 53, 55-63 (1994). Rats may be stimulated with the hair in the middle of the series (for example, 2.0 g) and consequent stimuli may be presented in consecutive order, either ascending or descending. A paw withdrawal response to the hair may result in presentation of the next weaker stimulus; absence of a paw withdrawal response may result in presentation of the next stronger stimulus. Administration of the compound may result in increased threshold for von Frey hair stimulation to induce paw withdrawal i.e. decreased mechanical allodynia.

Example 108: Neuropathic Pain

The analgesic efficacy of the compounds of the present application, for example, compound 3, 6B, 10, 11, 53, 56, 59, or 62, may be assessed using preclinical models of neuropathic pain in rats. Neurophysiological measures will be recorded in the spinal cord (dorsal horn) and brain (ventral posterolateral nucleus (VPL) of the thalamus) of anesthetized rats. The effects of systemic administration of compounds (e.g. by subcutaneous injection, intravenous etc.) that achieve appropriate plasma exposure will be assessed in spinal nerve ligated and sham operated rats, as recently described for oxcarbazepine (Kim, S. & Chung, J. An experimental model for peripheral neuropathy produced by segmental spinal nerve ligation in the rat. *Pain* 50, 355-363 (1992)). Spinal nerve ligation (SNL) of the left L5 and L6 spinal nerves may be performed to induce a model of unilateral peripheral neuropathic pain; sham rats will undergo all steps of this surgery, apart from the nerve isolation and ligation (Patel, R., Kucharczyk, M., Montagut-Bordas, C., Lockwood, S. & Dickenson, A. H. Neuropathy following spinal nerve injury shares features with the irritable nociceptor phenotype: A back-translational study of oxcarbazepine. *Eur J Pain* 23, 183-197 (2019)). After recovery from the SNL or sham surgery, thalamic recordings may be obtained by implanting parylene-coated tungsten electrodes into the right ventral posterolateral nucleus (VPL) of the thalamus. Spontaneous neuronal activity and neuronal activity evoked using natural stimuli, for example, dynamic brushing, mechanical pressure, cold or heat, to stimulate the receptive field may be recorded from sham and SNL rats at baseline and at various time points (e.g. 10-120 min) after administration of compounds. Extracellular recordings from deep dorsal horn laminae neurons may be made in anesthetized sham and SNL rats which have had a laminectomy to access L4-L6 segments of the spinal cord. Spontaneous neuronal activity and activity evoked by electrical stimuli (typically 2 ms pulses, 0.5 Hz) or natural stimuli (as described above) may be recorded at baseline and at various time points (e.g. 10-120 min) after administration of compounds. Spinal nerve ligation may result in exaggerated responses in the thalamus and dorsal horn to some modalities of stimulation (e.g. brushing, mechanical pressure, cold and heat). Administration of the compound may result in attenuation of these exaggerated responses in the thalamus and/or dorsal horn following stimulation compared to vehicle treated spinal nerve ligated rats. Furthermore, in a separate study, mechanical allodynia may be assessed in rats after spinal nerve ligation surgery. 1-2 weeks after surgery, mechanical allodynia will be assessed using the Up-Down method with von Frey hairs[1]. Rats may then be dosed chronically with systemic compound, for example compound 3, 6B, 10, 11, 53, 56, 59, or 62, (e.g. by oral gavage, subcutaneous injection, etc.) to achieve appropriate plasma exposure and mechanical allodynia may be assessed using the Up-Down method after the acute administration of the compound and subsequently at least once per week for 2 weeks. Administration of the compound may result in increased threshold for von Frey hair stimulation to induce paw withdrawal, i.e. decreased mechanical allodynia.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

The invention claimed is:
1. The compound:

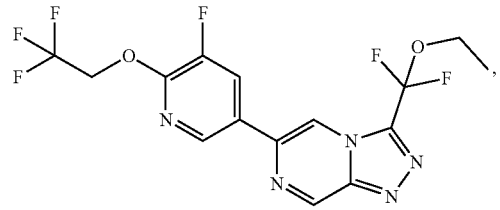

or a pharmaceutically acceptable salt thereof.

2. A pharmaceutical composition comprising a pharmaceutically acceptable carrier and the compound:

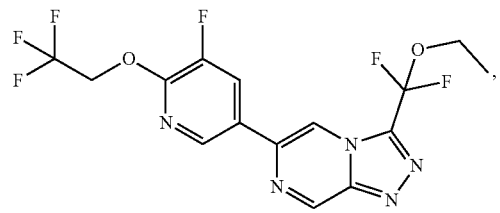 [SMILES: CCOC(F)(F)c1nnc2cnc(-c3cnc(OCC(F)(F)F)c(F)c3)cn12]

or a pharmaceutically acceptable salt thereof.

3. The compound:

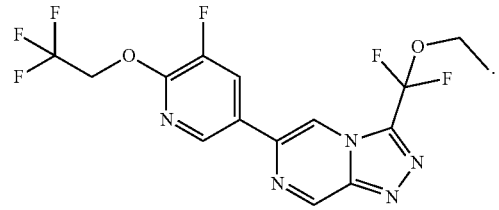 [SMILES: CCOC(F)(F)c1nnc2cnc(-c3cnc(OCC(F)(F)F)c(F)c3)cn12]

4. A pharmaceutical composition comprising a pharmaceutically acceptable carrier and the compound:

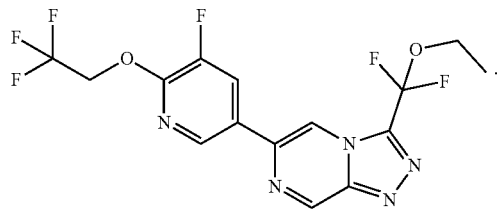

5. A crystalline form of the compound:

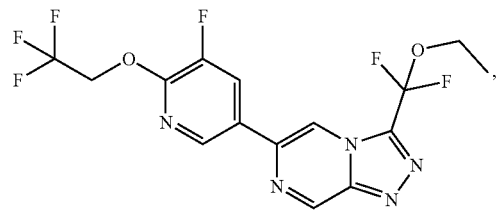

wherein the crystalline form is characterized by an X-ray powder diffraction pattern comprising X-ray power diffraction peaks at the following diffraction angles (° 2θ): 9.3°±0.2°, 18.8°±0.2°, and 21.4°±0.2° (2θ).

6. The crystalline form of claim 5, wherein the crystalline form is further characterized by an X-ray powder diffraction pattern comprising additional X-ray powder diffraction peaks at the following diffraction angles (° 2θ): 16.1°±0.2°, 21.1°±0.2°, and 21.6°±0.2° (2θ).

7. The crystalline form of claim 5, wherein the crystalline form is further characterized by an X-ray powder diffraction pattern comprising additional X-ray powder diffraction peaks at the following diffraction angles (° 2θ): 16.1°±0.2°, 21.1°±0.2°, 21.6°±0.2°, 22.6°±0.2°, 23.9°±0.2°, 26.0°±0.2°, and 26.4°±0.2° (2θ).

8. The crystalline form of claim 5, wherein the crystalline form is characterized by an X-ray powder diffraction pattern as shown in FIG. 1A.

9. The crystalline form of claim 5, wherein the X-ray powder diffraction pattern is obtained using Cu Kα radiation.

10. The crystalline form of claim 5, wherein the crystalline form has a melting point onset as determined by differential scanning calorimetry at 122° C.

11. The crystalline form of claim 5, wherein the crystalline form has a differential scanning calorimetry curve as shown in FIG. 1B.

12. A pharmaceutical composition comprising a pharmaceutically acceptable carrier and the crystalline form of claim 5.

13. A pharmaceutical composition comprising a pharmaceutically acceptable carrier and the crystalline form of claim 6.

14. A pharmaceutical composition comprising a pharmaceutically acceptable carrier and the crystalline form of claim 7.

15. A pharmaceutical composition comprising a pharmaceutically acceptable carrier and the crystalline form of claim 8.

16. A pharmaceutical composition comprising a pharmaceutically acceptable carrier and the crystalline form of claim 9.

17. A pharmaceutical composition comprising a pharmaceutically acceptable carrier and the crystalline form of claim 10.

18. A pharmaceutical composition comprising a pharmaceutically acceptable carrier and the crystalline form of claim 11.

* * * * *

UNITED STATES PATENT AND TRADEMARK OFFICE
CERTIFICATE OF CORRECTION

PATENT NO. : 11,014,931 B2
APPLICATION NO. : 17/102586
DATED : May 25, 2021
INVENTOR(S) : Griffin et al.

Page 1 of 1

It is certified that error appears in the above-identified patent and that said Letters Patent is hereby corrected as shown below:

In the Claims

Claim 5, Column 191, Line 2, "X-ray power" should be --X-ray powder--

Signed and Sealed this
Ninth Day of August, 2022

Katherine Kelly Vidal
*Director of the United States Patent and Trademark Office*